(12) United States Patent
Palmer

(10) Patent No.: US 6,900,237 B2
(45) Date of Patent: May 31, 2005

(54) SULFONAMIDE COMPOUNDS AS PROTEASE INHIBITORS

(75) Inventor: James Palmer, Corte Madera, CA (US)

(73) Assignee: Axys Pharmaceuticals, Inc., So. San Francisco, CA (US)

(*) Notice: Subject to any disclaimer, the term of this patent is extended or adjusted under 35 U.S.C. 154(b) by 0 days.

(21) Appl. No.: 10/237,509

(22) Filed: Sep. 9, 2002

(65) Prior Publication Data

US 2003/0158231 A1 Aug. 21, 2003

Related U.S. Application Data

(60) Provisional application No. 60/322,220, filed on Sep. 14, 2001.

(51) Int. Cl.$^7$ .................. A61K 31/604; C07D 209/404

(52) U.S. Cl. .................. 514/419; 548/491; 546/134; 546/268.1; 546/270.7; 544/106; 544/336

(58) Field of Search .................. 548/491; 514/419; 546/134, 268.1, 270.7; 544/106, 336

(56) References Cited

FOREIGN PATENT DOCUMENTS

| WO | WO 96/30353 | 10/1996 |
|----|-------------|---------|
| WO | WO 98/47523 | 10/1998 |
| WO | WO 00/48993 | 8/2000 |
| WO | WO 00/55144 | 9/2000 |

*Primary Examiner*—Golam M M Shameem
(74) *Attorney, Agent, or Firm*—Celera, an Applera Corporation Business; Rekha Bansal; Janice V. Wade

(57) ABSTRACT

The present invention relates to novel cysteine protease inhibitors; the pharmaceutically acceptable salts and N-oxides thereof; their uses as therapeutic agents and the methods of their making.

20 Claims, No Drawings

SULFONAMIDE COMPOUNDS AS PROTEASE INHIBITORS

CROSS-REFERENCE

This application claims priority under 35 USC 119(e) to U.S. Provisional application Ser. No. 60/322,220, filed on Sep. 14, 2001, the disclosure of which is incorporated herein by reference in its entirety.

BACKGROUND OF THE INVENTION

1. Field of the Invention

This application relates to compounds and compositions for treating diseases associated with cysteine protease activity, particularly diseases associated with activity of cathepsins B, K, L or S.

2. State of the Art

Cysteine proteases represent a class of peptidases characterized by the presence of a cysteine residue in the catalytic site of the enzyme. Cysteine proteases are associated with the normal degradation and processing of proteins. The aberrant activity of cysteine proteases, e.g., as a result of increased expression or enhanced activation, however, may have pathological consequences. In this regard, certain cysteine proteases are associated with a number of disease states, including arthritis, muscular dystrophy, inflammation, tumor invasion, glomerulonephritis, malaria, periodontal disease, metachromatic leukodystrophy and others. For example, increased cathepsin B levels and redistribution of the enzyme are found in tumors; thus, suggesting a role for the enzyme in tumor invasion and metastasis. In addition, aberrant cathepsin B activity is implicated in such disease states as rheumatoid arthritis, osteo arthritis, pneumocystis carinii, acute pancreatitis, inflammatory airway disease and bone and joint disorders.

The prominent expression of cathepsin K in osteoclasts and osteoclast-related multinucleated cells and its high collagenolytic activity suggest that the enzyme is involved in ososteoclast-mediated bone resorption and, hence, in bone abnormalities such as occurs in osteoporosis. In addition, cathepsin K expression in the lung and its elastinolytic activity suggest that the enzyme plays a role in pulmonary disorders as well.

Cathepsin L is implicated in normal lysosomal proteolysis as well as several disease states, including, but not limited to, metastasis of melanomas. Cathepsin S is implicated in Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis. In addition, cathepsin S is implicated in: allergic disorders, including, but not limited to asthma; and allogeneic immune reponses, including, but not limited to, rejection of organ transplants or tissue grafts.

In view of the number of diseases wherein it is recognized that an increase in cysteine protease activity contributes to the pathology and/or symptomatology of the disease, molecules which are shown to inhibit the activity of this class of enzymes, in particular molecules which are inhibitors of cathepsins B, K, L and/or S, will be useful as therapeutic agents.

SUMMARY OF THE INVENTION

In one aspect, this invention is directed to a compound of Formula I:

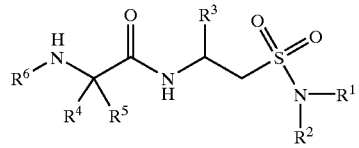

in which:

$R^1$ and $R^2$ independently are $-R^8$, $-X^2OR^8$, $-X^2SR^8$, $-X^2S(O)R^8$, $-X^2S(O)_2R^8$, $-X^2C(O)R^8$, $-X^2C(OR^7)R^7R^8$, $-X^2C(O)OR^8$, $-X^2NR^7R^8$, $-X^2NR^7C(O)OR^8$, $-X^2C(O)NR^7R^8$, $-X^2S(O)_2NR^7R^8$, $-X^2NR^7C(O)NR^7R^8$ or $-X^2NR^7C(NR^7)NR^7R^8$, wherein $X^2$ is $(C_{1-6})$alkylene, $R^7$ is hydrogen or $(C_{1-6})$alkyl; $R^8$ is hydrogen, $(C_{1-6})$alkyl, $(C_{3-12})$cycloalkyl$(C_{0-3})$alkyl, hetero$(C_{5-12})$cycloalkyl$(C_{0-3})$alkyl, $(C_{6-12})$aryl$(C_{0-3})$alkyl, hetero$(C_{5-12})$aryl$(C_{0-3})$alkyl, $(C_{9-12})$bicycloaryl$(C_{0-3})$alkyl or hetero$(C_{8-12})$bicyclo-aryl$(C_{0-3})$alkyl; wherein within $R^8$ said cycloalkyl, heterocycloalkyl, aryl, heteroaryl, bicycloaryl or heterobicycloaryl ring may be substituted with halo, $-R^9$, $-X^3OR^9$, $-X^3SR^9$, $-X^3S(O)R^9$, $-X^3S(O)_2R^9$, $-X^3C(O)R^9$, $-X^3C(OR^9)R^9$, $-X^3C(O)OR^9$, $-X^3NR^9R^{10}$, $-X^3NR^9C(O)OR^9$, $-X^3C(O)NR^9R^{10}$, $-X^3S(O)_2NR^9R^{10}$, $-X^3NR^9C(O)NR^9R^{10}$ or $-X^3NR^9C(NR^9)NR^9R^{10}$; wherein $X^3$ is a bond or $(C_{1-6})$alkylene, $R^9$ is hydrogen or $(C_{1-6})$alkyl and $R^{10}$ is cycloalkyl;

$R^3$ is $-R^{11}$, $-X^3OR^{11}$, $-X^3SR^{11}$, $-X^3S(O)R^{11}$, $-X^3S(O)_2R^{11}$, $-X^3C(O)R^{11}$, $-X^3C(O)OR^{11}$, $-X^3NR^{11}R^{12}$, $-X^3NR^{12}C(O)OR^{11}$, $-X^3C(O)NR^{11}R^{12}$, $-X^3S(O)_2NR^{11}R^{12}$, $-X^3NR^{12}C(O)NR^{11}R^{12}$ or $-X^3NR^{12}C(NR^{12})NR^{11}R^{12}$, wherein $X^3$ is as described above, $R^{11}$ is hydrogen, $(C_{1-6})$alkyl, halo$(C_{1-6})$alkyl, $(C_{3-12})$cycloalkyl$(C_{0-3})$alkyl, hetero$(C_{5-12})$cycloalkyl-$(C_{0-3})$alkyl, $(C_{6-12})$aryl$(C_{0-3})$alkyl, hetero$(C_{5-12})$aryl$(C_{0-3})$alkyl, $(C_{9-12})$bicycloary$(C_{0-3})$alkyl or hetero$(C_{8-12})$bicycloaryl$(C_{0-3})$alkyl and $R^{12}$ is hydrogen or $(C_{1-6})$alkyl, wherein any 1 to 3 annular atoms of any aromatic ring with available valences comprising $R^3$ are optionally independently substituted with halo, nitro, cyano, $(C_{1-6})$alkyl, halo-substituted$(C_{1-6})$alkyl, $-OR^7$, $-C(O)R^7$, $-C(O)OR^7$, $-C(O)NR^7R^7$, $-S(O)_2NR^7R^7$, $-X^2NR^7R^7$, $-X^2NR^7C(O)OR^7$, $-X^2NR^7C(O)NR^7R^7$ or $-X^2NR^7C(NR^7NR^7R^7$, wherein $X^2$ and $R^7$ are as defined above;

$R^4$ is hydrogen or $(C_{1-6})$alkyl;

$R^5$ is $(C_{1-6})$alkyl, halo$(C_{1-6})$alkyl, $(C_{3-12})$cycloalkyl$(C_{0-3})$alkyl, or $-X^2S(O)R^{14}$ where $X^2$ is as defined above and $R^{14}$ is $(C_{3-12})$cycloalkyl$(C_{0-3})$alkyl, hetero$(C_{5-12})$cycloalkyl$(C_{0-3})$alkyl, $(C_{6-12})$aryl$(C_{0-3})$alkyl, hetero$(C_{5-12})$aryl$(C_{0-3})$alkyl, $(C_{9-12})$bicycloaryl$(C_{0-3})$alkyl or hetero$(C_{8-12})$bicycloaryl$(C_{0-3})$alkyl; or $R^4$ and $R^5$ together with the carbon atom to which $R^4$ and $R^5$ are attached form $(C_{3-7})$cycloalkylene;

$R^6$ is hydrogen or $-X^4X^5R^{13}$, wherein $X^4$ is $-C(O)-$, $X^5$ is a bond, $-O-$ or $-NR^{12}-$, wherein $R^{12}$ is as defined above, and $R^{13}$ is $(C_{1-6})$alkyl, $-R^{14}$, $-X^3OR^{14}$, $-X^3SR^{14}$, $-X^3S(O)R^{14}$, $-X^3S(O)_2R^{14}$, $-X^3C(O)R^{14}$, $-X^3C(O)OR^{14}$, $-X^3NR^{14}R^{15}$, $-X^3NR^{15}C(O)OR^{14}$, $-X^3C(O)NR^{14}R^{15}$, $-X^3S(O)_2NR^{14}R^{15}$, $-X^3NR^{15}C(O)NR^{14}R^{15}$ or $-X^3NR^{15}C(NR^{15})NR^{14}R^{15}$, wherein $X^3$ is as defined above; $R^{14}$ is $(C_{3-12})$cycloalkyl$(C_{0-3})$alkyl, hetero$(C_{5-12})$cycloalkyl$(C_{0-3})$alkyl, $(C_{6-12})$aryl$(C_{0-3})$alkyl, hetero$(C_{5-12})$aryl$(C_{0-3})$alkyl, $(C_{9-12})$bicycloaryl$(C_{0-3})$alkyl or hetero$(C_{8-12})$bicycloaryl$(C_{0-3})$alkyl; $R^{15}$ is hydrogen or $(C_{1-6})$alkyl; and within $R^{14}$ said cycloalkyl, heterocycloalkyl, aryl, heteroaryl, bicycloaryl or heterobicycloaryl ring may be substituted with $-OCF_3$, $-CF_3$, $-OH$, halo, $-R^{16}$, $-X^3OR^{16}$, $-X^3OR^{15}$, $-X^3C(O)R^{15}$, $-X^3SR^{16}$, $-X^3S$ (O)R$^{16}$, —R$^{15}$, —X$^3$S(O)$_2$R$^{16}$, —X$^3$C(O)R$^{16}$, —X$^3$C(O) OR$^{15}$, —X$^3$NR$^{15}$R$^{15}$, —X$^3$NR$^{15}$C(O)OR$^{15}$, —X$^3$C(O) NR$^{15}$R$^{16}$, —X$^3$S(O)$_2$NR$^{15}$R$^{16}$, —X$^3$NR$^{15}$C(O)NR$^{15}$R$^{15}$ or —X$^3$NR$^{15}$C(NR$^{15}$)NR$^{15}$R$^{16}$, wherein X$^3$ and R$^{15}$ are as defined above and R$^{16}$ is (C$_{3\text{-}12}$)cycloalkyl(C$_{0\text{-}3}$)alkyl, hetero(C$_{5\text{-}12}$)cycloalkyl(C$_{0\text{-}3}$)alkyl, (C$_{6\text{-}12}$)aryl(C$_{0\text{-}3}$)alkyl, hetero(C$_{5\text{-}12}$)aryl(C$_{0\text{-}3}$)alkyl, (C$_{9\text{-}12}$)bicycloaryl(C$_{0\text{-}3}$)alkyl or hetero(C$_{8\text{-}12}$)bicycloaryl-(C$_{0\text{-}3}$)alkyl and within R$^{16}$ said cycloalkyl, heterocycloalkyl, aryl, heteroaryl, bicycloaryl or heterobicycloaryl ring may be substituted with —R$^{15}$, —R$^{17}$, —X$^3$OR$^{17}$, —X$^3$SR$^{17}$, —X$^3$S(O)R$^{17}$, —X$^3$S (O)$_2$R$^{17}$, —X$^3$C(O)R$^{17}$, —X$^3$C(O)OR$^{17}$, —X$^3$NR$^{15}$R$^{17}$, —X$^3$NR$^{15}$R$^{15}$, —X$^3$NR$^{15}$C(O)OR$^{17}$, —X$^3$C(O)NR$^{15}$R$^{17}$, —X$^3$S(O)$_2$NR$^{15}$R$^{17}$, —X$^3$NR$^{15}$C(O)NR$^{15}$R$^{17}$ or —X$^3$NR$^{15}$C(NR$^{15}$)NR$^{15}$R$^{17}$, wherein X$^3$ and R$^{15}$ are as defined above and R$^{17}$ is (C$_{3\text{-}12}$)cycloalkyl(C$_{0\text{-}3}$)alkyl, hetero(C$_{5\text{-}12}$)cycloalkyl(C$_{0\text{-}3}$)alkyl, (C$_{6\text{-}12}$)aryl(C$_{0\text{-}3}$)alkyl, hetero(C$_{5\text{-}12}$)aryl(C$_{0\text{-}3}$)alkyl, (C$_{9\text{-}12}$)bicycloaryl(C$_{0\text{-}3}$)alkyl or hetero(C$_{8\text{-}12}$)bicycloary(C$_{0\text{-}3}$)alkyl and within R$^{17}$ said cycloalkyl, heterocycloalkyl, aryl, heteroaryl, bicycloaryl or heterobicycloaryl ring may be substituted with —R$^{18}$, —X$^3$OR$^{18}$, —X$^3$SR$^{18}$, —X$^3$S(O)R$^{18}$, —X$^3$S(O)$_2$R$^{18}$, —X$^3$C(O)R$^{18}$, —X$^3$C(O)OR$^{18}$, —X$^3$NR$^{15}$R$^{18}$, —X$^3$NR$^{15}$C (O)OR$^{18}$, —X$^3$C(O)NR$^{15}$R$^{18}$, —X$^3$S(O)$_2$NR$^{15}$R$^{18}$, —X$^3$NR$^{15}$C(O)NR$^{15}$R$^{18}$ or —X$^3$NR$^{15}$C(NR$^{15}$)NR$^{15}$R$^{18}$, wherein X$^3$ and R$^{15}$ are as defined above and R$^{18}$ is (C$_{3\text{-}12}$)cycloalkyl(C$_{0\text{-}3}$)alkyl, hetero(C$_{5\text{-}12}$)cycloalkyl(C$_{0\text{-}3}$) alkyl, (C$_{6\text{-}12}$)aryl(C$_{0\text{-}3}$)alkyl, hetero(C$_{5\text{-}12}$)aryl(C$_{0\text{-}3}$)alkyl, (C$_{9\text{-}12}$)bicycloaryl(C$_{0\text{-}3}$)alkyl or hetero(C$_{8\text{-}12}$)bicycloaryl (C$_{0\text{-}3}$)alkyl; with the proviso that only one (C$_{9\text{-}12}$) bicycloaryl(C$_{0\text{-}3}$)alkyl or hetero(C$_{8\text{-}12}$)bicycloaryl(C$_{0\text{-}3}$) alkyl is present within R$^6$, or a pharmaceutically acceptable salt thereof.

A second aspect of this invention is a pharmaceutical composition that contains a compound of Formula I or a pharmaceutically acceptable salt thereof in admixture with one or more suitable excipients.

A third aspect of this invention is a method of treating a disease in an animal in which inhibition of a cysteine protease can prevent, inhibit or ameliorate the pathology and/or symptomatology of the disease. Said method comprises administering to the animal a therapeutically effective amount of compound of Formula I or a pharmaceutically acceptable salt thereof.

A fourth aspect of this invention is the processes for preparing compounds of Formula I and the pharmaceutically acceptable salts thereof as set forth in "Detailed Description of the Invention".

DETAILED DESCRIPTION OF THE INVENTION

Definitions:

Unless otherwise stated, the following terms used in the specification and claims are defined for the purposes of this Application and have the meanings given this Section:

"Aliphatic" means a moiety characterized by straight or branched chain arrangement of the constituent carbon atoms and may be saturated or partially unsaturated with two or more double or triple bonds.

"Alkyl" represented by itself means a straight or branched, saturated or unsaturated, aliphatic radical having the number of carbon atoms indicated (e.g., (C$_{1\text{-}6}$)alkyl includes methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl) means a straight or branched, saturated or unsaturated aliphatic divalent radical having the number of atoms indicated or when zero atoms are indicated means a bond (e.g., (C$_{6\text{-}12}$)aryl (C$_{0\text{-}3}$)alkyl includes phenyl, benzyl, phenethyl, 1-phenylethyl, 3-phenylpropyl, and the like).

"Alkylene", unless indicated otherwise, means a straight or branched, saturated or unsaturated, aliphatic, divalent radical having the number of carbon atoms indicated (e.g., (C$_{2\text{-}5}$)alkylene includes ethylene (—CH$_2$CH$_2$— or —CH (CH$_3$)—), 1-methylethylene (—CH(CH$_3$)CH$_2$—), trimethylene (—CH$_2$CH$_2$CH$_2$—), tetramethylene (—CH$_2$CH$_2$CH$_2$CH$_2$—), pentamethylene (—CH$_2$CH$_2$CH$_2$CH$_2$CH$_2$—), and the like.

"Alkyloxy" means the radical —OR, wherein R is alkyl as defined above, having the number of carbon atoms indicated (e.g., (C$_{1\text{-}6}$)alkyloxy includes the radicals methoxy, ethoxy, propoxy, isopropoxy, butoxy, sec-butoxy, isobutoxy, tert-butoxy, vinyloxy, allyloxy, 1-propenyloxy, isopropenyloxy, 1-butenyloxy, 2-butenyloxy, 3-butenyloxy, 2-methylallyloxy, ethynyloxy, 1-propynyloxy, 2-propynyloxy, and the like).

"Amino" means the radical —NH$_2$. Unless indicated otherwise, the compounds of the invention containing amino moieties include protected derivatives thereof. Suitable protecting groups for amino moieties include acetyl, tert-butoxycarbonyl, benzyloxycarbonyl, and the like.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring are sp$^2$ hybridized and the total number of pi electrons is equal to 4n+2.

"Aryl" means a monocyclic or bicyclic ring assembly (fused or linked by a single bond) containing the total number of ring carbon atoms indicated, wherein each ring is aromatic or when fused with another ring forms an aromatic ring assembly. For example, (C$_{6\text{-}12}$)aryl includes phenyl, naphthalenyl, and biphenylyl.

"Bicycloaryl" means a bicyclic ring assembly containing the number of annular carbon atoms indicated, wherein the rings are linked by a single bond or fused and one, but not both, of the rings comprising the assembly is aromatic, and any carbocyclic ketone, thioketone or iminoketone derivative thereof. For example, (C$_{9\text{-}12}$)bicycloaryl includes indanyl, indenyl, 1,2,3,4-tetrahydronaphthalenyl, 1,2-dihydronaphthalenyl, cyclohexylphenyl, phenylcyclohexyl, 2,4-dioxo-1,2,3,4-tetrahydro-naphthalenyl, or the like.

"Carbamoyl" means the radical —C(O)NH$_2$. Unless indicated otherwise, the compounds of the invention containing carbamoyl moieties include protected derivatives thereof. Suitable protecting groups for carbamoyl moieties include acetyl, tert-butoxycarbonyl, benzyloxycarbonyl, and the like and both the unprotected and protected derivatives fall within the scope of the invention.

"Cycloalkyl" means a saturated or partially unsaturated, monocyclic ring, bicyclic ring assembly (directly linked by a single bond or fused) or bridged polycyclic ring assembly containing the number of annular carbon atoms indicated, and any carbocyclic ketone, thioketone or iminoketone derivative thereof. For example, (C$_{3\text{-}12}$)cycloalkyl includes cyclopropyl, cyclobutyl, cyclopentyl, cyclohexyl, cyclohexenyl, 2,5-cyclohexadienyl, bicyclohexylyl, cyclopentylcyclohexyl, bicyclo[2.2.2]octyl, adamantan-1-yl, decahydronaphthalenyl, oxocyclohexyl, dioxocyclohexyl, thiocyclohexyl, 2-oxobicyclo-[2.2.1]hept-1-yl, and the like.

"Cycloalkylene" means a divalent saturated or partially unsaturated, monocyclic ring, bicyclic ring assembly (directly linked by a single bond or fused) or bridged polycyclic ring assembly containing the number of annular carbon atoms indicated, and any carbocyclic ketone, thioketone or iminoketone derivative thereof. For example, ($C_{3-12}$)cycloalkylene includes cyclopropylene, cyclobutylene, cyclopentylene, cyclohexylene, cyclohexenylene, 2,5-cyclohexadienylene, bicyclohexylylene, and the like.

"Disease" specifically includes any unhealthy condition of an animal or part thereof and includes an unhealthy condition that may be caused by, or incident to, medical or veterinary therapy applied to that animal, i.e., the "side effects" of such therapy.

"Halo" means fluoro, chloro, bromo or iodo.

"Haloalkyl" or "halo-substituted alkyl" means an alkyl group as defined above that is substituted with a halo group as defined above e.g., trifluoromethyl, fluoroethyl, fluoropropyl, fluorobutyl, and the like.

"Heteroaryl" means aryl, as defined herein, provided that one or more, preferably one to four, of the ring carbon atoms indicated, are replaced by a heteroatom moiety selected from —N═, —N$^+$(O$^-$)═, —NR—, —O— or —S—, wherein R is hydrogen, ($C_{1-6}$)alkyl or a protecting group, and each ring contained therein is comprised of 5 to 6 annular members (e.g., hetero($C_{5-14}$)aryl includes thienyl, furyl, pyrrolyl, pyrimidinyl, isoxazolyl, oxazolyl, indolyl, benzo[b]thienyl, isobenzofuranyl, purinyl, isoquinolyl, pterdinyl, perimidinyl, imidazolyl, 1-methylimidazolyl, 1-benzylimidazolyl, pyridyl, pyrazolyl, pyrazinyl, tetrazolyl, quinolyl, [2,4']bipyridinylyl, 2-phenylpyridyl, 4-thiazol-4-ylphenyl, 1H-imidazol-1-ylphenyl, and the like). Suitable protecting groups include tert-butoxycarbonyl, benzyloxycarbonyl, benzyl, 4-methoxybenzyl, 2-nitrobenzyl, and the like.

"Heterobicycloaryl" means bicycloaryl, as defined herein, except one or more of the annular carbon atoms indicated are replaced by a heteroatom moiety selected from —N—, —NR—, —O— or —S—, wherein R is hydrogen, ($C_{1-6}$) alkyl or a protecting group, and any carbocyclic ketone, thioketone or iminoketone derivative thereof. For example, hetero($C_{8-12}$)bicycloaryl includes 3,4-dihydro-2H-quinolinyl, 5,6,7,8-tetrahydroquinolinyl, 3,4-dihydro-2H-[1,8]naphthyridinyl, morpholinylpyridyl, piperidinylphenyl, 1,2,3,4,5,6-hexahydro-[2,2']bipyridinylyl, 2,4-dioxo-3,4-dihydro-2H-quinazolinyl, 3-oxo-2,3-dihydrobenzo-[1,4] oxazinyl, and the like.

"Heterocycloalkyl" means cycloalkyl, as defined herein, provided that one or more, preferably one to three, of the annular carbon atoms indicated is replaced by heteroatom moiety selected from —N—, —NR—, —O— or —S—, wherein R is hydrogen, ($C_{1-6}$)alkyl or a protecting group, and any carbocyclic ketone, thioketone or iminoketone derivative thereof (e.g., the term hetero($C_{3-14}$)cycloalkyl includes piperidyl, pyrrolidinyl, pyrrolinyl, imidazolidinyl, quinuclidinyl, morpholinyl, [1,4']bipiperidinylyl, 1',2'-dihydro-2H-[1,4']bipyridinylyl, 1-morpholin-4-ylpiperidinyl, and the like). Suitable protecting groups include tert-butoxycarbonyl, benzyloxycarbonyl, benzyl, 4-methoxybenzyl, 2-nitrobenzyl, and the like. For example, a compound of Formula I wherein $R^1$ is piperidin-4-ylcarbonyl may exist as either the unprotected or a protected derivative, e.g., wherein $R^1$ is 1-tert-butoxycarbonylpiperidin-4-ylcarbonyl, and both the unprotected and protected derivatives fall within the scope of the invention.

"Hydroxy" means the radical —OH. Unless indicated otherwise, the compounds of the invention containing hydroxy radicals include protected derivatives thereof. Suitable protecting groups for hydroxy moieties include benzyl and the like and both the unprotected and protected derivatives fall within the scope of the invention.

"Iminoketone derivative" means a derivative containing the moiety —C(NR)—, wherein R is hydrogen or ($C_{1-6}$) alkyl.

"Isomers" mean compounds of Formula I having identical molecular formulae but differ in the nature or sequence of bonding of their atoms or in the arrangement of their atoms in space. Isomers that differ in the arrangement of their atoms in space are termed "steroisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality is termed a "racemic mixture". A compound that has more than one chiral center has $2^{n-1}$ enantiomeric pairs, where n is the number of chiral centers. Compounds with more than one chiral center may exist as ether an individual diasteromer or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992). It is understood that the names and illustration used in this Application to describe compounds of Formula I are meant to encompass all possible stereoisomers and any mixture, racemic or otherwise, thereof.

"Ketone derivative" means a derivative containing the moiety —C(O)—.

"Leaving group" has the meaning conventionally associated with it in synthetic organic chemistry, i.e., an atom or group displaceable under alkylating conditions, and includes, halogen, hydroxy, alkyloxy, alkylsulfonyloxy (e.g., mesyloxy, ethanesulfonyloxy, or the like), arylsulfonyloxy (e.g., benzenesulfonyloxy and tosyloxy, thienyloxy), dihalophosphinoyloxy, tetrahalophosphaoxy, and the like.

"Nitro" means the radical —NO$_2$.

"Optional" or "optionally" means that the subsequently described event or circumstance may or may not occur, and that the description includes instances where the event or circumstance occurs and instances in which it does not. For example, the phrase "any 1 to 3 annular atoms of any aromatic ring with available valences comprising $R^6$ optionally independently is substituted" means that the aromatic ring referred to may or may not be substituted in order to fall within the scope of the invention.

"N-oxide derivatives" means derivatives of compounds of Formula I in which nitrogen atom(s) is in an oxidized state (i.e., N→O) and which possess the desired pharmacological activity. The n-oxide derivative of a compound of Formula I is within the scope of this invention.

"Oxo" means the radical ═O.

"Pathology" of a disease means the essential nature, causes and development of the disease as well as the structural and functional changes that result from the disease processes.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of Formula I which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartatic acid, citric acid, benzoic acid, o-(4-hydroxybenzoyl)benzoic acid, cinnamic acid, madelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Prodrug derivatives" means derivatives of compounds of Formula I which are converted in vivo to the corresponding non-derivatized form of a compound of Formula I. All prodrugs of a compound of Formula I are within the scope of this invention.

"Protected derivatives" means derivatives of compounds of Formula I in which a reactive site or sites are blocked with protective groups. Protected derivatives of compounds of Formula I are useful in the preparation of compounds of Formula I or in themselves may be active cysteine protease inhibitors. A comprehensive list of suitable protective groups can be found in T. W. Greene and P. G. M. Wuts, *Protective Groups in Organic Synthesis*, John Wiley & Sons, Inc. (3rd Edition) 1999. All protective derivatives of a compound of Formula I are within the scope of this invention.

"Therapeutically effective amount" means that amount which, when administered to an animal for treating a disease, is sufficient to effect such treatment for the disease.

"Thioketone derivative" means a derivative containing the moiety —C(S)—.

"Treatment" or "treating" means any administration of a compound of the present invention and includes:

preventing the disease from occurring in an animal which may be predisposed to the disease but does not yet experience or display the pathology or symptomatology of the disease, inhibiting the disease in an animal that is experiencing or displaying the pathology or symptomatology of the diseased (i.e., arresting further development of the pathology and/or symptomatology), or ameliorating the disease in an animal that is experiencing or displaying the pathology or symptomatology of the diseased (i.e., reversing the pathology and/or symptomatology).

Abbreviations used: acetonitrile (ACN); t-butyloxycarbonyl (BOC); dichloromethane (DCM); 2,3-dichloro-5,6-dicyano-1,4-benzoquinone (DDQ); diisopropylcarbodiimide (DIC); 4-dimethylamino-pyridine (DMAP); electrospray ionization (ESI); diethyl ether (Et$_2$O); High performance liquid chromatography (HPLC); Liquid Chromatography/Mass Spectroscopy (LC/MS); tetrahydrofuran (THF); trifluoroacetic acid (TFA); tetrapyrrolidinophosphonium hexafluorophosphate (PyBOP); N-{(dimethylamino)(1H-1,2,3-triazole[4,5-b]pyridin-1-yl)-methylene}-N-methylmethan-aminium hexafluorophosphate N-oxide (HATU); 4-dimethylamino-pyridine (DMAP); dicyclohexylcarbodiimide (DCC); dimethylformamide (DMF).

Nomenclature:

The compounds of Formula I and the intermediates and starting materials used in their preparation are named in accordance with IUPAC rules of nomenclature in which the characteristic groups have decreasing priority for citation as the principle group as follows: acids, esters, amides, etc. Alternatively, the compounds are named by AutoNom 2.1 or 4.0 (Beilstein Information System, Inc.). For example, compounds of Formula I in which:

$R^1$ is 4-methoxy-benzyl; $R^2$ is 4-phenylethyl; $R^3$ is cyclohexylmethyl; and $R^4$ is acetyl is named 2-acetylamino-3-cyclohexyl-N-[2-(4-methoxy-phenylsulfomoyl)-ethyl]-propionamide; or $R^1$ is 4-methoxy-benzyl; $R^2$ is 4-phenylethyl; $R^3$ is isobutyl; and $R^4$ is pyridine-3-carbonyl is named N-(1-{1-[(4-methoxy-phenylsulfamoyl)-methyl]-3-phenyl-propylcarbamoyl}-3-methyl-butyl)-nicotinamide.

Presently Preferred Embodiments:

While the broadest definition of this invention is set forth in the Summary of the Invention, certain aspects of the invention are preferred. Preferred aspects of the invention are $R^1$ is —$R^8$, —$X^2OR^8$, —$X^2C(O)R^8$, —$X^2C(OR^7)R^7R^8$, —$X^2NR^7R^8$ or —$X^2NR^7C(O)OR^8$; wherein $X^2$ is (C$_{1-6}$) alkylene; $R^7$ is hydrogen or (C$_{1-6}$)alkyl; $R^8$ is hydrogen, (C$_{1-6}$)alkyl, (C$_{3-12}$)cycloalkyl(C$_{0-3}$)alkyl, hetero(C$_{5-12}$) cycloalkyl(C$_{0-3}$)alkyl, (C$_{6-12}$)aryl(C$_{0-3}$)alkyl or hetero (C$_{5-12}$)aryl(C$_{0-3}$)alkyl; wherein within $R^8$ said cycloalkyl, heterocycloalkyl, aryl or heteroaryl ring may be substituted with halo, —$R^9$, —$X^3OR^9$, —$X^3C(O)R^9$, —$X^3C(OR^9)R^9$, —$X^3NR^9R^{10}$ or —$X^3NR^9C(O)OR^9$; wherein $X^3$ is a bond or (C$_{1-6}$)alkylene, $R^9$ is hydrogen or (C$_{1-6}$)alkyl and $R^{10}$ is cycloalkyl;

$R^2$ is hydrogen;

$R^3$ is —$R^{11}$, —$X^3NR^{11}R^{12}$ or —$X^3NR^{12}C(O)OR^{11}$; wherein $X^3$ is a bond or (C$_{1-6}$)alkylene, $R^{11}$ is hydrogen, (C$_{1-6}$)alkyl, halo(C$_{1-6}$)alkyl, (C$_{3-12}$)cycloalkyl(C$_{0-3}$)alkyl, hetero(C$_{5-12}$)cycloalkyl(C$_{0-3}$)alkyl, (C$_{6-12}$)aryl(C$_{0-3}$)alkyl, hetero(C$_{5-12}$)aryl(C$_{0-3}$)alkyl, (C$_{9-12}$)bicycloaryl(C$_{0-3}$)alkyl or hetero(C$_{8-12}$)bicycloaryl(C$_{0-3}$)alkyl and $R^{12}$ is hydrogen or (C$_{1-6}$)alkyl, wherein any 1 to 3 annular atoms of any aromatic ring with available valences comprising $R^3$ are optionally independently substituted with halo, nitro, cyano, (C$_{1-6}$)alkyl, halo-substituted(C$_{1-6}$)alkyl, —$OR^7$, —$C(O)R^7$, —$C(O)OR^7$, —$C(O)NR^7R^7$, —$S(O)_2NR^7R^7$, —$X^2NR^7R^7$, —$X^2NR^7C(O)OR^7$, —$X^2NR^7C(O)NR^7R^7$ or —$X^2NR^7C$ $(NR^7NR^7R^7$, wherein $X^2$ and $R^7$ are as defined above;

$R^4$ is hydrogen or (C$_{1-6}$)alkyl;

$R^5$ is (C$_{1-6}$)alkyl, halo(C$_{1-6}$)alkyl, (C$_{3-12}$)cycloalkyl(C$_{0-3}$) alkyl, or —$X^2S(O)R^{14}$ where $X^2$ is as defined above and $R^{14}$ is (C$_{3-12}$)cycloalkyl(C$_{0-3}$)alkyl, hetero(C$_{5-12}$)cycloalkyl (C$_{0-3}$)alkyl, (C$_{6-12}$)aryl(C$_{0-3}$)alkyl, hetero(C$_{5-12}$)aryl(C$_{0-3}$) alkyl, $(C_{9-12})$bicycloaryl$(C_{0-3})$alkyl or hetero$(C_{8-12})$bicycloaryl$(C_{0-3})$alkyl; preferably, $R^5$ is $(C_{1-6})$alkyl or $(C_{3-12})$cycloalkyl$(C_{0-3})$alkyl; or $R^4$ and $R^5$ together with the carbon atom to which $R^4$ and $R^5$ are attached form $(C_{3-7})$cycloalkylene;

$R^6$ is hydrogen or —$X^4X^5R^{13}$, wherein $X^4$ is —C(O)—, $X^5$ is a bond, —O— or —NR$^{12}$—, wherein $R^{12}$ is as defined above, and $R^{13}$ is $(C_{1-6})$alkyl or —$R^{14}$ wherein $R^{14}$ is $(C_{3-12})$cycloalkyl$(C_{0-3})$-alkyl, hetero$(C_{5-12})$cycloalkyl$(C_{0-3})$alkyl, $(C_{6-12})$aryl$(C_{0-3})$alkyl, hetero$(C_{5-12})$aryl$)C_{0-3})$alkyl, $(C_{9-12})$bicycloaryl$(C_{0-3})$alkyl or hetero$(C_{8-12})$bicycloaryl$(C_{0-3})$alkyl; and within $R^{14}$ said cycloalkyl, heterocycloalkyl, aryl, heteroaryl, bicycloaryl or heterobicycloaryl ring may be substituted with —OCF$_3$, —CF$_3$, —OH, halo, —$R^{16}$, —$X^3OR^{16}$, —$X^3OR^{15}$, —$X^3C(O)R^{15}$, —$R^{15}$, —$X^3C(O)R^{16}$, —$X^3C(O)OR^{15}$, —$X^3NR^{15}R^{15}$, —$X^3NR^{15}C(O)OR^{15}$, wherein $X^3$ is as defined above, $R^{15}$ is hydrogen or $(C_{1-6})$alkyl; and $R^{16}$ is $(C_{3-12})$cycloalkyl$(C_{0-3})$alkyl, hetero$(C_{5-12})$cycloalkyl-$(C_{0-3})$alkyl, $(C_{6-12})$aryl$(C_{0-3})$alkyl or hetero$(C_{5-12})$aryl$(C_{0-3})$alkyl, and within $R^{16}$ said cycloalkyl, heterocycloalkyl, aryl or heteroaryl ring may be substituted with —$R^{15}$, —$R^{17}$, —$X^3NR^{15}R^{17}$, —$X^3NR^{15}R^{15}$ wherein $X^3$ and $R^{15}$ are as defined above and $R^{17}$ is $(C_{3-12})$cycloalkyl$(C_{0-3})$alkyl, hetero$(C_{5-12})$cycloalkyl$(C_{0-3})$alkyl, $(C_{6-12})$aryl$(C_{0-3})$alkyl or hetero$(C_{5-12})$aryl$(C_{0-3})$alkyl; with the proviso that only one $(C_{9-12})$bicycloaryl$(C_{0-3})$alkyl or hetero$(C_{8-12})$bicycloaryl$(C_{0-3})$alkyl is present within $R^6$; and the pharmaceutically acceptable salts thereof.

More preferably, $R^1$ is 4-methoxyphenyl, 3-methoxyphenyl, 2-methoxyphenyl, 4-chlorophenyl, 3-chloro-phenyl, 2-chlorophenyl, 4-hydroxyphenyl, 2-acetylphenyl, 2-(1-hydroxyethyl)phenyl, 2-phenylaminoethyl, pyridin-4-ylphenyl, pyridin-3-ylphenyl, pyridin-2-ylphenyl, 1H-imidazol-2-yl, piperidin-4-yl or 1-methylpiperidin-4-yl;

$R^2$ is hydrogen;

$R^3$ is hydrogen, phenethyl, 4-aminobutyl, butyl or 4-benzyloxycarbonylaminobutyl;

$R^4$ is hydrogen;

$R^5$ is isobutyl, sec-butyl or cyclohexylmethyl; or $R^4$ and $R^5$ together with the carbon atom to which $R^4$ and $R^5$ are attached form cyclohexyl; and $R^6$ is selected from the group consisting of benzoyl, morpholin-4-ylcarbonyl, acetyl, furan-3-ylcarbonyl, 2-methoxybenzoyl, 3-methoxybenzoyl, naphthalen-2-ylcarbonyl, benzo[1,3]dioxol-5-ylcarbonyl, 3-pyridin-3-ylacryloyl, benzofuran-2-ylcarbonyl, furan-2-ylcarbonyl, tert-butoxycarbonyl, biphenyl-4-carbonyl, quinolin-2-ylcarbonyl, quinolin-3-ylcarbonyl, 3-acetylbenzoyl, 4-phenoxybenzoyl, 3-hydroxybenzoyl, 4-hydroxybenzoyl, pyridin-3-ylcarbonyl, 3-(tert-butoxycarbonylaminomethyl)benzoyl, 4-carbonylpiperazin-1-ylcarboxylic acid tert-butyl ester, 4-carbonylpiperazin-1-ylcarboxylic acid ethyl ester, 4-(furan-2-ylcarbonyl)piperazin-1-ylcarbonyl, pyridin-4-ylcarbonyl, 1-oxypyridin-4-ylcarbonyl, 1-oxypyridin-3-ylcarbonyl, thiophen-2-ylcarbonyl, thiophen-3-ylcarbonyl, 4-benzoylbenzoyl, 5-methylthiophen-2-ylcarbonyl, 3-chlorothiophen-2-ylcarbonyl, 3-bromothiophen-2-ylcarbonyl, 4-chlorobenzoyl, 3-flouro-4-methoxybenzoyl, 4-methoxy-benzoyl, 4-triflouromethoxybenzoyl, 3,4-diflourobenzoyl, 4-fluorobenzoyl, 3,4-dimethoxy-benzoyl, 3-methylbenzoyl, 4-bromobenzoyl, 4-triflouromethylbenzoyl, 3-benzoylbenzoyl, cyclopentanecarbonyl, benzo[b]thiophen-2-ylcarbonyl, 3-chlorobenzo[b]thiophen-2-ylcarbonyl, formamylmethyl ester, 4-methylpentanoyl, formamylisobutyl ester, formamylmonoallyl ester, formamylisopropyl ester, N,N-dimethylformamyl, N-isopropylformamyl, N-pyridin-4-ylformamyl, N-pyridin-3-ylformamyl, 3-phenylacryloyl, 1H-indol-5-ylcarbonyl, pyridin-2-ylcarbonyl, pyrazin-2-ylcarbonyl, 3-hydroxypyridin-2-ylcarbonyl, 2-aminopyridin-3-ylcarbonyl, 2-hydroxypyridin-3-ylcarbonyl, 6-aminopyridin-3-ylcarbonyl, 6-hydroxypyridin-3-ylcarbonyl, pyridazin-4-ylcarbonyl, 3-phenoxybenzoyl, 1-oxo-1,3-dihydroisoindol-2-ylcarbonyl, 4-(4-methylpiperazin-1-yl)benzoyl, 4-morpholin-4-ylbenzoyl, 4-[2-(pyridin-3-ylamino)thiazol-4-yl]-benzoyl, 3-aminobenzoyl, 4-methylpiperazin-1-ylcarbonyl and benzylacetyl.

More preferably, $R^1$ is 4-methoxyphenyl, 3-methoxyphenyl, 2-methoxyphenyl, 4-chlorophenyl, 3-chloro-phenyl, 2-chlorophenyl, 4-hydroxyphenyl, 2-acetylphenyl, 2-(1-hydroxyethyl)phenyl, 2-phenylaminoethyl, pyridin-4-ylphenyl, pyridin-3-ylphenyl, pyridin-2-ylphenyl, 1H-imidazol-2-yl, piperidin-4-yl or 1-methylpiperidin-4-yl;

$R^2$ is hydrogen;

$R^3$ is benzylsulfonylmethyl;

$R^4$ is hydrogen;

$R^5$ is isobutyl, sec-butyl or cyclohexylmethyl; or $R^4$ and $R^5$ together with the carbon atom to which $R^4$ and $R^5$ are attached form cyclohexyl; and $R^6$ is selected from the group consisting of $R^6$ is selected from the group consisting of benzoyl, morpholin-4-ylcarbonyl, acetyl, furan-3-ylcarbonyl, 2-methoxybenzoyl, 3-methoxybenzoyl, naphthalen-2-ylcarbonyl, benzo[1,3]dioxol-5-ylcarbonyl, 3-pyridin-3-ylacryloyl, benzofuran-2-ylcarbonyl, furan-2-ylcarbonyl, tert-butoxycarbonyl, biphenyl-4-carbonyl, quinolin-2-ylcarbonyl, quinolin-3-ylcarbonyl, 3-acetylbenzoyl, 4-phenoxybenzoyl, 3-hydroxybenzoyl, 4-hydroxybenzoyl, pyridin-3-ylcarbonyl, 3-(tert-butoxycarbonylaminomethyl)benzoyl, 4-carbonylpiperazin-1-ylcarboxylic acid tert-butyl ester, 4-carbonylpiperazin-1-ylcarboxylic acid ethyl ester, 4-(furan-2-ylcarbonyl)piperazin-1-ylcarbonyl, pyridin-4-ylcarbonyl, 1-oxypyridin-4-ylcarbonyl, 1-oxypyridin-3-ylcarbonyl, thiophen-2-ylcarbonyl, thiophen-3-ylcarbonyl, 4-benzoylbenzoyl, 5-methylthiophen-2-ylcarbonyl, 3-chlorothiophen-2-ylcarbonyl, 3-bromothiophen-2-ylcarbonyl, 4-chlorobenzoyl, 3-flouro-4-methoxybenzoyl, 4-methoxy-benzoyl, 4-triflouromethoxybenzoyl, 3,4-diflourobenzoyl, 4-fluorobenzoyl, 3,4-dimethoxy-benzoyl, 3-methylbenzoyl, 4-bromobenzoyl, 4-triflouromethylbenzoyl, 3-benzoylbenzoyl, cyclopentanecarbonyl, benzo[b]thiophen-2-ylcarbonyl, 3-chlorobenzo[b]thiophen-2-ylcarbonyl, formamylmethyl ester, 4-methylpentanoyl, formamylisobutyl ester, formamylmonoallyl ester, formamylisopropyl ester, N,N-dimethylformamyl, N-isopropylformamyl, N-pyridin-4-ylformamyl, N-pyridin-3-ylformamyl, 3-phenylacryloyl, 1H-indol-5-ylcarbonyl, pyridin-2-ylcarbonyl, pyrazin-2-ylcarbonyl, 3-hydroxypyridin-2-ylcarbonyl, 2-aminopyridin-3-ylcarbonyl, 2-hydroxypyridin-3-ylcarbonyl, 6-aminopyridin-3-ylcarbonyl, 6-hydroxypyridin-3-ylcarbonyl, pyridazin-4-ylcarbonyl, 3-phenoxybenzoyl, 1-oxo-1,3-dihydroisoindol-2-ylcarbonyl, 4-(4-methylpiperazin-1-yl)benzoyl, 4-morpholin-4-ylbenzoyl, 4-[2-(pyridin-3-ylamino)thiazol-4-yl]-benzoyl, 4-(2-dimethylaminothiazol-4-yl)benzoyl, quinolin-6-ylcarbonyl, 4-dimethylamino-benzoyl, 3-aminobenzoyl, 4-methylpiperazin-1-ylcarbonyl and benzylacetyl.

Even more preferably, $R^1$ is 4-methoxyphenyl, 3-acetylphenyl, 3-(1-hydroxyethyl)-phenyl, 2-(phenylamino)ethyl or 4-hydroxyphenyl;

$R^2$ is hydrogen;

$R^3$ is hydrogen, 2-phenethyl, 4-aminobutyl, or 4-benzyloxycarbonylaminobutyl;

$R^4$ is hydrogen;

$R^5$ is isobutyl, sec-butyl or cyclohexylmethyl; or $R^4$ and $R^5$ together with the carbon atom to which $R^4$ and $R^5$ are attached form cyclohexyl; and $R^6$ is selected from the group consisting of acetyl, pyridin-3-ylcarbonyl, 3-(tert-butoxycarbonylamino)benzoyl, pyridin-4-ylcarbonyl, 1H-indol-5-ylcarbonyl, benzyloxycarbonyl, 3-aminobenzoyl, 4-methylpiperazin-1-ylcarbonyl, quinolin-6-ylcarbonyl, 4-[2-(pyridin-3-ylamino)thiazol-4-yl]benzoyl, 4-dimethylaminobenzoyl, morpholin-4-yl-carbonyl, 4-(2-dimethylaminothiazol-4-yl)benzoyl, tert-butoxycarbonyl, 4-(4-ethylpiperazin-1-yl)-benzoyl, and 4-[2-(4-methylpiperazin-1-yl)thiazol-4-yl]benzoyl.

A number of different preferences have been given above, and following any one of these preferences results in a compound of this invention that is more presently preferred than a compound in which that particular preference is not followed. However, these preferences are generally independent [although some (alternative) preferences are mutually exclusive], and additive; and following more than one of these preferences may result in a more presently preferred compound than one in which fewer of the preferences are followed.

Particular compounds of the invention are selected from the compounds formed by joining C* of one of the fragments (A1 to A77) shown in Table 1 to the nitrogen atom (*N) of one of the fragments (B1 to B4) shown in Table 2, and joining the methine carbon atom (CH*) of one of the fragments (B1 to B4) shown in Table 2 to the acyl carbon atom (C*) of one of the fragments (C1 to C3 1) depicted in Table 3.

TABLE 1

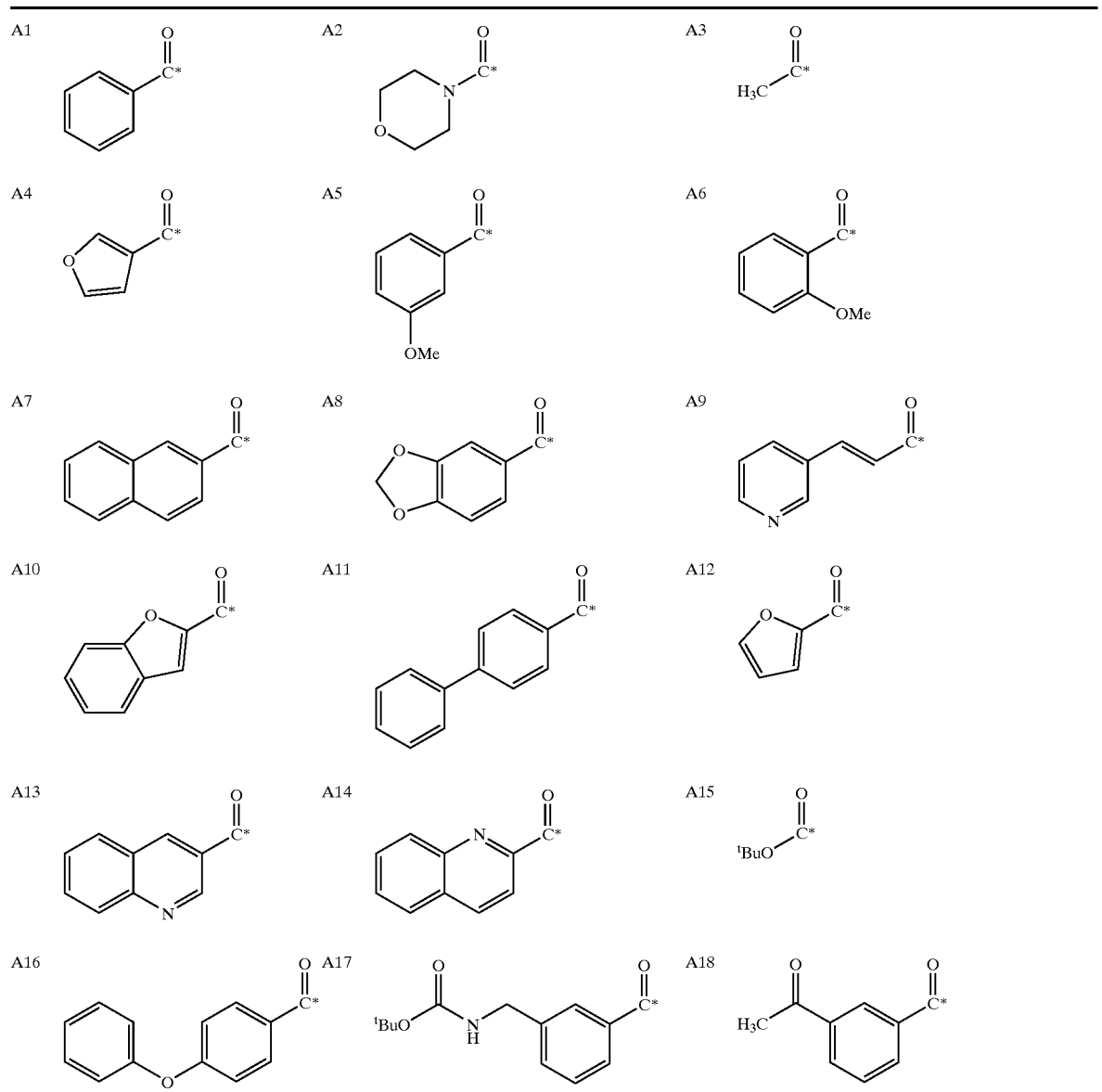

TABLE 1-continued
| A19 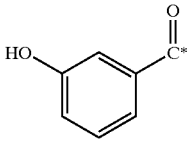 | A20 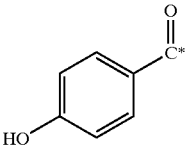 | A21 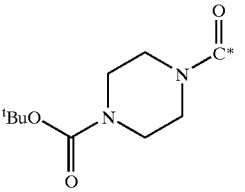 |
| --- | --- | --- |
| A22 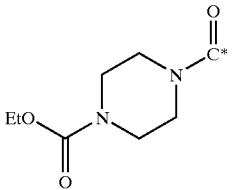 | A23 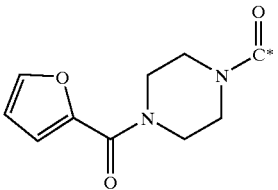 | A24 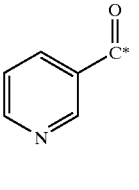 |
| A25 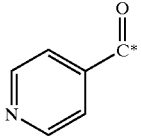 | A26 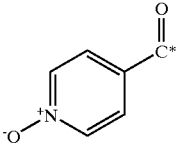 | A27 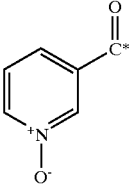 |
| A28 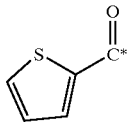 | A29 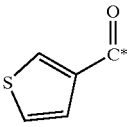 | A30 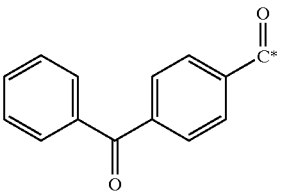 |
| A31 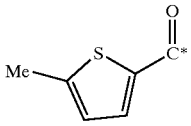 | A32 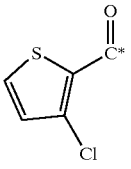 | A33 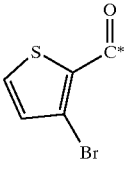 |
| A34 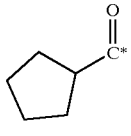 | A35 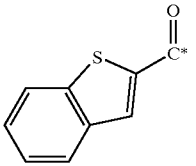 | A36 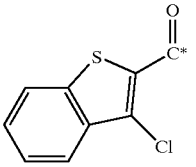 |
| A37 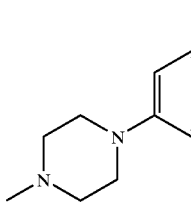 | A38 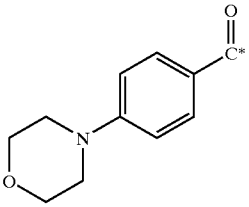 | A39 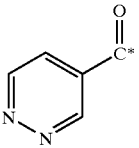 |
| A40 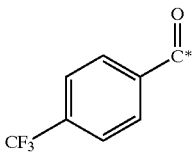 | A41 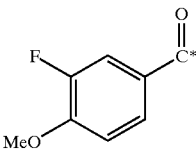 | A42 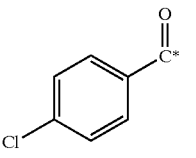 |

TABLE 1-continued
| A43  | A44  | A45  |
|---|---|---|
| A46  | A47  | A48  |
| A49  | A50  | A51  |
| A52  | A53  | A54  |
| A55  | A56  | A57  |
| A58  | A59  | A60  |
| A61  | A62  | A63  |
| A64  | A65  | A66  |
| A67  | A68  | A69  |

TABLE 1-continued
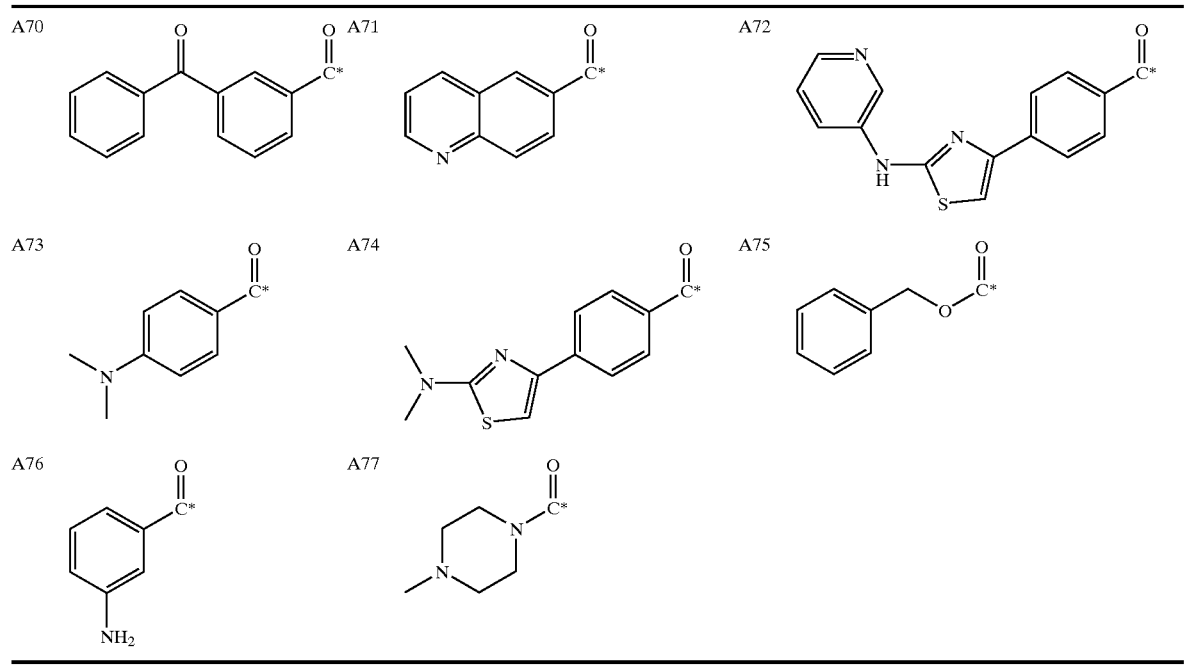
TABLE 2
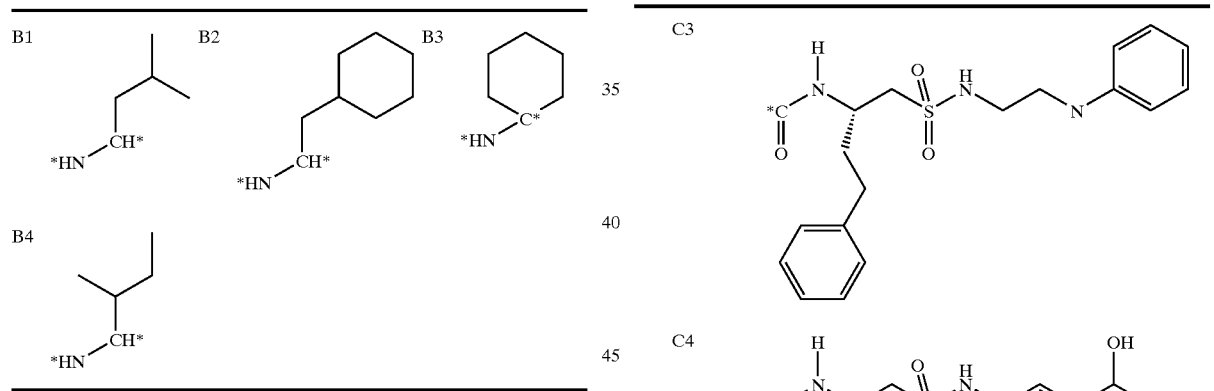
TABLE 3
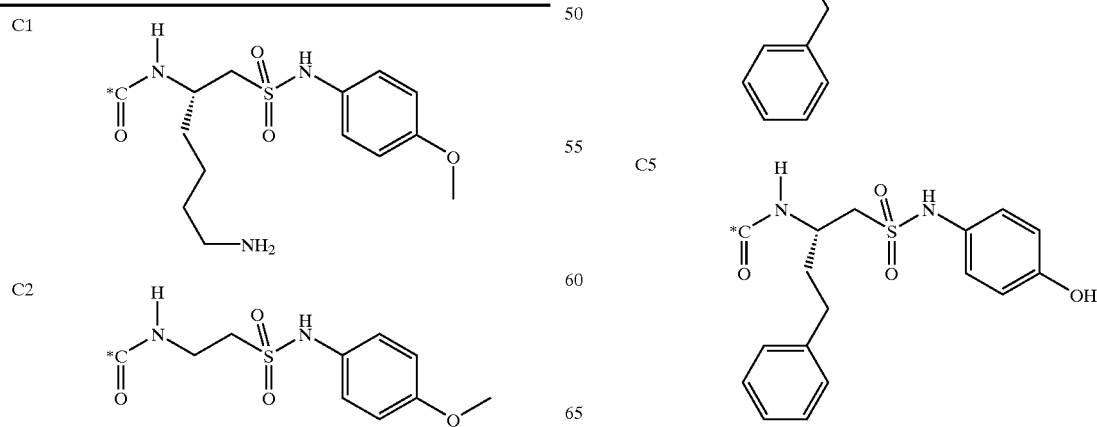

TABLE 3-continued
C6 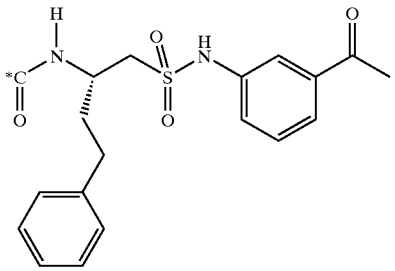
C7 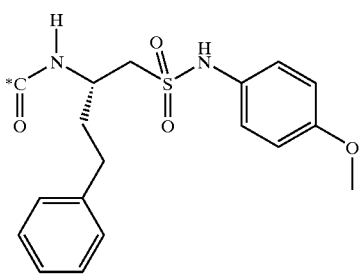
C8 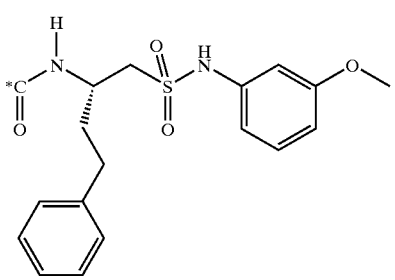
C9 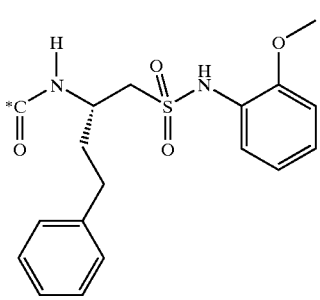
C10 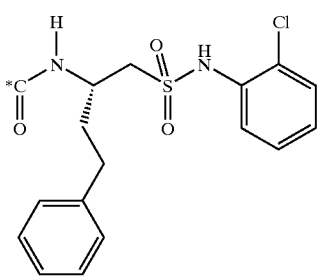
TABLE 3-continued
C11 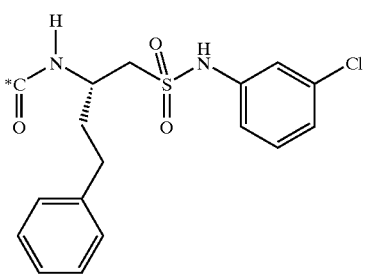
C12 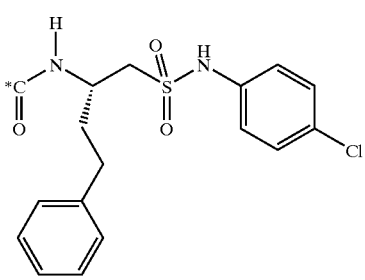
C13 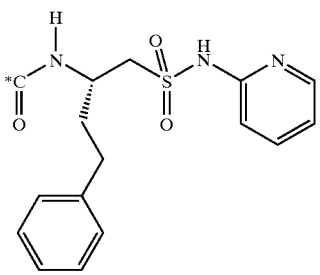
C14 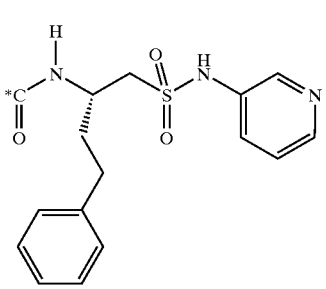
C15 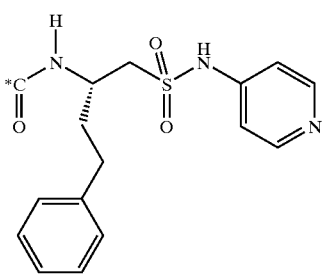

TABLE 3-continued
C16 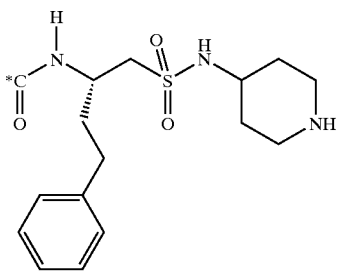
C17 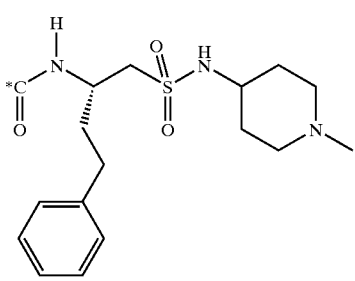
C18 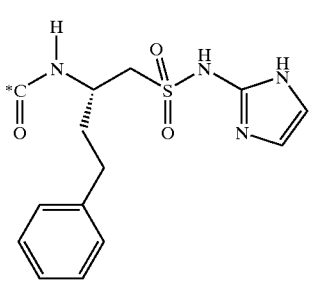
C19 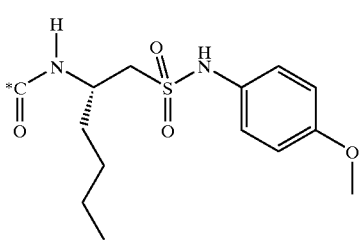
C20 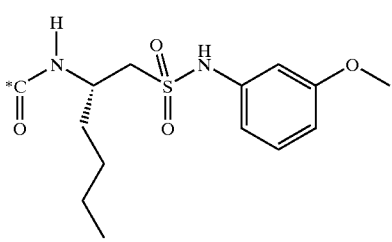
C21 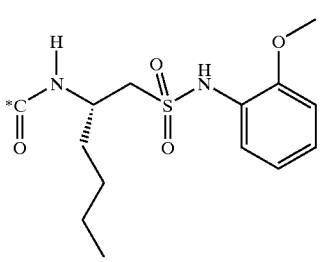
C22 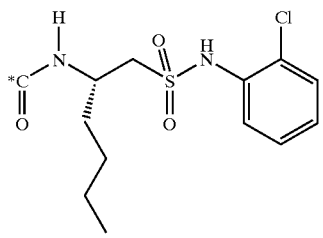
C23 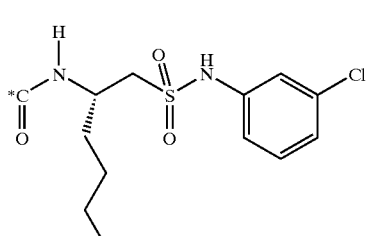
C24 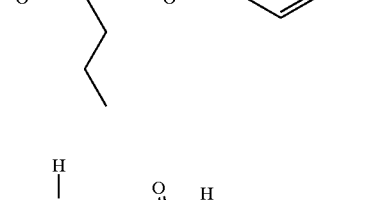
C25 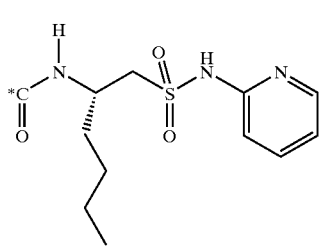
C26 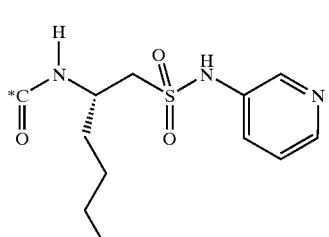
C27 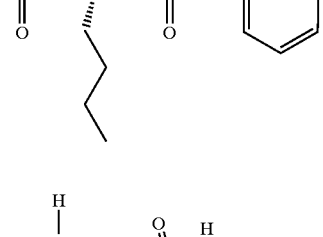

TABLE 3-continued

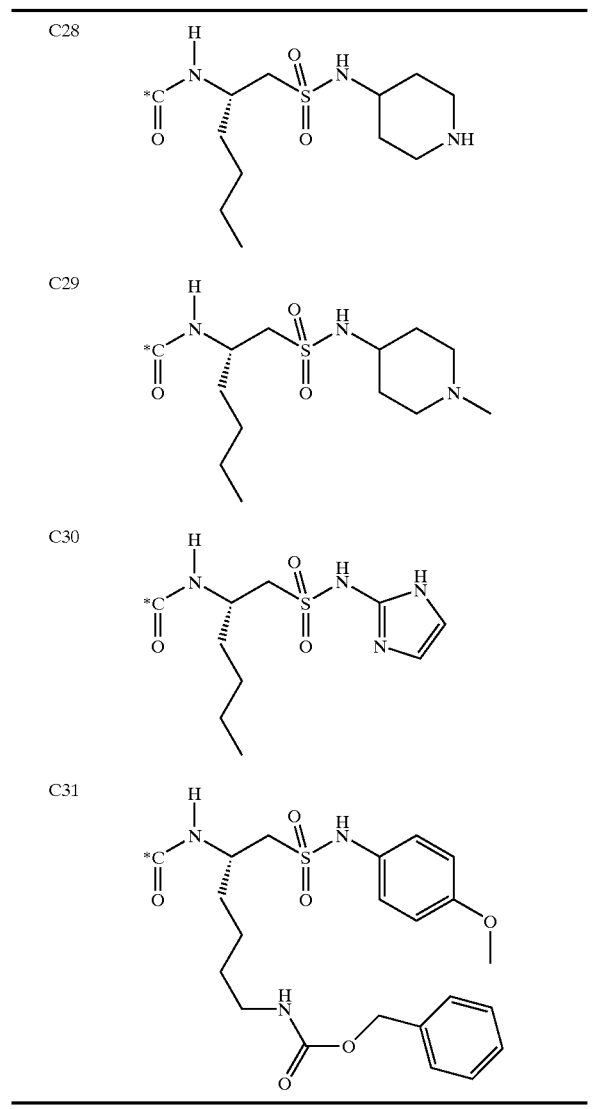

C28

C29

C30

C31

Particularly preferred compounds of "A", "B", and "C" combinations are illustrated in table 4, infra:

TABLE 4

| | | | |
|---|---|---|---|
| A1-B1-C1 | A12-B1-C1 | A23-B1-C1 | A34-B1-C1 |
| A2-B1-C1 | A13-B1-C1 | A24-B1-C1 | A35-B1-C1 |
| A3-B1-C1 | A14-B1-C1 | A25-B1-C1 | A36-B1-C1 |
| A4-B1-C1 | A15-B1-C1 | A26-B1-C1 | A37-B1-C1 |
| A5-B1-C1 | A16-B1-C1 | A27-B1-C1 | A38-B1-C1 |
| A6-B1-C1 | A17-B1-C1 | A28-B1-C1 | A39-B1-C1 |
| A7-B1-C1 | A18-B1-C1 | A29-B1-C1 | A40-B1-C1 |
| A8-B1-C1 | A19-B1-C1 | A30-B1-C1 | A41-B1-C1 |
| A9-B1-C1 | A20-B1-C1 | A31-B1-C1 | A42-B1-C1 |
| A10-B1-C1 | A21-B1-C1 | A32-B1-C1 | A43-B1-C1 |
| A11-B1-C1 | A22-B1-C1 | A33-B1-C1 | A44-B1-C1 |
| A45-B1-C1 | A35-B2-C1 | A25-B3-C1 | A15-B4-C1 |
| A46-B1-C1 | A36-B2-C1 | A26-B3-C1 | A16-B4-C1 |
| A47-B1-C1 | A37-B2-C1 | A27-B3-C1 | A17-B4-C1 |
| A48-B1-C1 | A38-B2-C1 | A28-B3-C1 | A18-B4-C1 |
| A49-B1-C1 | A39-B2-C1 | A29-B3-C1 | A19-B4-C1 |
| A50-B1-C1 | A40-B2-C1 | A30-B3-C1 | A20-B4-C1 |
| A51-B1-C1 | A41-B2-C1 | A31-B3-C1 | A21-B4-C1 |
| A52-B1-C1 | A42-B2-C1 | A32-B3-C1 | A22-B4-C1 |
| A53-B1-C1 | A43-B2-C1 | A33-B3-C1 | A23-B4-C1 |

TABLE 4-continued

| | | | |
|---|---|---|---|
| A54-B1-C1 | A44-B2-C1 | A34-B3-C1 | A24-B4-C1 |
| A55-B1-C1 | A45-B2-C1 | A35-B3-C1 | A25-B4-C1 |
| A56-B1-C1 | A46-B2-C1 | A36-B3-C1 | A26-B4-C1 |
| A57-B1-C1 | A47-B2-C1 | A37-B3-C1 | A27-B4-C1 |
| A58-B1-C1 | A48-B2-C1 | A38-B3-C1 | A28-B4-C1 |
| A59-B1-C1 | A49-B2-C1 | A39-B3-C1 | A29-B4-C1 |
| A60-B1-C1 | A50-B2-C1 | A40-B3-C1 | A30-B4-C1 |
| A61-B1-C1 | A51-B2-C1 | A41-B3-C1 | A31-B4-C1 |
| A62-B1-C1 | A52-B2-C1 | A42-B3-C1 | A32-B4-C1 |
| A63-B1-C1 | A53-B2-C1 | A43-B3-C1 | A33-B4-C1 |
| A64-B1-C1 | A54-B2-C1 | A44-B3-C1 | A34-B4-C1 |
| A65-B1-C1 | A55-B2-C1 | A45-B3-C1 | A35-B4-C1 |
| A66-B1-C1 | A56-B2-C1 | A46-B3-C1 | A36-B4-C1 |
| A67-B1-C1 | A57-B2-C1 | A47-B3-C1 | A37-B4-C1 |
| A68-B1-C1 | A58-B2-C1 | A48-B3-C1 | A38-B4-C1 |
| A69-B1-C1 | A59-B2-C1 | A49-B3-C1 | A39-B4-C1 |
| A70-B1-C1 | A60-B2-C1 | A50-B3-C1 | A40-B4-C1 |
| A71-B1-C1 | A61-B2-C1 | A51-B3-C1 | A41-B4-C1 |
| A72-B1-C1 | A62-B2-C1 | A52-B3-C1 | A42-B4-C1 |
| A73-B1-C1 | A63-B2-C1 | A53-B3-C1 | A43-B4-C1 |
| A74-B1-C1 | A64-B2-C1 | A54-B3-C1 | A44-B4-C1 |
| A75-B1-C1 | A65-B2-C1 | A55-B3-C1 | A45-B4-C1 |
| A76-B1-C1 | A66-B2-C1 | A56-B3-C1 | A46-B4-C1 |
| A77-B1-C1 | A67-B2-C1 | A57-B3-C1 | A47-B4-C1 |
| A1-B2-C1 | A68-B2-C1 | A58-B3-C1 | A48-B4-C1 |
| A2-B2-C1 | A69-B2-C1 | A59-B3-C1 | A49-B4-C1 |
| A3-B2-C1 | A70-B2-C1 | A60-B3-C1 | A50-B4-C1 |
| A4-B2-C1 | A71-B2-C1 | A61-B3-C1 | A51-B4-C1 |
| A5-B2-C1 | A72-B2-C1 | A62-B3-C1 | A52-B4-C1 |
| A6-B2-C1 | A73-B2-C1 | A63-B3-C1 | A53-B4-C1 |
| A7-B2-C1 | A74-B2-C1 | A64-B3-C1 | A54-B4-C1 |
| A8-B2-C1 | A75-B2-C1 | A65-B3-C1 | A55-B4-C1 |
| A9-B2-C1 | A76-B2-C1 | A66-B3-C1 | A56-B4-C1 |
| A10-B2-C1 | A77-B2-C1 | A67-B3-C1 | A57-B4-C1 |
| A11-B2-C1 | A1-B3-C1 | A68-B3-C1 | A58-B4-C1 |
| A12-B2-C1 | A2-B3-C1 | A69-B3-C1 | A59-B4-C1 |
| A13-B2-C1 | A3-B3-C1 | A70-B3-C1 | A60-B4-C1 |
| A14-B2-C1 | A4-B3-C1 | A71-B3-C1 | A61-B4-C1 |
| A15-B2-C1 | A5-B3-C1 | A72-B3-C1 | A62-B4-C1 |
| A16-B2-C1 | A6-B3-C1 | A73-B3-C1 | A63-B4-C1 |
| A17-B2-C1 | A7-B3-C1 | A74-B3-C1 | A64-B4-C1 |
| A18-B2-C1 | A8-B3-C1 | A75-B3-C1 | A65-B4-C1 |
| A19-B2-C1 | A9-B3-C1 | A76-B3-C1 | A66-B4-C1 |
| A20-B2-C1 | A10-B3-C1 | A77-B3-C1 | A67-B4-C1 |
| A21-B2-C1 | A11-B3-C1 | A1-B4-C1 | A68-B4-C1 |
| A22-B2-C1 | A12-B3-C1 | A2-B4-C1 | A69-B4-C1 |
| A23-B2-C1 | A13-B3-C1 | A3-B4-C1 | A70-B4-C1 |
| A24-B2-C1 | A14-B3-C1 | A4-B4-C1 | A71-B4-C1 |
| A25-B2-C1 | A15-B3-C1 | A5-B4-C1 | A72-B4-C1 |
| A26-B2-C1 | A16-B3-C1 | A6-B4-C1 | A73-B4-C1 |
| A27-B2-C1 | A17-B3-C1 | A7-B4-C1 | A74-B4-C1 |
| A28-B2-C1 | A18-B3-C1 | A8-B4-C1 | A75-B4-C1 |
| A29-B2-C1 | A19-B3-C1 | A9-B4-C1 | A76-B4-C1 |
| A30-B2-C1 | A20-B3-C1 | A10-B4-C1 | A77-B4-C1 |
| A31-B2-C1 | A21-B3-C1 | A11-B4-C1 | A1-B1-C2 |
| A32-B2-C1 | A22-B3-C1 | A12-B4-C1 | A2-B1-C2 |
| A33-B2-C1 | A23-B3-C1 | A13-B4-C1 | A3-B1-C2 |
| A34-B2-C1 | A24-B3-C1 | A14-B4-C1 | A4-B1-C2 |
| A5-B1-C2 | A72-B1-C2 | A62-B2-C2 | A52-B3-C2 |
| A6-B1-C2 | A73-B1-C2 | A63-B2-C2 | A53-B3-C2 |
| A7-B1-C2 | A74-B1-C2 | A64-B2-C2 | A54-B3-C2 |
| A8-B1-C2 | A75-B1-C2 | A65-B2-C2 | A55-B3-C2 |
| A9-B1-C2 | A76-B1-C2 | A66-B2-C2 | A56-B3-C2 |
| A10-B1-C2 | A77-B1-C2 | A67-B2-C2 | A57-B3-C2 |
| A11-B1-C2 | A1-B2-C2 | A68-B2-C2 | A58-B3-C2 |
| A12-B1-C2 | A2-B2-C2 | A69-B2-C2 | A59-B3-C2 |
| A13-B1-C2 | A3-B2-C2 | A70-B2-C2 | A60-B3-C2 |
| A14-B1-C2 | A4-B2-C2 | A71-B2-C2 | A61-B3-C2 |
| A15-B1-C2 | A5-B2-C2 | A72-B2-C2 | A62-B3-C2 |
| A16-B1-C2 | A6-B2-C2 | A73-B2-C2 | A63-B3-C2 |
| A17-B1-C2 | A7-B2-C2 | A74-B2-C2 | A64-B3-C2 |
| A18-B1-C2 | A8-B2-C2 | A75-B2-C2 | A65-B3-C2 |
| A19-B1-C2 | A9-B2-C2 | A76-B2-C2 | A66-B3-C2 |
| A20-B1-C2 | A10-B2-C2 | A77-B2-C2 | A67-B3-C2 |
| A21-B1-C2 | A11-B2-C2 | A1-B3-C2 | A68-B3-C2 |
| A22-B1-C2 | A12-B2-C2 | A2-B3-C2 | A69-B3-C2 |
| A23-B1-C2 | A13-B2-C2 | A3-B3-C2 | A70-B3-C2 |
| A24-B1-C2 | A14-B2-C2 | A4-B3-C2 | A71-B3-C2 |
| A25-B1-C2 | A15-B2-C2 | A5-B3-C2 | A72-B3-C2 |

TABLE 4-continued

| | | | |
|---|---|---|---|
| A26-B1-C2 | A16-B2-C2 | A6-B3-C2 | A73-B3-C2 |
| A27-B1-C2 | A17-B2-C2 | A7-B3-C2 | A74-B3-C2 |
| A28-B1-C2 | A18-B2-C2 | A8-B3-C2 | A75-B3-C2 |
| A29-B1-C2 | A19-B2-C2 | A9-B3-C2 | A76-B3-C2 |
| A30-B1-C2 | A20-B2-C2 | A10-B3-C2 | A77-B3-C2 |
| A31-B1-C2 | A21-B2-C2 | A11-B3-C2 | A1-B4-C2 |
| A32-B1-C2 | A22-B2-C2 | A12-B3-C2 | A2-B4-C2 |
| A33-B1-C2 | A23-B2-C2 | A13-B3-C2 | A3-B4-C2 |
| A34-B1-C2 | A24-B2-C2 | A14-B3-C2 | A4-B4-C2 |
| A35-B1-C2 | A25-B2-C2 | A15-B3-C2 | A5-B4-C2 |
| A36-B1-C2 | A26-B2-C2 | A16-B3-C2 | A6-B4-C2 |
| A37-B1-C2 | A27-B2-C2 | A17-B3-C2 | A7-B4-C2 |
| A38-B1-C2 | A28-B2-C2 | A18-B3-C2 | A8-B4-C2 |
| A39-B1-C2 | A29-B2-C2 | A19-B3-C2 | A9-B4-C2 |
| A40-B1-C2 | A30-B2-C2 | A20-B3-C2 | A10-B4-C2 |
| A41-B1-C2 | A31-B2-C2 | A21-B3-C2 | A11-B4-C2 |
| A42-B1-C2 | A32-B2-C2 | A22-B3-C2 | A12-B4-C2 |
| A43-B1-C2 | A33-B2-C2 | A23-B3-C2 | A13-B4-C2 |
| A44-B1-C2 | A34-B2-C2 | A24-B3-C2 | A14-B4-C2 |
| A45-B1-C2 | A35-B2-C2 | A25-B3-C2 | A15-B4-C2 |
| A46-B1-C2 | A36-B2-C2 | A26-B3-C2 | A16-B4-C2 |
| A47-B1-C2 | A37-B2-C2 | A27-B3-C2 | A17-B4-C2 |
| A48-B1-C2 | A38-B2-C2 | A28-B3-C2 | A18-B4-C2 |
| A49-B1-C2 | A39-B2-C2 | A29-B3-C2 | A19-B4-C2 |
| A50-B1-C2 | A40-B2-C2 | A30-B3-C2 | A20-B4-C2 |
| A51-B1-C2 | A41-B2-C2 | A31-B3-C2 | A21-B4-C2 |
| A52-B1-C2 | A42-B2-C2 | A32-B3-C2 | A22-B4-C2 |
| A53-B1-C2 | A43-B2-C2 | A33-B3-C2 | A23-B4-C2 |
| A54-B1-C2 | A44-B2-C2 | A34-B3-C2 | A24-B4-C2 |
| A55-B1-C2 | A45-B2-C2 | A35-B3-C2 | A25-B4-C2 |
| A56-B1-C2 | A46-B2-C2 | A36-B3-C2 | A26-B4-C2 |
| A57-B1-C2 | A47-B2-C2 | A37-B3-C2 | A27-B4-C2 |
| A58-B1-C2 | A48-B2-C2 | A38-B3-C2 | A28-B4-C2 |
| A59-B1-C2 | A49-B2-C2 | A39-B3-C2 | A29-B4-C2 |
| A60-B1-C2 | A50-B2-C2 | A40-B3-C2 | A30-B4-C2 |
| A61-B1-C2 | A51-B2-C2 | A41-B3-C2 | A31-B4-C2 |
| A62-B1-C2 | A52-B2-C2 | A42-B3-C2 | A32-B4-C2 |
| A63-B1-C2 | A53-B2-C2 | A43-B3-C2 | A33-B4-C2 |
| A64-B1-C2 | A54-B2-C2 | A44-B3-C2 | A34-B4-C2 |
| A65-B1-C2 | A55-B2-C2 | A45-B3-C2 | A35-B4-C2 |
| A66-B1-C2 | A56-B2-C2 | A46-B3-C2 | A36-B4-C2 |
| A67-B1-C2 | A57-B2-C2 | A47-B3-C2 | A37-B4-C2 |
| A68-B1-C2 | A58-B2-C2 | A48-B3-C2 | A38-B4-C2 |
| A69-B1-C2 | A59-B2-C2 | A49-B3-C2 | A39-B4-C2 |
| A70-B1-C2 | A60-B2-C2 | A50-B3-C2 | A40-B4-C2 |
| A71-B1-C2 | A61-B2-C2 | A51-B3-C2 | A41-B4-C2 |
| A42-B4-C2 | A32-B1-C3 | A22-B2-C3 | A12-B3-C3 |
| A43-B4-C2 | A33-B1-C3 | A23-B2-C3 | A13-B3-C3 |
| A44-B4-C2 | A34-B1-C3 | A24-B2-C3 | A14-B3-C3 |
| A45-B4-C2 | A35-B1-C3 | A25-B2-C3 | A15-B3-C3 |
| A46-B4-C2 | A36-B1-C3 | A26-B2-C3 | A16-B3-C3 |
| A47-B4-C2 | A37-B1-C3 | A27-B2-C3 | A17-B3-C3 |
| A48-B4-C2 | A38-B1-C3 | A28-B2-C3 | A18-B3-C3 |
| A49-B4-C2 | A39-B1-C3 | A29-B2-C3 | A19-B3-C3 |
| A50-B4-C2 | A40-B1-C3 | A30-B2-C3 | A20-B3-C3 |
| A51-B4-C2 | A41-B1-C3 | A31-B2-C3 | A21-B3-C3 |
| A52-B4-C2 | A42-B1-C3 | A32-B2-C3 | A22-B3-C3 |
| A53-B4-C2 | A43-B1-C3 | A33-B2-C3 | A23-B3-C3 |
| A54-B4-C2 | A44-B1-C3 | A34-B2-C3 | A24-B3-C3 |
| A55-B4-C2 | A45-B1-C3 | A35-B2-C3 | A25-B3-C3 |
| A56-B4-C2 | A46-B1-C3 | A36-B2-C3 | A26-B3-C3 |
| A57-B4-C2 | A47-B1-C3 | A37-B2-C3 | A27-B3-C3 |
| A58-B4-C2 | A48-B1-C3 | A38-B2-C3 | A28-B3-C3 |
| A59-B4-C2 | A49-B1-C3 | A39-B2-C3 | A29-B3-C3 |
| A60-B4-C2 | A50-B1-C3 | A40-B2-C3 | A30-B3-C3 |
| A61-B4-C2 | A51-B1-C3 | A41-B2-C3 | A31-B3-C3 |
| A62-B4-C2 | A52-B1-C3 | A42-B2-C3 | A32-B3-C3 |
| A63-B4-C2 | A53-B1-C3 | A43-B2-C3 | A33-B3-C3 |
| A64-B4-C2 | A54-B1-C3 | A44-B2-C3 | A34-B3-C3 |
| A65-B4-C2 | A55-B1-C3 | A45-B2-C3 | A35-B3-C3 |
| A66-B4-C2 | A56-B1-C3 | A46-B2-C3 | A36-B3-C3 |
| A67-B4-C2 | A57-B1-C3 | A47-B2-C3 | A37-B3-C3 |
| A68-B4-C2 | A58-B1-C3 | A48-B2-C3 | A38-B3-C3 |
| A69-B4-C2 | A59-B1-C3 | A49-B2-C3 | A39-B3-C3 |
| A70-B4-C2 | A60-B1-C3 | A50-B2-C3 | A40-B3-C3 |
| A71-B4-C2 | A61-B1-C3 | A51-B2-C3 | A41-B3-C3 |
| A72-B4-C2 | A62-B1-C3 | A52-B2-C3 | A42-B3-C3 |
| A73-B4-C2 | A63-B1-C3 | A53-B2-C3 | A43-B3-C3 |
| A74-B4-C2 | A64-B1-C3 | A54-B2-C3 | A44-B3-C3 |

TABLE 4-continued

| | | | |
|---|---|---|---|
| A75-B4-C2 | A65-B1-C3 | A55-B2-C3 | A45-B3-C3 |
| A76-B4-C2 | A66-B1-C3 | A56-B2-C3 | A46-B3-C3 |
| A77-B4-C2 | A67-B1-C3 | A57-B2-C3 | A47-B3-C3 |
| A1-B1-C3 | A68-B1-C3 | A58-B2-C3 | A48-B3-C3 |
| A2-B1-C3 | A69-B1-C3 | A59-B2-C3 | A49-B3-C3 |
| A3-B1-C3 | A70-B1-C3 | A60-B2-C3 | A50-B3-C3 |
| A4-B1-C3 | A71-B1-C3 | A61-B2-C3 | A51-B3-C3 |
| A5-B1-C3 | A72-B1-C3 | A62-B2-C3 | A52-B3-C3 |
| A6-B1-C3 | A73-B1-C3 | A63-B2-C3 | A53-B3-C3 |
| A7-B1-C3 | A74-B1-C3 | A64-B2-C3 | A54-B3-C3 |
| A8-B1-C3 | A75-B1-C3 | A65-B2-C3 | A55-B3-C3 |
| A9-B1-C3 | A76-B1-C3 | A66-B2-C3 | A56-B3-C3 |
| A10-B1-C3 | A77-B1-C3 | A67-B2-C3 | A57-B3-C3 |
| A11-B1-C3 | A1-B2-C3 | A68-B2-C3 | A58-B3-C3 |
| A12-B1-C3 | A2-B2-C3 | A69-B2-C3 | A59-B3-C3 |
| A13-B1-C3 | A3-B2-C3 | A70-B2-C3 | A60-B3-C3 |
| A14-B1-C3 | A4-B2-C3 | A71-B2-C3 | A61-B3-C3 |
| A15-B1-C3 | A5-B2-C3 | A72-B2-C3 | A62-B3-C3 |
| A16-B1-C3 | A6-B2-C3 | A73-B2-C3 | A63-B3-C3 |
| A17-B1-C3 | A7-B2-C3 | A74-B2-C3 | A64-B3-C3 |
| A18-B1-C3 | A8-B2-C3 | A75-B2-C3 | A65-B3-C3 |
| A19-B1-C3 | A9-B2-C3 | A76-B2-C3 | A66-B3-C3 |
| A20-B1-C3 | A10-B2-C3 | A77-B2-C3 | A67-B3-C3 |
| A21-B1-C3 | A11-B2-C3 | A1-B3-C3 | A68-B3-C3 |
| A22-B1-C3 | A12-B2-C3 | A2-B3-C3 | A69-B3-C3 |
| A23-B1-C3 | A13-B2-C3 | A3-B3-C3 | A70-B3-C3 |
| A24-B1-C3 | A14-B2-C3 | A4-B3-C3 | A71-B3-C3 |
| A25-B1-C3 | A15-B2-C3 | A5-B3-C3 | A72-B3-C3 |
| A26-B1-C3 | A16-B2-C3 | A6-B3-C3 | A73-B3-C3 |
| A27-B1-C3 | A17-B2-C3 | A7-B3-C3 | A74-B3-C3 |
| A28-B1-C3 | A18-B2-C3 | A8-B3-C3 | A75-B3-C3 |
| A29-B1-C3 | A19-B2-C3 | A9-B3-C3 | A76-B3-C3 |
| A30-B1-C3 | A20-B2-C3 | A10-B3-C3 | A77-B3-C3 |
| A31-B1-C3 | A21-B2-C3 | A11-B3-C3 | A1-B4-C3 |
| A2-B4-C3 | A69-B4-C3 | A59-B1-C4 | A49-B2-C4 |
| A3-B4-C3 | A70-B4-C3 | A60-B1-C4 | A50-B2-C4 |
| A4-B4-C3 | A71-B4-C3 | A61-B1-C4 | A51-B2-C4 |
| A5-B4-C3 | A72-B4-C3 | A62-B1-C4 | A52-B2-C4 |
| A6-B4-C3 | A73-B4-C3 | A63-B1-C4 | A53-B2-C4 |
| A7-B4-C3 | A74-B4-C3 | A64-B1-C4 | A54-B2-C4 |
| A8-B4-C3 | A75-B4-C3 | A65-B1-C4 | A55-B2-C4 |
| A9-B4-C3 | A76-B4-C3 | A66-B1-C4 | A56-B2-C4 |
| A10-B4-C3 | A77-B4-C3 | A67-B1-C4 | A57-B2-C4 |
| A11-B4-C3 | A1-B1-C4 | A68-B1-C4 | A58-B2-C4 |
| A12-B4-C3 | A2-B1-C4 | A69-B1-C4 | A59-B2-C4 |
| A13-B4-C3 | A3-B1-C4 | A70-B1-C4 | A60-B2-C4 |
| A14-B4-C3 | A4-B1-C4 | A71-B1-C4 | A61-B2-C4 |
| A15-B4-C3 | A5-B1-C4 | A72-B1-C4 | A62-B2-C4 |
| A16-B4-C3 | A6-B1-C4 | A73-B1-C4 | A63-B2-C4 |
| A17-B4-C3 | A7-B1-C4 | A74-B1-C4 | A64-B2-C4 |
| A18-B4-C3 | A8-B1-C4 | A75-B1-C4 | A65-B2-C4 |
| A19-B4-C3 | A9-B1-C4 | A76-B1-C4 | A66-B2-C4 |
| A20-B4-C3 | A10-B1-C4 | A77-B1-C4 | A67-B2-C4 |
| A21-B4-C3 | A11-B1-C4 | A1-B2-C4 | A68-B2-C4 |
| A22-B4-C3 | A12-B1-C4 | A2-B2-C4 | A69-B2-C4 |
| A23-B4-C3 | A13-B1-C4 | A3-B2-C4 | A70-B2-C4 |
| A24-B4-C3 | A14-B1-C4 | A4-B2-C4 | A71-B2-C4 |
| A25-B4-C3 | A15-B1-C4 | A5-B2-C4 | A72-B2-C4 |
| A26-B4-C3 | A16-B1-C4 | A6-B2-C4 | A73-B2-C4 |
| A27-B4-C3 | A17-B1-C4 | A7-B2-C4 | A74-B2-C4 |
| A28-B4-C3 | A18-B1-C4 | A8-B2-C4 | A75-B2-C4 |
| A29-B4-C3 | A19-B1-C4 | A9-B2-C4 | A76-B2-C4 |
| A30-B4-C3 | A20-B1-C4 | A10-B2-C4 | A77-B2-C4 |
| A31-B4-C3 | A21-B1-C4 | A11-B2-C4 | A1-B3-C4 |
| A32-B4-C3 | A22-B1-C4 | A12-B2-C4 | A2-B3-C4 |
| A33-B4-C3 | A23-B1-C4 | A13-B2-C4 | A3-B3-C4 |
| A34-B4-C3 | A24-B1-C4 | A14-B2-C4 | A4-B3-C4 |
| A35-B4-C3 | A25-B1-C4 | A15-B2-C4 | A5-B3-C4 |
| A36-B4-C3 | A26-B1-C4 | A16-B2-C4 | A6-B3-C4 |
| A37-B4-C3 | A27-B1-C4 | A17-B2-C4 | A7-B3-C4 |
| A38-B4-C3 | A28-B1-C4 | A18-B2-C4 | A8-B3-C4 |
| A39-B4-C3 | A29-B1-C4 | A19-B2-C4 | A9-B3-C4 |
| A40-B4-C3 | A30-B1-C4 | A20-B2-C4 | A10-B3-C4 |
| A41-B4-C3 | A31-B1-C4 | A21-B2-C4 | A11-B3-C4 |
| A42-B4-C3 | A32-B1-C4 | A22-B2-C4 | A12-B3-C4 |
| A43-B4-C3 | A33-B1-C4 | A23-B2-C4 | A13-B3-C4 |
| A44-B4-C3 | A34-B1-C4 | A24-B2-C4 | A14-B3-C4 |
| A45-B4-C3 | A35-B1-C4 | A25-B2-C4 | A15-B3-C4 |
| A46-B4-C3 | A36-B1-C4 | A26-B2-C4 | A16-B3-C4 |

TABLE 4-continued

| | | | |
|---|---|---|---|
| A47-B4-C3 | A37-B1-C4 | A27-B2-C4 | A17-B3-C4 |
| A48-B4-C3 | A38-B1-C4 | A28-B2-C4 | A18-B3-C4 |
| A49-B4-C3 | A39-B1-C4 | A29-B2-C4 | A19-B3-C4 |
| A50-B4-C3 | A40-B1-C4 | A30-B2-C4 | A20-B3-C4 |
| A51-B4-C3 | A41-B1-C4 | A31-B2-C4 | A21-B3-C4 |
| A52-B4-C3 | A42-B1-C4 | A32-B2-C4 | A22-B3-C4 |
| A53-B4-C3 | A43-B1-C4 | A33-B2-C4 | A23-B3-C4 |
| A54-B4-C3 | A44-B1-C4 | A34-B2-C4 | A24-B3-C4 |
| A55-B4-C3 | A45-B1-C4 | A35-B2-C4 | A25-B3-C4 |
| A56-B4-C3 | A46-B1-C4 | A36-B2-C4 | A26-B3-C4 |
| A57-B4-C3 | A47-B1-C4 | A37-B2-C4 | A27-B3-C4 |
| A58-B4-C3 | A48-B1-C4 | A38-B2-C4 | A28-B3-C4 |
| A59-B4-C3 | A49-B1-C4 | A39-B2-C4 | A29-B3-C4 |
| A60-B4-C3 | A50-B1-C4 | A40-B2-C4 | A30-B3-C4 |
| A61-B4-C3 | A51-B1-C4 | A41-B2-C4 | A31-B3-C4 |
| A62-B4-C3 | A52-B1-C4 | A42-B2-C4 | A32-B3-C4 |
| A63-B4-C3 | A53-B1-C4 | A43-B2-C4 | A33-B3-C4 |
| A64-B4-C3 | A54-B1-C4 | A44-B2-C4 | A34-B3-C4 |
| A65-B4-C3 | A55-B1-C4 | A45-B2-C4 | A35-B3-C4 |
| A66-B4-C3 | A56-B1-C4 | A46-B2-C4 | A36-B3-C4 |
| A67-B4-C3 | A57-B1-C4 | A47-B2-C4 | A37-B3-C4 |
| A68-B4-C3 | A58-B1-C4 | A48-B2-C4 | A38-B3-C4 |
| A39-B3-C4 | A29-B4-C4 | A19-B1-C5 | A9-B2-C5 |
| A40-B3-C4 | A30-B4-C4 | A20-B1-C5 | A10-B2-C5 |
| A41-B3-C4 | A31-B4-C4 | A21-B1-C5 | A11-B2-C5 |
| A42-B3-C4 | A32-B4-C4 | A22-B1-C5 | A12-B2-C5 |
| A43-B3-C4 | A33-B4-C4 | A23-B1-C5 | A13-B2-C5 |
| A44-B3-C4 | A34-B4-C4 | A24-B1-C5 | A14-B2-C5 |
| A45-B3-C4 | A35-B4-C4 | A25-B1-C5 | A15-B2-C5 |
| A46-B3-C4 | A36-B4-C4 | A26-B1-C5 | A16-B2-C5 |
| A47-B3-C4 | A37-B4-C4 | A27-B1-C5 | A17-B2-C5 |
| A48-B3-C4 | A38-B4-C4 | A28-B1-C5 | A18-B2-C5 |
| A49-B3-C4 | A39-B4-C4 | A29-B1-C5 | A19-B2-C5 |
| A50-B3-C4 | A40-B4-C4 | A30-B1-C5 | A20-B2-C5 |
| A51-B3-C4 | A41-B4-C4 | A31-B1-C5 | A21-B2-C5 |
| A52-B3-C4 | A42-B4-C4 | A32-B1-C5 | A22-B2-C5 |
| A53-B3-C4 | A43-B4-C4 | A33-B1-C5 | A23-B2-C5 |
| A54-B3-C4 | A44-B4-C4 | A34-B1-C5 | A24-B2-C5 |
| A55-B3-C4 | A45-B4-C4 | A35-B1-C5 | A25-B2-C5 |
| A56-B3-C4 | A46-B4-C4 | A36-B1-C5 | A26-B2-C5 |
| A57-B3-C4 | A47-B4-C4 | A37-B1-C5 | A27-B2-C5 |
| A58-B3-C4 | A48-B4-C4 | A38-B1-C5 | A28-B2-C5 |
| A59-B3-C4 | A49-B4-C4 | A39-B1-C5 | A29-B2-C5 |
| A60-B3-C4 | A50-B4-C4 | A40-B1-C5 | A30-B2-C5 |
| A61-B3-C4 | A51-B4-C4 | A41-B1-C5 | A31-B2-C5 |
| A62-B3-C4 | A52-B4-C4 | A42-B1-C5 | A32-B2-C5 |
| A63-B3-C4 | A53-B4-C4 | A43-B1-C5 | A33-B2-C5 |
| A64-B3-C4 | A54-B4-C4 | A44-B1-C5 | A34-B2-C5 |
| A65-B3-C4 | A55-B4-C4 | A45-B1-C5 | A35-B2-C5 |
| A66-B3-C4 | A56-B4-C4 | A46-B1-C5 | A36-B2-C5 |
| A67-B3-C4 | A57-B4-C4 | A47-B1-C5 | A37-B2-C5 |
| A68-B3-C4 | A58-B4-C4 | A48-B1-C5 | A38-B2-C5 |
| A69-B3-C4 | A59-B4-C4 | A49-B1-C5 | A39-B2-C5 |
| A70-B3-C4 | A60-B4-C4 | A50-B1-C5 | A40-B2-C5 |
| A71-B3-C4 | A61-B4-C4 | A51-B1-C5 | A41-B2-C5 |
| A72-B3-C4 | A62-B4-C4 | A52-B1-C5 | A42-B2-C5 |
| A73-B3-C4 | A63-B4-C4 | A53-B1-C5 | A43-B2-C5 |
| A74-B3-C4 | A64-B4-C4 | A54-B1-C5 | A44-B2-C5 |
| A75-B3-C4 | A65-B4-C4 | A55-B1-C5 | A45-B2-C5 |
| A76-B3-C4 | A66-B4-C4 | A56-B1-C5 | A46-B2-C5 |
| A77-B3-C4 | A67-B4-C4 | A57-B1-C5 | A47-B2-C5 |
| A1-B4-C4 | A68-B4-C4 | A58-B1-C5 | A48-B2-C5 |
| A2-B4-C4 | A69-B4-C4 | A59-B1-C5 | A49-B2-C5 |
| A3-B4-C4 | A70-B4-C4 | A60-B1-C5 | A50-B2-C5 |
| A4-B4-C4 | A71-B4-C4 | A61-B1-C5 | A51-B2-C5 |
| A5-B4-C4 | A72-B4-C4 | A62-B1-C5 | A52-B2-C5 |
| A6-B4-C4 | A73-B4-C4 | A63-B1-C5 | A53-B2-C5 |
| A7-B4-C4 | A74-B4-C4 | A64-B1-C5 | A54-B2-C5 |
| A8-B4-C4 | A75-B4-C4 | A65-B1-C5 | A55-B2-C5 |
| A9-B4-C4 | A76-B4-C4 | A66-B1-C5 | A56-B2-C5 |
| A10-B4-C4 | A77-B4-C4 | A67-B1-C5 | A57-B2-C5 |
| A11-B4-C4 | A1-B1-C5 | A68-B1-C5 | A58-B2-C5 |
| A12-B4-C4 | A2-B1-C5 | A69-B1-C5 | A59-B2-C5 |
| A13-B4-C4 | A3-B1-C5 | A70-B1-C5 | A60-B2-C5 |
| A14-B4-C4 | A4-B1-C5 | A71-B1-C5 | A61-B2-C5 |
| A15-B4-C4 | A5-B1-C5 | A72-B1-C5 | A62-B2-C5 |
| A16-B4-C4 | A6-B1-C5 | A73-B1-C5 | A63-B2-C5 |
| A17-B4-C4 | A7-B1-C5 | A74-B1-C5 | A64-B2-C5 |
| A18-B4-C4 | A8-B1-C5 | A75-B1-C5 | A65-B2-C5 |
| A19-B4-C4 | A9-B1-C5 | A76-B1-C5 | A66-B2-C5 |
| A20-B4-C4 | A10-B1-C5 | A77-B1-C5 | A67-B2-C5 |
| A21-B4-C4 | A11-B1-C5 | A1-B2-C5 | A68-B2-C5 |
| A22-B4-C4 | A12-B1-C5 | A2-B2-C5 | A69-B2-C5 |
| A23-B4-C4 | A13-B1-C5 | A3-B2-C5 | A70-B2-C5 |
| A24-B4-C4 | A14-B1-C5 | A4-B2-C5 | A71-B2-C5 |
| A25-B4-C4 | A15-B1-C5 | A5-B2-C5 | A72-B2-C5 |
| A26-B4-C4 | A16-B1-C5 | A6-B2-C5 | A73-B2-C5 |
| A27-B4-C4 | A17-B1-C5 | A7-B2-C5 | A74-B2-C5 |
| A28-B4-C4 | A18-B1-C5 | A8-B2-C5 | A75-B2-C5 |
| A76-B2-C5 | A66-B3-C5 | A56-B4-C5 | A46-B1-C6 |
| A77-B2-C5 | A67-B3-C5 | A57-B4-C5 | A47-B1-C6 |
| A1-B3-C5 | A68-B3-C5 | A58-B4-C5 | A48-B1-C6 |
| A2-B3-C5 | A69-B3-C5 | A59-B4-C5 | A49-B1-C6 |
| A3-B3-C5 | A70-B3-C5 | A60-B4-C5 | A50-B1-C6 |
| A4-B3-C5 | A71-B3-C5 | A61-B4-C5 | A51-B1-C6 |
| A5-B3-C5 | A72-B3-C5 | A62-B4-C5 | A52-B1-C6 |
| A6-B3-C5 | A73-B3-C5 | A63-B4-C5 | A53-B1-C6 |
| A7-B3-C5 | A74-B3-C5 | A64-B4-C5 | A54-B1-C6 |
| A8-B3-C5 | A75-B3-C5 | A65-B4-C5 | A55-B1-C6 |
| A9-B3-C5 | A76-B3-C5 | A66-B4-C5 | A56-B1-C6 |
| A10-B3-C5 | A77-B3-C5 | A67-B4-C5 | A57-B1-C6 |
| A11-B3-C5 | A1-B4-C5 | A68-B4-C5 | A58-B1-C6 |
| A12-B3-C5 | A2-B4-C5 | A69-B4-C5 | A59-B1-C6 |
| A13-B3-C5 | A3-B4-C5 | A70-B4-C5 | A60-B1-C6 |
| A14-B3-C5 | A4-B4-C5 | A71-B4-C5 | A61-B1-C6 |
| A15-B3-C5 | A5-B4-C5 | A72-B4-C5 | A62-B1-C6 |
| A16-B3-C5 | A6-B4-C5 | A73-B4-C5 | A63-B1-C6 |
| A17-B3-C5 | A7-B4-C5 | A74-B4-C5 | A64-B1-C6 |
| A18-B3-C5 | A8-B4-C5 | A75-B4-C5 | A65-B1-C6 |
| A19-B3-C5 | A9-B4-C5 | A76-B4-C5 | A66-B1-C6 |
| A20-B3-C5 | A10-B4-C5 | A77-B4-C5 | A67-B1-C6 |
| A21-B3-C5 | A11-B4-C5 | A1-B1-C6 | A68-B1-C6 |
| A22-B3-C5 | A12-B4-C5 | A2-B1-C6 | A69-B1-C6 |
| A23-B3-C5 | A13-B4-C5 | A3-B1-C6 | A70-B1-C6 |
| A24-B3-C5 | A14-B4-C5 | A4-B1-C6 | A71-B1-C6 |
| A25-B3-C5 | A15-B4-C5 | A5-B1-C6 | A72-B1-C6 |
| A26-B3-C5 | A16-B4-C5 | A6-B1-C6 | A73-B1-C6 |
| A27-B3-C5 | A17-B4-C5 | A7-B1-C6 | A74-B1-C6 |
| A28-B3-C5 | A18-B4-C5 | A8-B1-C6 | A75-B1-C6 |
| A29-B3-C5 | A19-B4-C5 | A9-B1-C6 | A76-B1-C6 |
| A30-B3-C5 | A20-B4-C5 | A10-B1-C6 | A77-B1-C6 |
| A31-B3-C5 | A21-B4-C5 | A11-B1-C6 | A1-B2-C6 |
| A32-B3-C5 | A22-B4-C5 | A12-B1-C6 | A2-B2-C6 |
| A33-B3-C5 | A23-B4-C5 | A13-B1-C6 | A3-B2-C6 |
| A34-B3-C5 | A24-B4-C5 | A14-B1-C6 | A4-B2-C6 |
| A35-B3-C5 | A25-B4-C5 | A15-B1-C6 | A5-B2-C6 |
| A36-B3-C5 | A26-B4-C5 | A16-B1-C6 | A6-B2-C6 |
| A37-B3-C5 | A27-B4-C5 | A17-B1-C6 | A7-B2-C6 |
| A38-B3-C5 | A28-B4-C5 | A18-B1-C6 | A8-B2-C6 |
| A39-B3-C5 | A29-B4-C5 | A19-B1-C6 | A9-B2-C6 |
| A40-B3-C5 | A30-B4-C5 | A20-B1-C6 | A10-B2-C6 |
| A41-B3-C5 | A31-B4-C5 | A21-B1-C6 | A11-B2-C6 |
| A42-B3-C5 | A32-B4-C5 | A22-B1-C6 | A12-B2-C6 |
| A43-B3-C5 | A33-B4-C5 | A23-B1-C6 | A13-B2-C6 |
| A44-B3-C5 | A34-B4-C5 | A24-B1-C6 | A14-B2-C6 |
| A45-B3-C5 | A35-B4-C5 | A25-B1-C6 | A15-B2-C6 |
| A46-B3-C5 | A36-B4-C5 | A26-B1-C6 | A16-B2-C6 |
| A47-B3-C5 | A37-B4-C5 | A27-B1-C6 | A17-B2-C6 |
| A48-B3-C5 | A38-B4-C5 | A28-B1-C6 | A18-B2-C6 |
| A49-B3-C5 | A39-B4-C5 | A29-B1-C6 | A19-B2-C6 |
| A50-B3-C5 | A40-B4-C5 | A30-B1-C6 | A20-B2-C6 |
| A51-B3-C5 | A41-B4-C5 | A31-B1-C6 | A21-B2-C6 |
| A52-B3-C5 | A42-B4-C5 | A32-B1-C6 | A22-B2-C6 |
| A53-B3-C5 | A43-B4-C5 | A33-B1-C6 | A23-B2-C6 |
| A54-B3-C5 | A44-B4-C5 | A34-B1-C6 | A24-B2-C6 |
| A55-B3-C5 | A45-B4-C5 | A35-B1-C6 | A25-B2-C6 |
| A56-B3-C5 | A46-B4-C5 | A36-B1-C6 | A26-B2-C6 |
| A57-B3-C5 | A47-B4-C5 | A37-B1-C6 | A27-B2-C6 |
| A58-B3-C5 | A48-B4-C5 | A38-B1-C6 | A28-B2-C6 |
| A59-B3-C5 | A49-B4-C5 | A39-B1-C6 | A29-B2-C6 |
| A60-B3-C5 | A50-B4-C5 | A40-B1-C6 | A30-B2-C6 |
| A61-B3-C5 | A51-B4-C5 | A41-B1-C6 | A31-B2-C6 |
| A62-B3-C5 | A52-B4-C5 | A42-B1-C6 | A32-B2-C6 |
| A63-B3-C5 | A53-B4-C5 | A43-B1-C6 | A33-B2-C6 |
| A64-B3-C5 | A54-B4-C5 | A44-B1-C6 | A34-B2-C6 |
| A65-B3-C5 | A55-B4-C5 | A45-B1-C6 | A35-B2-C6 |
| A36-B2-C6 | A26-B3-C6 | A16-B4-C6 | A6-B1-C7 |
| A37-B2-C6 | A27-B3-C6 | A17-B4-C6 | A7-B1-C7 |

TABLE 4-continued

| | | | |
|---|---|---|---|
| A38-B2-C6 | A28-B3-C6 | A18-B4-C6 | A8-B1-C7 |
| A39-B2-C6 | A29-B3-C6 | A19-B4-C6 | A9-B1-C7 |
| A40-B2-C6 | A30-B3-C6 | A20-B4-C6 | A10-B1-C7 |
| A41-B2-C6 | A31-B3-C6 | A21-B4-C6 | A11-B1-C7 |
| A42-B2-C6 | A32-B3-C6 | A22-B4-C6 | A12-B1-C7 |
| A43-B2-C6 | A33-B3-C6 | A23-B4-C6 | A13-B1-C7 |
| A44-B2-C6 | A34-B3-C6 | A24-B4-C6 | A14-B1-C7 |
| A45-B2-C6 | A35-B3-C6 | A25-B4-C6 | A15-B1-C7 |
| A46-B2-C6 | A36-B3-C6 | A26-B4-C6 | A16-B1-C7 |
| A47-B2-C6 | A37-B3-C6 | A27-B4-C6 | A17-B1-C7 |
| A48-B2-C6 | A38-B3-C6 | A28-B4-C6 | A18-B1-C7 |
| A49-B2-C6 | A39-B3-C6 | A29-B4-C6 | A19-B1-C7 |
| A50-B2-C6 | A40-B3-C6 | A30-B4-C6 | A20-B1-C7 |
| A51-B2-C6 | A41-B3-C6 | A31-B4-C6 | A21-B1-C7 |
| A52-B2-C6 | A42-B3-C6 | A32-B4-C6 | A22-B1-C7 |
| A53-B2-C6 | A43-B3-C6 | A33-B4-C6 | A23-B1-C7 |
| A54-B2-C6 | A44-B3-C6 | A34-B4-C6 | A24-B1-C7 |
| A55-B2-C6 | A45-B3-C6 | A35-B4-C6 | A25-B1-C7 |
| A56-B2-C6 | A46-B3-C6 | A36-B4-C6 | A26-B1-C7 |
| A57-B2-C6 | A47-B3-C6 | A37-B4-C6 | A27-B1-C7 |
| A58-B2-C6 | A48-B3-C6 | A38-B4-C6 | A28-B1-C7 |
| A59-B2-C6 | A49-B3-C6 | A39-B4-C6 | A29-B1-C7 |
| A60-B2-C6 | A50-B3-C6 | A40-B4-C6 | A30-B1-C7 |
| A61-B2-C6 | A51-B3-C6 | A41-B4-C6 | A31-B1-C7 |
| A62-B2-C6 | A52-B3-C6 | A42-B4-C6 | A32-B1-C7 |
| A63-B2-C6 | A53-B3-C6 | A43-B4-C6 | A33-B1-C7 |
| A64-B2-C6 | A54-B3-C6 | A44-B4-C6 | A34-B1-C7 |
| A65-B2-C6 | A55-B3-C6 | A45-B4-C6 | A35-B1-C7 |
| A66-B2-C6 | A56-B3-C6 | A46-B4-C6 | A36-B1-C7 |
| A67-B2-C6 | A57-B3-C6 | A47-B4-C6 | A37-B1-C7 |
| A68-B2-C6 | A58-B3-C6 | A48-B4-C6 | A38-B1-C7 |
| A69-B2-C6 | A59-B3-C6 | A49-B4-C6 | A39-B1-C7 |
| A70-B2-C6 | A60-B3-C6 | A50-B4-C6 | A40-B1-C7 |
| A71-B2-C6 | A61-B3-C6 | A51-B4-C6 | A41-B1-C7 |
| A72-B2-C6 | A62-B3-C6 | A52-B4-C6 | A42-B1-C7 |
| A73-B2-C6 | A63-B3-C6 | A53-B4-C6 | A43-B1-C7 |
| A74-B2-C6 | A64-B3-C6 | A54-B4-C6 | A44-B1-C7 |
| A75-B2-C6 | A65-B3-C6 | A55-B4-C6 | A45-B1-C7 |
| A76-B2-C6 | A66-B3-C6 | A56-B4-C6 | A46-B1-C7 |
| A77-B2-C6 | A67-B3-C6 | A57-B4-C6 | A47-B1-C7 |
| A1-B3-C6 | A68-B3-C6 | A58-B4-C6 | A48-B1-C7 |
| A2-B3-C6 | A69-B3-C6 | A59-B4-C6 | A49-B1-C7 |
| A3-B3-C6 | A70-B3-C6 | A60-B4-C6 | A50-B1-C7 |
| A4-B3-C6 | A71-B3-C6 | A61-B4-C6 | A51-B1-C7 |
| A5-B3-C6 | A72-B3-C6 | A62-B4-C6 | A52-B1-C7 |
| A6-B3-C6 | A73-B3-C6 | A63-B4-C6 | A53-B1-C7 |
| A7-B3-C6 | A74-B3-C6 | A64-B4-C6 | A54-B1-C7 |
| A8-B3-C6 | A75-B3-C6 | A65-B4-C6 | A55-B1-C7 |
| A9-B3-C6 | A76-B3-C6 | A66-B4-C6 | A56-B1-C7 |
| A10-B3-C6 | A77-B3-C6 | A67-B4-C6 | A57-B1-C7 |
| A11-B3-C6 | A1-B4-C6 | A68-B4-C6 | A58-B1-C7 |
| A12-B3-C6 | A2-B4-C6 | A69-B4-C6 | A59-B1-C7 |
| A13-B3-C6 | A3-B4-C6 | A70-B4-C6 | A60-B1-C7 |
| A14-B3-C6 | A4-B4-C6 | A71-B4-C6 | A61-B1-C7 |
| A15-B3-C6 | A5-B4-C6 | A72-B4-C6 | A62-B1-C7 |
| A16-B3-C6 | A6-B4-C6 | A73-B4-C6 | A63-B1-C7 |
| A17-B3-C6 | A7-B4-C6 | A74-B4-C6 | A64-B1-C7 |
| A18-B3-C6 | A8-B4-C6 | A75-B4-C6 | A65-B1-C7 |
| A19-B3-C6 | A9-B4-C6 | A76-B4-C6 | A66-B1-C7 |
| A20-B3-C6 | A10-B4-C6 | A77-B4-C6 | A67-B1-C7 |
| A21-B3-C6 | A11-B4-C6 | A1-B1-C7 | A68-B1-C7 |
| A22-B3-C6 | A12-B4-C6 | A2-B1-C7 | A69-B1-C7 |
| A23-B3-C6 | A13-B4-C6 | A3-B1-C7 | A70-B1-C7 |
| A24-B3-C6 | A14-B4-C6 | A4-B1-C7 | A71-B1-C7 |
| A25-B3-C6 | A15-B4-C6 | A5-B1-C7 | A72-B1-C7 |
| A73-B1-C7 | A63-B2-C7 | A53-B3-C7 | A43-B4-C7 |
| A74-B1-C7 | A64-B2-C7 | A54-B3-C7 | A44-B4-C7 |
| A75-B1-C7 | A65-B2-C7 | A55-B3-C7 | A45-B4-C7 |
| A76-B1-C7 | A66-B2-C7 | A56-B3-C7 | A46-B4-C7 |
| A77-B1-C7 | A67-B2-C7 | A57-B3-C7 | A47-B4-C7 |
| A1-B2-C7 | A68-B2-C7 | A58-B3-C7 | A48-B4-C7 |
| A2-B2-C7 | A69-B2-C7 | A59-B3-C7 | A49-B4-C7 |
| A3-B2-C7 | A70-B2-C7 | A60-B3-C7 | A50-B4-C7 |
| A4-B2-C7 | A71-B2-C7 | A61-B3-C7 | A51-B4-C7 |
| A5-B2-C7 | A72-B2-C7 | A62-B3-C7 | A52-B4-C7 |
| A6-B2-C7 | A73-B2-C7 | A63-B3-C7 | A53-B4-C7 |
| A7-B2-C7 | A74-B2-C7 | A64-B3-C7 | A54-B4-C7 |
| A8-B2-C7 | A75-B2-C7 | A65-B3-C7 | A55-B4-C7 |
| A9-B2-C7 | A76-B2-C7 | A66-B3-C7 | A56-B4-C7 |

TABLE 4-continued

| | | | |
|---|---|---|---|
| A10-B2-C7 | A77-B2-C7 | A67-B3-C7 | A57-B4-C7 |
| A11-B2-C7 | A1-B3-C7 | A68-B3-C7 | A58-B4-C7 |
| A12-B2-C7 | A2-B3-C7 | A69-B3-C7 | A59-B4-C7 |
| A13-B2-C7 | A3-B3-C7 | A70-B3-C7 | A60-B4-C7 |
| A14-B2-C7 | A4-B3-C7 | A71-B3-C7 | A61-B4-C7 |
| A15-B2-C7 | A5-B3-C7 | A72-B3-C7 | A62-B4-C7 |
| A16-B2-C7 | A6-B3-C7 | A73-B3-C7 | A63-B4-C7 |
| A17-B2-C7 | A7-B3-C7 | A74-B3-C7 | A64-B4-C7 |
| A18-B2-C7 | A8-B3-C7 | A75-B3-C7 | A65-B4-C7 |
| A19-B2-C7 | A9-B3-C7 | A76-B3-C7 | A66-B4-C7 |
| A20-B2-C7 | A10-B3-C7 | A77-B3-C7 | A67-B4-C7 |
| A21-B2-C7 | A11-B3-C7 | A1-B4-C7 | A68-B4-C7 |
| A22-B2-C7 | A12-B3-C7 | A2-B4-C7 | A69-B4-C7 |
| A23-B2-C7 | A13-B3-C7 | A3-B4-C7 | A70-B4-C7 |
| A24-B2-C7 | A14-B3-C7 | A4-B4-C7 | A71-B4-C7 |
| A25-B2-C7 | A15-B3-C7 | A5-B4-C7 | A72-B4-C7 |
| A26-B2-C7 | A16-B3-C7 | A6-B4-C7 | A73-B4-C7 |
| A27-B2-C7 | A17-B3-C7 | A7-B4-C7 | A74-B4-C7 |
| A28-B2-C7 | A18-B3-C7 | A8-B4-C7 | A75-B4-C7 |
| A29-B2-C7 | A19-B3-C7 | A9-B4-C7 | A76-B4-C7 |
| A30-B2-C7 | A20-B3-C7 | A10-B4-C7 | A77-B4-C7 |
| A31-B2-C7 | A21-B3-C7 | A11-B4-C7 | A1-B1-C8 |
| A32-B2-C7 | A22-B3-C7 | A12-B4-C7 | A2-B1-C8 |
| A33-B2-C7 | A23-B3-C7 | A13-B4-C7 | A3-B1-C8 |
| A34-B2-C7 | A24-B3-C7 | A14-B4-C7 | A4-B1-C8 |
| A35-B2-C7 | A25-B3-C7 | A15-B4-C7 | A5-B1-C8 |
| A36-B2-C7 | A26-B3-C7 | A16-B4-C7 | A6-B1-C8 |
| A37-B2-C7 | A27-B3-C7 | A17-B4-C7 | A7-B1-C8 |
| A38-B2-C7 | A28-B3-C7 | A18-B4-C7 | A8-B1-C8 |
| A39-B2-C7 | A29-B3-C7 | A19-B4-C7 | A9-B1-C8 |
| A40-B2-C7 | A30-B3-C7 | A20-B4-C7 | A10-B1-C8 |
| A41-B2-C7 | A31-B3-C7 | A21-B4-C7 | A11-B1-C8 |
| A42-B2-C7 | A32-B3-C7 | A22-B4-C7 | A12-B1-C8 |
| A43-B2-C7 | A33-B3-C7 | A23-B4-C7 | A13-B1-C8 |
| A44-B2-C7 | A34-B3-C7 | A24-B4-C7 | A14-B1-C8 |
| A45-B2-C7 | A35-B3-C7 | A25-B4-C7 | A15-B1-C8 |
| A46-B2-C7 | A36-B3-C7 | A26-B4-C7 | A16-B1-C8 |
| A47-B2-C7 | A37-B3-C7 | A27-B4-C7 | A17-B1-C8 |
| A48-B2-C7 | A38-B3-C7 | A28-B4-C7 | A18-B1-C8 |
| A49-B2-C7 | A39-B3-C7 | A29-B4-C7 | A19-B1-C8 |
| A50-B2-C7 | A40-B3-C7 | A30-B4-C7 | A20-B1-C8 |
| A51-B2-C7 | A41-B3-C7 | A31-B4-C7 | A21-B1-C8 |
| A52-B2-C7 | A42-B3-C7 | A32-B4-C7 | A22-B1-C8 |
| A53-B2-C7 | A43-B3-C7 | A33-B4-C7 | A23-B1-C8 |
| A54-B2-C7 | A44-B3-C7 | A34-B4-C7 | A24-B1-C8 |
| A55-B2-C7 | A45-B3-C7 | A35-B4-C7 | A25-B1-C8 |
| A56-B2-C7 | A46-B3-C7 | A36-B4-C7 | A26-B1-C8 |
| A57-B2-C7 | A47-B3-C7 | A37-B4-C7 | A27-B1-C8 |
| A58-B2-C7 | A48-B3-C7 | A38-B4-C7 | A28-B1-C8 |
| A59-B2-C7 | A49-B3-C7 | A39-B4-C7 | A29-B1-C8 |
| A60-B2-C7 | A50-B3-C7 | A40-B4-C7 | A30-B1-C8 |
| A61-B2-C7 | A51-B3-C7 | A41-B4-C7 | A31-B1-C8 |
| A62-B2-C7 | A52-B3-C7 | A42-B4-C7 | A32-B1-C8 |
| A33-B1-C8 | A23-B2-C8 | A13-B3-C8 | A3-B4-C8 |
| A34-B1-C8 | A24-B2-C8 | A14-B3-C8 | A4-B4-C8 |
| A35-B1-C8 | A25-B2-C8 | A15-B3-C8 | A5-B4-C8 |
| A36-B1-C8 | A26-B2-C8 | A16-B3-C8 | A6-B4-C8 |
| A37-B1-C8 | A27-B2-C8 | A17-B3-C8 | A7-B4-C8 |
| A38-B1-C8 | A28-B2-C8 | A18-B3-C8 | A8-B4-C8 |
| A39-B1-C8 | A29-B2-C8 | A19-B3-C8 | A9-B4-C8 |
| A40-B1-C8 | A30-B2-C8 | A20-B3-C8 | A10-B4-C8 |
| A41-B1-C8 | A31-B2-C8 | A21-B3-C8 | A11-B4-C8 |
| A42-B1-C8 | A32-B2-C8 | A22-B3-C8 | A12-B4-C8 |
| A43-B1-C8 | A33-B2-C8 | A23-B3-C8 | A13-B4-C8 |
| A44-B1-C8 | A34-B2-C8 | A24-B3-C8 | A14-B4-C8 |
| A45-B1-C8 | A35-B2-C8 | A25-B3-C8 | A15-B4-C8 |
| A46-B1-C8 | A36-B2-C8 | A26-B3-C8 | A16-B4-C8 |
| A47-B1-C8 | A37-B2-C8 | A27-B3-C8 | A17-B4-C8 |
| A48-B1-C8 | A38-B2-C8 | A28-B3-C8 | A18-B4-C8 |
| A49-B1-C8 | A39-B2-C8 | A29-B3-C8 | A19-B4-C8 |
| A50-B1-C8 | A40-B2-C8 | A30-B3-C8 | A20-B4-C8 |
| A51-B1-C8 | A41-B2-C8 | A31-B3-C8 | A21-B4-C8 |
| A52-B1-C8 | A42-B2-C8 | A32-B3-C8 | A22-B4-C8 |
| A53-B1-C8 | A43-B2-C8 | A33-B3-C8 | A23-B4-C8 |
| A54-B1-C8 | A44-B2-C8 | A34-B3-C8 | A24-B4-C8 |
| A55-B1-C8 | A45-B2-C8 | A35-B3-C8 | A25-B4-C8 |
| A56-B1-C8 | A46-B2-C8 | A36-B3-C8 | A26-B4-C8 |
| A57-B1-C8 | A47-B2-C8 | A37-B3-C8 | A27-B4-C8 |
| A58-B1-C8 | A48-B2-C8 | A38-B3-C8 | A28-B4-C8 |

TABLE 4-continued

| | | | |
|---|---|---|---|
| A59-B1-C8 | A49-B2-C8 | A39-B3-C8 | A29-B4-CB |
| A60-B1-C8 | A50-B2-C8 | A40-B3-C8 | A30-B4-C8 |
| A61-B1-C8 | A51-B2-C8 | A41-B3-C8 | A31-B4-C8 |
| A62-B1-C8 | A52-B2-C8 | A42-B3-C8 | A32-B4-C8 |
| A63-B1-C8 | A53-B2-C8 | A43-B3-C8 | A33-B4-C8 |
| A64-B1-C8 | A54-B2-C8 | A44-B3-C8 | A34-B4-C8 |
| A65-B1-C8 | A55-B2-C8 | A45-B3-C8 | A35-B4-C8 |
| A66-B1-C8 | A56-B2-C8 | A46-B3-C8 | A36-B4-C8 |
| A67-B1-C8 | A57-B2-C8 | A47-B3-C8 | A37-B4-C8 |
| A68-B1-C8 | A58-B2-C8 | A48-B3-C8 | A38-B4-C8 |
| A69-B1-C8 | A59-B2-C8 | A49-B3-C8 | A39-B4-C8 |
| A70-B1-C8 | A60-B2-C8 | A50-B3-C8 | A40-B4-C8 |
| A71-B1-C8 | A61-B2-C8 | A51-B3-C8 | A41-B4-C8 |
| A72-B1-C8 | A62-B2-C8 | A52-B3-C8 | A42-B4-C8 |
| A73-B1-C8 | A63-B2-C8 | A53-B3-C8 | A43-B4-C8 |
| A74-B1-C8 | A64-B2-C8 | A54-B3-C8 | A44-B4-C8 |
| A75-B1-C8 | A65-B2-C8 | A55-B3-C8 | A45-B4-C8 |
| A76-B1-C8 | A66-B2-C8 | A56-B3-C8 | A46-B4-C8 |
| A77-B1-C8 | A67-B2-C8 | A57-B3-C8 | A47-B4-C8 |
| A1-B2-C8 | A68-B2-C8 | A58-B3-C8 | A48-B4-C8 |
| A2-B2-C8 | A69-B2-C8 | A59-B3-C8 | A49-B4-C8 |
| A3-B2-C8 | A70-B2-C8 | A60-B3-C8 | A50-B4-C8 |
| A4-B2-C8 | A71-B2-C8 | A61-B3-C8 | A51-B4-C8 |
| A5-B2-C8 | A72-B2-C8 | A62-B3-C8 | A52-B4-C8 |
| A6-B2-C8 | A73-B2-C8 | A63-B3-C8 | A53-B4-C8 |
| A7-B2-C8 | A74-B2-C8 | A64-B3-C8 | A54-B4-C8 |
| A8-B2-C8 | A75-B2-C8 | A65-B3-C8 | A55-B4-C8 |
| A9-B2-C8 | A76-B2-C8 | A66-B3-C8 | A56-B4-C8 |
| A10-B2-C8 | A77-B2-C8 | A67-B3-C8 | A57-B4-C8 |
| A11-B2-C8 | A1-B3-C8 | A68-B3-C8 | A58-B4-C8 |
| A12-B2-C8 | A2-B3-C8 | A69-B3-C8 | A59-B4-C8 |
| A13-B2-C8 | A3-B3-C8 | A70-B3-C8 | A60-B4-C8 |
| A14-B2-C8 | A4-B3-C8 | A71-B3-C8 | A61-B4-C8 |
| A15-B2-C8 | A5-B3-C8 | A72-B3-C8 | A62-B4-C8 |
| A16-B2-C8 | A6-B3-C8 | A73-B3-C8 | A63-B4-C8 |
| A17-B2-C8 | A7-B3-C8 | A74-B3-C8 | A64-B4-C8 |
| A18-B2-C8 | A8-B3-C8 | A75-B3-C8 | A65-B4-C8 |
| A19-B2-C8 | A9-B3-C8 | A76-B3-C8 | A66-B4-C8 |
| A20-B2-C8 | A10-B3-C8 | A77-B3-C8 | A67-B4-C8 |
| A21-B2-C8 | A11-B3-C8 | A1-B4-C8 | A68-B4-C8 |
| A22-B2-C8 | A12-B3-C8 | A2-B4-C8 | A69-B4-C8 |
| A70-B4-C8 | A60-B1-C9 | A50-B2-C9 | A40-B3-C9 |
| A71-B4-C8 | A61-B1-C9 | A51-B2-C9 | A41-B3-C9 |
| A72-B4-C8 | A62-B1-C9 | A52-B2-C9 | A42-B3-C9 |
| A73-B4-C8 | A63-B1-C9 | A53-B2-C9 | A43-B3-C9 |
| A74-B4-C8 | A64-B1-C9 | A54-B2-C9 | A44-B3-C9 |
| A75-B4-C8 | A65-B1-C9 | A55-B2-C9 | A45-B3-C9 |
| A76-B4-C8 | A66-B1-C9 | A56-B2-C9 | A46-B3-C9 |
| A77-B4-C8 | A67-B1-C9 | A57-B2-C9 | A47-B3-C9 |
| A1-B1-C9 | A68-B1-C9 | A58-B2-C9 | A48-B3-C9 |
| A2-B1-C9 | A69-B1-C9 | A59-B2-C9 | A49-B3-C9 |
| A3-B1-C9 | A70-B1-C9 | A60-B2-C9 | A50-B3-C9 |
| A4-B1-C9 | A71-B1-C9 | A61-B2-C9 | A51-B3-C9 |
| A5-B1-C9 | A72-B1-C9 | A62-B2-C9 | A52-B3-C9 |
| A6-B1-C9 | A73-B1-C9 | A63-B2-C9 | A53-B3-C9 |
| A7-B1-C9 | A74-B1-C9 | A64-B2-C9 | A54-B3-C9 |
| A8-B1-C9 | A75-B1-C9 | A65-B2-C9 | A55-B3-C9 |
| A9-B1-C9 | A76-B1-C9 | A66-B2-C9 | A56-B3-C9 |
| A10-B1-C9 | A77-B1-C9 | A67-B2-C9 | A57-B3-C9 |
| A11-B1-C9 | A1-B2-C9 | A68-B2-C9 | A58-B3-C9 |
| A12-B1-C9 | A2-B2-C9 | A69-B2-C9 | A59-B3-C9 |
| A13-B1-C9 | A3-B2-C9 | A70-B2-C9 | A60-B3-C9 |
| A14-B1-C9 | A4-B2-C9 | A71-B2-C9 | A61-B3-C9 |
| A15-B1-C9 | A5-B2-C9 | A72-B2-C9 | A62-B3-C9 |
| A16-B1-C9 | A6-B2-C9 | A73-B2-C9 | A63-B3-C9 |
| A17-B1-C9 | A7-B2-C9 | A74-B2-C9 | A64-B3-C9 |
| A18-B1-C9 | A8-B2-C9 | A75-B2-C9 | A65-B3-C9 |
| A19-B1-C9 | A9-B2-C9 | A76-B2-C9 | A66-B3-C9 |
| A20-B1-C9 | A10-B2-C9 | A77-B2-C9 | A67-B3-C9 |
| A21-B1-C9 | A11-B2-C9 | A1-B3-C9 | A68-B3-C9 |
| A22-B1-C9 | A12-B2-C9 | A2-B3-C9 | A69-B3-C9 |
| A23-B1-C9 | A13-B2-C9 | A3-B3-C9 | A70-B3-C9 |
| A24-B1-C9 | A14-B2-C9 | A4-B3-C9 | A71-B3-C9 |
| A25-B1-C9 | A15-B2-C9 | A5-B3-C9 | A72-B3-C9 |
| A26-B1-C9 | A16-B2-C9 | A6-B3-C9 | A73-B3-C9 |
| A27-B1-C9 | A17-B2-C9 | A7-B3-C9 | A74-B3-C9 |
| A28-B1-C9 | A18-B2-C9 | A8-B3-C9 | A75-B3-C9 |
| A29-B1-C9 | A19-B2-C9 | A9-B3-C9 | A76-B3-C9 |
| A30-B1-C9 | A20-B2-C9 | A10-B3-C9 | A77-B3-C9 |
| A31-B1-C9 | A21-B2-C9 | A11-B3-C9 | A1-B4-C9 |
| A32-B1-C9 | A22-B2-C9 | A12-B3-C9 | A2-B4-C9 |
| A33-B1-C9 | A23-B2-C9 | A13-B3-C9 | A3-B4-C9 |
| A34-B1-C9 | A24-B2-C9 | A14-B3-C9 | A4-B4-C9 |
| A35-B1-C9 | A25-B2-C9 | A15-B3-C9 | A5-B4-C9 |
| A36-B1-C9 | A26-B2-C9 | A16-B3-C9 | A6-B4-C9 |
| A37-B1-C9 | A27-B2-C9 | A17-B3-C9 | A7-B4-C9 |
| A38-B1-C9 | A28-B2-C9 | A18-B3-C9 | A8-B4-C9 |
| A39-B1-C9 | A29-B2-C9 | A19-B3-C9 | A9-B4-C9 |
| A40-B1-C9 | A30-B2-C9 | A20-B3-C9 | A10-B4-C9 |
| A41-B1-C9 | A31-B2-C9 | A21-B3-C9 | A11-B4-C9 |
| A42-B1-C9 | A32-B2-C9 | A22-B3-C9 | A12-B4-C9 |
| A43-B1-C9 | A33-B2-C9 | A23-B3-C9 | A13-B4-C9 |
| A44-B1-C9 | A34-B2-C9 | A24-B3-C9 | A14-B4-C9 |
| A45-B1-C9 | A35-B2-C9 | A25-B3-C9 | A15-B4-C9 |
| A46-B1-C9 | A36-B2-C9 | A26-B3-C9 | A16-B4-C9 |
| A47-B1-C9 | A37-B2-C9 | A27-B3-C9 | A17-B4-C9 |
| A48-B1-C9 | A38-B2-C9 | A28-B3-C9 | A18-B4-C9 |
| A49-B1-C9 | A39-B2-C9 | A29-B3-C9 | A19-B4-C9 |
| A50-B1-C9 | A40-B2-C9 | A30-B3-C9 | A20-B4-C9 |
| A51-B1-C9 | A41-B2-C9 | A31-B3-C9 | A21-B4-C9 |
| A52-B1-C9 | A42-B2-C9 | A32-B3-C9 | A22-B4-C9 |
| A53-B1-C9 | A43-B2-C9 | A33-B3-C9 | A23-B4-C9 |
| A54-B1-C9 | A44-B2-C9 | A34-B3-C9 | A24-B4-C9 |
| A55-B1-C9 | A45-B2-C9 | A35-B3-C9 | A25-B4-C9 |
| A56-B1-C9 | A46-B2-C9 | A36-B3-C9 | A26-B4-C9 |
| A57-B1-C9 | A47-B2-C9 | A37-B3-C9 | A27-B4-C9 |
| A58-B1-C9 | A48-B2-C9 | A38-B3-C9 | A28-B4-C9 |
| A59-B1-C9 | A49-B2-C9 | A39-B3-C9 | A29-B4-C9 |
| A30-B4-C9 | A20-B1-C10 | A10-B2-C10 | A77-B2-C10 |
| A31-B4-C9 | A21-B1-C10 | A11-B2-C10 | A1-B3-C10 |
| A32-B4-C9 | A22-B1-C10 | A12-B2-C10 | A2-B3-C10 |
| A33-B4-C9 | A23-B1-C10 | A13-B2-C10 | A3-B3-C10 |
| A34-B4-C9 | A24-B1-C10 | A14-B2-C10 | A4-B3-C10 |
| A35-B4-C9 | A25-B1-C10 | A15-B2-C10 | A5-B3-C10 |
| A36-B4-C9 | A26-B1-C10 | A16-B2-C10 | A6-B3-C10 |
| A37-B4-C9 | A27-B1-C10 | A17-B2-C10 | A7-B3-C10 |
| A38-B4-C9 | A28-B1-C10 | A18-B2-C10 | A8-B3-C10 |
| A39-B4-C9 | A29-B1-C10 | A19-B2-C10 | A9-B3-C10 |
| A40-B4-C9 | A30-B1-C10 | A20-B2-C10 | A10-B3-C10 |
| A41-B4-C9 | A31-B1-C10 | A21-B2-C10 | A11-B3-C10 |
| A42-B4-C9 | A32-B1-C10 | A22-B2-C10 | A12-B3-C10 |
| A43-B4-C9 | A33-B1-C10 | A23-B2-C10 | A13-B3-C10 |
| A44-B4-C9 | A34-B1-C10 | A24-B2-C10 | A14-B3-C10 |
| A45-B4-C9 | A35-B1-C10 | A25-B2-C10 | A15-B3-C10 |
| A46-B4-C9 | A36-B1-C10 | A26-B2-C10 | A16-B3-C10 |
| A47-B4-C9 | A37-B1-C10 | A27-B2-C10 | A17-B3-C10 |
| A48-B4-C9 | A38-B1-C10 | A28-B2-C10 | A18-B3-C10 |
| A49-B4-C9 | A39-B1-C10 | A29-B2-C10 | A19-B3-C10 |
| A50-B4-C9 | A40-B1-C10 | A30-B2-C10 | A20-B3-C10 |
| A51-B4-C9 | A41-B1-C10 | A31-B2-C10 | A21-B3-C10 |
| A52-B4-C9 | A42-B1-C10 | A32-B2-C10 | A22-B3-C10 |
| A53-B4-C9 | A43-B1-C10 | A33-B2-C10 | A23-B3-C10 |
| A54-B4-C9 | A44-B1-C10 | A34-B2-C10 | A24-B3-C10 |
| A55-B4-C9 | A45-B1-C10 | A35-B2-C10 | A25-B3-C10 |
| A56-B4-C9 | A46-B1-C10 | A36-B2-C10 | A26-B3-C10 |
| A57-B4-C9 | A47-B1-C10 | A37-B2-C10 | A27-B3-C10 |
| A58-B4-C9 | A48-B1-C10 | A38-B2-C10 | A28-B3-C10 |
| A59-B4-C9 | A49-B1-C10 | A39-B2-C10 | A29-B3-C10 |
| A60-B4-C9 | A50-B1-C10 | A40-B2-C10 | A30-B3-C10 |
| A61-B4-C9 | A51-B1-C10 | A41-B2-C10 | A31-B3-C10 |
| A62-B4-C9 | A52-B1-C10 | A42-B2-C10 | A32-B3-C10 |
| A63-B4-C9 | A53-B1-C10 | A43-B2-C10 | A33-B3-C10 |
| A64-B4-C9 | A54-B1-C10 | A44-B2-C10 | A34-B3-C10 |
| A65-B4-C9 | A55-B1-C10 | A45-B2-C10 | A35-B3-C10 |
| A66-B4-C9 | A56-B1-C10 | A46-B2-C10 | A36-B3-C10 |
| A67-B4-C9 | A57-B1-C10 | A47-B2-C10 | A37-B3-C10 |
| A68-B4-C9 | A58-B1-C10 | A48-B2-C10 | A38-B3-C10 |
| A69-B4-C9 | A59-B1-C10 | A49-B2-C10 | A39-B3-C10 |
| A70-B4-C9 | A60-B1-C10 | A50-B2-C10 | A40-B3-C10 |
| A71-B4-C9 | A61-B1-C10 | A51-B2-C10 | A41-B3-C10 |
| A72-B4-C9 | A62-B1-C10 | A52-B2-C10 | A42-B3-C10 |
| A73-B4-C9 | A63-B1-C10 | A53-B2-C10 | A43-B3-C10 |
| A74-B4-C9 | A64-B1-C10 | A54-B2-C10 | A44-B3-C10 |
| A75-B4-C9 | A65-B1-C10 | A55-B2-C10 | A45-B3-C10 |
| A76-B4-C9 | A66-B1-C10 | A56-B2-C10 | A46-B3-C10 |
| A77-B4-C9 | A67-B1-C10 | A57-B2-C10 | A47-B3-C10 |
| A1-B1-C10 | A68-B1-C10 | A58-B2-C10 | A48-B3-C10 |
| A2-B1-C10 | A69-B1-C10 | A59-B2-C10 | A49-B3-C10 |

TABLE 4-continued

| | | | |
|---|---|---|---|
| A3-B1-C10 | A70-B1-C10 | A60-B2-C10 | A50-B3-C10 |
| A4-B1-C10 | A71-B1-C10 | A61-B2-C10 | A51-B3-C10 |
| A5-B1-C10 | A72-B1-C10 | A62-B2-C10 | A52-B3-C10 |
| A6-B1-C10 | A73-B1-C10 | A63-B2-C10 | A53-B3-C10 |
| A7-B1-C10 | A74-B1-C10 | A64-B2-C10 | A54-B3-C10 |
| A8-B1-C10 | A75-B1-C10 | A65-B2-C10 | A55-B3-C10 |
| A9-B1-C10 | A76-B1-C10 | A66-B2-C10 | A56-B3-C10 |
| A10-B1-C10 | A77-B1-C10 | A67-B2-C10 | A57-B3-C10 |
| A11-B1-C10 | A1-B2-C10 | A68-B2-C10 | A58-B3-C10 |
| A12-B1-C10 | A2-B2-C10 | A69-B2-C10 | A59-B3-C10 |
| A13-B1-C10 | A3-B2-C10 | A70-B2-C10 | A60-B3-C10 |
| A14-B1-C10 | A4-B2-C10 | A71-B2-C10 | A61-B3-C10 |
| A15-B1-C10 | A5-B2-C10 | A72-B2-C10 | A62-B3-C10 |
| A16-B1-C10 | A6-B2-C10 | A73-B2-C10 | A63-B3-C10 |
| A17-B1-C10 | A7-B2-C10 | A74-B2-C10 | A64-B3-C10 |
| A18-B1-C10 | A8-B2-C10 | A75-B2-C10 | A65-B3-C10 |
| A19-B1-C10 | A9-B2-C10 | A76-B2-C10 | A66-B3-C10 |
| A67-B3-C10 | A57-B4-C10 | A47-B1-C11 | A37-B2-C11 |
| A68-B3-C10 | A58-B4-C10 | A48-B1-C11 | A38-B2-C11 |
| A69-B3-C10 | A59-B4-C10 | A49-B1-C11 | A39-B2-C11 |
| A70-B3-C10 | A60-B4-C10 | A50-B1-C11 | A40-B2-C11 |
| A71-B3-C10 | A61-B4-C10 | A51-B1-C11 | A41-B2-C11 |
| A72-B3-C10 | A62-B4-C10 | A52-B1-C11 | A42-B2-C11 |
| A73-B3-C10 | A63-B4-C10 | A53-B1-C11 | A43-B2-C11 |
| A74-B3-C10 | A64-B4-C10 | A54-B1-C11 | A44-B2-C11 |
| A75-B3-C10 | A65-B4-C10 | A55-B1-C11 | A45-B2-C11 |
| A76-B3-C10 | A66-B4-C10 | A56-B1-C11 | A46-B2-C11 |
| A77-B3-C10 | A67-B4-C10 | A57-B1-C11 | A47-B2-C11 |
| A1-B4-C10 | A68-B4-C10 | A58-B1-C11 | A48-B2-C11 |
| A2-B4-C10 | A69-B4-C10 | A59-B1-C11 | A49-B2-C11 |
| A3-B4-C10 | A70-B4-C10 | A60-B1-C11 | A50-B2-C11 |
| A4-B4-C10 | A71-B4-C10 | A61-B1-C11 | A51-B2-C11 |
| A5-B4-C10 | A72-B4-C10 | A62-B1-C11 | A52-B2-C11 |
| A6-B4-C10 | A73-B4-C10 | A63-B1-C11 | A53-B2-C11 |
| A7-B4-C10 | A74-B4-C10 | A64-B1-C11 | A54-B2-C11 |
| A8-B4-C10 | A75-B4-C10 | A65-B1-C11 | A55-B2-C11 |
| A9-B4-C10 | A76-B4-C10 | A66-B1-C11 | A56-B2-C11 |
| A10-B4-C10 | A77-B4-C10 | A67-B1-C11 | A57-B2-C11 |
| A11-B4-C10 | A1-B1-C11 | A68-B1-C11 | A58-B2-C11 |
| A12-B4-C10 | A2-B1-C11 | A69-B1-C11 | A59-B2-C11 |
| A13-B4-C10 | A3-B1-C11 | A70-B1-C11 | A60-B2-C11 |
| A14-B4-C10 | A4-B1-C11 | A71-B1-C11 | A61-B2-C11 |
| A15-B4-C10 | A5-B1-C11 | A72-B1-C11 | A62-B2-C11 |
| A16-B4-C10 | A6-B1-C11 | A73-B1-C11 | A63-B2-C11 |
| A17-B4-C10 | A7-B1-C11 | A74-B1-C11 | A64-B2-C11 |
| A18-B4-C10 | A8-B1-C11 | A75-B1-C11 | A65-B2-C11 |
| A19-B4-C10 | A9-B1-C11 | A76-B1-C11 | A66-B2-C11 |
| A20-B4-C10 | A10-B1-C11 | A77-B1-C11 | A67-B2-C11 |
| A21-B4-C10 | A11-B1-C11 | A1-B2-C11 | A68-B2-C11 |
| A22-B4-C10 | A12-B1-C11 | A2-B2-C11 | A69-B2-C11 |
| A23-B4-C10 | A13-B1-C11 | A3-B2-C11 | A70-B2-C11 |
| A24-B4-C10 | A14-B1-C11 | A4-B2-C11 | A71-B2-C11 |
| A25-B4-C10 | A15-B1-C11 | A5-B2-C11 | A72-B2-C11 |
| A26-B4-C10 | A16-B1-C11 | A6-B2-C11 | A73-B2-C11 |
| A27-B4-C10 | A17-B1-C11 | A7-B2-C11 | A74-B2-C11 |
| A28-B4-C10 | A18-B1-C11 | A8-B2-C11 | A75-B2-C11 |
| A29-B4-C10 | A19-B1-C11 | A9-B2-C11 | A76-B2-C11 |
| A30-B4-C10 | A20-B1-C11 | A10-B2-C11 | A77-B2-C11 |
| A31-B4-C10 | A21-B1-C11 | A11-B2-C11 | A1-B3-C11 |
| A32-B4-C10 | A22-B1-C11 | A12-B2-C11 | A2-B3-C11 |
| A33-B4-C10 | A23-B1-C11 | A13-B2-C11 | A3-B3-C11 |
| A34-B4-C10 | A24-B1-C11 | A14-B2-C11 | A4-B3-C11 |
| A35-B4-C10 | A25-B1-C11 | A15-B2-C11 | A5-B3-C11 |
| A36-B4-C10 | A26-B1-C11 | A16-B2-C11 | A6-B3-C11 |
| A37-B4-C10 | A27-B1-C11 | A17-B2-C11 | A7-B3-C11 |
| A38-B4-C10 | A28-B1-C11 | A18-B2-C11 | A8-B3-C11 |
| A39-B4-C10 | A29-B1-C11 | A19-B2-C11 | A9-B3-C11 |
| A40-B4-C10 | A30-B1-C11 | A20-B2-C11 | A10-B3-C11 |
| A41-B4-C10 | A31-B1-C11 | A21-B2-C11 | A11-B3-C11 |
| A42-B4-C10 | A32-B1-C11 | A22-B2-C11 | A12-B3-C11 |
| A43-B4-C10 | A33-B1-C11 | A23-B2-C11 | A13-B3-C11 |
| A44-B4-C10 | A34-B1-C11 | A24-B2-C11 | A14-B3-C11 |
| A45-B4-C10 | A35-B1-C11 | A25-B2-C11 | A15-B3-C11 |
| A46-B4-C10 | A36-B1-C11 | A26-B2-C11 | A16-B3-C11 |
| A47-B4-C10 | A37-B1-C11 | A27-B2-C11 | A17-B3-C11 |
| A48-B4-C10 | A38-B1-C11 | A28-B2-C11 | A18-B3-C11 |
| A49-B4-C10 | A39-B1-C11 | A29-B2-C11 | A19-B3-C11 |
| A50-B4-C10 | A40-B1-C11 | A30-B2-C11 | A20-B3-C11 |
| A51-B4-C10 | A41-B1-C11 | A31-B2-C11 | A21-B3-C11 |
| A52-B4-C10 | A42-B1-C11 | A32-B2-C11 | A22-B3-C11 |
| A53-B4-C10 | A43-B1-C11 | A33-B2-C11 | A23-B3-C11 |
| A54-B4-C10 | A44-B1-C11 | A34-B2-C11 | A24-B3-C11 |
| A55-B4-C10 | A45-B1-C11 | A35-B2-C11 | A25-B3-C11 |
| A56-B4-C10 | A46-B1-C11 | A36-B2-C11 | A26-B3-C11 |
| A27-B3-C11 | A17-B4-C11 | A7-B1-C12 | A74-B1-C12 |
| A28-B3-C11 | A18-B4-C11 | A8-B1-C12 | A75-B1-C12 |
| A29-B3-C11 | A19-B4-C11 | A9-B1-C12 | A76-B1-C12 |
| A30-B3-C11 | A20-B4-C11 | A10-B1-C12 | A77-B1-C12 |
| A31-B3-C11 | A21-B4-C11 | A11-B1-C12 | A1-B2-C12 |
| A32-B3-C11 | A22-B4-C11 | A12-B1-C12 | A2-B2-C12 |
| A33-B3-C11 | A23-B4-C11 | A13-B1-C12 | A3-B2-C12 |
| A34-B3-C11 | A24-B4-C11 | A14-B1-C12 | A4-B2-C12 |
| A35-B3-C11 | A25-B4-C11 | A15-B1-C12 | A5-B2-C12 |
| A36-B3-C11 | A26-B4-C11 | A16-B1-C12 | A6-B2-C12 |
| A37-B3-C11 | A27-B4-C11 | A17-B1-C12 | A7-B2-C12 |
| A38-B3-C11 | A28-B4-C11 | A18-B1-C12 | A8-B2-C12 |
| A39-B3-C11 | A29-B4-C11 | A19-B1-C12 | A9-B2-C12 |
| A40-B3-C11 | A30-B4-C11 | A20-B1-C12 | A10-B2-C12 |
| A41-B3-C11 | A31-B4-C11 | A21-B1-C12 | A11-B2-C12 |
| A42-B3-C11 | A32-B4-C11 | A22-B1-C12 | A12-B2-C12 |
| A43-B3-C11 | A33-B4-C11 | A23-B1-C12 | A13-B2-C12 |
| A44-B3-C11 | A34-B4-C11 | A24-B1-C12 | A14-B2-C12 |
| A45-B3-C11 | A35-B4-C11 | A25-B1-C12 | A15-B2-C12 |
| A46-B3-C11 | A36-B4-C11 | A26-B1-C12 | A16-B2-C12 |
| A47-B3-C11 | A37-B4-C11 | A27-B1-C12 | A17-B2-C12 |
| A48-B3-C11 | A38-B4-C11 | A28-B1-C12 | A18-B2-C12 |
| A49-B3-C11 | A39-B4-C11 | A29-B1-C12 | A19-B2-C12 |
| A50-B3-C11 | A40-B4-C11 | A30-B1-C12 | A20-B2-C12 |
| A51-B3-C11 | A41-B4-C11 | A31-B1-C12 | A21-B2-C12 |
| A52-B3-C11 | A42-B4-C11 | A32-B1-C12 | A22-B2-C12 |
| A53-B3-C11 | A43-B4-C11 | A33-B1-C12 | A23-B2-C12 |
| A54-B3-C11 | A44-B4-C11 | A34-B1-C12 | A24-B2-C12 |
| A55-B3-C11 | A45-B4-C11 | A35-B1-C12 | A25-B2-C12 |
| A56-B3-C11 | A46-B4-C11 | A36-B1-C12 | A26-B2-C12 |
| A57-B3-C11 | A47-B4-C11 | A37-B1-C12 | A27-B2-C12 |
| A58-B3-C11 | A48-B4-C11 | A38-B1-C12 | A28-B2-C12 |
| A59-B3-C11 | A49-B4-C11 | A39-B1-C12 | A29-B2-C12 |
| A60-B3-C11 | A50-B4-C11 | A40-B1-C12 | A30-B2-C12 |
| A61-B3-C11 | A51-B4-C11 | A41-B1-C12 | A31-B2-C12 |
| A62-B3-C11 | A52-B4-C11 | A42-B1-C12 | A32-B2-C12 |
| A63-B3-C11 | A53-B4-C11 | A43-B1-C12 | A33-B2-C12 |
| A64-B3-C11 | A54-B4-C11 | A44-B1-C12 | A34-B2-C12 |
| A65-B3-C11 | A55-B4-C11 | A45-B1-C12 | A35-B2-C12 |
| A66-B3-C11 | A56-B4-C11 | A46-B1-C12 | A36-B2-C12 |
| A67-B3-C11 | A57-B4-C11 | A47-B1-C12 | A37-B2-C12 |
| A68-B3-C11 | A58-B4-C11 | A48-B1-C12 | A38-B2-C12 |
| A69-B3-C11 | A59-B4-C11 | A49-B1-C12 | A39-B2-C12 |
| A70-B3-C11 | A60-B4-C11 | A50-B1-C12 | A40-B2-C12 |
| A71-B3-C11 | A61-B4-C11 | A51-B1-C12 | A41-B2-C12 |
| A72-B3-C11 | A62-B4-C11 | A52-B1-C12 | A42-B2-C12 |
| A73-B3-C11 | A63-B4-C11 | A53-B1-C12 | A43-B2-C12 |
| A74-B3-C11 | A64-B4-C11 | A54-B1-C12 | A44-B2-C12 |
| A75-B3-C11 | A65-B4-C11 | A55-B1-C12 | A45-B2-C12 |
| A76-B3-C11 | A66-B4-C11 | A56-B1-C12 | A46-B2-C12 |
| A77-B3-C11 | A67-B4-C11 | A57-B1-C12 | A47-B2-C12 |
| A1-B4-C11 | A68-B4-C11 | A58-B1-C12 | A48-B2-C12 |
| A2-B4-C11 | A69-B4-C11 | A59-B1-C12 | A49-B2-C12 |
| A3-B4-C11 | A70-B4-C11 | A60-B1-C12 | A50-B2-C12 |
| A4-B4-C11 | A71-B4-C11 | A61-B1-C12 | A51-B2-C12 |
| A5-B4-C11 | A72-B4-C11 | A62-B1-C12 | A52-B2-C12 |
| A6-B4-C11 | A73-B4-C11 | A63-B1-C12 | A53-B2-C12 |
| A7-B4-C11 | A74-B4-C11 | A64-B1-C12 | A54-B2-C12 |
| A8-B4-C11 | A75-B4-C11 | A65-B1-C12 | A55-B2-C12 |
| A9-B4-C11 | A76-B4-C11 | A66-B1-C12 | A56-B2-C12 |
| A10-B4-C11 | A77-B4-C11 | A67-B1-C12 | A57-B2-C12 |
| A11-B4-C11 | A1-B1-C12 | A68-B1-C12 | A58-B2-C12 |
| A12-B4-C11 | A2-B1-C12 | A69-B1-C12 | A59-B2-C12 |
| A13-B4-C11 | A3-B1-C12 | A70-B1-C12 | A60-B2-C12 |
| A14-B4-C11 | A4-B1-C12 | A71-B1-C12 | A61-B2-C12 |
| A15-B4-C11 | A5-B1-C12 | A72-B1-C12 | A62-B2-C12 |
| A16-B4-C11 | A6-B1-C12 | A73-B1-C12 | A63-B2-C12 |
| A64-B2-C12 | A54-B3-C12 | A44-B4-C12 | A34-B1-C13 |
| A65-B2-C12 | A55-B3-C12 | A45-B4-C12 | A35-B1-C13 |
| A66-B2-C12 | A56-B3-C12 | A46-B4-C12 | A36-B1-C13 |
| A67-B2-C12 | A57-B3-C12 | A47-B4-C12 | A37-B1-C13 |
| A68-B2-C12 | A58-B3-C12 | A48-B4-C12 | A38-B1-C13 |
| A69-B2-C12 | A59-B3-C12 | A49-B4-C12 | A39-B1-C13 |
| A70-B2-C12 | A60-B3-C12 | A50-B4-C12 | A40-B1-C13 |

TABLE 4-continued

| | | | |
|---|---|---|---|
| A71-B2-C12 | A61-B3-C12 | A51-B4-C12 | A41-B1-C13 |
| A72-B2-C12 | A62-B3-C12 | A52-B4-C12 | A42-B1-C13 |
| A73-B2-C12 | A63-B3-C12 | A53-B4-C12 | A43-B1-C13 |
| A74-B2-C12 | A64-B3-C12 | A54-B4-C12 | A44-B1-C13 |
| A75-B2-C12 | A65-B3-C12 | A55-B4-C12 | A45-B1-C13 |
| A76-B2-C12 | A66-B3-C12 | A56-B4-C12 | A46-B1-C13 |
| A77-B2-C12 | A67-B3-C12 | A57-B4-C12 | A47-B1-C13 |
| A1-B3-C12 | A68-B3-C12 | A58-B4-C12 | A48-B1-C13 |
| A2-B3-C12 | A69-B3-C12 | A59-B4-C12 | A49-B1-C13 |
| A3-B3-C12 | A70-B3-C12 | A60-B4-C12 | A50-B1-C13 |
| A4-B3-C12 | A71-B3-C12 | A61-B4-C12 | A51-B1-C13 |
| A5-B3-C12 | A72-B3-C12 | A62-B4-C12 | A52-B1-C13 |
| A6-B3-C12 | A73-B3-C12 | A63-B4-C12 | A53-B1-C13 |
| A7-B3-C12 | A74-B3-C12 | A64-B4-C12 | A54-B1-C13 |
| A8-B3-C12 | A75-B3-C12 | A65-B4-C12 | A55-B1-C13 |
| A9-B3-C12 | A76-B3-C12 | A66-B4-C12 | A56-B1-C13 |
| A10-B3-C12 | A77-B3-C12 | A67-B4-C12 | A57-B1-C13 |
| A11-B3-C12 | A1-B4-C12 | A68-B4-C12 | A58-B1-C13 |
| A12-B3-C12 | A2-B4-C12 | A69-B4-C12 | A59-B1-C13 |
| A13-B3-C12 | A3-B4-C12 | A70-B4-C12 | A60-B1-C13 |
| A14-B3-C12 | A4-B4-C12 | A71-B4-C12 | A61-B1-C13 |
| A15-B3-C12 | A5-B4-C12 | A72-B4-C12 | A62-B1-C13 |
| A16-B3-C12 | A6-B4-C12 | A73-B4-C12 | A63-B1-C13 |
| A17-B3-C12 | A7-B4-C12 | A74-B4-C12 | A64-B1-C13 |
| A18-B3-C12 | A8-B4-C12 | A75-B4-C12 | A65-B1-C13 |
| A19-B3-C12 | A9-B4-C12 | A76-B4-C12 | A66-B1-C13 |
| A20-B3-C12 | A10-B4-C12 | A77-B4-C12 | A67-B1-C13 |
| A21-B3-C12 | A11-B4-C12 | A1-B1-C13 | A68-B1-C13 |
| A22-B3-C12 | A12-B4-C12 | A2-B1-C13 | A69-B1-C13 |
| A23-B3-C12 | A13-B4-C12 | A3-B1-C13 | A70-B1-C13 |
| A24-B3-C12 | A14-B4-C12 | A4-B1-C13 | A71-B1-C13 |
| A25-B3-C12 | A15-B4-C12 | A5-B1-C13 | A72-B1-C13 |
| A26-B3-C12 | A16-B4-C12 | A6-B1-C13 | A73-B1-C13 |
| A27-B3-C12 | A17-B4-C12 | A7-B1-C13 | A74-B1-C13 |
| A28-B3-C12 | A18-B4-C12 | A8-B1-C13 | A75-B1-C13 |
| A29-B3-C12 | A19-B4-C12 | A9-B1-C13 | A76-B1-C13 |
| A30-B3-C12 | A20-B4-C12 | A10-B1-C13 | A77-B1-C13 |
| A31-B3-C12 | A21-B4-C12 | A11-B1-C13 | A1-B2-C13 |
| A32-B3-C12 | A22-B4-C12 | A12-B1-C13 | A2-B2-C13 |
| A33-B3-C12 | A23-B4-C12 | A13-B1-C13 | A3-B2-C13 |
| A34-B3-C12 | A24-B4-C12 | A14-B1-C13 | A4-B2-C13 |
| A35-B3-C12 | A25-B4-C12 | A15-B1-C13 | A5-B2-C13 |
| A36-B3-C12 | A26-B4-C12 | A16-B1-C13 | A6-B2-C13 |
| A37-B3-C12 | A27-B4-C12 | A17-B1-C13 | A7-B2-C13 |
| A38-B3-C12 | A28-B4-C12 | A18-B1-C13 | A8-B2-C13 |
| A39-B3-C12 | A29-B4-C12 | A19-B1-C13 | A9-B2-C13 |
| A40-B3-C12 | A30-B4-C12 | A20-B1-C13 | A10-B2-C13 |
| A41-B3-C12 | A31-B4-C12 | A21-B1-C13 | A11-B2-C13 |
| A42-B3-C12 | A32-B4-C12 | A22-B1-C13 | A12-B2-C13 |
| A43-B3-C12 | A33-B4-C12 | A23-B1-C13 | A13-B2-C13 |
| A44-B3-C12 | A34-B4-C12 | A24-B1-C13 | A14-B2-C13 |
| A45-B3-C12 | A35-B4-C12 | A25-B1-C13 | A15-B2-C13 |
| A46-B3-C12 | A36-B4-C12 | A26-B1-C13 | A16-B2-C13 |
| A47-B3-C12 | A37-B4-C12 | A27-B1-C13 | A17-B2-C13 |
| A48-B3-C12 | A38-B4-C12 | A28-B1-C13 | A18-B2-C13 |
| A49-B3-C12 | A39-B4-C12 | A29-B1-C13 | A19-B2-C13 |
| A50-B3-C12 | A40-B4-C12 | A30-B1-C13 | A20-B2-C13 |
| A51-B3-C12 | A41-B4-C12 | A31-B1-C13 | A21-B2-C13 |
| A52-B3-C12 | A42-B4-C12 | A32-B1-C13 | A22-B2-C13 |
| A53-B3-C12 | A43-B4-C12 | A33-B1-C13 | A23-B2-C13 |
| A24-B2-C13 | A14-B3-C13 | A4-B4-C13 | A71-B4-C13 |
| A25-B2-C13 | A15-B3-C13 | A5-B4-C13 | A72-B4-C13 |
| A26-B2-C13 | A16-B3-C13 | A6-B4-C13 | A73-B4-C13 |
| A27-B2-C13 | A17-B3-C13 | A7-B4-C13 | A74-B4-C13 |
| A28-B2-C13 | A18-B3-C13 | A8-B4-C13 | A75-B4-C13 |
| A29-B2-C13 | A19-B3-C13 | A9-B4-C13 | A76-B4-C13 |
| A30-B2-C13 | A20-B3-C13 | A10-B4-C13 | A77-B4-C13 |
| A31-B2-C13 | A21-B3-C13 | A11-B4-C13 | A1-B1-C14 |
| A32-B2-C13 | A22-B3-C13 | A12-B4-C13 | A2-B1-C14 |
| A33-B2-C13 | A23-B3-C13 | A13-B4-C13 | A3-B1-C14 |
| A34-B2-C13 | A24-B3-C13 | A14-B4-C13 | A4-B1-C14 |
| A35-B2-C13 | A25-B3-C13 | A15-B4-C13 | A5-B1-C14 |
| A36-B2-C13 | A26-B3-C13 | A16-B4-C13 | A6-B1-C14 |
| A37-B2-C13 | A27-B3-C13 | A17-B4-C13 | A7-B1-C14 |
| A38-B2-C13 | A28-B3-C13 | A18-B4-C13 | A8-B1-C14 |
| A39-B2-C13 | A29-B3-C13 | A19-B4-C13 | A9-B1-C14 |
| A40-B2-C13 | A30-B3-C13 | A20-B4-C13 | A10-B1-C14 |
| A41-B2-C13 | A31-B3-C13 | A21-B4-C13 | A11-B1-C14 |
| A42-B2-C13 | A32-B3-C13 | A22-B4-C13 | A12-B1-C14 |
| A43-B2-C13 | A33-B3-C13 | A23-B4-C13 | A13-B1-C14 |
| A44-B2-C13 | A34-B3-C13 | A24-B4-C13 | A14-B1-C14 |
| A45-B2-C13 | A35-B3-C13 | A25-B4-C13 | A15-B1-C14 |
| A46-B2-C13 | A36-B3-C13 | A26-B4-C13 | A16-B1-C14 |
| A47-B2-C13 | A37-B3-C13 | A27-B4-C13 | A17-B1-C14 |
| A48-B2-C13 | A38-B3-C13 | A28-B4-C13 | A18-B1-C14 |
| A49-B2-C13 | A39-B3-C13 | A29-B4-C13 | A19-B1-C14 |
| A50-B2-C13 | A40-B3-C13 | A30-B4-C13 | A20-B1-C14 |
| A51-B2-C13 | A41-B3-C13 | A31-B4-C13 | A21-B1-C14 |
| A52-B2-C13 | A42-B3-C13 | A32-B4-C13 | A22-B1-C14 |
| A53-B2-C13 | A43-B3-C13 | A33-B4-C13 | A23-B1-C14 |
| A54-B2-C13 | A44-B3-C13 | A34-B4-C13 | A24-B1-C14 |
| A55-B2-C13 | A45-B3-C13 | A35-B4-C13 | A25-B1-C14 |
| A56-B2-C13 | A46-B3-C13 | A36-B4-C13 | A26-B1-C14 |
| A57-B2-C13 | A47-B3-C13 | A37-B4-C13 | A27-B1-C14 |
| A58-B2-C13 | A48-B3-C13 | A38-B4-C13 | A28-B1-C14 |
| A59-B2-C13 | A49-B3-C13 | A39-B4-C13 | A29-B1-C14 |
| A60-B2-C13 | A50-B3-C13 | A40-B4-C13 | A30-B1-C14 |
| A61-B2-C13 | A51-B3-C13 | A41-B4-C13 | A31-B1-C14 |
| A62-B2-C13 | A52-B3-C13 | A42-B4-C13 | A32-B1-C14 |
| A63-B2-C13 | A53-B3-C13 | A43-B4-C13 | A33-B1-C14 |
| A64-B2-C13 | A54-B3-C13 | A44-B4-C13 | A34-B1-C14 |
| A65-B2-C13 | A55-B3-C13 | A45-B4-C13 | A35-B1-C14 |
| A66-B2-C13 | A56-B3-C13 | A46-B4-C13 | A36-B1-C14 |
| A67-B2-C13 | A57-B3-C13 | A47-B4-C13 | A37-B1-C14 |
| A68-B2-C13 | A58-B3-C13 | A48-B4-C13 | A38-B1-C14 |
| A69-B2-C13 | A59-B3-C13 | A49-B4-C13 | A39-B1-C14 |
| A70-B2-C13 | A60-B3-C13 | A50-B4-C13 | A40-B1-C14 |
| A71-B2-613 | A61-B3-C13 | A51-B4-C13 | A41-B1-C14 |
| A72-B2-C13 | A62-B3-C13 | A52-B4-C13 | A42-B1-C14 |
| A73-B2-C13 | A63-B3-C13 | A53-B4-C13 | A43-B1-C14 |
| A74-B2-C13 | A64-B3-C13 | A54-B4-C13 | A44-B1-C14 |
| A75-B2-C13 | A65-B3-C13 | A55-B4-C13 | A45-B1-C14 |
| A76-B2-C13 | A66-B3-C13 | A56-B4-C13 | A46-B1-C14 |
| A77-B2-C13 | A67-B3-C13 | A57-B4-C13 | A47-B1-C14 |
| A1-B3-C13 | A68-B3-C13 | A58-B4-C13 | A48-B1-C14 |
| A2-B3-C13 | A69-B3-C13 | A59-B4-C13 | A49-B1-C14 |
| A3-B3-C13 | A70-B3-C13 | A60-B4-C13 | A50-B1-C14 |
| A4-B3-C13 | A71-B3-C13 | A61-B4-C13 | A51-B1-C14 |
| A5-B3-C13 | A72-B3-C13 | A62-B4-C13 | A52-B1-C14 |
| A6-B3-C13 | A73-B3-C13 | A63-B4-C13 | A53-B1-C14 |
| A7-B3-C13 | A74-B3-C13 | A64-B4-C13 | A54-B1-C14 |
| A8-B3-C13 | A75-B3-C13 | A65-B4-C13 | A55-B1-C14 |
| A9-B3-C13 | A76-B3-C13 | A66-B4-C13 | A56-B1-C14 |
| A10-B3-C13 | A77-B3-C13 | A67-B4-C13 | A57-B1-C14 |
| A11-B3-C13 | A1-B4-C13 | A68-B4-C13 | A58-B1-C14 |
| A12-B3-C13 | A2-B4-C13 | A69-B4-C13 | A59-B1-C14 |
| A13-B3-C13 | A3-B4-C13 | A70-B4-C13 | A60-B1-C14 |
| A61-B1-C14 | A51-B2-C14 | A41-B3-C14 | A31-B4-C14 |
| A62-B1-C14 | A52-B2-C14 | A42-B3-C14 | A32-B4-C14 |
| A63-B1-C14 | A53-B2-C14 | A43-B3-C14 | A33-B4-C14 |
| A64-B1-C14 | A54-B2-C14 | A44-B3-C14 | A34-B4-C14 |
| A65-B1-C14 | A55-B2-C14 | A45-B3-C14 | A35-B4-C14 |
| A66-B1-C14 | A56-B2-C14 | A46-B3-C14 | A36-B4-C14 |
| A67-B1-C14 | A57-B2-C14 | A47-B3-C14 | A37-B4-C14 |
| A68-B1-C14 | A58-B2-C14 | A48-B3-C14 | A38-B4-C14 |
| A69-B1-C14 | A59-B2-C14 | A49-B3-C14 | A39-B4-C14 |
| A70-B1-C14 | A60-B2-C14 | A50-B3-C14 | A40-B4-C14 |
| A71-B1-C14 | A61-B2-C14 | A51-B3-C14 | A41-B4-C14 |
| A72-B1-C14 | A62-B2-C14 | A52-B3-C14 | A42-B4-C14 |
| A73-B1-C14 | A63-B2-C14 | A53-B3-C14 | A43-B4-C14 |
| A74-B1-C14 | A64-B2-C14 | A54-B3-C14 | A44-B4-C14 |
| A75-B1-C14 | A65-B2-C14 | A55-B3-C14 | A45-B4-C14 |
| A76-B1-C14 | A66-B2-C14 | A56-B3-C14 | A46-B4-C14 |
| A77-B1-C14 | A67-B2-C14 | A57-B3-C14 | A47-B4-C14 |
| A1-B2-C14 | A68-B2-C14 | A58-B3-C14 | A48-B4-C14 |
| A2-B2-C14 | A69-B2-C14 | A59-B3-C14 | A49-B4-C14 |
| A3-B2-C14 | A70-B2-C14 | A60-B3-C14 | A50-B4-C14 |
| A4-B2-C14 | A71-B2-C14 | A61-B3-C14 | A51-B4-C14 |
| A5-B2-C14 | A72-B2-C14 | A62-B3-C14 | A52-B4-C14 |
| A6-B2-C14 | A73-B2-C14 | A63-B3-C14 | A53-B4-C14 |
| A7-B2-C14 | A74-B2-C14 | A64-B3-C14 | A54-B4-C14 |
| A8-B2-C14 | A75-B2-C14 | A65-B3-C14 | A55-B4-C14 |
| A9-B2-C14 | A76-B2-C14 | A66-B3-C14 | A56-B4-C14 |
| A10-B2-C14 | A77-B2-C14 | A67-B3-C14 | A57-B4-C14 |
| A11-B2-C14 | A1-B3-C14 | A68-B3-C14 | A58-B4-C14 |
| A12-B2-C14 | A2-B3-C14 | A69-B3-C14 | A59-B4-C14 |
| A13-B2-C14 | A3-B3-C14 | A70-B3-C14 | A60-B4-C14 |
| A14-B2-C14 | A4-B3-C14 | A71-B3-C14 | A61-B4-C14 |

TABLE 4-continued

| | | | |
|---|---|---|---|
| A15-B2-C14 | A5-B3-C14 | A72-B3-C14 | A62-B4-C14 |
| A16-B2-C14 | A6-B3-C14 | A73-B3-C14 | A63-B4-C14 |
| A17-B2-C14 | A7-B3-C14 | A74-B3-C14 | A64-B4-C14 |
| A18-B2-C14 | A8-B3-C14 | A75-B3-C14 | A65-B4-C14 |
| A19-B2-C14 | A9-B3-C14 | A76-B3-C14 | A66-B4-C14 |
| A20-B2-C14 | A10-B3-C14 | A77-B3-C14 | A67-B4-C14 |
| A21-B2-C14 | A11-B3-C14 | A1-B4-C14 | A68-B4-C14 |
| A22-B2-C14 | A12-B3-C14 | A2-B4-C14 | A69-B4-C14 |
| A23-B2-C14 | A13-B3-C14 | A3-B4-C14 | A70-B4-C14 |
| A24-B2-C14 | A14-B3-C14 | A4-B4-C14 | A71-B4-C14 |
| A25-B2-C14 | A15-B3-C14 | A5-B4-C14 | A72-B4-C14 |
| A26-B2-C14 | A16-B3-C14 | A6-B4-C14 | A73-B4-C14 |
| A27-B2-C14 | A17-B3-C14 | A7-B4-C14 | A74-B4-C14 |
| A28-B2-C14 | A18-B3-C14 | A8-B4-C14 | A75-B4-C14 |
| A29-B2-C14 | A19-B3-C14 | A9-B4-C14 | A76-B4-C14 |
| A30-B2-C14 | A20-B3-C14 | A10-B4-C14 | A77-B4-C14 |
| A31-B2-C14 | A21-B3-C14 | A11-B4-C14 | A1-B1-C15 |
| A32-B2-C14 | A22-B3-C14 | A12-B4-C14 | A2-B1-C15 |
| A33-B2-C14 | A23-B3-C14 | A13-B4-C14 | A3-B1-C15 |
| A34-B2-C14 | A24-B3-C14 | A14-B4-C14 | A4-B1-C15 |
| A35-B2-C14 | A25-B3-C14 | A15-B4-C14 | A5-B1-C15 |
| A36-B2-C14 | A26-B3-C14 | A16-B4-C14 | A6-B1-C15 |
| A37-B2-C14 | A27-B3-C14 | A17-B4-C14 | A7-B1-C15 |
| A38-B2-C14 | A28-B3-C14 | A18-B4-C14 | A8-B1-C15 |
| A39-B2-C14 | A29-B3-C14 | A19-B4-C14 | A9-B1-C15 |
| A40-B2-C14 | A30-B3-C14 | A20-B4-C14 | A10-B1-C15 |
| A41-B2-C14 | A31-B3-C14 | A21-B4-C14 | A11-B1-C15 |
| A42-B2-C14 | A32-B3-C14 | A22-B4-C14 | A12-B1-C15 |
| A43-B2-C14 | A33-B3-C14 | A23-B4-C14 | A13-B1-C15 |
| A44-B2-C14 | A34-B3-C14 | A24-B4-C14 | A14-B1-C15 |
| A45-B2-C14 | A35-B3-C14 | A25-B4-C14 | A15-B1-C15 |
| A46-B2-C14 | A36-B3-C14 | A26-B4-C14 | A16-B1-C15 |
| A47-B2-C14 | A37-B3-C14 | A27-B4-C14 | A17-B1-C15 |
| A48-B2-C14 | A38-B3-C14 | A28-B4-C14 | A18-B1-C15 |
| A49-B2-C14 | A39-B3-C14 | A29-B4-C14 | A19-B1-C15 |
| A50-B2-C14 | A40-B3-C14 | A30-B4-C14 | A20-B1-C15 |
| A21-B1-C15 | A11-B2-C15 | A1-B3-C15 | A68-B3-C15 |
| A22-B1-C15 | A12-B2-C15 | A2-B3-C15 | A69-B3-C15 |
| A23-B1-C15 | A13-B2-C15 | A3-B3-C15 | A70-B3-C15 |
| A24-B1-C15 | A14-B2-C15 | A4-B3-C15 | A71-B3-C15 |
| A25-B1-C15 | A15-B2-C15 | A5-B3-C15 | A72-B3-C15 |
| A26-B1-C15 | A16-B2-C15 | A6-B3-C15 | A73-B3-C15 |
| A27-B1-C15 | A17-B2-C15 | A7-B3-C15 | A74-B3-C15 |
| A28-B1-C15 | A18-B2-C15 | A8-B3-C15 | A75-B3-C15 |
| A29-B1-C15 | A19-B2-C15 | A9-B3-C15 | A76-B3-C15 |
| A30-B1-C15 | A20-B2-C15 | A10-B3-C15 | A77-B3-C15 |
| A31-B1-C15 | A21-B2-C15 | A11-B3-C15 | A1-B4-C15 |
| A32-B1-C15 | A22-B2-C15 | A12-B3-C15 | A2-B4-C15 |
| A33-B1-C15 | A23-B2-C15 | A13-B3-C15 | A3-B4-C15 |
| A34-B1-C15 | A24-B2-C15 | A14-B3-C15 | A4-B4-C15 |
| A35-B1-C15 | A25-B2-C15 | A15-B3-C15 | A5-B4-C15 |
| A36-B1-C15 | A26-B2-C15 | A16-B3-C15 | A6-B4-C15 |
| A37-B1-C15 | A27-B2-C15 | A17-B3-C15 | A7-B4-C15 |
| A38-B1-C15 | A28-B2-C15 | A18-B3-C15 | A8-B4-C15 |
| A39-B1-C15 | A29-B2-C15 | A19-B3-C15 | A9-B4-C15 |
| A40-B1-C15 | A30-B2-C15 | A20-B3-C15 | A10-B4-C15 |
| A41-B1-C15 | A31-B2-C15 | A21-B3-C15 | A11-B4-C15 |
| A42-B1-C15 | A32-B2-C15 | A22-B3-C15 | A12-B4-C15 |
| A43-B1-C15 | A33-B2-C15 | A23-B3-C15 | A13-B4-C15 |
| A44-B1-C15 | A34-B2-C15 | A24-B3-C15 | A14-B4-C15 |
| A45-B1-C15 | A35-B2-C15 | A25-B3-C15 | A15-B4-C15 |
| A46-B1-C15 | A36-B2-C15 | A26-B3-C15 | A16-B4-C15 |
| A47-B1-C15 | A37-B2-C15 | A27-B3-C15 | A17-B4-C15 |
| A48-B1-C15 | A38-B2-C15 | A28-B3-C15 | A18-B4-C15 |
| A49-B1-C15 | A39-B2-C15 | A29-B3-C15 | A19-B4-C15 |
| A50-B1-C15 | A40-B2-C15 | A30-B3-C15 | A20-B4-C15 |
| A51-B1-C15 | A41-B2-C15 | A31-B3-C15 | A21-B4-C15 |
| A52-B1-C15 | A42-B2-C15 | A32-B3-C15 | A22-B4-C15 |
| A53-B1-C15 | A43-B2-C15 | A33-B3-C15 | A23-B4-C15 |
| A54-B1-C15 | A44-B2-C15 | A34-B3-C15 | A24-B4-C15 |
| A55-B1-C15 | A45-B2-C15 | A35-B3-C15 | A25-B4-C15 |
| A56-B1-C15 | A46-B2-C15 | A36-B3-C15 | A26-B4-C15 |
| A57-B1-C15 | A47-B2-C15 | A37-B3-C15 | A27-B4-C15 |
| A58-B1-C15 | A48-B2-C15 | A38-B3-C15 | A28-B4-C15 |
| A59-B1-C15 | A49-B2-C15 | A39-B3-C15 | A29-B4-C15 |
| A60-B1-C15 | A50-B2-C15 | A40-B3-C15 | A30-B4-C15 |
| A61-B1-C15 | A51-B2-C15 | A41-B3-C15 | A31-B4-C15 |
| A62-B1-C15 | A52-B2-C15 | A42-B3-C15 | A32-B4-C15 |
| A63-B1-C15 | A53-B2-C15 | A43-B3-C15 | A33-B4-C15 |
| A64-B1-C15 | A54-B2-C15 | A44-B3-C15 | A34-B4-C15 |
| A65-B1-C15 | A55-B2-C15 | A45-B3-C15 | A35-B4-C15 |
| A66-B1-C15 | A56-B2-C15 | A46-B3-C15 | A36-B4-C15 |
| A67-B1-C15 | A57-B2-C15 | A47-B3-C15 | A37-B4-C15 |
| A68-B1-C15 | A58-B2-C15 | A48-B3-C15 | A38-B4-C15 |
| A69-B1-C15 | A59-B2-C15 | A49-B3-C15 | A39-B4-C15 |
| A70-B1-C15 | A60-B2-C15 | A50-B3-C15 | A40-B4-C15 |
| A71-B1-C15 | A61-B2-C15 | A51-B3-C15 | A41-B4-C15 |
| A72-B1-C15 | A62-B2-C15 | A52-B3-C15 | A42-B4-C15 |
| A73-B1-C15 | A63-B2-C15 | A53-B3-C15 | A43-B4-C15 |
| A74-B1-C15 | A64-B2-C15 | A54-B3-C15 | A44-B4-C15 |
| A75-B1-C15 | A65-B2-C15 | A55-B3-C15 | A45-B4-C15 |
| A76-B1-C15 | A66-B2-C15 | A56-B3-C15 | A46-B4-C15 |
| A77-B1-C15 | A67-B2-C15 | A57-B3-C15 | A47-B4-C15 |
| A1-B2-C15 | A68-B2-C15 | A58-B3-C15 | A48-B4-C15 |
| A2-B2-C15 | A69-B2-C15 | A59-B3-C15 | A49-B4-C15 |
| A3-B2-C15 | A70-B2-C15 | A60-B3-C15 | A50-B4-C15 |
| A4-B2-C15 | A71-B2-C15 | A61-B3-C15 | A51-B4-C15 |
| A5-B2-C15 | A72-B2-C15 | A62-B3-C15 | A52-B4-C15 |
| A6-B2-C15 | A73-B2-C15 | A63-B3-C15 | A53-B4-C15 |
| A7-B2-C15 | A74-B2-C15 | A64-B3-C15 | A54-B4-C15 |
| A8-B2-C15 | A75-B2-C15 | A65-B3-C15 | A55-B4-C15 |
| A9-B2-C15 | A76-B2-C15 | A66-B3-C15 | A56-B4-C15 |
| A10-B2-C15 | A77-B2-C15 | A67-B3-C15 | A57-B4-C15 |
| A58-B4-C15 | A48-B1-C16 | A38-B2-C16 | A28-B3-C16 |
| A59-B4-C15 | A49-B1-C16 | A39-B2-C16 | A29-B3-C16 |
| A60-B4-C15 | A50-B1-C16 | A40-B2-C16 | A30-B3-C16 |
| A61-B4-C15 | A51-B1-C16 | A41-B2-C16 | A31-B3-C16 |
| A62-B4-C15 | A52-B1-C16 | A42-B2-C16 | A32-B3-C16 |
| A63-B4-C15 | A53-B1-C16 | A43-B2-C16 | A33-B3-C16 |
| A64-B4-C15 | A54-B1-C16 | A44-B2-C16 | A34-B3-C16 |
| A65-B4-C15 | A55-B1-C16 | A45-B2-C16 | A35-B3-C16 |
| A66-B4-C15 | A56-B1-C16 | A46-B2-C16 | A36-B3-C16 |
| A67-B4-C15 | A57-B1-C16 | A47-B2-C16 | A37-B3-C16 |
| A68-B4-C15 | A58-B1-C16 | A48-B2-C16 | A38-B3-C16 |
| A69-B4-C15 | A59-B1-C16 | A49-B2-C16 | A39-B3-C16 |
| A70-B4-C15 | A60-B1-C16 | A50-B2-C16 | A40-B3-C16 |
| A71-B4-C15 | A61-B1-C16 | A51-B2-C16 | A41-B3-C16 |
| A72-B4-C15 | A62-B1-C16 | A52-B2-C16 | A42-B3-C16 |
| A73-B4-C15 | A63-B1-C16 | A53-B2-C16 | A43-B3-C16 |
| A74-B4-C15 | A64-B1-C16 | A54-B2-C16 | A44-B3-C16 |
| A75-B4-C15 | A65-B1-C16 | A55-B2-C16 | A45-B3-C16 |
| A76-B4-C15 | A66-B1-C16 | A56-B2-C16 | A46-B3-C16 |
| A77-B4-C15 | A67-B1-C16 | A57-B2-C16 | A47-B3-C16 |
| A1-B1-C16 | A68-B1-C16 | A58-B2-C16 | A48-B3-C16 |
| A2-B1-C16 | A69-B1-C16 | A59-B2-C16 | A49-B3-C16 |
| A3-B1-C16 | A70-B1-C16 | A60-B2-C16 | A50-B3-C16 |
| A4-B1-C16 | A71-B1-C16 | A61-B2-C16 | A51-B3-C16 |
| A5-B1-C16 | A72-B1-C16 | A62-B2-C16 | A52-B3-C16 |
| A6-B1-C16 | A73-B1-C16 | A63-B2-C16 | A53-B3-C16 |
| A7-B1-C16 | A74-B1-C16 | A64-B2-C16 | A54-B3-C16 |
| A8-B1-C16 | A75-B1-C16 | A65-B2-C16 | A55-B3-C16 |
| A9-B1-C16 | A76-B1-C16 | A66-B2-C16 | A56-B3-C16 |
| A10-B1-C16 | A77-B1-C16 | A67-B2-C16 | A57-B3-C16 |
| A11-B1-C16 | A1-B2-C16 | A68-B2-C16 | A58-B3-C16 |
| A12-B1-C16 | A2-B2-C16 | A69-B2-C16 | A59-B3-C16 |
| A13-B1-C16 | A3-B2-C16 | A70-B2-C16 | A60-B3-C16 |
| A14-B1-C16 | A4-B2-C16 | A71-B2-C16 | A61-B3-C16 |
| A15-B1-C16 | A5-B2-C16 | A72-B2-C16 | A62-B3-C16 |
| A16-B1-C16 | A6-B2-C16 | A73-B2-C16 | A63-B3-C16 |
| A17-B1-C16 | A7-B2-C16 | A74-B2-C16 | A64-B3-C16 |
| A18-B1-C16 | A8-B2-C16 | A75-B2-C16 | A65-B3-C16 |
| A19-B1-C16 | A9-B2-C16 | A76-B2-C16 | A66-B3-C16 |
| A20-B1-C16 | A10-B2-C16 | A77-B2-C16 | A67-B3-C16 |
| A21-B1-C16 | A11-B2-C16 | A1-B3-C16 | A68-B3-C16 |
| A22-B1-C16 | A12-B2-C16 | A2-B3-C16 | A69-B3-C16 |
| A23-B1-C16 | A13-B2-C16 | A3-B3-C16 | A70-B3-C16 |
| A24-B1-C16 | A14-B2-C16 | A4-B3-C16 | A71-B3-C16 |
| A25-B1-C16 | A15-B2-C16 | A5-B3-C16 | A72-B3-C16 |
| A26-B1-C16 | A16-B2-C16 | A6-B3-C16 | A73-B3-C16 |
| A27-B1-C16 | A17-B2-C16 | A7-B3-C16 | A74-B3-C16 |
| A28-B1-C16 | A18-B2-C16 | A8-B3-C16 | A75-B3-C16 |
| A29-B1-C16 | A19-B2-C16 | A9-B3-C16 | A76-B3-C16 |
| A30-B1-C16 | A20-B2-C16 | A10-B3-C16 | A77-B3-C16 |
| A31-B1-C16 | A21-B2-C16 | A11-B3-C16 | A1-B4-C16 |
| A32-B1-C16 | A22-B2-C16 | A12-B3-C16 | A2-B4-C16 |
| A33-B1-C16 | A23-B2-C16 | A13-B3-C16 | A3-B4-C16 |
| A34-B1-C16 | A24-B2-C16 | A14-B3-C16 | A4-B4-C16 |
| A35-B1-C16 | A25-B2-C16 | A15-B3-C16 | A5-B4-C16 |

TABLE 4-continued

| | | | |
|---|---|---|---|
| A36-B1-C16 | A26-B2-C16 | A16-B3-C16 | A6-B4-C16 |
| A37-B1-C16 | A27-B2-C16 | A17-B3-C16 | A7-B4-C16 |
| A38-B1-C16 | A28-B2-C16 | A18-B3-C16 | A8-B4-C16 |
| A39-B1-C16 | A29-B2-C16 | A19-B3-C16 | A9-B4-C16 |
| A40-B1-C16 | A30-B2-C16 | A20-B3-C16 | A10-B4-C16 |
| A41-B1-C16 | A31-B2-C16 | A21-B3-C16 | A11-B4-C16 |
| A42-B1-C16 | A32-B2-C16 | A22-B3-C16 | A12-B4-C16 |
| A43-B1-C16 | A33-B2-C16 | A23-B3-C16 | A13-B4-C16 |
| A44-B1-C16 | A34-B2-C16 | A24-B3-C16 | A14-B4-C16 |
| A45-B1-C16 | A35-B2-C16 | A25-B3-C16 | A15-B4-C16 |
| A46-B1-C16 | A36-B2-C16 | A26-B3-C16 | A16-B4-C16 |
| A47-B1-C16 | A37-B2-C16 | A27-B3-C16 | A17-B4-C16 |
| A18-B4-C16 | A8-B1-C17 | A75-B1-C17 | A65-B2-C17 |
| A19-B4-C16 | A9-B1-C17 | A76-B1-C17 | A66-B2-C17 |
| A20-B4-C16 | A10-B1-C17 | A77-B1-C17 | A67-B2-C17 |
| A21-B4-C16 | A11-B1-C17 | A1-B2-C17 | A68-B2-C17 |
| A22-B4-C16 | A12-B1-C17 | A2-B2-C17 | A69-B2-C17 |
| A23-B4-C16 | A13-B1-C17 | A3-B2-C17 | A70-B2-C17 |
| A24-B4-C16 | A14-B1-C17 | A4-B2-C17 | A71-B2-C17 |
| A25-B4-C16 | A15-B1-C17 | A5-B2-C17 | A72-B2-C17 |
| A26-B4-C16 | A16-B1-C17 | A6-B2-C17 | A73-B2-C17 |
| A27-B4-C16 | A17-B1-C17 | A7-B2-C17 | A74-B2-C17 |
| A28-B4-C16 | A18-B1-C17 | A8-B2-C17 | A75-B2-C17 |
| A29-B4-C16 | A19-B1-C17 | A9-B2-C17 | A76-B2-C17 |
| A30-B4-C16 | A20-B1-C17 | A10-B2-C17 | A77-B2-C17 |
| A31-B4-C16 | A21-B1-C17 | A11-B2-C17 | A1-B3-C17 |
| A32-B4-C16 | A22-B1-C17 | A12-B2-C17 | A2-B3-C17 |
| A33-B4-C16 | A23-B1-C17 | A13-B2-C17 | A3-B3-C17 |
| A34-B4-C16 | A24-B1-C17 | A14-B2-C17 | A4-B3-C17 |
| A35-B4-C16 | A25-B1-C17 | A15-B2-C17 | A5-B3-C17 |
| A36-B4-C16 | A26-B1-C17 | A16-B2-C17 | A6-B3-C17 |
| A37-B4-C16 | A27-B1-C17 | A17-B2-C17 | A7-B3-C17 |
| A38-B4-C16 | A28-B1-C17 | A18-B2-C17 | A8-B3-C17 |
| A39-B4-C16 | A29-B1-C17 | A19-B2-C17 | A9-B3-C17 |
| A40-B4-C16 | A30-B1-C17 | A20-B2-C17 | A10-B3-C17 |
| A41-B4-C16 | A31-B1-C17 | A21-B2-C17 | A11-B3-C17 |
| A42-B4-C16 | A32-B1-C17 | A22-B2-C17 | A12-B3-C17 |
| A43-B4-C16 | A33-B1-C17 | A23-B2-C17 | A13-B3-C17 |
| A44-B4-C16 | A34-B1-C17 | A24-B2-C17 | A14-B3-C17 |
| A45-B4-C16 | A35-B1-C17 | A25-B2-C17 | A15-B3-C17 |
| A46-B4-C16 | A36-B1-C17 | A26-B2-C17 | A16-B3-C17 |
| A47-B4-C16 | A37-B1-C17 | A27-B2-C17 | A17-B3-C17 |
| A48-B4-C16 | A38-B1-C17 | A28-B2-C17 | A18-B3-C17 |
| A49-B4-C16 | A39-B1-C17 | A29-B2-C17 | A19-B3-C17 |
| A50-B4-C16 | A40-B1-C17 | A30-B2-C17 | A20-B3-C17 |
| A51-B4-C16 | A41-B1-C17 | A31-B2-C17 | A21-B3-C17 |
| A52-B4-C16 | A42-B1-C17 | A32-B2-C17 | A22-B3-C17 |
| A53-B4-C16 | A43-B1-C17 | A33-B2-C17 | A23-B3-C17 |
| A54-B4-C16 | A44-B1-C17 | A34-B2-C17 | A24-B3-C17 |
| A55-B4-C16 | A45-B1-C17 | A35-B2-C17 | A25-B3-C17 |
| A56-B4-C16 | A46-B1-C17 | A36-B2-C17 | A26-B3-C17 |
| A57-B4-C16 | A47-B1-C17 | A37-B2-C17 | A27-B3-C17 |
| A58-B4-C16 | A48-B1-C17 | A38-B2-C17 | A28-B3-C17 |
| A59-B4-C16 | A49-B1-C17 | A39-B2-C17 | A29-B3-C17 |
| A60-B4-C16 | A50-B1-C17 | A40-B2-C17 | A30-B3-C17 |
| A61-B4-C16 | A51-B1-C17 | A41-B2-C17 | A31-B3-C17 |
| A62-B4-C16 | A52-B1-C17 | A42-B2-C17 | A32-B3-C17 |
| A63-B4-C16 | A53-B1-C17 | A43-B2-C17 | A33-B3-C17 |
| A64-B4-C16 | A54-B1-C17 | A44-B2-C17 | A34-B3-C17 |
| A65-B4-C16 | A55-B1-C17 | A45-B2-C17 | A35-B3-C17 |
| A66-B4-C16 | A56-B1-C17 | A46-B2-C17 | A36-B3-C17 |
| A67-B4-C16 | A57-B1-C17 | A47-B2-C17 | A37-B3-C17 |
| A68-B4-C16 | A58-B1-C17 | A48-B2-C17 | A38-B3-C17 |
| A69-B4-C16 | A59-B1-C17 | A49-B2-C17 | A39-B3-C17 |
| A70-B4-C16 | A60-B1-C17 | A50-B2-C17 | A40-B3-C17 |
| A71-B4-C16 | A61-B1-C17 | A51-B2-C17 | A41-B3-C17 |
| A72-B4-C16 | A62-B1-C17 | A52-B2-C17 | A42-B3-C17 |
| A73-B4-C16 | A63-B1-C17 | A53-B2-C17 | A43-B3-C17 |
| A74-B4-C16 | A64-B1-C17 | A54-B2-C17 | A44-B3-C17 |
| A75-B4-C16 | A65-B1-C17 | A55-B2-C17 | A45-B3-C17 |
| A76-B4-C16 | A66-B1-C17 | A56-B2-C17 | A46-B3-C17 |
| A77-B4-C16 | A67-B1-C17 | A57-B2-C17 | A47-B3-C17 |
| A1-B1-C17 | A68-B1-C17 | A58-B2-C17 | A48-B3-C17 |
| A2-B1-C17 | A69-B1-C17 | A59-B2-C17 | A49-B3-C17 |
| A3-B1-C17 | A70-B1-C17 | A60-B2-C17 | A50-B3-C17 |
| A4-B1-C17 | A71-B1-C17 | A61-B2-C17 | A51-B3-C17 |
| A5-B1-C17 | A72-B1-C17 | A62-B2-C17 | A52-B3-C17 |
| A6-B1-C17 | A73-B1-C17 | A63-B2-C17 | A53-B3-C17 |
| A7-B1-C17 | A74-B1-C17 | A64-B2-C17 | A54-B3-C17 |
| A55-B3-C17 | A45-B4-C17 | A35-B1-C18 | A25-B2-C18 |
| A56-B3-C17 | A46-B4-C17 | A36-B1-C18 | A26-B2-C18 |
| A57-B3-C17 | A47-B4-C17 | A37-B1-C18 | A27-B2-C18 |
| A58-B3-C17 | A48-B4-C17 | A38-B1-C18 | A28-B2-C18 |
| A59-B3-C17 | A49-B4-C17 | A39-B1-C18 | A29-B2-C18 |
| A60-B3-C17 | A50-B4-C17 | A40-B1-C18 | A30-B2-C18 |
| A61-B3-C17 | A51-B4-C17 | A41-B1-C18 | A31-B2-C18 |
| A62-B3-C17 | A52-B4-C17 | A42-B1-C18 | A32-B2-C18 |
| A63-B3-C17 | A53-B4-C17 | A43-B1-C18 | A33-B2-C18 |
| A64-B3-C17 | A54-B4-C17 | A44-B1-C18 | A34-B2-C18 |
| A65-B3-C17 | A55-B4-C17 | A45-B1-C18 | A35-B2-C18 |
| A66-B3-C17 | A56-B4-C17 | A46-B1-C18 | A36-B2-C18 |
| A67-B3-C17 | A57-B4-C17 | A47-B1-C18 | A37-B2-C18 |
| A68-B3-C17 | A58-B4-C17 | A48-B1-C18 | A38-B2-C18 |
| A69-B3-C17 | A59-B4-C17 | A49-B1-C18 | A39-B2-C18 |
| A70-B3-C17 | A60-B4-C17 | A50-B1-C18 | A40-B2-C18 |
| A71-B3-C17 | A61-B4-C17 | A51-B1-C18 | A41-B2-C18 |
| A72-B3-C17 | A62-B4-C17 | A52-B1-C18 | A42-B2-C18 |
| A73-B3-C17 | A63-B4-C17 | A53-B1-C18 | A43-B2-C18 |
| A74-B3-C17 | A64-B4-C17 | A54-B1-C18 | A44-B2-C18 |
| A75-B3-C17 | A65-B4-C17 | A55-B1-C18 | A45-B2-C18 |
| A76-B3-C17 | A66-B4-C17 | A56-B1-C18 | A46-B2-C18 |
| A77-B3-C17 | A67-B4-C17 | A57-B1-C18 | A47-B2-C18 |
| A1-B4-C17 | A68-B4-C17 | A58-B1-C18 | A48-B2-C18 |
| A2-B4-C17 | A69-B4-C17 | A59-B1-C18 | A49-B2-C18 |
| A3-B4-C17 | A70-B4-C17 | A60-B1-C18 | A50-B2-C18 |
| A4-B4-C17 | A71-B4-C17 | A61-B1-C18 | A51-B2-C18 |
| A5-B4-C17 | A72-B4-C17 | A62-B1-C18 | A52-B2-C18 |
| A6-B4-C17 | A73-B4-C17 | A63-B1-C18 | A53-B2-C18 |
| A7-B4-C17 | A74-B4-C17 | A64-B1-C18 | A54-B2-C18 |
| A8-B4-C17 | A75-B4-C17 | A65-B1-C18 | A55-B2-C18 |
| A9-B4-C17 | A76-B4-C17 | A66-B1-C18 | A56-B2-C18 |
| A10-B4-C17 | A77-B4-C17 | A67-B1-C18 | A57-B2-C18 |
| A11-B4-C17 | A1-B1-C18 | A68-B1-C18 | A58-B2-C18 |
| A12-B4-C17 | A2-B1-C18 | A69-B1-C18 | A59-B2-C18 |
| A13-B4-C17 | A3-B1-C18 | A70-B1-C18 | A60-B2-C18 |
| A14-B4-C17 | A4-B1-C18 | A71-B1-C18 | A61-B2-C18 |
| A15-B4-C17 | A5-B1-C18 | A72-B1-C18 | A62-B2-C18 |
| A16-B4-C17 | A6-B1-C18 | A73-B1-C18 | A63-B2-C18 |
| A17-B4-C17 | A7-B1-C18 | A74-B1-C18 | A64-B2-C18 |
| A18-B4-C17 | A8-B1-C18 | A75-B1-C18 | A65-B2-C18 |
| A19-B4-C17 | A9-B1-C18 | A76-B1-C18 | A66-B2-C18 |
| A20-B4-C17 | A10-B1-C18 | A77-B1-C18 | A67-B2-C18 |
| A21-B4-C17 | A11-B1-C18 | A1-B2-C18 | A68-B2-C18 |
| A22-B4-C17 | A12-B1-C18 | A2-B2-C18 | A69-B2-C18 |
| A23-B4-C17 | A13-B1-C18 | A3-B2-C18 | A70-B2-C18 |
| A24-B4-C17 | A14-B1-C18 | A4-B2-C18 | A71-B2-C18 |
| A25-B4-C17 | A15-B1-C18 | A5-B2-C18 | A72-B2-C18 |
| A26-B4-C17 | A16-B1-C18 | A6-B2-C18 | A73-B2-C18 |
| A27-B4-C17 | A17-B1-C18 | A7-B2-C18 | A74-B2-C18 |
| A28-B4-C17 | A18-B1-C18 | A8-B2-C18 | A75-B2-C18 |
| A29-B4-C17 | A19-B1-C18 | A9-B2-C18 | A76-B2-C18 |
| A30-B4-C17 | A20-B1-C18 | A10-B2-C18 | A77-B2-C18 |
| A31-B4-C17 | A21-B1-C18 | A11-B2-C18 | A1-B3-C18 |
| A32-B4-C17 | A22-B1-C18 | A12-B2-C18 | A2-B3-C18 |
| A33-B4-C17 | A23-B1-C18 | A13-B2-C18 | A3-B3-C18 |
| A34-B4-C17 | A24-B1-C18 | A14-B2-C18 | A4-B3-C18 |
| A35-B4-C17 | A25-B1-C18 | A15-B2-C18 | A5-B3-C18 |
| A36-B4-C17 | A26-B1-C18 | A16-B2-C18 | A6-B3-C18 |
| A37-B4-C17 | A27-B1-C18 | A17-B2-C18 | A7-B3-C18 |
| A38-B4-C17 | A28-B1-C18 | A18-B2-C18 | A8-B3-C18 |
| A39-B4-C17 | A29-B1-C18 | A19-B2-C1B | A9-B3-C18 |
| A40-B4-C17 | A30-B1-C18 | A20-B2-C18 | A10-B3-C18 |
| A41-B4-C17 | A31-B1-C18 | A21-B2-C18 | A11-B3-C18 |
| A42-B4-C17 | A32-B1-C18 | A22-B2-C18 | A12-B3-C18 |
| A43-B4-C17 | A33-B1-C18 | A23-B2-C18 | A13-B3-C18 |
| A44-B4-C17 | A34-B1-C18 | A24-B2-C18 | A14-B3-C18 |
| A15-B3-C18 | A5-B4-C18 | A72-B4-C18 | A62-B1-C19 |
| A16-B3-C18 | A6-B4-C18 | A73-B4-C18 | A63-B1-C19 |
| A17-B3-C18 | A7-B4-C18 | A74-B4-C18 | A64-B1-C19 |
| A18-B3-C18 | A8-B4-C18 | A75-B4-C18 | A65-B1-C19 |
| A19-B3-C18 | A9-B4-C18 | A76-B4-C18 | A66-B1-C19 |
| A20-B3-C18 | A10-B4-C18 | A77-B4-C18 | A67-B1-C19 |
| A21-B3-C18 | A11-B4-C18 | A1-B1-C19 | A68-B1-C19 |
| A22-B3-C18 | A12-B4-C18 | A2-B1-C19 | A69-B1-C19 |
| A23-B3-C18 | A13-B4-C18 | A3-B1-C19 | A70-B1-C19 |
| A24-B3-C18 | A14-B4-C18 | A4-B1-C19 | A71-B1-C19 |
| A25-B3-C18 | A15-B4-C18 | A5-B1-C19 | A72-B1-C19 |
| A26-B3-C18 | A16-B4-C18 | A6-B1-C19 | A73-B1-C19 |

TABLE 4-continued

| | | | |
|---|---|---|---|
| A27-B3-C18 | A17-B4-C18 | A7-B1-C19 | A74-B1-C19 |
| A28-B3-C18 | A18-B4-C18 | A8-B1-C19 | A75-B1-C19 |
| A29-B3-C18 | A19-B4-C18 | A9-B1-C19 | A76-B1-C19 |
| A30-B3-C18 | A20-B4-C18 | A10-B1-C19 | A77-B1-C19 |
| A31-B3-C18 | A21-B4-C18 | A11-B1-C19 | A1-B2-C19 |
| A32-B3-C18 | A22-B4-C18 | A12-B1-C19 | A2-B2-C19 |
| A33-B3-C18 | A23-B4-C18 | A13-B1-C19 | A3-B2-C19 |
| A34-B3-C18 | A24-B4-C18 | A14-B1-C19 | A4-B2-C19 |
| A35-B3-C18 | A25-B4-C18 | A15-B1-C19 | A5-B2-C19 |
| A36-B3-C18 | A26-B4-C18 | A16-B1-C19 | A6-B2-C19 |
| A37-B3-C18 | A27-B4-C18 | A17-B1-C19 | A7-B2-C19 |
| A38-B3-C18 | A28-B4-C18 | A18-B1-C19 | A8-B2-C19 |
| A39-B3-C18 | A29-B4-C18 | A19-B1-C19 | A9-B2-C19 |
| A40-B3-C18 | A30-B4-C18 | A20-B1-C19 | A10-B2-C19 |
| A41-B3-C18 | A31-B4-C18 | A21-B1-C19 | A11-B2-C19 |
| A42-B3-C18 | A32-B4-C18 | A22-B1-C19 | A12-B2-C19 |
| A43-B3-C18 | A33-B4-C18 | A23-B1-C19 | A13-B2-C19 |
| A44-B3-C18 | A34-B4-C18 | A24-B1-C19 | A14-B2-C19 |
| A45-B3-C18 | A35-B4-C18 | A25-B1-C19 | A15-B2-C19 |
| A46-B3-C18 | A36-B4-C18 | A26-B1-C19 | A16-B2-C19 |
| A47-B3-C18 | A37-B4-C18 | A27-B1-C19 | A17-B2-C19 |
| A48-B3-C18 | A38-B4-C18 | A28-B1-C19 | A18-B2-C19 |
| A49-B3-C18 | A39-B4-C18 | A29-B1-C19 | A19-B2-C19 |
| A50-B3-C18 | A40-B4-C18 | A30-B1-C19 | A20-B2-C19 |
| A51-B3-C18 | A41-B4-C18 | A31-B1-C19 | A21-B2-C19 |
| A52-B3-C18 | A42-B4-C18 | A32-B1-C19 | A22-B2-C19 |
| A53-B3-C18 | A43-B4-C18 | A33-B1-C19 | A23-B2-C19 |
| A54-B3-C18 | A44-B4-C18 | A34-B1-C19 | A24-B2-C19 |
| A55-B3-C18 | A45-B4-C18 | A35-B1-C19 | A25-B2-C19 |
| A56-B3-C18 | A46-B4-C18 | A36-B1-C19 | A26-B2-C19 |
| A57-B3-C18 | A47-B4-C18 | A37-B1-C19 | A27-B2-C19 |
| A58-B3-C18 | A48-B4-C18 | A38-B1-C19 | A28-B2-C19 |
| A59-B3-C18 | A49-B4-C18 | A39-B1-C19 | A29-B2-C19 |
| A60-B3-C18 | A50-B4-C18 | A40-B1-C19 | A30-B2-C19 |
| A61-B3-C18 | A51-B4-C18 | A41-B1-C19 | A31-B2-C19 |
| A62-B3-C18 | A52-B4-C18 | A42-B1-C19 | A32-B2-C19 |
| A63-B3-C18 | A53-B4-C18 | A43-B1-C19 | A33-B2-C19 |
| A64-B3-C18 | A54-B4-C18 | A44-B1-C19 | A34-B2-C19 |
| A65-B3-C18 | A55-B4-C18 | A45-B1-C19 | A35-B2-C19 |
| A66-B3-C18 | A56-B4-C18 | A46-B1-C19 | A36-B2-C19 |
| A67-B3-C18 | A57-B4-C18 | A47-B1-C19 | A37-B2-C19 |
| A68-B3-C18 | A58-B4-C18 | A48-B1-C19 | A38-B2-C19 |
| A69-B3-C18 | A59-B4-C18 | A49-B1-C19 | A39-B2-C19 |
| A70-B3-C18 | A60-B4-C18 | A50-B1-C19 | A40-B2-C19 |
| A71-B3-C18 | A61-B4-C18 | A51-B1-C19 | A41-B2-C19 |
| A72-B3-C18 | A62-B4-C18 | A52-B1-C19 | A42-B2-C19 |
| A73-B3-C18 | A63-B4-C18 | A53-B1-C19 | A43-B2-C19 |
| A74-B3-C18 | A64-B4-C18 | A54-B1-C19 | A44-B2-C19 |
| A75-B3-C18 | A65-B4-C18 | A55-B1-C19 | A45-B2-C19 |
| A76-B3-C18 | A66-B4-C18 | A56-B1-C19 | A46-B2-C19 |
| A77-B3-C18 | A67-B4-C18 | A57-B1-C19 | A47-B2-C19 |
| A1-B4-C18 | A68-B4-C18 | A58-B1-C19 | A48-B2-C19 |
| A2-B4-C18 | A69-B4-C18 | A59-B1-C19 | A49-B2-C19 |
| A3-B4-C18 | A70-B4-C18 | A60-B1-C19 | A50-B2-C19 |
| A4-B4-C18 | A71-B4-C18 | A61-B1-C19 | A51-B2-C19 |
| A52-B2-C19 | A42-B3-C19 | A32-B4-C19 | A22-B1-C20 |
| A53-B2-C19 | A43-B3-C19 | A33-B4-C19 | A23-B1-C20 |
| A54-B2-C19 | A44-B3-C19 | A34-B4-C19 | A24-B1-C20 |
| A55-B2-C19 | A45-B3-C19 | A35-B4-C19 | A25-B1-C20 |
| A56-B2-C19 | A46-B3-C19 | A36-B4-C19 | A26-B1-C20 |
| A57-B2-C19 | A47-B3-C19 | A37-B4-C19 | A27-B1-C20 |
| A58-B2-C19 | A48-B3-C19 | A38-B4-C19 | A28-B1-C20 |
| A59-B2-C19 | A49-B3-C19 | A39-B4-C19 | A29-B1-C20 |
| A60-B2-C19 | A50-B3-C19 | A40-B4-C19 | A30-B1-C20 |
| A61-B2-C19 | A51-B3-C19 | A41-B4-C19 | A31-B1-C20 |
| A62-B2-C19 | A52-B3-C19 | A42-B4-C19 | A32-B1-C20 |
| A63-B2-C19 | A53-B3-C19 | A43-B4-C19 | A33-B1-C20 |
| A64-B2-C19 | A54-B3-C19 | A44-B4-C19 | A34-B1-C20 |
| A65-B2-C19 | A55-B3-C19 | A45-B4-C19 | A35-B1-C20 |
| A66-B2-C19 | A56-B3-C19 | A46-B4-C19 | A36-B1-C20 |
| A67-B2-C19 | A57-B3-C19 | A47-B4-C19 | A37-B1-C20 |
| A68-B2-C19 | A58-B3-C19 | A48-B4-C19 | A38-B1-C20 |
| A69-B2-C19 | A59-B3-C19 | A49-B4-C19 | A39-B1-C20 |
| A70-B2-C19 | A60-B3-C19 | A50-B4-C19 | A40-B1-C20 |
| A71-B2-C19 | A61-B3-C19 | A51-B4-C19 | A41-B1-C20 |
| A72-B2-C19 | A62-B3-C19 | A52-B4-C19 | A42-B1-C20 |
| A73-B2-C19 | A63-B3-C19 | A53-B4-C19 | A43-B1-C20 |
| A74-B2-C19 | A64-B3-C19 | A54-B4-C19 | A44-B1-C20 |
| A75-B2-C19 | A65-B3-C19 | A55-B4-C19 | A45-B1-C20 |

TABLE 4-continued

| | | | |
|---|---|---|---|
| A76-B2-C19 | A66-B3-C19 | A56-B4-C19 | A46-B1-C20 |
| A77-B2-C19 | A67-B3-C19 | A57-B4-C19 | A47-B1-C20 |
| A1-B3-C19 | A68-B3-C19 | A58-B4-C19 | A48-B1-C20 |
| A2-B3-C19 | A69-B3-C19 | A59-B4-C19 | A49-B1-C20 |
| A3-B3-C19 | A70-B3-C19 | A60-B4-C19 | A50-B1-C20 |
| A4-B3-C19 | A71-B3-C19 | A61-B4-C19 | A51-B1-C20 |
| A5-B3-C19 | A72-B3-C19 | A62-B4-C19 | A52-B1-C20 |
| A6-B3-C19 | A73-B3-C19 | A63-B4-C19 | A53-B1-C20 |
| A7-B3-C19 | A74-B3-C19 | A64-B4-C19 | A54-B1-C20 |
| A8-B3-C19 | A75-B3-C19 | A65-B4-C19 | A55-B1-C20 |
| A9-B3-C19 | A76-B3-C19 | A66-B4-C19 | A56-B1-C20 |
| A10-B3-C19 | A77-B3-C19 | A67-B4-C19 | A57-B1-C20 |
| A11-B3-C19 | A1-B4-C19 | A68-B4-C19 | A58-B1-C20 |
| A12-B3-C19 | A2-B4-C19 | A69-B4-C19 | A59-B1-C20 |
| A13-B3-C19 | A3-B4-C19 | A70-B4-C19 | A60-B1-C20 |
| A14-B3-C19 | A4-B4-C19 | A71-B4-C19 | A61-B1-C20 |
| A15-B3-C19 | A5-B4-C19 | A72-B4-C19 | A62-B1-C20 |
| A16-B3-C19 | A6-B4-C19 | A73-B4-C19 | A63-B1-C20 |
| A17-B3-C19 | A7-B4-C19 | A74-B4-C19 | A64-B1-C20 |
| A18-B3-C19 | A8-B4-C19 | A75-B4-C19 | A65-B1-C20 |
| A19-B3-C19 | A9-B4-C19 | A76-B4-C19 | A66-B1-C20 |
| A20-B3-C19 | A10-B4-C19 | A77-B4-C19 | A67-B1-C20 |
| A21-B3-C19 | A11-B4-C19 | A1-B1-C20 | A68-B1-C20 |
| A22-B3-C19 | A12-B4-C19 | A2-B1-C20 | A69-B1-C20 |
| A23-B3-C19 | A13-B4-C19 | A3-B1-C20 | A70-B1-C20 |
| A24-B3-C19 | A14-B4-C19 | A4-B1-C20 | A71-B1-C20 |
| A25-B3-C19 | A15-B4-C19 | A5-B1-C20 | A72-B1-C20 |
| A26-B3-C19 | A16-B4-C19 | A6-B1-C20 | A73-B1-C20 |
| A27-B3-C19 | A17-B4-C19 | A7-B1-C20 | A74-B1-C20 |
| A28-B3-C19 | A18-B4-C19 | A8-B1-C20 | A75-B1-C20 |
| A29-B3-C19 | A19-B4-C19 | A9-B1-C20 | A76-B1-C20 |
| A30-B3-C19 | A20-B4-C19 | A10-B1-C20 | A77-B1-C20 |
| A31-B3-C19 | A21-B4-C19 | A11-B1-C20 | A1-B2-C20 |
| A32-B3-C19 | A22-B4-C19 | A12-B1-C20 | A2-B2-C20 |
| A33-B3-C19 | A23-B4-C19 | A13-B1-C20 | A3-B2-C20 |
| A34-B3-C19 | A24-B4-C19 | A14-B1-C20 | A4-B2-C20 |
| A35-B3-C19 | A25-B4-C19 | A15-B1-C20 | A5-B2-C20 |
| A36-B3-C19 | A26-B4-C19 | A16-B1-C20 | A6-B2-C20 |
| A37-B3-C19 | A27-B4-C19 | A17-B1-C20 | A7-B2-C20 |
| A38-B3-C19 | A28-B4-C19 | A18-B1-C20 | A8-B2-C20 |
| A39-B3-C19 | A29-B4-C19 | A19-B1-C20 | A9-B2-C20 |
| A40-B3-C19 | A30-B4-C19 | A20-B1-C20 | A10-B2-C20 |
| A41-B3-C19 | A31-B4-C19 | A21-B1-C20 | A11-B2-C20 |
| A12-B2-C20 | A2-B3-C20 | A69-B3-C20 | A59-B4-C20 |
| A13-B2-C20 | A3-B3-C20 | A70-B3-C20 | A60-B4-C20 |
| A14-B2-C20 | A4-B3-C20 | A71-B3-C20 | A61-B4-C20 |
| A15-B2-C20 | A5-B3-C20 | A72-B3-C20 | A62-B4-C20 |
| A16-B2-C20 | A6-B3-C20 | A73-B3-C20 | A63-B4-C20 |
| A17-B2-C20 | A7-B3-C20 | A74-B3-C20 | A64-B4-C20 |
| A18-B2-C20 | A8-B3-C20 | A75-B3-C20 | A65-B4-C20 |
| A19-B2-C20 | A9-B3-C20 | A76-B3-C20 | A66-B4-C20 |
| A20-B2-C20 | A10-B3-C20 | A77-B3-C20 | A67-B4-C20 |
| A21-B2-C20 | A11-B3-C20 | A1-B4-C20 | A68-B4-C20 |
| A22-B2-C20 | A12-B3-C20 | A2-B4-C20 | A69-B4-C20 |
| A23-B2-C20 | A13-B3-C20 | A3-B4-C20 | A70-B4-C20 |
| A24-B2-C20 | A14-B3-C20 | A4-B4-C20 | A71-B4-C20 |
| A25-B2-C20 | A15-B3-C20 | A5-B4-C20 | A72-B4-C20 |
| A26-B2-C20 | A16-B3-C20 | A6-B4-C20 | A73-B4-C20 |
| A27-B2-C20 | A17-B3-C20 | A7-B4-C20 | A74-B4-C20 |
| A28-B2-C20 | A18-B3-C20 | A8-B4-C20 | A75-B4-C20 |
| A29-B2-C20 | A19-B3-C20 | A9-B4-C20 | A76-B4-C20 |
| A30-B2-C20 | A20-B3-C20 | A10-B4-C20 | A77-B4-C20 |
| A31-B2-C20 | A21-B3-C20 | A11-B4-C20 | A1-B1-C21 |
| A32-B2-C20 | A22-B3-C20 | A12-B4-C20 | A2-B1-C21 |
| A33-B2-C20 | A23-B3-C20 | A13-B4-C20 | A3-B1-C21 |
| A34-B2-C20 | A24-B3-C20 | A14-B4-C20 | A4-B1-C21 |
| A35-B2-C20 | A25-B3-C20 | A15-B4-C20 | A5-B1-C21 |
| A36-B2-C20 | A26-B3-C20 | A16-B4-C20 | A6-B1-C21 |
| A37-B2-C20 | A27-B3-C20 | A17-B4-C20 | A7-B1-C21 |
| A38-B2-C20 | A28-B3-C20 | A18-B4-C20 | A8-B1-C21 |
| A39-B2-C20 | A29-B3-C20 | A19-B4-C20 | A9-B1-C21 |
| A40-B2-C20 | A30-B3-C20 | A20-B4-C20 | A10-B1-C21 |
| A41-B2-C20 | A31-B3-C20 | A21-B4-C20 | A11-B1-C21 |
| A42-B2-C20 | A32-B3-C20 | A22-B4-C20 | A12-B1-C21 |
| A43-B2-C20 | A33-B3-C20 | A23-B4-C20 | A13-B1-C21 |
| A44-B2-C20 | A34-B3-C20 | A24-B4-C20 | A14-B1-C21 |
| A45-B2-C20 | A35-B3-C20 | A25-B4-C20 | A15-B1-C21 |
| A46-B2-C20 | A36-B3-C20 | A26-B4-C20 | A16-B1-C21 |
| A47-B2-C20 | A37-B3-C20 | A27-B4-C20 | A17-B1-C21 |

TABLE 4-continued

| | | | |
|---|---|---|---|
| A48-B2-C20 | A38-B3-C20 | A28-B4-C20 | A18-B1-C21 |
| A49-B2-C20 | A39-B3-C20 | A29-B4-C20 | A19-B1-C21 |
| A50-B2-C20 | A40-B3-C20 | A30-B4-C20 | A20-B1-C21 |
| A51-B2-C20 | A41-B3-C20 | A31-B4-C20 | A21-B1-C21 |
| A52-B2-C20 | A42-B3-C20 | A32-B4-C20 | A22-B1-C21 |
| A53-B2-C20 | A43-B3-C20 | A33-B4-C20 | A23-B1-C21 |
| A54-B2-C20 | A44-B3-C20 | A34-B4-C20 | A24-B1-C21 |
| A55-B2-C20 | A45-B3-C20 | A35-B4-C20 | A25-B1-C21 |
| A56-B2-C20 | A46-B3-C20 | A36-B4-C20 | A26-B1-C21 |
| A57-B2-C20 | A47-B3-C20 | A37-B4-C20 | A27-B1-C21 |
| A58-B2-C20 | A48-B3-C20 | A38-B4-C20 | A28-B1-C21 |
| A59-B2-C20 | A49-B3-C20 | A39-B4-C20 | A29-B1-C21 |
| A60-B2-C20 | A50-B3-C20 | A40-B4-C20 | A30-B1-C21 |
| A61-B2-C20 | A51-B3-C20 | A41-B4-C20 | A31-B1-C21 |
| A62-B2-C20 | A52-B3-C20 | A42-B4-C20 | A32-B1-C21 |
| A63-B2-C20 | A53-B3-C20 | A43-B4-C20 | A33-B1-C21 |
| A64-B2-C20 | A54-B3-C20 | A44-B4-C20 | A34-B1-C21 |
| A65-B2-C20 | A55-B3-C20 | A45-B4-C20 | A35-B1-C21 |
| A66-B2-C20 | A56-B3-C20 | A46-B4-C20 | A36-B1-C21 |
| A67-B2-C20 | A57-B3-C20 | A47-B4-C20 | A37-B1-C21 |
| A68-B2-C20 | A58-B3-C20 | A48-B4-C20 | A38-B1-C21 |
| A69-B2-C20 | A59-B3-C20 | A49-B4-C20 | A39-B1-C21 |
| A70-B2-C20 | A60-B3-C20 | A50-B4-C20 | A40-B1-C21 |
| A71-B2-C20 | A61-B3-C20 | A51-B4-C20 | A41-B1-C21 |
| A72-B2-C20 | A62-B3-C20 | A52-B4-C20 | A42-B1-C21 |
| A73-B2-C20 | A63-B3-C20 | A53-B4-C20 | A43-B1-C21 |
| A74-B2-C20 | A64-B3-C20 | A54-B4-C20 | A44-B1-C21 |
| A75-B2-C20 | A65-B3-C20 | A55-B4-C20 | A45-B1-C21 |
| A76-B2-C20 | A66-B3-C20 | A56-B4-C20 | A46-B1-C21 |
| A77-B2-C20 | A67-B3-C20 | A57-B4-C20 | A47-B1-C21 |
| A1-B3-C20 | A68-B3-C20 | A58-B4-C20 | A48-B1-C21 |
| A49-B1-C21 | A39-B2-C21 | A29-B3-C21 | A19-B4-C21 |
| A50-B1-C21 | A40-B2-C21 | A30-B3-C21 | A20-B4-C21 |
| A51-B1-C21 | A41-B2-C21 | A31-B3-C21 | A21-B4-C21 |
| A52-B1-C21 | A42-B2-C21 | A32-B3-C21 | A22-B4-C21 |
| A53-B1-C21 | A43-B2-C21 | A33-B3-C21 | A23-B4-C21 |
| A54-B1-C21 | A44-B2-C21 | A34-B3-C21 | A24-B4-C21 |
| A55-B1-C21 | A45-B2-C21 | A35-B3-C21 | A25-B4-C21 |
| A56-B1-C21 | A46-B2-C21 | A36-B3-C21 | A26-B4-C21 |
| A57-B1-C21 | A47-B2-C21 | A37-B3-C21 | A27-B4-C21 |
| A58-B1-C21 | A48-B2-C21 | A38-B3-C21 | A28-B4-C21 |
| A59-B1-C21 | A49-B2-C21 | A39-B3-C21 | A29-B4-C21 |
| A60-B1-C21 | A50-B2-C21 | A40-B3-C21 | A30-B4-C21 |
| A61-B1-C21 | A51-B2-C21 | A41-B3-C21 | A31-B4-C21 |
| A62-B1-C21 | A52-B2-C21 | A42-B3-C21 | A32-B4-C21 |
| A63-B1-C21 | A53-B2-C21 | A43-B3-C21 | A33-B4-C21 |
| A64-B1-C21 | A54-B2-C21 | A44-B3-C21 | A34-B4-C21 |
| A65-B1-C21 | A55-B2-C21 | A45-B3-C21 | A35-B4-C21 |
| A66-B1-C21 | A56-B2-C21 | A46-B3-C21 | A36-B4-C21 |
| A67-B1-C21 | A57-B2-C21 | A47-B3-C21 | A37-B4-C21 |
| A68-B1-C21 | A58-B2-C21 | A48-B3-C21 | A38-B4-C21 |
| A69-B1-C21 | A59-B2-C21 | A49-B3-C21 | A39-B4-C21 |
| A70-B1-C21 | A60-B2-C21 | A50-B3-C21 | A40-B4-C21 |
| A71-B1-C21 | A61-B2-C21 | A51-B3-C21 | A41-B4-C21 |
| A72-B1-C21 | A62-B2-C21 | A52-B3-C21 | A42-B4-C21 |
| A73-B1-C21 | A63-B2-C21 | A53-B3-C21 | A43-B4-C21 |
| A74-B1-C21 | A64-B2-C21 | A54-B3-C21 | A44-B4-C21 |
| A75-B1-C21 | A65-B2-C21 | A55-B3-C21 | A45-B4-C21 |
| A76-B1-C21 | A66-B2-C21 | A56-B3-C21 | A46-B4-C21 |
| A77-B1-C21 | A67-B2-C21 | A57-B3-C21 | A47-B4-C21 |
| A1-B2-C21 | A68-B2-C21 | A58-B3-C21 | A48-B4-C21 |
| A2-B2-C21 | A69-B2-C21 | A59-B3-C21 | A49-B4-C21 |
| A3-B2-C21 | A70-B2-C21 | A60-B3-C21 | A50-B4-C21 |
| A4-B2-C21 | A71-B2-C21 | A61-B3-C21 | A51-B4-C21 |
| A5-B2-C21 | A72-B2-C21 | A62-B3-C21 | A52-B4-C21 |
| A6-B2-C21 | A73-B2-C21 | A63-B3-C21 | A53-B4-C21 |
| A7-B2-C21 | A74-B2-C21 | A64-B3-C21 | A54-B4-C21 |
| A8-B2-C21 | A75-B2-C21 | A65-B3-C21 | A55-B4-C21 |
| A9-B2-C21 | A76-B2-C21 | A66-B3-C21 | A56-B4-C21 |
| A10-B2-C21 | A77-B2-C21 | A67-B3-C21 | A57-B4-C21 |
| A11-B2-C21 | A1-B3-C21 | A68-B3-C21 | A58-B4-C21 |
| A12-B2-C21 | A2-B3-C21 | A69-B3-C21 | A59-B4-C21 |
| A13-B2-C21 | A3-B3-C21 | A70-B3-C21 | A60-B4-C21 |
| A14-B2-C21 | A4-B3-C21 | A71-B3-C21 | A61-B4-C21 |
| A15-B2-C21 | A5-B3-C21 | A72-B3-C21 | A62-B4-C21 |
| A16-B2-C21 | A6-B3-C21 | A73-B3-C21 | A63-B4-C21 |
| A17-B2-C21 | A7-B3-C21 | A74-B3-C21 | A64-B4-C21 |
| A18-B2-C21 | A8-B3-C21 | A75-B3-C21 | A65-B4-C21 |
| A19-B2-C21 | A9-B3-C21 | A76-B3-C21 | A66-B4-C21 |

TABLE 4-continued

| | | | |
|---|---|---|---|
| A20-B2-C21 | A10-B3-C21 | A77-B3-C21 | A67-B4-C21 |
| A21-B2-C21 | A11-B3-C21 | A1-B4-C21 | A68-B4-C21 |
| A22-B2-C21 | A12-B3-C21 | A2-B4-C21 | A69-B4-C21 |
| A23-B2-C21 | A13-B3-C21 | A3-B4-C21 | A70-B4-C21 |
| A24-B2-C21 | A14-B3-C21 | A4-B4-C21 | A71-B4-C21 |
| A25-B2-C21 | A15-B3-C21 | A5-B4-C21 | A72-B4-C21 |
| A26-B2-C21 | A16-B3-C21 | A6-B4-C21 | A73-B4-C21 |
| A27-B2-C21 | A17-B3-C21 | A7-B4-C21 | A74-B4-C21 |
| A28-B2-C21 | A18-B3-C21 | A8-B4-C21 | A75-B4-C21 |
| A29-B2-C21 | A19-B3-C21 | A9-B4-C21 | A76-B4-C21 |
| A30-B2-C21 | A20-B3-C21 | A10-B4-C21 | A77-B4-C21 |
| A31-B2-C21 | A21-B3-C21 | A11-B4-C21 | A1-B1-C22 |
| A32-B2-C21 | A22-B3-C21 | A12-B4-C21 | A2-B1-C22 |
| A33-B2-C21 | A23-B3-C21 | A13-B4-C21 | A3-B1-C22 |
| A34-B2-C21 | A24-B3-C21 | A14-B4-C21 | A4-B1-C22 |
| A35-B2-C21 | A25-B3-C21 | A15-B4-C21 | A5-B1-C22 |
| A36-B2-C21 | A26-B3-C21 | A16-B4-C21 | A6-B1-C22 |
| A37-B2-C21 | A27-B3-C21 | A17-B4-C21 | A7-B1-C22 |
| A38-B2-C21 | A28-B3-C21 | A18-B4-C21 | A8-B1-C22 |
| A9-B1-C22 | A76-B1-C22 | A66-B2-C22 | A56-B3-C22 |
| A10-B1-C22 | A77-B1-C22 | A67-B2-C22 | A57-B3-C22 |
| A11-B1-C22 | A1-B2-C22 | A68-B2-C22 | A58-B3-C22 |
| A12-B1-C22 | A2-B2-C22 | A69-B2-C22 | A59-B3-C22 |
| A13-B1-C22 | A3-B2-C22 | A70-B2-C22 | A60-B3-C22 |
| A14-B1-C22 | A4-B2-C22 | A71-B2-C22 | A61-B3-C22 |
| A15-B1-C22 | A5-B2-C22 | A72-B2-C22 | A62-B3-C22 |
| A16-B1-C22 | A6-B2-C22 | A73-B2-C22 | A63-B3-C22 |
| A17-B1-C22 | A7-B2-C22 | A74-B2-C22 | A64-B3-C22 |
| A18-B1-C22 | A8-B2-C22 | A75-B2-C22 | A65-B3-C22 |
| A19-B1-C22 | A9-B2-C22 | A76-B2-C22 | A66-B3-C22 |
| A20-B1-C22 | A10-B2-C22 | A77-B2-C22 | A67-B3-C22 |
| A21-B1-C22 | A11-B2-C22 | A1-B3-C22 | A68-B3-C22 |
| A22-B1-C22 | A12-B2-C22 | A2-B3-C22 | A69-B3-C22 |
| A23-B1-C22 | A13-B2-C22 | A3-B3-C22 | A70-B3-C22 |
| A24-B1-C22 | A14-B2-C22 | A4-B3-C22 | A71-B3-C22 |
| A25-B1-C22 | A15-B2-C22 | A5-B3-C22 | A72-B3-C22 |
| A26-B1-C22 | A16-B2-C22 | A6-B3-C22 | A73-B3-C22 |
| A27-B1-C22 | A17-B2-C22 | A7-B3-C22 | A74-B3-C22 |
| A28-B1-C22 | A18-B2-C22 | A8-B3-C22 | A75-B3-C22 |
| A29-B1-C22 | A19-B2-C22 | A9-B3-C22 | A76-B3-C22 |
| A30-B1-C22 | A20-B2-C22 | A10-B3-C22 | A77-B3-C22 |
| A31-B1-C22 | A21-B2-C22 | A11-B3-C22 | A1-B4-C22 |
| A32-B1-C22 | A22-B2-C22 | A12-B3-C22 | A2-B4-C22 |
| A33-B1-C22 | A23-B2-C22 | A13-B3-C22 | A3-B4-C22 |
| A34-B1-C22 | A24-B2-C22 | A14-B3-C22 | A4-B4-C22 |
| A35-B1-C22 | A25-B2-C22 | A15-B3-C22 | A5-B4-C22 |
| A36-B1-C22 | A26-B2-C22 | A16-B3-C22 | A6-B4-C22 |
| A37-B1-C22 | A27-B2-C22 | A17-B3-C22 | A7-B4-C22 |
| A38-B1-C22 | A28-B2-C22 | A18-B3-C22 | A8-B4-C22 |
| A39-B1-C22 | A29-B2-C22 | A19-B3-C22 | A9-B4-C22 |
| A40-B1-C22 | A30-B2-C22 | A20-B3-C22 | A10-B4-C22 |
| A41-B1-C22 | A31-B2-C22 | A21-B3-C22 | A11-B4-C22 |
| A42-B1-C22 | A32-B2-C22 | A22-B3-C22 | A12-B4-C22 |
| A43-B1-C22 | A33-B2-C22 | A23-B3-C22 | A13-B4-C22 |
| A44-B1-C22 | A34-B2-C22 | A24-B3-C22 | A14-B4-C22 |
| A45-B1-C22 | A35-B2-C22 | A25-B3-C22 | A15-B4-C22 |
| A46-B1-C22 | A36-B2-C22 | A26-B3-C22 | A16-B4-C22 |
| A47-B1-C22 | A37-B2-C22 | A27-B3-C22 | A17-B4-C22 |
| A48-B1-C22 | A38-B2-C22 | A28-B3-C22 | A18-B4-C22 |
| A49-B1-C22 | A39-B2-C22 | A29-B3-C22 | A19-B4-C22 |
| A50-B1-C22 | A40-B2-C22 | A30-B3-C22 | A20-B4-C22 |
| A51-B1-C22 | A41-B2-C22 | A31-B3-C22 | A21-B4-C22 |
| A52-B1-C22 | A42-B2-C22 | A32-B3-C22 | A22-B4-C22 |
| A53-B1-C22 | A43-B2-C22 | A33-B3-C22 | A23-B4-C22 |
| A54-B1-C22 | A44-B2-C22 | A34-B3-C22 | A24-B4-C22 |
| A55-B1-C22 | A45-B2-C22 | A35-B3-C22 | A25-B4-C22 |
| A56-B1-C22 | A46-B2-C22 | A36-B3-C22 | A26-B4-C22 |
| A57-B1-C22 | A47-B2-C22 | A37-B3-C22 | A27-B4-C22 |
| A58-B1-C22 | A48-B2-C22 | A38-B3-C22 | A28-B4-C22 |
| A59-B1-C22 | A49-B2-C22 | A39-B3-C22 | A29-B4-C22 |
| A60-B1-C22 | A50-B2-C22 | A40-B3-C22 | A30-B4-C22 |
| A61-B1-C22 | A51-B2-C22 | A41-B3-C22 | A31-B4-C22 |
| A62-B1-C22 | A52-B2-C22 | A42-B3-C22 | A32-B4-C22 |
| A63-B1-C22 | A53-B2-C22 | A43-B3-C22 | A33-B4-C22 |
| A64-B1-C22 | A54-B2-C22 | A44-B3-C22 | A34-B4-C22 |
| A65-B1-C22 | A55-B2-C22 | A45-B3-C22 | A35-B4-C22 |
| A66-B1-C22 | A56-B2-C22 | A46-B3-C22 | A36-B4-C22 |
| A67-B1-C22 | A57-B2-C22 | A47-B3-C22 | A37-B4-C22 |
| A68-B1-C22 | A58-B2-C22 | A48-B3-C22 | A38-B4-C22 |

TABLE 4-continued

| | | | |
|---|---|---|---|
| A69-B1-C22 | A59-B2-C22 | A49-B3-C22 | A39-B4-C22 |
| A70-B1-C22 | A60-B2-C22 | A50-B3-C22 | A40-B4-C22 |
| A71-B1-C22 | A61-B2-C22 | A51-B3-C22 | A41-B4-C22 |
| A72-B1-C22 | A62-B2-C22 | A52-B3-C22 | A42-B4-C22 |
| A73-B1-C22 | A63-B2-C22 | A53-B3-C22 | A43-B4-C22 |
| A74-B1-C22 | A64-B2-C22 | A54-B3-C22 | A44-B4-C22 |
| A75-B1-C22 | A65-B2-C22 | A55-B3-C22 | A45-B4-C22 |
| A46-B4-C22 | A36-B1-C23 | A26-B2-C23 | A16-B3-C23 |
| A47-B4-C22 | A37-B1-C23 | A27-B2-C23 | A17-B3-C23 |
| A48-B4-C22 | A38-B1-C23 | A28-B2-C23 | A18-B3-C23 |
| A49-B4-C22 | A39-B1-C23 | A29-B2-C23 | A19-B3-C23 |
| A50-B4-C22 | A40-B1-C23 | A30-B2-C23 | A20-B3-C23 |
| A51-B4-C22 | A41-B1-C23 | A31-B2-C23 | A21-B3-C23 |
| A52-B4-C22 | A42-B1-C23 | A32-B2-C23 | A22-B3-C23 |
| A53-B4-C22 | A43-B1-C23 | A33-B2-C23 | A23-B3-C23 |
| A54-B4-C22 | A44-B1-C23 | A34-B2-C23 | A24-B3-C23 |
| A55-B4-C22 | A45-B1-C23 | A35-B2-C23 | A25-B3-C23 |
| A56-B4-C22 | A46-B1-C23 | A36-B2-C23 | A26-B3-C23 |
| A57-B4-C22 | A47-B1-C23 | A37-B2-C23 | A27-B3-C23 |
| A58-B4-C22 | A48-B1-C23 | A38-B2-C23 | A28-B3-C23 |
| A59-B4-C22 | A49-B1-C23 | A39-B2-C23 | A29-B3-C23 |
| A60-B4-C22 | A50-B1-C23 | A40-B2-C23 | A30-B3-C23 |
| A61-B4-C22 | A51-B1-C23 | A41-B2-C23 | A31-B3-C23 |
| A62-B4-C22 | A52-B1-C23 | A42-B2-C23 | A32-B3-C23 |
| A63-B4-C22 | A53-B1-C23 | A43-B2-C23 | A33-B3-C23 |
| A64-B4-C22 | A54-B1-C23 | A44-B2-C23 | A34-B3-C23 |
| A65-B4-C22 | A55-B1-C23 | A45-B2-C23 | A35-B3-C23 |
| A66-B4-C22 | A56-B1-C23 | A46-B2-C23 | A36-B3-C23 |
| A67-B4-C22 | A57-B1-C23 | A47-B2-C23 | A37-B3-C23 |
| A68-B4-C22 | A58-B1-C23 | A48-B2-C23 | A38-B3-C23 |
| A69-B4-C22 | A59-B1-C23 | A49-B2-C23 | A39-B3-C23 |
| A70-B4-C22 | A60-B1-C23 | A50-B2-C23 | A40-B3-C23 |
| A71-B4-C22 | A61-B2-C23 | A51-B2-C23 | A41-B3-C23 |
| A72-B4-C22 | A62-B1-C23 | A52-B2-C23 | A42-B3-C23 |
| A73-B4-C22 | A63-B1-C23 | A53-B2-C23 | A43-B3-C23 |
| A74-B4-C22 | A64-B1-C23 | A54-B2-C23 | A44-B3-C23 |
| A75-B4-C22 | A65-B1-C23 | A55-B2-C23 | A45-B3-C23 |
| A76-B4-C22 | A66-B1-C23 | A56-B2-C23 | A46-B3-C23 |
| A77-B4-C22 | A67-B1-C23 | A57-B2-C23 | A47-B3-C23 |
| A1-B1-C23 | A68-B1-C23 | A58-B2-C23 | A48-B3-C23 |
| A2-B1-C23 | A69-B1-C23 | A59-B2-C23 | A49-B3-C23 |
| A3-B1-C23 | A70-B1-C23 | A60-B2-C23 | A50-B3-C23 |
| A4-B1-C23 | A71-B1-C23 | A61-B2-C23 | A51-B3-C23 |
| A5-B1-C23 | A72-B1-C23 | A62-B2-C23 | A52-B3-C23 |
| A6-B1-C23 | A73-B1-C23 | A63-B2-C23 | A53-B3-C23 |
| A7-B1-C23 | A74-B1-C23 | A64-B2-C23 | A54-B3-C23 |
| A8-B1-C23 | A75-B1-C23 | A65-B2-C23 | A55-B3-C23 |
| A9-B1-C23 | A76-B1-C23 | A66-B2-C23 | A56-B3-C23 |
| A10-B1-C23 | A77-B1-C23 | A67-B2-C23 | A57-B3-C23 |
| A11-B1-C23 | A1-B2-C23 | A68-B2-C23 | A58-B3-C23 |
| A12-B1-C23 | A2-B2-C23 | A69-B2-C23 | A59-B3-C23 |
| A13-B1-C23 | A3-B2-C23 | A70-B2-C23 | A60-B3-C23 |
| A14-B1-C23 | A4-B2-C23 | A71-B2-C23 | A61-B3-C23 |
| A15-B1-C23 | A5-B2-C23 | A72-B2-C23 | A62-B3-C23 |
| A16-B1-C23 | A6-B2-C23 | A73-B2-C23 | A63-B3-C23 |
| A17-B1-C23 | A7-B2-C23 | A74-B2-C23 | A64-B3-C23 |
| A18-B1-C23 | A8-B2-C23 | A75-B2-C23 | A65-B3-C23 |
| A19-B1-C23 | A9-B2-C23 | A76-B2-C23 | A66-B3-C23 |
| A20-B1-C23 | A10-B2-C23 | A77-B2-C23 | A67-B3-C23 |
| A21-B1-C23 | A11-B2-C23 | A1-B3-C23 | A68-B3-C23 |
| A22-B1-C23 | A12-B2-C23 | A2-B3-C23 | A69-B3-C23 |
| A23-B1-C23 | A13-B2-C23 | A3-B3-C23 | A70-B3-C23 |
| A24-B1-C23 | A14-B2-C23 | A4-B3-C23 | A71-B3-C23 |
| A25-B1-C23 | A15-B2-C23 | A5-B3-C23 | A72-B3-C23 |
| A26-B1-C23 | A16-B2-C23 | A6-B3-C23 | A73-B3-C23 |
| A27-B1-C23 | A17-B2-C23 | A7-B3-C23 | A74-B3-C23 |
| A28-B1-C23 | A18-B2-C23 | A8-B3-C23 | A75-B3-C23 |
| A29-B1-C23 | A19-B2-C23 | A9-B3-C23 | A76-B3-C23 |
| A30-B1-C23 | A20-B2-C23 | A10-B3-C23 | A77-B3-C23 |
| A31-B1-C23 | A21-B2-C23 | A11-B3-C23 | A1-B4-C23 |
| A32-B1-C23 | A22-B2-C23 | A12-B3-C23 | A2-B4-C23 |
| A33-B1-C23 | A23-B2-C23 | A13-B3-C23 | A3-B4-C23 |
| A34-B1-C23 | A24-B2-C23 | A14-B3-C23 | A4-B4-C23 |
| A35-B1-C23 | A25-B2-C23 | A15-B3-C23 | A5-B4-C23 |
| A6-B4-C23 | A73-B4-C23 | A63-B1-C24 | A53-B2-C24 |
| A7-B4-C23 | A74-B4-C23 | A64-B1-C24 | A54-B2-C24 |
| A8-B4-C23 | A75-B4-C23 | A65-B1-C24 | A55-B2-C24 |
| A9-B4-C23 | A76-B4-c23 | A66-B1-C24 | A56-B2-C24 |
| A10-B4-C23 | A77-B4-C23 | A67-B1-C24 | A57-B2-C24 |

TABLE 4-continued

| | | | |
|---|---|---|---|
| A11-B4-C23 | A1-B1-C24 | A68-B1-C24 | A58-B2-C24 |
| A12-B4-C23 | A2-B1-C24 | A69-B1-C24 | A59-B2-C24 |
| A13-B4-C23 | A3-B1-C24 | A70-B1-C24 | A60-B2-C24 |
| A14-B4-C23 | A4-B1-C24 | A71-B1-C24 | A61-B2-C24 |
| A15-B4-C23 | A5-B1-C24 | A72-B1-C24 | A62-B2-C24 |
| A16-B4-C23 | A6-B1-C24 | A73-B1-C24 | A63-B2-C24 |
| A17-B4-C23 | A7-B1-C24 | A74-B1-C24 | A64-B2-C24 |
| A18-B4-C23 | A8-B1-C24 | A75-B1-C24 | A65-B2-C24 |
| A19-B4-C23 | A9-B1-C24 | A76-B1-C24 | A66-B2-C24 |
| A20-B4-C23 | A10-B1-C24 | A77-B1-C24 | A67-B2-C24 |
| A21-B4-C23 | A11-B1-C24 | A1-B2-C24 | A68-B2-C24 |
| A22-B4-C23 | A12-B1-C24 | A2-B2-C24 | A69-B2-C24 |
| A23-B4-C23 | A13-B1-C24 | A3-B2-C24 | A70-B2-C24 |
| A24-B4-C23 | A14-B1-C24 | A4-B2-C24 | A71-B2-C24 |
| A25-B4-C23 | A15-B1-C24 | A5-B2-C24 | A72-B2-C24 |
| A26-B4-C23 | A16-B1-C24 | A6-B2-C24 | A73-B2-C24 |
| A27-B4-C23 | A17-B1-C24 | A7-B2-C24 | A74-B2-C24 |
| A28-B4-C23 | A18-B1-C24 | A8-B2-C24 | A75-B2-C24 |
| A29-B4-C23 | A19-B1-C24 | A9-B2-C24 | A76-B2-C24 |
| A30-B4-C23 | A20-B1-C24 | A10-B2-C24 | A77-B2-C24 |
| A31-B4-C23 | A21-B1-C24 | A11-B2-C24 | A1-B3-C24 |
| A32-B4-C23 | A22-B1-C24 | A12-B2-C24 | A2-B3-C24 |
| A33-B4-C23 | A23-B1-C24 | A13-B2-C24 | A3-B3-C24 |
| A34-B4-C23 | A24-B1-C24 | A14-B2-C24 | A4-B3-C24 |
| A35-B4-C23 | A25-B1-C24 | A15-B2-C24 | A5-B3-C24 |
| A36-B4-C23 | A26-B1-C24 | A16-B2-C24 | A6-B3-C24 |
| A37-B4-C23 | A27-B1-C24 | A17-B2-C24 | A7-B3-C24 |
| A38-B4-C23 | A28-B1-C24 | A18-B2-C24 | A8-B3-C24 |
| A39-B4-C23 | A29-B1-C24 | A19-B2-C24 | A9-B3-C24 |
| A40-B4-C23 | A30-B1-C24 | A20-B2-C24 | A10-B3-C24 |
| A41-B4-C23 | A31-B1-C24 | A21-B2-C24 | A11-B3-C24 |
| A42-B4-C23 | A32-B1-C24 | A22-B2-C24 | A12-B3-C24 |
| A43-B4-C23 | A33-B1-C24 | A23-B2-C24 | A13-B3-C24 |
| A44-B4-C23 | A34-B1-C24 | A24-B2-C24 | A14-B3-C24 |
| A45-B4-C23 | A35-B1-C24 | A25-B2-C24 | A15-B3-C24 |
| A46-B4-C23 | A36-B1-C24 | A26-B2-C24 | A16-B3-C24 |
| A47-B4-C23 | A37-B1-C24 | A27-B2-C24 | A17-B3-C24 |
| A48-B4-C23 | A38-B1-C24 | A28-B2-C24 | A18-B3-C24 |
| A49-B4-C23 | A39-B1-C24 | A29-B2-C24 | A19-B3-C24 |
| A50-B4-C23 | A40-B1-C24 | A30-B2-C24 | A20-B3-C24 |
| A51-B4-C23 | A41-B1-C24 | A31-B2-C24 | A21-B3-C24 |
| A52-B4-C23 | A42-B1-C24 | A32-B2-C24 | A22-B3-C24 |
| A53-B4-C23 | A43-B1-C24 | A33-B2-C24 | A23-B3-C24 |
| A54-B4-C23 | A44-B1-C24 | A34-B2-C24 | A24-B3-C24 |
| A55-B4-C23 | A45-B1-C24 | A35-B2-C24 | A25-B3-C24 |
| A56-B4-C23 | A46-B1-C24 | A36-B2-C24 | A26-B3-C24 |
| A57-B4-C23 | A47-B1-C24 | A37-B2-C24 | A27-B3-C24 |
| A58-B4-C23 | A48-B1-C24 | A38-B2-C24 | A28-B3-C24 |
| A59-B4-C23 | A49-B1-C24 | A39-B2-C24 | A29-B3-C24 |
| A60-B4-C23 | A50-B1-C24 | A40-B2-C24 | A30-B3-C24 |
| A61-B4-C23 | A51-B1-C24 | A41-B2-C24 | A31-B3-C24 |
| A62-B4-C23 | A52-B1-C24 | A42-B2-C24 | A32-B3-C24 |
| A63-B4-C23 | A53-B1-C24 | A43-B2-C24 | A33-B3-C24 |
| A64-B4-C23 | A54-B1-C24 | A44-B2-C24 | A34-B3-C24 |
| A65-B4-C23 | A55-B1-C24 | A45-B2-C24 | A35-B3-C24 |
| A66-B4-C23 | A56-B1-C24 | A46-B2-C24 | A36-B3-C24 |
| A67-B4-C23 | A57-B1-C24 | A47-B2-C24 | A37-B3-C24 |
| A68-B4-C23 | A58-B1-C24 | A48-B2-C24 | A38-B3-C24 |
| A69-B4-C23 | A59-B1-C24 | A49-B2-C24 | A39-B3-C24 |
| A70-B4-C23 | A60-B1-C24 | A50-B2-C24 | A40-B3-C24 |
| A71-B4-C23 | A61-B1-C24 | A51-B2-C24 | A41-B3-C24 |
| A72-B4-C23 | A62-B1-C24 | A52-B2-C24 | A42-B3-C24 |
| A43-B3-C24 | A33-B4-C24 | A23-B1-C25 | A13-B2-C25 |
| A44-B3-C24 | A34-B4-C24 | A24-B1-C25 | A14-B2-C25 |
| A45-B3-C24 | A35-B4-C24 | A25-B1-C25 | A15-B2-C25 |
| A46-B3-C24 | A36-B4-C24 | A26-B1-C25 | A16-B2-C25 |
| A47-B3-C24 | A37-B4-C24 | A27-B1-C25 | A17-B2-C25 |
| A48-B3-C24 | A38-B4-C24 | A28-B1-C25 | A18-B2-C25 |
| A49-B3-C24 | A39-B4-C24 | A29-B1-C25 | A19-B2-C25 |
| A50-B3-C24 | A40-B4-C24 | A30-B1-C25 | A20-B2-C25 |
| A51-B3-C24 | A41-B4-C24 | A31-B1-C25 | A21-B2-C25 |
| A52-B3-C24 | A42-B4-C24 | A32-B1-C25 | A22-B2-C25 |
| A53-B3-C24 | A43-B4-C24 | A33-B1-C25 | A23-B2-C25 |
| A54-B3-C24 | A44-B4-C24 | A34-B1-C25 | A24-B2-C25 |
| A55-B3-C24 | A45-B4-C24 | A35-B1-C25 | A25-B2-C25 |
| A56-B3-C24 | A46-B4-C24 | A36-B1-C25 | A26-B2-C25 |
| A57-B3-C24 | A47-B4-C24 | A37-B1-C25 | A27-B2-C25 |
| A58-B3-C24 | A48-B4-C24 | A38-B1-C25 | A28-B2-C25 |
| A59-B3-C24 | A49-B4-C24 | A39-B1-C25 | A29-B2-C25 |

TABLE 4-continued

| | | | |
|---|---|---|---|
| A60-B3-C24 | A50-B4-C24 | A40-B1-C25 | A30-B2-C25 |
| A61-B3-C24 | A51-B4-C24 | A41-B1-C25 | A31-B2-C25 |
| A62-B3-C24 | A52-B4-C24 | A42-B1-C25 | A32-B2-C25 |
| A63-B3-C24 | A53-B4-C24 | A43-B1-C25 | A33-B2-C25 |
| A64-B3-C24 | A54-B4-C24 | A44-B1-C25 | A34-B2-C25 |
| A65-B3-C24 | A55-B4-C24 | A45-B1-C25 | A35-B2-C25 |
| A66-B3-C24 | A56-B4-C24 | A46-B1-C25 | A36-B2-C25 |
| A67-B3-C24 | A57-B4-C24 | A47-B1-C25 | A37-B2-C25 |
| A68-B3-C24 | A58-B4-C24 | A48-B1-C25 | A38-B2-C25 |
| A69-B3-C24 | A59-B4-C24 | A49-B1-C25 | A39-B2-C25 |
| A70-B3-C24 | A60-B4-C24 | A50-B1-C25 | A40-B2-C25 |
| A71-B3-C24 | A61-B4-C24 | A51-B1-C25 | A41-B2-C25 |
| A72-B3-C24 | A62-B4-C24 | A52-B1-C25 | A42-B2-C25 |
| A73-B3-C24 | A63-B4-C24 | A53-B1-C25 | A43-B2-C25 |
| A74-B3-C24 | A64-B4-C24 | A54-B1-C25 | A44-B2-C25 |
| A75-B3-C24 | A65-B4-C24 | A55-B1-C25 | A45-B2-C25 |
| A76-B3-C24 | A66-B4-C24 | A56-B1-C25 | A46-B2-C25 |
| A77-B3-C24 | A67-B4-C24 | A57-B1-C25 | A47-B2-C25 |
| A1-B4-C24 | A68-B4-C24 | A58-B1-C25 | A48-B2-C25 |
| A2-B4-C24 | A69-B4-C24 | A59-B1-C25 | A49-B2-C25 |
| A3-B4-C24 | A70-B4-C24 | A60-B1-C25 | A50-B2-C25 |
| A4-B4-C24 | A71-B4-C24 | A61-B1-C25 | A51-B2-C25 |
| A5-B4-C24 | A72-B4-C24 | A62-B1-C25 | A52-B2-C25 |
| A6-B4-C24 | A73-B4-C24 | A63-B1-C25 | A53-B2-C25 |
| A7-B4-C24 | A74-B4-C24 | A64-B1-C25 | A54-B2-C25 |
| A8-B4-C24 | A75-B4-C24 | A65-B1-C25 | A55-B2-C25 |
| A9-B4-C24 | A76-B4-C24 | A66-B1-C25 | A56-B2-C25 |
| A10-B4-C24 | A77-B4-C24 | A67-B1-C25 | A57-B2-C25 |
| A11-B4-C24 | A1-B1-C25 | A68-B1-C25 | A58-B2-C25 |
| A12-B4-C24 | A2-B1-C25 | A69-B1-C25 | A59-B2-C25 |
| A13-B4-C24 | A3-B1-C25 | A70-B1-C25 | A60-B2-C25 |
| A14-B4-C24 | A4-B1-C25 | A71-B1-C25 | A61-B2-C25 |
| A15-B4-C24 | A5-B1-C25 | A72-B1-C25 | A62-B2-C25 |
| A16-B4-C24 | A6-B1-C25 | A73-B1-C25 | A63-B2-C25 |
| A17-B4-C24 | A7-B1-C25 | A74-B1-C25 | A64-B2-C25 |
| A18-B4-C24 | A8-B1-C25 | A75-B1-C25 | A65-B2-C25 |
| A19-B4-C24 | A9-B1-C25 | A76-B1-C25 | A66-B2-C25 |
| A20-B4-C24 | A10-B1-C25 | A77-B1-C25 | A67-B2-C25 |
| A21-B4-C24 | A11-B1-C25 | A1-B2-C25 | A68-B2-C25 |
| A22-B4-C24 | A12-B1-C25 | A2-B2-C25 | A69-B2-C25 |
| A23-B4-C24 | A13-B1-C25 | A3-B2-C25 | A70-B2-C25 |
| A24-B4-C24 | A14-B1-C25 | A4-B2-C25 | A71-B2-C25 |
| A25-B4-C24 | A15-B1-C25 | A5-B2-C25 | A72-B2-C25 |
| A26-B4-C24 | A16-B1-C25 | A6-B2-C25 | A73-B2-C25 |
| A27-B4-C24 | A17-B1-C25 | A7-B2-C25 | A74-B2-C25 |
| A28-B4-C24 | A18-B1-C25 | A8-B2-C25 | A75-B2-C25 |
| A29-B4-C24 | A19-B1-C25 | A9-B2-C25 | A76-B2-C25 |
| A30-B4-C24 | A20-B1-C25 | A10-B2-C25 | A77-B2-C25 |
| A31-B4-C24 | A21-B1-C25 | A11-B2-C25 | A1-B3-C25 |
| A32-B4-C24 | A22-B1-C25 | A12-B2-C25 | A2-B3-C25 |
| A3-B3-C25 | A70-B3-C25 | A60-B4-C25 | A50-B1-C26 |
| A4-B3-C25 | A71-B3-C25 | A61-B4-C25 | A51-B1-C26 |
| A5-B3-C25 | A72-B3-C25 | A62-B4-C25 | A52-B1-C26 |
| A6-B3-C25 | A73-B3-C25 | A63-B4-C25 | A53-B1-C26 |
| A7-B3-C25 | A74-B3-C25 | A64-B4-C25 | A54-B1-C26 |
| A8-B3-C25 | A75-B3-C25 | A65-B4-C25 | A55-B1-C26 |
| A9-B3-C25 | A76-B3-C25 | A66-B4-C25 | A56-B1-C26 |
| A10-B3-C25 | A77-B3-C25 | A67-B4-C25 | A57-B1-C26 |
| A11-B3-C25 | A1-B4-C25 | A68-B4-C25 | A58-B1-C26 |
| A12-B3-C25 | A2-B4-C25 | A69-B4-C25 | A59-B1-C26 |
| A13-B3-C25 | A3-B4-C25 | A70-B4-C25 | A60-B1-C26 |
| A14-B3-C25 | A4-B4-C25 | A71-B4-C25 | A61-B1-C26 |
| A15-B3-C25 | A5-B4-C25 | A72-B4-C25 | A62-B1-C26 |
| A16-B3-C25 | A6-B4-C25 | A73-B4-C25 | A63-B1-C26 |
| A17-B3-C25 | A7-B4-C25 | A74-B4-C25 | A64-B1-C26 |
| A18-B3-C25 | A8-B4-C25 | A75-B4-C25 | A65-B1-C26 |
| A19-B3-C25 | A9-B4-C25 | A76-B4-C25 | A66-B1-C26 |
| A20-B3-C25 | A10-B4-C25 | A77-B4-C25 | A67-B1-C26 |
| A21-B3-C25 | A11-B4-C25 | A1-B1-C26 | A68-B1-C26 |
| A22-B3-C25 | A12-B4-C25 | A2-B1-C26 | A69-B1-C26 |
| A23-B3-C25 | A13-B4-C25 | A3-B1-C26 | A70-B1-C26 |
| A24-B3-C25 | A14-B4-C25 | A4-B1-C26 | A71-B1-C26 |
| A25-B3-C25 | A15-B4-C25 | A5-B1-C26 | A72-B1-C26 |
| A26-B3-C25 | A16-B4-C25 | A6-B1-C26 | A73-B1-C26 |
| A27-B3-C25 | A17-B4-C25 | A7-B1-C26 | A74-B1-C26 |
| A28-B3-C25 | A18-B4-C25 | A8-B1-C26 | A75-B1-C26 |
| A29-B3-C25 | A19-B4-C25 | A9-B1-C26 | A76-B1-C26 |
| A30-B3-C25 | A20-B4-C25 | A10-B1-C26 | A77-B1-C26 |
| A31-B3-C25 | A21-B4-C25 | A11-B1-C26 | A1-B2-C26 |
| A32-B3-C25 | A22-B4-C25 | A12-B1-C26 | A2-B2-C26 |
| A33-B3-C25 | A23-B4-C25 | A13-B1-C26 | A3-B2-C26 |
| A34-B3-C25 | A24-B4-C25 | A14-B1-C26 | A4-B2-C26 |
| A35-B3-C25 | A25-B4-C25 | A15-B1-C26 | A5-B2-C26 |
| A36-B3-C25 | A26-B4-C25 | A16-B1-C26 | A6-B2-C26 |
| A37-B3-C25 | A27-B4-C25 | A17-B1-C26 | A7-B2-C26 |
| A38-B3-C25 | A28-B4-C25 | A18-B1-C26 | A8-B2-C26 |
| A39-B3-C25 | A29-B4-C25 | A19-B1-C26 | A9-B2-C26 |
| A40-B3-C25 | A30-B4-C25 | A20-B1-C26 | A10-B2-C26 |
| A41-B3-C25 | A31-B4-C25 | A21-B1-C26 | A11-B2-C26 |
| A42-B3-C25 | A32-B4-C25 | A22-B1-C26 | A12-B2-C26 |
| A43-B3-C25 | A33-B4-C25 | A23-B1-C26 | A13-B2-C26 |
| A44-B3-C25 | A34-B4-C25 | A24-B1-C26 | A14-B2-C26 |
| A45-B3-C25 | A35-B4-C25 | A25-B1-C26 | A15-B2-C26 |
| A46-B3-C25 | A36-B4-C25 | A26-B1-C26 | A16-B2-C26 |
| A47-B3-C25 | A37-B4-C25 | A27-B1-C26 | A17-B2-C26 |
| A48-B3-C25 | A38-B4-C25 | A28-B1-C26 | A18-B2-C26 |
| A49-B3-C25 | A39-B4-C25 | A29-B1-C26 | A19-B2-C26 |
| A50-B3-C25 | A40-B4-C25 | A30-B1-C26 | A20-B2-C26 |
| A51-B3-C25 | A41-B4-C25 | A31-B1-C26 | A21-B2-C26 |
| A52-B3-C25 | A42-B4-C25 | A32-B1-C26 | A22-B2-C26 |
| A53-B3-C25 | A43-B4-C25 | A33-B1-C26 | A23-B2-C26 |
| A54-B3-C25 | A44-B4-C25 | A34-B1-C26 | A24-B2-C26 |
| A55-B3-C25 | A45-B4-C25 | A35-B1-C26 | A25-B2-C26 |
| A56-B3-C25 | A46-B4-C25 | A36-B1-C26 | A26-B2-C26 |
| A57-B3-C25 | A47-B4-C25 | A37-B1-C26 | A27-B2-C26 |
| A58-B3-C25 | A48-B4-C25 | A38-B1-C26 | A28-B2-C26 |
| A59-B3-C25 | A49-B4-C25 | A39-B1-C26 | A29-B2-C26 |
| A60-B3-C25 | A50-B4-C25 | A40-B1-C26 | A30-B2-C26 |
| A61-B3-C25 | A51-B4-C25 | A41-B1-C26 | A31-B2-C26 |
| A62-B3-C25 | A52-B4-C25 | A42-B1-C26 | A32-B2-C26 |
| A63-B3-C25 | A53-B4-C25 | A43-B1-C26 | A33-B2-C26 |
| A64-B3-C25 | A54-B4-C25 | A44-B1-C26 | A34-B2-C26 |
| A65-B3-C25 | A55-B4-C25 | A45-B1-C26 | A35-B2-C26 |
| A66-B3-C25 | A56-B4-C25 | A46-B1-C26 | A36-B2-C26 |
| A67-B3-C25 | A57-B4-C25 | A47-B1-C26 | A37-B2-C26 |
| A68-B3-C25 | A58-B4-C25 | A48-B1-C26 | A38-B2-C26 |
| A69-B3-C25 | A59-B4-C25 | A49-B1-C26 | A39-B2-C26 |
| A40-B2-C26 | A30-B3-C26 | A20-B4-C26 | A10-B1-C27 |
| A41-B2-C26 | A31-B3-C26 | A21-B4-C26 | A11-B1-C27 |
| A42-B2-C26 | A32-B3-C26 | A22-B4-C26 | A12-B1-C27 |
| A43-B2-C26 | A33-B3-C26 | A23-B4-C26 | A13-B1-C27 |
| A44-B2-C26 | A34-B3-C26 | A24-B4-C26 | A14-B1-C27 |
| A45-B2-C26 | A35-B3-C26 | A25-B4-C26 | A15-B1-C27 |
| A46-B2-C26 | A36-B3-C26 | A26-B4-C26 | A16-B1-C27 |
| A47-B2-C26 | A37-B3-C26 | A27-B4-C26 | A17-B1-C27 |
| A48-B2-C26 | A38-B3-C26 | A28-B4-C26 | A18-B1-C27 |
| A49-B2-C26 | A39-B3-C26 | A29-B4-C26 | A19-B1-C27 |
| A50-B2-C26 | A40-B3-C26 | A30-B4-C26 | A20-B1-C27 |
| A51-B2-C26 | A41-B3-C26 | A31-B4-C26 | A21-B1-C27 |
| A52-B2-C26 | A42-B3-C26 | A32-B4-C26 | A22-B1-C27 |
| A53-B2-C26 | A43-B3-C26 | A33-B4-C26 | A23-B1-C27 |
| A54-B2-C26 | A44-B3-C26 | A34-B4-C26 | A24-B1-C27 |
| A55-B2-C26 | A45-B3-C26 | A35-B4-C26 | A25-B1-C27 |
| A56-B2-C26 | A46-B3-C26 | A36-B4-C26 | A26-B1-C27 |
| A57-B2-C26 | A47-B3-C26 | A37-B4-C26 | A27-B1-C27 |
| A58-B2-C26 | A48-B3-C26 | A38-B4-C26 | A28-B1-C27 |
| A59-B2-C26 | A49-B3-C26 | A39-B4-C26 | A29-B1-C27 |
| A60-B2-C26 | A50-B3-C26 | A40-B4-C26 | A30-B1-C27 |
| A61-B2-C26 | A51-B3-C26 | A41-B4-C26 | A31-B1-C27 |
| A62-B2-C26 | A52-B3-C26 | A42-B4-C26 | A32-B1-C27 |
| A63-B2-C26 | A53-B3-C26 | A43-B4-C26 | A33-B1-C27 |
| A64-B2-C26 | A54-B3-C26 | A44-B4-C26 | A34-B1-C27 |
| A65-B2-C26 | A55-B3-C26 | A45-B4-C26 | A35-B1-C27 |
| A66-B2-C26 | A56-B3-C26 | A46-B4-C26 | A36-B1-C27 |
| A67-B2-C26 | A57-B3-C26 | A47-B4-C26 | A37-B1-C27 |
| A68-B2-C26 | A58-B3-C26 | A48-B4-C26 | A38-B1-C27 |
| A69-B2-C26 | A59-B3-C26 | A49-B4-C26 | A39-B1-C27 |
| A70-B2-C26 | A60-B3-C26 | A50-B4-C26 | A40-B1-C27 |
| A71-B2-C26 | A61-B3-C26 | A51-B4-C26 | A41-B1-C27 |
| A72-B2-C26 | A62-B3-C26 | A52-B4-C26 | A42-B1-C27 |
| A73-B2-C26 | A63-B3-C26 | A53-B4-C26 | A43-B1-C27 |
| A74-B2-C26 | A64-B3-C26 | A54-B4-C26 | A44-B1-C27 |
| A75-B2-C26 | A65-B3-C26 | A55-B4-C26 | A45-B1-C27 |
| A76-B2-C26 | A66-B3-C26 | A56-B4-C26 | A46-B1-C27 |
| A77-B2-C26 | A67-B3-C26 | A57-B4-C26 | A47-B1-C27 |
| A1-B3-C26 | A68-B3-C26 | A58-B4-C26 | A48-B1-C27 |
| A2-B3-C26 | A69-B3-C26 | A59-B4-C26 | A49-B1-C27 |
| A3-B3-C26 | A70-B3-C26 | A60-B4-C26 | A50-B1-C27 |

TABLE 4-continued

| | | | |
|---|---|---|---|
| A4-B3-C26 | A71-B3-C26 | A61-B4-C26 | A51-B1-C27 |
| A5-B3-C26 | A72-B3-C26 | A62-B4-C26 | A52-B1-C27 |
| A6-B3-C26 | A73-B3-C26 | A63-B4-C26 | A53-B1-C27 |
| A7-B3-C26 | A74-B3-C26 | A64-B4-C26 | A54-B1-C27 |
| A8-B3-C26 | A75-B3-C26 | A65-B4-C26 | A55-B1-C27 |
| A9-B3-C26 | A76-B3-C26 | A66-B4-C26 | A56-B1-C27 |
| A10-B3-C26 | A77-B3-C26 | A67-B4-C26 | A57-B1-C27 |
| A11-B3-C26 | A1-B4-C26 | A68-B4-C26 | A58-B1-C27 |
| A12-B3-C26 | A2-B4-C26 | A69-B4-C26 | A59-B1-C27 |
| A13-B3-C26 | A3-B4-C26 | A70-B4-C26 | A60-B1-C27 |
| A14-B3-C26 | A4-B4-C26 | A71-B4-C26 | A61-B1-C27 |
| A15-B3-C26 | A5-B4-C26 | A72-B4-C26 | A62-B1-C27 |
| A16-B3-C26 | A6-B4-C26 | A73-B4-C26 | A63-B1-C27 |
| A17-B3-C26 | A7-B4-C26 | A74-B4-C26 | A64-B1-C27 |
| A18-B3-C26 | A8-B4-C26 | A75-B4-C26 | A65-B1-C27 |
| A19-B3-C26 | A9-B4-C26 | A76-B4-C26 | A66-B1-C27 |
| A20-B3-C26 | A10-B4-C26 | A77-B4-C26 | A67-B1-C27 |
| A21-B3-C26 | A11-B4-C26 | A1-B1-C27 | A68-B1-C27 |
| A22-B3-C26 | A12-B4-C26 | A2-B1-C27 | A69-B1-C27 |
| A23-B3-C26 | A13-B4-C26 | A3-B1-C27 | A70-B1-C27 |
| A24-B3-C26 | A14-B4-C26 | A4-B1-C27 | A71-B1-C27 |
| A25-B3-C26 | A15-B4-C26 | A5-B1-C27 | A72-B1-C27 |
| A26-B3-C26 | A16-B4-C26 | A6-B1-C27 | A73-B1-C27 |
| A27-B3-C26 | A17-B4-C26 | A7-B1-C27 | A74-B1-C27 |
| A28-B3-C26 | A18-B4-C26 | A8-B1-C27 | A75-B1-C27 |
| A29-B3-C26 | A19-B4-C26 | A9-B1-C27 | A76-B1-C27 |
| A77-B1-C27 | A67-B2-C27 | A57-B3-C27 | A47-B4-C27 |
| A1-B2-C27 | A68-B2-C27 | A58-B3-C27 | A48-B4-C27 |
| A2-B2-C27 | A69-B2-C27 | A59-B3-C27 | A49-B4-C27 |
| A3-B2-C27 | A70-B2-C27 | A60-B3-C27 | A50-B4-C27 |
| A4-B2-C27 | A71-B2-C27 | A61-B3-C27 | A51-B4-C27 |
| A5-B2-C27 | A72-B2-C27 | A62-B3-C27 | A52-B4-C27 |
| A6-B2-C27 | A73-B2-C27 | A63-B3-C27 | A53-B4-C27 |
| A7-B2-C27 | A74-B2-C27 | A64-B3-C27 | A54-B4-C27 |
| A8-B2-C27 | A75-B2-C27 | A65-B3-C27 | A55-B4-C27 |
| A9-B2-C27 | A76-B2-C27 | A66-B3-C27 | A56-B4-C27 |
| A10-B2-C27 | A77-B2-C27 | A67-B3-C27 | A57-B4-C27 |
| A11-B2-C27 | A1-B3-C27 | A68-B3-C27 | A58-B4-C27 |
| A12-B2-C27 | A2-B3-C27 | A69-B3-C27 | A59-B4-C27 |
| A13-B2-C27 | A3-B3-C27 | A70-B3-C27 | A60-B4-C27 |
| A14-B2-C27 | A4-B3-C27 | A71-B3-C27 | A61-B4-C27 |
| A15-B2-C27 | A5-B3-C27 | A72-B3-C27 | A62-B4-C27 |
| A16-B2-C27 | A6-B3-C27 | A73-B3-C27 | A63-B4-C27 |
| A17-B2-C27 | A7-B3-C27 | A74-B3-C27 | A64-B4-C27 |
| A18-B2-C27 | A8-B3-C27 | A75-B3-C27 | A65-B4-C27 |
| A19-B2-C27 | A9-B3-C27 | A76-B3-C27 | A66-B4-C27 |
| A20-B2-C27 | A10-B3-C27 | A77-B3-C27 | A67-B4-C27 |
| A21-B2-C27 | A11-B3-C27 | A1-B4-C27 | A68-B4-C27 |
| A22-B2-C27 | A12-B3-C27 | A2-B4-C27 | A69-B4-C27 |
| A23-B2-C27 | A13-B3-C27 | A3-B4-C27 | A70-B4-C27 |
| A24-B2-C27 | A14-B3-C27 | A4-B4-C27 | A71-B4-C27 |
| A25-B2-C27 | A15-B3-C27 | A5-B4-C27 | A72-B4-C27 |
| A26-B2-C27 | A16-B3-C27 | A6-B4-C27 | A73-B4-C27 |
| A27-B2-C27 | A17-B3-C27 | A7-B4-C27 | A74-B4-C27 |
| A28-B2-C27 | A18-B3-C27 | A8-B4-C27 | A75-B4-C27 |
| A29-B2-C27 | A19-B3-C27 | A9-B4-C27 | A76-B4-C27 |
| A30-B2-C27 | A20-B3-C27 | A10-B4-C27 | A77-B4-C27 |
| A31-B2-C27 | A21-B3-C27 | A11-B4-C27 | A1-B1-C28 |
| A32-B2-C27 | A22-B3-C27 | A12-B4-C27 | A2-B1-C28 |
| A33-B2-C27 | A23-B3-C27 | A13-B4-C27 | A3-B1-C28 |
| A34-B2-C27 | A24-B3-C27 | A14-B4-C27 | A4-B1-C28 |
| A35-B2-C27 | A25-B3-C27 | A15-B4-C27 | A5-B1-C28 |
| A36-B2-C27 | A26-B3-C27 | A16-B4-C27 | A6-B1-C28 |
| A37-B2-C27 | A27-B3-C27 | A17-B4-C27 | A7-B1-C28 |
| A38-B2-C27 | A28-B3-C27 | A18-B4-C27 | A8-B1-C28 |
| A39-B2-C27 | A29-B3-C27 | A19-B4-C27 | A9-B1-C28 |
| A40-B2-C27 | A30-B3-C27 | A20-B4-C27 | A10-B1-C28 |
| A41-B2-C27 | A31-B3-C27 | A21-B4-C27 | A11-B1-C28 |
| A42-B2-C27 | A32-B3-C27 | A22-B4-C27 | A12-B1-C28 |
| A43-B2-C27 | A33-B3-C27 | A23-B4-C27 | A13-B1-C28 |
| A44-B2-C27 | A34-B3-C27 | A24-B4-C27 | A14-B1-C28 |
| A45-B2-C27 | A35-B3-C27 | A25-B4-C27 | A15-B1-C28 |
| A46-B2-C27 | A36-B3-C27 | A26-B4-C27 | A16-B1-C28 |
| A47-B2-C27 | A37-B3-C27 | A27-B4-C27 | A17-B1-C28 |
| A48-B2-C27 | A38-B3-C27 | A28-B4-C27 | A18-B1-C28 |
| A49-B2-C27 | A39-B3-C27 | A29-B4-C27 | A19-B1-C28 |
| A50-B2-C27 | A40-B3-C27 | A30-B4-C27 | A20-B1-C28 |
| A51-B2-C27 | A41-B3-C27 | A31-B4-C27 | A21-B1-C28 |
| A52-B2-C27 | A42-B3-C27 | A32-B4-C27 | A22-B1-C28 |
| A53-B2-C27 | A43-B3-C27 | A33-B4-C27 | A23-B1-C28 |
| A54-B2-C27 | A44-B3-C27 | A34-B4-C27 | A24-B1-C28 |
| A55-B2-C27 | A45-B3-C27 | A35-B4-C27 | A25-B1-C28 |
| A56-B2-C27 | A46-B3-C27 | A36-B4-C27 | A26-B1-C28 |
| A57-B2-C27 | A47-B3-C27 | A37-B4-C27 | A27-B1-C28 |
| A58-B2-C27 | A48-B3-C27 | A38-B4-C27 | A28-B1-C28 |
| A59-B2-C27 | A49-B3-C27 | A39-B4-C27 | A29-B1-C28 |
| A60-B2-C27 | A50-B3-C27 | A40-B4-C27 | A30-B1-C28 |
| A61-B2-C27 | A51-B3-C27 | A41-B4-C27 | A31-B1-C28 |
| A62-B2-C27 | A52-B3-C27 | A42-B4-C27 | A32-B1-C28 |
| A63-B2-C27 | A53-B3-C27 | A43-B4-C27 | A33-B1-C28 |
| A64-B2-C27 | A54-B3-C27 | A44-B4-C27 | A34-B1-C28 |
| A65-B2-C27 | A55-B3-C27 | A45-B4-C27 | A35-B1-C28 |
| A66-B2-C27 | A56-B3-C27 | A46-B4-C27 | A36-B1-C28 |
| A37-B1-C28 | A27-B2-C28 | A17-B3-C28 | A7-B4-C28 |
| A38-B1-C28 | A28-B2-C28 | A18-B3-C28 | A8-B4-C28 |
| A39-B1-C28 | A29-B2-C28 | A19-B3-C28 | A9-B4-C28 |
| A40-B1-C28 | A30-B2-C28 | A20-B3-C28 | A10-B4-C28 |
| A41-B1-C28 | A31-B2-C28 | A21-B3-C28 | A11-B4-C28 |
| A42-B1-C28 | A32-B2-C28 | A22-B3-C28 | A12-B4-C28 |
| A43-B1-C28 | A33-B2-C28 | A23-B3-C28 | A13-B4-C28 |
| A44-B1-C28 | A34-B2-C28 | A24-B3-C28 | A14-B4-C28 |
| A45-B1-C28 | A35-B2-C28 | A25-B3-C28 | A15-B4-C28 |
| A46-B1-C28 | A36-B2-C28 | A26-B3-C28 | A16-B4-C28 |
| A47-B1-C28 | A37-B2-C28 | A27-B3-C28 | A17-B4-C28 |
| A48-B1-C28 | A38-B2-C28 | A28-B3-C28 | A18-B4-C28 |
| A49-B1-C28 | A39-B2-C28 | A29-B3-C28 | A19-B4-C28 |
| A50-B1-C28 | A40-B2-C28 | A30-B3-C28 | A20-B4-C28 |
| A51-B1-C28 | A41-B2-C28 | A31-B3-C28 | A21-B4-C28 |
| A52-B1-C28 | A42-B2-C28 | A32-B3-C28 | A22-B4-C28 |
| A53-B1-C28 | A43-B2-C28 | A33-B3-C28 | A23-B4-C28 |
| A54-B1-C28 | A44-B2-C28 | A34-B3-C28 | A24-B4-C28 |
| A55-B1-C28 | A45-B2-C28 | A35-B3-C28 | A25-B4-C28 |
| A56-B1-C28 | A46-B2-C28 | A36-B3-C28 | A26-B4-C28 |
| A57-B1-C28 | A47-B2-C28 | A37-B3-C28 | A27-B4-C28 |
| A58-B1-C28 | A48-B2-C28 | A38-B3-C28 | A28-B4-C28 |
| A59-B1-C28 | A49-B2-C28 | A39-B3-C28 | A29-B4-C28 |
| A60-B1-C28 | A50-B2-C28 | A40-B3-C28 | A30-B4-C28 |
| A61-B1-C28 | A51-B2-C28 | A41-B3-C28 | A31-B4-C28 |
| A62-B1-C28 | A52-B2-C28 | A42-B3-C28 | A32-B4-C28 |
| A63-B1-C28 | A53-B2-C28 | A43-B3-C28 | A33-B4-C28 |
| A64-B1-C28 | A54-B2-C28 | A44-B3-C28 | A34-B4-C28 |
| A65-B1-C28 | A55-B2-C28 | A45-B3-C28 | A35-B4-C28 |
| A66-B1-C28 | A56-B2-C28 | A46-B3-C28 | A36-B4-C28 |
| A67-B1-C28 | A57-B2-C28 | A47-B3-C28 | A37-B4-C28 |
| A68-B1-C28 | A58-B2-C28 | A48-B3-C28 | A38-B4-C28 |
| A69-B1-C28 | A59-B2-C28 | A49-B3-C28 | A39-B4-C28 |
| A70-B1-C28 | A60-B2-C28 | A50-B3-C28 | A40-B4-C28 |
| A71-B1-C28 | A61-B2-C28 | A51-B3-C28 | A41-B4-C28 |
| A72-B1-C28 | A62-B2-C28 | A52-B3-C28 | A42-B4-C28 |
| A73-B1-C28 | A63-B2-C28 | A53-B3-C28 | A43-B4-C28 |
| A74-B1-C28 | A64-B2-C28 | A54-B3-C28 | A44-B4-C28 |
| A75-B1-C28 | A65-B2-C28 | A55-B3-C28 | A45-B4-C28 |
| A76-B1-C28 | A66-B2-C28 | A56-B3-C28 | A46-B4-C28 |
| A77-B1-C28 | A67-B2-C28 | A57-B3-C28 | A47-B4-C28 |
| A1-B2-C28 | A68-B2-C28 | A58-B3-C28 | A48-B4-C28 |
| A2-B2-C28 | A69-B2-C28 | A59-B3-C28 | A49-B4-C28 |
| A3-B2-C28 | A70-B2-C28 | A60-B3-C28 | A50-B4-C28 |
| A4-B2-C28 | A71-B2-C28 | A61-B3-C28 | A51-B4-C28 |
| A5-B2-C28 | A72-B2-C28 | A62-B3-C28 | A52-B4-C28 |
| A6-B2-C28 | A73-B2-C28 | A63-B3-C28 | A53-B4-C28 |
| A7-B2-C28 | A74-B2-C28 | A64-B3-C28 | A54-B4-C28 |
| A8-B2-C28 | A75-B2-C28 | A65-B3-C28 | A55-B4-C28 |
| A9-B2-C28 | A76-B2-C28 | A66-B3-C28 | A56-B4-C28 |
| A10-B2-C28 | A77-B2-C28 | A67-B3-C28 | A57-B4-C28 |
| A11-B2-C28 | A1-B3-C28 | A68-B3-C28 | A58-B4-C28 |
| A12-B2-C28 | A2-B3-C28 | A69-B3-C28 | A59-B4-C28 |
| A13-B2-C28 | A3-B3-C28 | A70-B3-C28 | A60-B4-C28 |
| A14-B2-C28 | A4-B3-C28 | A71-B3-C28 | A61-B4-C28 |
| A15-B2-C28 | A5-B3-C28 | A72-B3-C28 | A62-B4-C28 |
| A16-B2-C28 | A6-B3-C28 | A73-B3-C28 | A63-B4-C28 |
| A17-B2-C28 | A7-B3-C28 | A74-B3-C28 | A64-B4-C28 |
| A18-B2-C28 | A8-B3-C28 | A75-B3-C28 | A65-B4-C28 |
| A19-B2-C28 | A9-B3-C28 | A76-B3-C28 | A66-B4-C28 |
| A20-B2-C28 | A10-B3-C28 | A77-B3-C28 | A67-B4-C28 |
| A21-B2-C28 | A11-B3-C28 | A1-B4-C28 | A68-B4-C28 |
| A22-B2-C28 | A12-B3-C28 | A2-B4-C28 | A69-B4-C28 |
| A23-B2-C28 | A13-B3-C28 | A3-B4-C28 | A70-B4-C28 |
| A24-B2-C28 | A14-B3-C28 | A4-B4-C28 | A71-B4-C28 |

TABLE 4-continued

| | | | |
|---|---|---|---|
| A25-B2-C28 | A15-B3-C28 | A5-B4-C28 | A72-B4-C28 |
| A26-B2-C28 | A16-B3-C28 | A6-B4-C28 | A73-B4-C28 |
| A74-B4-C28 | A64-B1-C29 | A54-B2-C29 | A44-B3-C29 |
| A75-B4-C28 | A65-B1-C29 | A55-B2-C29 | A45-B3-C29 |
| A76-B4-C28 | A66-B1-C29 | A56-B2-C29 | A46-B3-C29 |
| A77-B4-C28 | A67-B1-C29 | A57-B2-C29 | A47-B3-C29 |
| A1-B1-C29 | A68-B1-C29 | A58-B2-C29 | A48-B3-C29 |
| A2-B1-C29 | A69-B1-C29 | A59-B2-C29 | A49-B3-C29 |
| A3-B1-C29 | A70-B1-C29 | A60-B2-C29 | A50-B3-C29 |
| A4-B1-C29 | A71-B1-C29 | A61-B2-C29 | A51-B3-C29 |
| A5-B1-C29 | A72-B1-C29 | A62-B2-C29 | A52-B3-C29 |
| A6-B1-C29 | A73-B1-C29 | A63-B2-C29 | A53-B3-C29 |
| A7-B1-C29 | A74-B1-C29 | A64-B2-C29 | A54-B3-C29 |
| A8-B1-C29 | A75-B1-C29 | A65-B2-C29 | A55-B3-C29 |
| A9-B1-C29 | A76-B1-C29 | A66-B2-C29 | A56-B3-C29 |
| A10-B1-C29 | A77-B1-C29 | A67-B2-C29 | A57-B3-C29 |
| A11-B1-C29 | A1-B2-C29 | A68-B2-C29 | A58-B3-C29 |
| A12-B1-C29 | A2-B2-C29 | A69-B2-C29 | A59-B3-C29 |
| A13-B1-C29 | A3-B2-C29 | A70-B2-C29 | A60-B3-C29 |
| A14-B1-C29 | A4-B2-C29 | A71-B2-C29 | A61-B3-C29 |
| A15-B1-C29 | A5-B2-C29 | A72-B2-C29 | A62-B3-C29 |
| A16-B1-C29 | A6-B2-C29 | A73-B2-C29 | A63-B3-C29 |
| A17-B1-C29 | A7-B2-C29 | A74-B2-C29 | A64-B3-C29 |
| A18-B1-C29 | A8-B2-C29 | A75-B2-C29 | A65-B3-C29 |
| A19-B1-C29 | A9-B2-C29 | A76-B2-C29 | A66-B3-C29 |
| A20-B1-C29 | A10-B2-C29 | A77-B2-C29 | A67-B3-C29 |
| A21-B1-C29 | A11-B2-C29 | A1-B3-C29 | A68-B3-C29 |
| A22-B1-C29 | A12-B2-C29 | A2-B3-C29 | A69-B3-C29 |
| A23-B1-C29 | A13-B2-C29 | A3-B3-C29 | A70-B3-C29 |
| A24-B1-C29 | A14-B2-C29 | A4-B3-C29 | A71-B3-C29 |
| A25-B1-C29 | A15-B2-C29 | A5-B3-C29 | A72-B3-C29 |
| A26-B1-C29 | A16-B2-C29 | A6-B3-C29 | A73-B3-C29 |
| A27-B1-C29 | A17-B2-C29 | A7-B3-C29 | A74-B3-C29 |
| A28-B1-C29 | A18-B2-C29 | A8-B3-C29 | A75-B3-C29 |
| A29-B1-C29 | A19-B2-C29 | A9-B3-C29 | A76-B3-C29 |
| A30-B1-C29 | A20-B2-C29 | A10-B3-C29 | A77-B3-C29 |
| A31-B1-C29 | A21-B2-C29 | A11-B3-C29 | A1-B4-C29 |
| A32-B1-C29 | A22-B2-C29 | A12-B3-C29 | A2-B4-C29 |
| A33-B1-C29 | A23-B2-C29 | A13-B3-C29 | A3-B4-C29 |
| A34-B1-C29 | A24-B2-C29 | A14-B3-C29 | A4-B4-C29 |
| A35-B1-C29 | A25-B2-C29 | A15-B3-C29 | A5-B4-C29 |
| A36-B1-C29 | A26-B2-C29 | A16-B3-C29 | A6-B4-C29 |
| A37-B1-C29 | A27-B2-C29 | A17-B3-C29 | A7-B4-C29 |
| A38-B1-C29 | A28-B2-C29 | A18-B3-C29 | A8-B4-C29 |
| A39-B1-C29 | A29-B2-C29 | A19-B3-C29 | A9-B4-C29 |
| A40-B1-C29 | A30-B2-C29 | A20-B3-C29 | A10-B4-C29 |
| A41-B1-C29 | A31-B2-C29 | A21-B3-C29 | A11-B4-C29 |
| A42-B1-C29 | A32-B2-C29 | A22-B3-C29 | A12-B4-C29 |
| A43-B1-C29 | A33-B2-C29 | A23-B3-C29 | A13-B4-C29 |
| A44-B1-C29 | A34-B2-C29 | A24-B3-C29 | A14-B4-C29 |
| A45-B1-C29 | A35-B2-C29 | A25-B3-C29 | A15-B4-C29 |
| A46-B1-C29 | A36-B2-C29 | A26-B3-C29 | A16-B4-C29 |
| A47-B1-C29 | A37-B2-C29 | A27-B3-C29 | A17-B4-C29 |
| A48-B1-C29 | A38-B2-C29 | A28-B3-C29 | A18-B4-C29 |
| A49-B1-C29 | A39-B2-C29 | A29-B3-C29 | A19-B4-C29 |
| A50-B1-C29 | A40-B2-C29 | A30-B3-C29 | A20-B4-C29 |
| A51-B1-C29 | A41-B2-C29 | A31-B3-C29 | A21-B4-C29 |
| A52-B1-C29 | A42-B2-C29 | A32-B3-C29 | A22-B4-C29 |
| A53-B1-C29 | A43-B2-C29 | A33-B3-C29 | A23-B4-C29 |
| A54-B1-C29 | A44-B2-C29 | A34-B3-C29 | A24-B4-C29 |
| A55-B1-C29 | A45-B2-C29 | A35-B3-C29 | A25-B4-C29 |
| A56-B1-C29 | A46-B2-C29 | A36-B3-C29 | A26-B4-C29 |
| A57-B1-C29 | A47-B2-C29 | A37-B3-C29 | A27-B4-C29 |
| A58-B1-C29 | A48-B2-C29 | A38-B3-C29 | A28-B4-C29 |
| A59-B1-C29 | A49-B2-C29 | A39-B3-C29 | A29-B4-C29 |
| A60-B1-C29 | A50-B2-C29 | A40-B3-C29 | A30-B4-C29 |
| A61-B1-C29 | A51-B2-C29 | A41-B3-C29 | A31-B4-C29 |
| A62-B1-C29 | A52-B2-C29 | A42-B3-C29 | A32-B4-C29 |
| A63-B1-C29 | A53-B2-C29 | A43-B3-C29 | A33-B4-C29 |
| A34-B4-C29 | A24-B1-C30 | A14-B2-C30 | A4-B3-C30 |
| A35-B4-C29 | A25-B1-C30 | A15-B2-C30 | A5-B3-C30 |
| A36-B4-C29 | A26-B1-C30 | A16-B2-C30 | A6-B3-C30 |
| A37-B4-C29 | A27-B1-C30 | A17-B2-C30 | A7-B3-C30 |
| A38-B4-C29 | A28-B1-C30 | A18-B2-C30 | A8-B3-C30 |
| A39-B4-C29 | A29-B1-C30 | A19-B2-C30 | A9-B3-C30 |
| A40-B4-C29 | A30-B1-C30 | A20-B2-C30 | A10-B3-C30 |
| A41-B4-C29 | A31-B1-C30 | A21-B2-C30 | A11-B3-C30 |
| A42-B4-C29 | A32-B1-C30 | A22-B2-C30 | A12-B3-C30 |
| A43-B4-C29 | A33-B1-C30 | A23-B2-C30 | A13-B3-C30 |
| A44-B4-C29 | A34-B1-C30 | A24-B2-C30 | A14-B3-C30 |
| A45-B4-C29 | A35-B1-C30 | A25-B2-C30 | A15-B3-C30 |
| A46-B4-C29 | A36-B1-C30 | A26-B2-C30 | A16-B3-C30 |
| A47-B4-C29 | A37-B1-C30 | A27-B2-C30 | A17-B3-C30 |
| A48-B4-C29 | A38-B1-C30 | A28-B2-C30 | A18-B3-C30 |
| A49-B4-C29 | A39-B1-C30 | A29-B2-C30 | A19-B3-C30 |
| A50-B4-C29 | A40-B1-C30 | A30-B2-C30 | A20-B3-C30 |
| A51-B4-C29 | A41-B1-C30 | A31-B2-C30 | A21-B3-C30 |
| A52-B4-C29 | A42-B1-C30 | A32-B2-C30 | A22-B3-C30 |
| A53-B4-C29 | A43-B1-C30 | A33-B2-C30 | A23-B3-C30 |
| A54-B4-C29 | A44-B1-C30 | A34-B2-C30 | A24-B3-C30 |
| A55-B4-C29 | A45-B1-C30 | A35-B2-C30 | A25-B3-C30 |
| A56-B4-C29 | A46-B1-C30 | A36-B2-C30 | A26-B3-C30 |
| A57-B4-C29 | A47-B1-C30 | A37-B2-C30 | A27-B3-C30 |
| A58-B4-C29 | A48-B1-C30 | A38-B2-C30 | A28-B3-C30 |
| A59-B4-C29 | A49-B1-C30 | A39-B2-C30 | A29-B3-C30 |
| A60-B4-C29 | A50-B1-C30 | A40-B2-C30 | A30-B3-C30 |
| A61-B4-C29 | A51-B1-C30 | A41-B2-C30 | A31-B3-C30 |
| A62-B4-C29 | A52-B1-C30 | A42-B2-C30 | A32-B3-C30 |
| A63-B4-C29 | A53-B1-C30 | A43-B2-C30 | A33-B3-C30 |
| A64-B4-C29 | A54-B1-C30 | A44-B2-C30 | A34-B3-C30 |
| A65-B4-C29 | A55-B1-C30 | A45-B2-C30 | A35-B3-C30 |
| A66-B4-C29 | A56-B1-C30 | A46-B2-C30 | A36-B3-C30 |
| A67-B4-C29 | A57-B1-C30 | A47-B2-C30 | A37-B3-C30 |
| A68-B4-C29 | A58-B1-C30 | A48-B2-C30 | A38-B3-C30 |
| A69-B4-C29 | A59-B1-C30 | A49-B2-C30 | A39-B3-C30 |
| A70-B4-C29 | A60-B1-C30 | A50-B2-C30 | A40-B3-C30 |
| A71-B4-C29 | A61-B1-C30 | A51-B2-C30 | A41-B3-C30 |
| A72-B4-C29 | A62-B1-C30 | A52-B2-C30 | A42-B3-C30 |
| A73-B4-C29 | A63-B1-C30 | A53-B2-C30 | A43-B3-C30 |
| A74-B4-C29 | A64-B1-C30 | A54-B2-C30 | A44-B3-C30 |
| A75-B4-C29 | A65-B1-C30 | A55-B2-C30 | A45-B3-C30 |
| A76-B4-C29 | A66-B1-C30 | A56-B2-C30 | A46-B3-C30 |
| A77-B4-C29 | A67-B1-C30 | A57-B2-C30 | A47-B3-C30 |
| A1-B1-C30 | A68-B1-C30 | A58-B2-C30 | A48-B3-C30 |
| A2-B1-C30 | A69-B1-C30 | A59-B2-C30 | A49-B3-C30 |
| A3-B1-C30 | A70-B1-C30 | A60-B2-C30 | A50-B3-C30 |
| A4-B1-C30 | A71-B1-C30 | A61-B2-C30 | A51-B3-C30 |
| A5-B1-C30 | A72-B1-C30 | A62-B2-C30 | A52-B3-C30 |
| A6-B1-C30 | A73-B1-C30 | A63-B2-C30 | A53-B3-C30 |
| A7-B1-C30 | A74-B1-C30 | A64-B2-C30 | A54-B3-C30 |
| A8-B1-C30 | A75-B1-C30 | A65-B2-C30 | A55-B3-C30 |
| A9-B1-C30 | A76-B1-C30 | A66-B2-C30 | A56-B3-C30 |
| A10-B1-C30 | A77-B1-C30 | A67-B2-C30 | A57-B3-C30 |
| A11-B1-C30 | A1-B2-C30 | A68-B2-C30 | A58-B3-C30 |
| A12-B1-C30 | A2-B2-C30 | A69-B2-C30 | A59-B3-C30 |
| A13-B1-C30 | A3-B2-C30 | A70-B2-C30 | A60-B3-C30 |
| A14-B1-C30 | A4-B2-C30 | A71-B2-C30 | A61-B3-C30 |
| A15-B1-C30 | A5-B2-C30 | A72-B2-C30 | A62-B3-C30 |
| A16-B1-C30 | A6-B2-C30 | A73-B2-C30 | A63-B3-C30 |
| A17-B1-C30 | A7-B2-C30 | A74-B2-C30 | A64-B3-C30 |
| A18-B1-C30 | A8-B2-C30 | A75-B2-C30 | A65-B3-C30 |
| A19-B1-C30 | A9-B2-C30 | A76-B2-C30 | A66-B3-C30 |
| A20-B1-C30 | A10-B2-C30 | A77-B2-C30 | A67-B3-C30 |
| A21-B1-C30 | A11-B2-C30 | A1-B3-C30 | A68-B3-C30 |
| A22-B1-C30 | A12-B2-C30 | A2-B3-C30 | A69-B3-C30 |
| A23-B1-C30 | A13-B2-C30 | A3-B3-C30 | A70-B3-C30 |
| A71-B3-C30 | A61-B4-C30 | A51-B1-C31 | A41-B2-C31 |
| A72-B3-C30 | A62-B4-C30 | A52-B1-C31 | A42-B2-C31 |
| A73-B3-C30 | A63-B4-C30 | A53-B1-C31 | A43-B2-C31 |
| A74-B3-C30 | A64-B4-C30 | A54-B1-C31 | A44-B2-C31 |
| A75-B3-C30 | A65-B4-C30 | A55-B1-C31 | A45-B2-C31 |
| A76-B3-C30 | A66-B4-C30 | A56-B1-C31 | A46-B2-C31 |
| A77-B3-C30 | A67-B4-C30 | A57-B1-C31 | A47-B2-C31 |
| A1-B4-C30 | A68-B4-C30 | A58-B1-C31 | A48-B2-C31 |
| A2-B4-C30 | A69-B4-C30 | A59-B1-C31 | A49-B2-C31 |
| A3-B4-C30 | A70-B4-C30 | A60-B1-C31 | A50-B2-C31 |
| A4-B4-C30 | A71-B4-C30 | A61-B1-C31 | A51-B2-C31 |
| A5-B4-C30 | A72-B4-C30 | A62-B1-C31 | A52-B2-C31 |
| A6-B4-C30 | A73-B4-C30 | A63-B1-C31 | A53-B2-C31 |
| A7-B4-C30 | A74-B4-C30 | A64-B1-C31 | A54-B2-C31 |
| A8-B4-C30 | A75-B4-C30 | A65-B1-C31 | A55-B2-C31 |
| A9-B4-C30 | A76-B4-C30 | A66-B1-C31 | A56-B2-C31 |
| A10-B4-C30 | A77-B4-C30 | A67-B1-C31 | A57-B2-C31 |
| A11-B4-C30 | A1-B1-C31 | A68-B1-C31 | A58-B2-C31 |
| A12-B4-C30 | A2-B1-C31 | A69-B1-C31 | A59-B2-C31 |
| A13-B4-C30 | A3-B1-C31 | A70-B1-C31 | A60-B2-C31 |
| A14-B4-C30 | A4-B1-C31 | A71-B1-C31 | A61-B2-C31 |
| A15-B4-C30 | A5-B1-C31 | A72-B1-C31 | A62-B2-C31 |

TABLE 4-continued

| | | | |
|---|---|---|---|
| A16-B4-C30 | A6-B1-C31 | A73-B1-C31 | A63-B2-C31 |
| A17-B4-C30 | A7-B1-C31 | A74-B1-C31 | A64-B2-C31 |
| A18-B4-C30 | A8-B1-C31 | A75-B1-C31 | A65-B2-C31 |
| A19-B4-C30 | A9-B1-C31 | A76-B1-C31 | A66-B2-C31 |
| A20-B4-C30 | A10-B1-C31 | A77-B1-C31 | A67-B2-C31 |
| A21-B4-C30 | A11-B1-C31 | A1-B2-C31 | A68-B2-C31 |
| A22-B4-C30 | A12-B1-C31 | A2-B2-C31 | A69-B2-C31 |
| A23-B4-C30 | A13-B1-C31 | A3-B2-C31 | A70-B2-C31 |
| A24-B4-C30 | A14-B1-C31 | A4-B2-C31 | A71-B2-C31 |
| A25-B4-C30 | A15-B1-C31 | A5-B2-C31 | A72-B2-C31 |
| A26-B4-C30 | A16-B1-C31 | A6-B2-C31 | A73-B2-C31 |
| A27-B4-C30 | A17-B1-C31 | A7-B2-C31 | A74-B2-C31 |
| A28-B4-C30 | A18-B1-C31 | A8-B2-C31 | A75-B2-C31 |
| A29-B4-C30 | A19-B1-C31 | A9-B2-C31 | A76-B2-C31 |
| A30-B4-C30 | A20-B1-C31 | A10-B2-C31 | A77-B2-C31 |
| A31-B4-C30 | A21-B1-C31 | A11-B2-C31 | A1-B3-C31 |
| A32-B4-C30 | A22-B1-C31 | A12-B2-C31 | A2-B3-C31 |
| A33-B4-C30 | A23-B1-C31 | A13-B2-C31 | A3-B3-C31 |
| A34-B4-C30 | A24-B1-C31 | A14-B2-C31 | A4-B3-C31 |
| A35-B4-C30 | A25-B1-C31 | A15-B2-C31 | A5-B3-C31 |
| A36-B4-C30 | A26-B1-C31 | A16-B2-C31 | A6-B3-C31 |
| A37-B4-C30 | A27-B1-C31 | A17-B2-C31 | A7-B3-C31 |
| A38-B4-C30 | A28-B1-C31 | A18-B2-C31 | A8-B3-C31 |
| A39-B4-C30 | A29-B1-C31 | A19-B2-C31 | A9-B3-C31 |
| A40-B4-C30 | A30-B1-C31 | A20-B2-C31 | A10-B3-C31 |
| A41-B4-C30 | A31-B1-C31 | A21-B2-C31 | A11-B3-C31 |
| A42-B4-C30 | A32-B1-C31 | A22-B2-C31 | A12-B3-C31 |
| A43-B4-C30 | A33-B1-C31 | A23-B2-C31 | A13-B3-C31 |
| A44-B4-C30 | A34-B1-C31 | A24-B2-C31 | A14-B3-C31 |
| A45-B4-C30 | A35-B1-C31 | A25-B2-C31 | A15-B3-C31 |
| A46-B4-C30 | A36-B1-C31 | A26-B2-C31 | A16-B3-C31 |
| A47-B4-C30 | A37-B1-C31 | A27-B2-C31 | A17-B3-C31 |
| A48-B4-C30 | A38-B1-C31 | A28-B2-C31 | A18-B3-C31 |
| A49-B4-C30 | A39-B1-C31 | A29-B2-C31 | A19-B3-C31 |
| A50-B4-C30 | A40-B1-C31 | A30-B2-C31 | A20-B3-C31 |
| A51-B4-C30 | A41-B1-C31 | A31-B2-C31 | A21-B3-C31 |
| A52-B4-C30 | A42-B1-C31 | A32-B2-C31 | A22-B3-C31 |
| A53-B4-C30 | A43-B1-C31 | A33-B2-C31 | A23-B3-C31 |
| A54-B4-C30 | A44-B1-C31 | A34-B2-C31 | A24-B3-C31 |
| A55-B4-C30 | A45-B1-C31 | A35-B2-C31 | A25-B3-C31 |
| A56-B4-C30 | A46-B1-C31 | A36-B2-C31 | A26-B3-C31 |
| A57-B4-C30 | A47-B1-C31 | A37-B2-C31 | A27-B3-C31 |
| A58-B4-C30 | A48-B1-C31 | A38-B2-C31 | A28-B3-C31 |
| A59-B4-C30 | A49-B1-C31 | A39-B2-C31 | A29-B3-C31 |
| A60-B4-C30 | A50-B1-C31 | A40-B2-C31 | A30-B3-C31 |
| A31-B3-C31 | A62-B3-C31 | A16-B4-C31 | A47-B4-C31 |
| A32-B3-C31 | A63-B3-C31 | A17-B4-C31 | A48-B4-C31 |
| A33-B3-C31 | A64-B3-C31 | A18-B4-C31 | A49-B4-C31 |
| A34-B3-C31 | A65-B3-c31 | A19-B4-C31 | A50-B4-C31 |
| A35-B3-C31 | A66-B3-C31 | A20-B4-C31 | A51-B4-C31 |
| A36-B3-C31 | A67-B3-C31 | A21-B4-C31 | A52-B4-C31 |
| A37-B3-C31 | A68-B3-C31 | A22-B4-C31 | A53-B4-C31 |
| A38-B3-C31 | A69-B3-C31 | A23-B4-C31 | A54-B4-C31 |
| A39-B3-C31 | A70-B3-C31 | A24-B4-C31 | A55-B4-C31 |
| A40-B3-C31 | A71-B3-C31 | A25-B4-C31 | A56-B4-C31 |
| A41-B3-C31 | A72-B3-C31 | A26-B4-C31 | A57-B4-C31 |
| A42-B3-C31 | A73-B3-C31 | A27-B4-C31 | A58-B4-C31 |
| A43-B3-C31 | A74-B3-C31 | A28-B4-C31 | A59-B4-C31 |
| A44-B3-C31 | A75-B3-C31 | A29-B4-C31 | A60-B4-C31 |
| A45-B3-C31 | A76-B3-C31 | A30-B4-C31 | A61-B4-C31 |
| A46-B3-C31 | A77-B3-C31 | A31-B4-C31 | A62-B4-C31 |
| A47-B3-C31 | A1-B4-C31 | A32-B4-C31 | A63-B4-C31 |
| A48-B3-C31 | A2-B4-C31 | A33-B4-C31 | A64-B4-C31 |
| A49-B3-C31 | A3-B4-C31 | A34-B4-C31 | A65-B4-C31 |
| A50-B3-C31 | A4-B4-C31 | A35-B4-C31 | A66-B4-C31 |
| A51-B3-C31 | A5-B4-C31 | A36-B4-C31 | A67-B4-C31 |
| A52-B3-C31 | A6-B4-C31 | A37-B4-C31 | A68-B4-C31 |
| A53-B3-C31 | A7-B4-C31 | A38-B4-C31 | A69-B4-C31 |
| A54-B3-C31 | A8-B4-C31 | A39-B4-C31 | A70-B4-C31 |
| A55-B3-C31 | A9-B4-C31 | A40-B4-C31 | A71-B4-C31 |
| A56-B3-C31 | A10-B4-C31 | A41-B4-C31 | A72-B4-C31 |
| A57-B3-C31 | A11-B4-C31 | A42-B4-C31 | A73-B4-C31 |
| A58-B3-C31 | A12-B4-C31 | A43-B4-C31 | A74-B4-C31 |
| A59-B3-C31 | A13-B4-C31 | A44-B4-C31 | A75-B4-C31 |
| A60-B3-C31 | A14-B4-C31 | A45-B4-C31 | A76-B4-C31 |
| A61-B3-C31 | A15-B4-C31 | A46-B4-C31 | A77-B4-C31 |

Thus, for example, in table 4 the compound denoted as A60-B1-C7 is the product of the combination of group A60 in Table 1 and B1 in Table 2 and C7 in Table 3, namely 1H-indole-5-carboxylic acid (1-{1-[(4-methoxyphenylsulfamoyl)-methyl]-3-phenyl-propylcarbamoyl}-3-methyl-butyl)-amide:

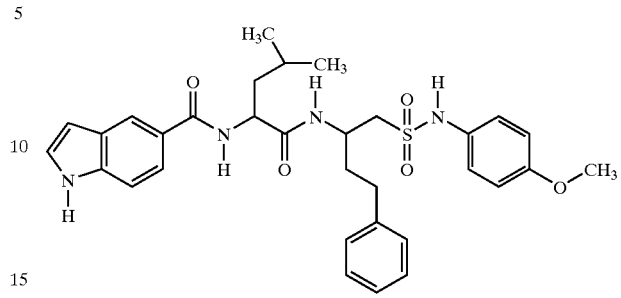

Further preferred are compounds selected from the group consisting of:

benzyl (1S-{1S-[(4-methoxyphenylsulfamoyl)-methyl]-3-phenyl-propylcarbamoyl}-3-methyl-butyl)-carbamate (Compound 1);

benzyl (1S-{1S-[(4-methoxyphenylsulfamoyl)-methyl]-3-phenyl-propylcarbamoyl}-2-methyl-butyl)-carbamate (Compound 2);

tert-butyl (1S-{1S-[(4-methoxyphenylsulfamoyl)-methyl]-3-phenyl-propylcarbamoyl}-3-methyl-butyl)-carbamate (Compound 3);

benzyl (1S-{1S-[(3-acetyl-phenylsulfamoyl)-methyl]-3-phenyl-propylcarbamoyl}-3-methyl-butyl)-carbamate (Compound 4);

N-{1S-[1S-(4-methoxyphenylsulfamoylmethyl)-3-phenylpropylcarbamoyl]-2-methylbutyl}-4-methylpiperazine-1-carboxamide (Compound 5);

benzyl {1S-[2-(4-methoxyphenylsulfamoyl)-ethylcarbamoyl]-2-methyl-butyl}-carbamate (Compound 6);

(2-cyclohexyl-1S-{3-phenyl-1S-[(2-phenylaminoethylsulfamoyl)-methyl]-propylcarbamoyl}ethyl)-carbamic acid tert-butyl ester (Compound 7);

4-dimethylamino-N-(1S-{1S-[(4-methoxyphenylsulfamoyl)methyl]-3-phenyl-propylcarbamoyl}-3-methylbutyl)-benzamide (Compound 8);

quinoline-6-carboxylic acid (1S-{1S-[(4-metboxyphenylsulfamoyl)methyl]-3-phenyl-propylcarbamoyl}-3-methyl-butyl)-amide (Compound 9);

morpholine-4-carboxylic acid (2-cyclohexyl-1S-{3-phenyl-1S-[(2-phenylamino-ethylsulfamoyl)methyl]-propylcarbamoyl}-ethyl)-amide (Compound 10);

4-(2-dimethylaminothiazol-4-yl)-N-{1S-[2-(4-methoxyphenylsulfamoyl)-ethylcarbamoyl]-3-methyl-butyl}benzamide (Compound 11);

2S-acetylamino-3-cyclohexyl-N-{1-[(4-methoxyphenylsulfamoyl)-methyl]-3-phenyl-propyl}propionamide (Compound 12);

2R-acetylamino-3-cyclohexyl-N-{1-[(4-methoxyphenylsulfamoyl)methyl]-3-phenyl-propyl}propionamide (Compound 13);

2RS-acetylamino-3-cyclohexyl-N-{1-[(4-hydroxyphenylsulfamoyl)methyl]-3-phenyl-propyl}-propionamide (Compound 14);

benzyl [6-(4-methoxyphenylsulfamoyl)-5S-(4-methyl-2S-{4-[2-(pyridin-3-ylamino)thiazol-4-yl]-benzoylamino}pentanoylamino)hexyl]carbamate (Compound 15);

N-(1S-{1S-[(4-methoxyphenylsulfamoyl)methyl]-3-phenylpropylcarbamoyl}-3-methyl-butyl)-4-[2-(pyridin-3-ylamino)thiazol-4-yl]-benzamide (Compound 16);

N-(1S-{1S-[(4-methoxyphenylsulfamoyl)methyl]-3-phenyl-propylcarbamoyl}-3-methyl-butyl)-nicotinamide (Compound 19);

N-(1S-{1S-[(4-methoxyphenylsulfamoyl)-methyl]-3-phenylpropylcarbamoyl}-3-methyl-butyl)-isonicotinamide (Compound 20);

N-{1-[1-(4-methoxyphenylsulfamoylmethyl)-3-phenylpropylcarbamoyl]-3-methylbutyl}-1H-indole-5-carboxamide (Compound 21);

tert-butyl [3-(1S-{1S-[(4-methoxyphenylsulfamoyl)-methyl]-3-phenylpropylcarbamoyl}-3-methyl-butylcarbamoyl)phenyl]-carbamate (Compound 22);

3-amino-N-(1S-{1S-[(4-methoxyphenylsulfamoyl)-methyl]-3-phenylpropylcarbamoyl}-3-methyl-butyl)-benzamide (Compound 23);

N-(1S-{5-amino-1S-[(4-methoxyphenylsulfamoyl)methyl]pentylcarbamoyl}-3-methyl-butyl)-4-[2-(pyridin-3-ylamino)-thiazol-4-yl]-benzamide (Compound 24);

benzyl [1S-(1S-{[3-(1-hydroxyethyl)phenylsulfamoyl]methyl}-3-phenylpropyl-carbamoyl)-3-methylbutyl]-carbamate (Compound 26);

morpholine 4-carboxylic acid (1S-{5-amino-1S-[(4-methoxyphenylsulfamoyl)methyl]-pentylcarbamoyl}-2-phenylmethanesulfonylethyl)amide;

(5S-[2S-(morpholin-4-ylcarbonyl)amino]-3-phenylmethanesulfonylpropionylamino}-6-phenylsulfamoylhexyl)carbamic acid benzyl ester;

morpholine 4-carboxylic acid (1S-{1S-[(4-methoxyphenylsulfamoyl)methyl]-3-phenylpropylcarbamoyl}-2-phenylmethanesulfonylethyl)amide;

N-(1S-{1S-[(4-methoxy-phenylsulfamoyl)-methyl]-3-phenyl-propylcarbamoyl}-cyclohexyl)-4-[2-(4-methylpiperazin-1-yl)thiazol-4-yl]benzamide; and N-(1S-{1S-[(4-methoxy-phenylsulfamoyl)-methyl]-3-phenyl-propylcarbamoyl}-cyclohexyl)-4-(4-propylpiperazin-1-yl)-benzamide.

The names of these compounds were generated using Autonom Version 2.1 or 4.0.

General Synthesis

Compounds of this invention can be made by the methods depicted in the reaction schemes shown below.

The starting materials and reagents used in preparing these compounds are either available from commercial suppliers such as Aldrich Chemical Co., (Milwaukee, Wis.), or Bachem (Torrance, Calif.), or are prepared by methods known to those skilled in the art following procedures set forth in references such as Fieser and Fieser's Reagents for Organic Synthesis, Volumes 1–17 (John Wiley and Sons, 1991); Rodd's Chemistry of Carbon Compounds, Volumes 1–5 and Supplementals (Elsevier Science Publishers, 1989); Organic Reactions, Volumes 1–40 (John Wiley and Sons, 1991), March's Advanced Organic Chemistry, (John Wiley and Sons, 4$^{th}$ Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Compounds of Formula I can be prepared by the procedure illustrated and described in Schemes 1 and 2 below:

Compounds of Formula I in which $R^1$, $R^2$, $R^3$, $R^4$, $R^5$ and $R^6$ are as defined in the Summary of the Invention can be prepared by proceeding as in the following Scheme 1 below.

Scheme 1

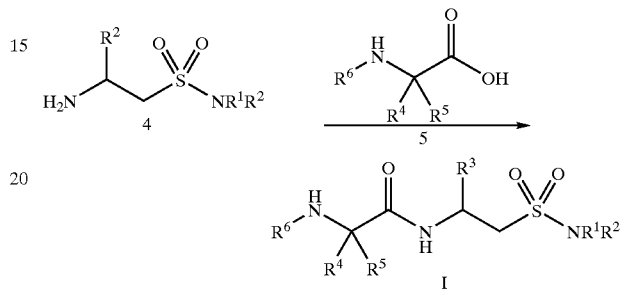

Compounds of Formula I can be prepared by condensing a compound of formula 4 with a compound of formula 5. The compound of formula 4 may be in a free base or an acid addition salt form, preferably an acid addition salt form (e.g. p-toluenesulfonic acid salt, or the like). Typically, the condensation reaction is carried out under nitrogen in the presence of a suitable condensing agent (e.g. isobutyl chloroformate, PyBOP, HATU, or the like), a non-nucleophilic base (e.g. 4-methylmorpholine, triethylamine, or the like) and a suitable solvent (e.g., THF, DMF, or the like), at −20 to 0° C., preferably at about −10° C., and requires 45 minutes to 12 hours to complete. A detailed description of the condensation reaction is found in the Examples, infra.

Compounds of formula 4 in which $R^3$ is as defined in the Summary of the Invention for Formula I can be prepared as illustrated and described below.

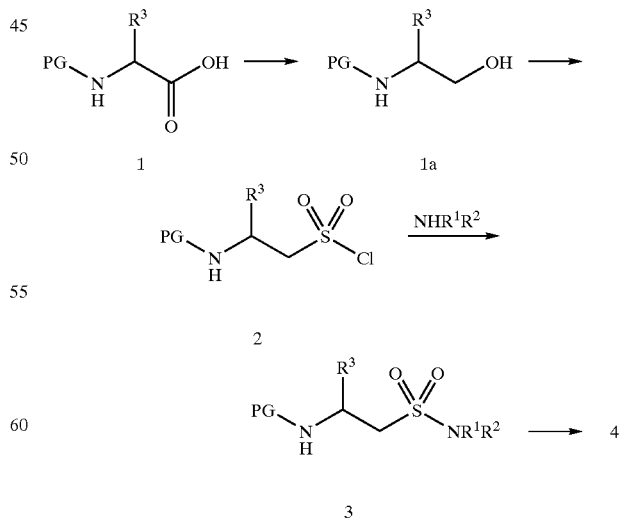

Treatment of an N-protected alpha amino acid compound of formula 1 with a condensing agent (e.g., isobutyl chloroformate, or the like) in the presence of a suitable base (e.g., 4-methylmorpholine, or the like) in a suitable solvent (e.g., THF, etc.) at a temperature of about −10 to 10° C., preferably 0° C., for about 5 to 20 hours, followed by reaction of the resulting anhydride intermediate with a suitable reducing agent (e.g., sodium borohydride, and the like) provides a 2-N-protected aminoethanol intermediate of formula 1a. Compounds of formula 1 are commercially available or they can be prepared by methods well known in the art.

Treatment of 1a with an alkylsulfonyl halide (e.g., methanesulfonylchloride, or the like) in the presence of a suitable base (e.g., triethylamine, etc.) and in a suitable solvent (e.g., DCM, and the like) and at a temperature of about −10 to 10° C., preferably 0° C., for about 5 to 20 hours provides the corresponding alkylsulfonyloxy derivative. Treatment of the alkylsulfonyloxy derivative with an acylating agent (e.g., cesium thiolacetate, or the like) in a suitable solvent (e.g., DMF, and the like) and at a temperature of about 10 to 30° C., preferably 20° C., for about 5 to 20 hours provides a thioester which upon reaction with chlorine gas in a suitable solvent (e.g., DCM, and the like) at a temperature of about 10 to 30° C., preferably 20° C., for about 15 minutes to about 2 hours provides a compound of formula 2.

Compounds of formula 3 can be prepared by reacting a compound of formula 2 with an amine of the formula $NHR^1R^2$ and then removing the protecting group (PG) to yield a compound of formula 4. Typically, the reaction with the amine is carried out in the presence of a suitable solvent (e.g., DCM, or the like) and at a temperature of about −10 to 10° C., preferably 0° C., for about 5 to 20 hours. Deprotection can be effected by any means that removes the protecting group and gives the desired product in reasonable yield. For example, when the protecting group is t-butoxycarbonyl, deprotecting can be effected with a suitable anhydrous acid (e.g., anhydrous hydrogen chloride, anhydrous p-toluenesulfonic acid, or the like) at ambient temperature for about 12 to 24 hours.

Compounds of formula 5 are either commercially available or they can be prepared by methods well known in the art. For examples, t-BOC alanine, t-BOC-leucine, t-BOC-isoleucine are commercially available. Compounds of formula 5 where $R^6$ is other groups within the scope of the invention sacan be readily prepared commercially available alpha amino acids by methods well known in the art. Some such methods are disclosed in U.S. Pat. No. 6,136,844 the disclosure of which is incorporated by reference in its entirety.

Compounds of Formula I in which $R^1$, $R^2$, $R^3$, $R^4$, $R^5$ and $R^6$ are as defined in the Summary of the Invention can also be prepared from compounds of formula 6 as illustrated and described in Scheme 2 below.

Scheme 2

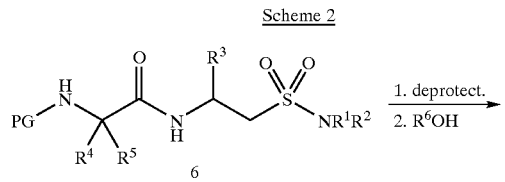

6

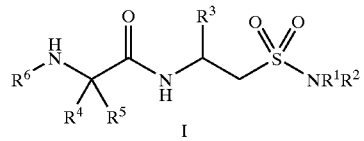

I

Compounds of Formula I can also be prepared by deprotecting a compound of formula 6 and then treating the resulting free amine with an acid of formula $R^6OH$ or its acid derivative such as acid chloride. The compound of formula 6 may be in a free base or an acid addition salt form, preferably an acid addition salt form (e.g. p-toluenesulfonic acid salt, or the like).

Deprotection can be effected by any means that removes the protecting group and gives the desired product in reasonable yield. A detailed description of the techniques applicable to the creation of protective groups and their removal can be found in T. W. Greene and P. G. M. Wuts, *Protective Groups in Organic Synthesis*, John Wiley & Sons, Inc. (3rd Edition) 1999. For example, when the protecting group is BOC, deprotection can be effected by treating with anhydrous hydrogen chloride in a suitable solvent (e.g., dichloromethane, diethyl ether, dioxane, or the like), at 10 to 30° C., preferably at about 20° C., and requires about 5 to 10 hours to complete. A detailed description of the deprotection reaction is found in Example 5, infra.

The reaction conditions employed for the coupling of the free amine of compound 6 with $R^6OH$ depend on the nature of $R^6OH$. For example, if an acid is used, then the reaction is carried out in the presence of a coupling agent such as PyBOP as described in Scheme 1 above. If an acid chloride is used then the reaction is carried out in the presence of a base such as triethylamine, pyridine, and the like and in a suitable organic solvent such as tetrahydrofuran, methylene chloride, and the like.

The reaction can be carried out at temperatures from about 10 to about 30° C., preferably at about 20° C., and requires 3 to 20 hours to complete. A detailed description of the step 2 reaction is found in the Examples, infra.

Additional Processes for Preparing Compounds of Formula I:

Compounds of Formula I in which $R^6$ is hydrogen can be prepared by deacylating a compound of Formula I in which $R^6$ is $—X^3X^4R^{13}$. For example, deacylation of a compound of Formula I in which $R^5$ is t-butyloxycarbonyl or benzyloxycarbonyl can be effected by treating with anhydrous hydrogen chloride or hydrogen bromide in a suitable solvent (e.g., DCM, dioxane, glacial acetic acid, or the like) at 10 to 30° C., preferable at about 20° C., for 5 to 20 hours. A detailed description of the reaction is found in the Examples, infra.

Compounds of Formula I can be further treated with a reducing agent (e.g., $NaBH_4$, $LiALH_4$, or the like), in the presence of a suitable solvent (e.g., tetrahydrofuran (THF), dimethylformamide (DMF) or the like), at 10 to 30° C., preferably at about 20° C., and requires 15 minutes to 2 hours to complete. A detailed description of the reduction reaction is found in the Examples, infra.

A compound of Formula I can be prepared as a pharmaceutically acceptable acid addition salt by reacting the free base form of the compound with a pharmaceutically acceptable inorganic or organic acid. Alternatively, a pharmaceutically acceptable base addition salt of a compound of Formula I can be prepared by reacting the free acid form of the compound with a pharmaceutically acceptable inorganic or organic base. Inorganic and organic acids and bases suitable for the preparation of the pharmaceutically acceptable salts of compounds of Formula I are set forth in the definitions section of this application. Alternatively, the salt forms of the compounds of Formula I can be prepared using salts of the starting materials or intermediates.

The free acid or free base forms of the compounds of Formula I can be prepared from the corresponding base addition salt or acid addition salt form. For example, a compound of Formula I in an acid addition salt form may be converted to the corresponding free base by treating with a suitable base (e.g., ammonium hydroxide solution, sodium hydroxide, or the like). A compound of Formula I in a base addition salt form can be converted to the corresponding free acid by treating with a suitable acid (e.g., hydrochloric acid, or the like).

The N-oxides of compounds of Formula I can be prepared by methods known to those of ordinary skill in the art. For example, N-oxides can be prepared by treating an unoxidized form of the compound of Formula I with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as methylene chloride) at approximately 0° C. Alternatively, the N-oxides of the compounds of Formula I can be prepared from the N-oxide of an appropriate starting material.

Compounds of Formula I in unoxidized form can be prepared from N-oxides of compounds of Formula I by treating with a reducing agent (e.g. sulfur, sulfur dioxide, triphenyl phosphine, lithium borohydride, sodium borohydride, phosphorus trichloride, tribromide, or the like) in a suitable organic solvent (e.g., acetonitrile, ethanol, aqueous dioxane, or the like) at 0 to 80° C.

Prodrug derivatives of the compounds of Formula I can be made by means known to those of ordinary skill in the art (e.g., for further details see Saulnier et al. (1994), *Bioorganic and Medicinal Chemistry Letters*. No. 16, Vol. 4, pp. 1985–1990). For example, appropriate drugs can be prepared by reacting a non-derivatized compound of Formula I with a suitable carbamylating agent (e.g., 1,1-acyloxyalkylcarbonochloridate, para-nitrophenyl carbonate, or the like).

Protected derivatives of the compounds of Formula I can be made by means known to those of ordinary skill in the art. A detailed description of the techniques applicable to the creation of protective groups and their removal can be found in T. W. Greene and P. G. M. Wuts, *Protective Groups in Organic Synthesis*, John Wiley & Sons, Inc. (3rd Edition) 1999.

Compounds of Formula I can be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of compounds of Formula I, dissociable complexes are preferred (e.g., crystalline diastereoisomeric salts). Diastereomers have distinct physical properties (e.g., melting points, boiling points, solubilities, reactivity, and the like) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

In Summary, the compounds of Formula I are made by a process which comprises:

(A) reacting a compound of formula 4:

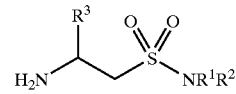

with a compound of formula 5:

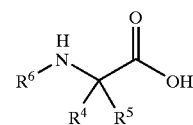

in which $R^1$, $R^2$, $R^3$, $R^4$, $R^5$ and $R^6$ are as defined in the Summary of the Invention; or (B) reacting a compound of formula 7:

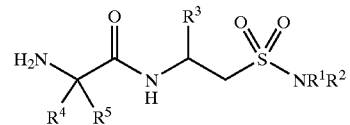

with an acid compound of formula $R^6OH$ or an acid derivative thereof, wherein $R^1$, $R^2$, $R^3$, $R^4$, $R^5$ and $R^6$ are defined in the Summary of the Invention; and (C) optionally converting a compound of Formula I into a pharmaceutically acceptable salt;

(D) optionally converting a salt form of a compound of Formula I to non-salt form;

(E) optionally converting an unoxidized form of a compound of Formula I into a pharmaceutically acceptable N-oxide;

(F) optionally converting an N-oxide form of a compound of Formula I its unoxidized form;

(G) optionally resolving an individual isomer of a compound of Formula I from a mixture of isomers;

(H) optionally converting a non-derivatized compound of Formula I into a pharmaceutically prodrug derivative;

optionally converting a prodrug derivative of a compound of Formula I to its non-derivatized form; and (J) optionally modifying any of the $R^1$, $R^2$, $R^3$, $R^4$, $R^5$ and $R^6$ groups.

Pharmacology and Utility

The compounds of the invention are cysteine protease inhibitors. In particular the compounds of the invention inhibit the activity of cathepsins B, L, K and/or S and, as such, are useful for treating diseases in which cathepsin B, L, K and/or S activity contributes to the pathology and/or symptomatology of the disease. For example, the compounds of the invention are useful in treating tumor invasion and metastasis, in particular as anti-angiogenic agents, rheumatoid arthritis, osteo arthritis, pneumocystis carinii, acute pancreatitis, inflammatory airway disease and bone and joint disorders. Furthermore, the compounds of the invention are useful in treating bone resorption disorders, e.g., osteoporosis. The compounds of the invention also are useful in treating autoimmune disorders, including, but not limited to juvenile onset diabetes, multiple sclerosis, pemphigus vulgaris, Graves disease, myasthenia gravis, systemic lupus erythemotasus, rheumatoid arthritis and Hashimoto's thyroiditis. The compounds of the invention also are useful in treating allergic disorders, including, but not limited to asthma; and allogeneic immune reponses, including, but not limited to, organ transplants or tissue grafts.

The cysteine protease inhibitory activities of the compounds of the invention can be determined by methods known to those of ordinary skill in the art. Suitable in vitro assays for measuring protease activity and the inhibition thereof by test compounds are known. Typically, the assay measures protease-induced hydrolysis of a peptide-based substrate. Details of assays for measuring protease inhibitory activity are set forth in Examples 9, 10, 11 and 12, infra.

Administration and Pharmaceutical Compositions

In general, compounds of Formula I will be administered in therapeutically effective amounts via any of the usual and acceptable modes known in the art, either singly or in combination with another therapeutic agent. A therapeutically effective amount may vary widely depending on the severity of the disease, the age and relative health of the subject, the potency of the compound used and other factors. For example, therapeutically effective amounts of a compound of Formula I may range from 0.1 micrograms per kilogram body weight (µg/kg) per day to 10 milligram per kilogram body weight (mg/kg) per day, typically 1 µg/kg/day to 1 mg/kg/day. Therefore, a therapeutically effective amount for a 80 kg human patient may range from 10 µg/day to 100 mg/day, typically 0.1 mg/day to 10 mg/day. In general, one of ordinary skill in the art, acting in reliance upon personal knowledge and the disclosure of this Application, will be able to ascertain a therapeutically effective amount of a compound of Formula I for treating a given disease.

The compounds of Formula I can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula I in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, or the like). Preferred liquid carriers, particularly for injectable solutions, include water, saline, aqueous dextrose and glycols.

The amount of a compound of Formula I in the composition may vary widely depending upon the type of formulation, size of a unit dosage, kind of excipients and other factors known to those of skill in the art of pharmaceutical sciences. In general, a composition of a compound of Formula I for treating a given disease will comprise from 0.01% w to 10% w, preferably 0.3% w to 1% w, of active ingredient with the remainder being the excipient or excipients. Preferably the pharmaceutical compositions is administered in a single unit dosage form for continuous treatment or in a single unit dosage form ad libitum when relief of symptoms is specifically required. Representative pharmaceutical formulations containing a compound of Formula I are described in Example 13.

The compounds of Formula I can be administered alone or in combination with other compounds of Formula I or in combination with one or more other active ingredient(s). For example, the compounds of Formula I can be administered in combination with a therapeutically active amount of a bisphosphonic acid or acid ester derivative or any pharmaceutically acceptable salt thereof. Suitable bisphosphonic acids and acid ester derivatives include compounds corresponding to the following formula:

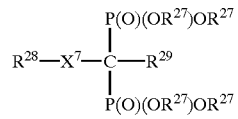

wherein $X^7$ is a bond or $(C_{1-7})$alkylene, each $R^{27}$ independently is hydrogen or $(C_{1-30})$alkyl, $R^{28}$ and $R^{29}$ are selected independently from a group consisting of hydrogen, halo, optionally substituted $(C_{1-30})$alkyl, $(C_{3-30})$cycloalkyl, hetero $(C_{5-30})$cycloalkyl, optionally substituted $(C_{6-10})$aryl, hetero $(C_{6-10})$aryl, $NR^{30}R^{30}$, $OR^{30}$, $SR^{30}$, wherein each $R^{30}$ independently is hydrogen, $(C_{1-10})$alkyl, $(C_{3-10})$cycloalkyl, optionally substituted $(C_{6-10})$aryl, provided that both $R^{28}$ and $R^{29}$ are not selected from hydrogen or hydroxy when $X^7$ is a bond; or $R^{28}$ and $R^{29}$ taken together form $(C_{2-9})$alkylene; wherein $(C_{3-10})$cycloalkyl includes adamantyl and the like, hetero$(C_{5-10})$cycloalkyl includes pyrrolidinyl and the like, $(C_{6-10})$aryl includes phenyl and naphthyl, and hetero$(C_{6-10})$aryl includes quinolyl, isoquinolyl, pyridyl, furyl, imidazolyl, imidazopyridyl and the like.

Instances wherein $R^{28}$ and/or $R^{29}$ are substituted $(C_{1-30})$ alkyl may include, but are not limited to, $(C_{1-30})$alkyl substituted by hetero$(C_{5-10})$cycloalkyl, $(C_{6-10})$aryl, hetero $(C_{6-10})$aryl, $NR^{31}R^{31}$, $OR^{31}$ and $SR^{31}$, wherein each $R^{31}$ is independently hydrogen or $(C_{1-10})$alkyl; wherein hetero$(C_{5-10})$cycloalkyl includes pyrrolidinyl and the like, $(C_{6-10})$aryl includes phenyl and naphthyl, and hetero$(C_{6-10})$aryl includes quinolyl, isoquinolyl, pyridyl, furyl, imidazolyl, imidazopyridyl and the like. Suitable optionally substituted aryl groups include, but are not limited to, halo-substituted phenyl.

A non-limiting class of bisphosphonic acids and acid ester derivatives thereof suitable for administration in combination with compounds of Formula I include those in which $R^{28}$ is selected from the group consisting of hydrogen, hydroxy or halo, and $R^{29}$ is selected from the group consisting of optionally substituted $(C_{1-30})$alkyl, halo and $SR^{30}$, wherein $R^{30}$ is $(C_{1-10})$alkyl or phenyl.

A non-limiting subclass of bisphosphonic acids and acid ester derivatives thereof suitable for administration in combination with compounds of Formula I include those in which $R^{28}$ is selected from the group consisting of hydrogen, hydroxy and chloro and $R^{29}$ is selected from the group consisting of optionally substituted $(C_{1-30})$alkyl, chloro and chlorophenylthio.

A non-limiting example of a bisphosphonic acid suitable for administration in combination with compounds of Formula I include that in which $X^7$ is a bond, each $R^{27}$ is hydrogen, $R^{28}$ is hydroxy and $R^{29}$ is 3-aminopropyl, namely 4-amino-1-hydroxybutylidene-1,1-bisphosphonic acid (aka alendronic acid), or the monosodium trihydrate salt thereof, namely 4-amino-1-hydroxybutylidene-1,1-bisphosphonate monosodium trihydrate (aka alendronate monosodium trihydrate), described in U.S. Pat. No. 4,922,007, to Kieczykowski et al., issued May 1, 1990; U.S. Pat. No. 5,019,651, to Kieczykowski et al., issued May 28, 1991; U.S. Pat. No. 5,510,517, to Dauer et al., issued Apr. 23, 1996; U.S. Pat. No. 5,648,491, to Dauer et al., issued Jul. 15, 1997, all of which patents are incorporated by reference herein in their entirety.

Further non-limiting examples of bisphosphonic acids suitable for administration in combination with compounds of Formula I include the following:

cycloheptylaminomethylene-1,1-bisphosphonic acid (aka cimadronic acid), described in U.S. Pat. No. 4,970,335, to Isomura et al., issued Nov. 13, 1990;

1,1-dichloromethylene-1,1-diphosphonic acid (aka clodronic acid) and the disodium salt thereof, namely clodronate disodium, described in Belgium Patent 672,205 (1966) and J. Org. Chem 32, 4111 (1967);

1-hydroxy-3-pyrrolidin-1-ylpropylidene-1,1-bisphosphonic acid (aka EB-1053);

1-hydroxyethylidene-1,1-diphosphonic acid (aka etidronic acid);

1-hydroxy-3-(N-methyl-N-pentylamino)propylidene-1,1-bisphosphonic acid (aka ibandronic acid), described in U.S. Pat. No. 4,927,814, issued May 22, 1990;

6-amino-1-hydroxyhexylidene-1,1-bisphosphonic acid (aka neridronic acid);

3-(dimethylamino)-1-hydroxypropylidene-1,1-bisphosphonic acid (aka olpadronic acid);

3-amino-1-hydroxypropylidene-1,1-bisphosphonic acid (aka pamidronic acid);

2-pyrid-2-ylethylidene-1,1-bisphosphonic acid (aka piridronic acid), described in U.S. Pat. No. 4,761,406;

1-hydroxy-2-pyrid-3-ylethylidene-1,1-bisphosphonic acid (aka risedronic acid);

4-chlorophenylthiomethylenebisphosphonic acid (aka tiludronic acid), described in U.S. Pat. No. 4,876,248, to Breliere et al., Oct. 24, 1989; and 1-hydroxy-2-(1H-imidazol-1-yl)ethylidene-1,1-bisphosphonic acid (aka zoledronic acid); all of which patents and other documents referred to above are incorporated by reference herein in their entirety.

A non-limiting subclass of bisphosphonic acids suitable for administration in combination with compounds of Formula I include those selected from the group consisting of alendronic acid, cimadronic acid, clodronic acid, tiludronic acid, etidronic acid, ibandronic acid, risedronic acid, piridronic acid, pamidronic acid, zolendronic acid, pharmaceutically acceptable salts thereof, and mixtures thereof. A further example of a bisphosphonic acid suitable for administration in combination with compounds of Formula I is alendronic acid or a pharmaceutically acceptable salt thereof, and mixtures thereof. A further non-limiting example is alendronate monosodium trihydrate.

Compounds of Formula I can be administered in combination with a therapeutically active amount of an estrogen receptor agonist. Non-limiting examples of estrogen receptor agonists suitable for administration in combination with the compounds of Formula I include naturally occurring estrogens such as estradiol, estrone and estroil, or synthetic estrogen receptor agonists such as [6-hydroxy-2-(4-hydroxyphenyl)benzo[b]thien-3-yl][4-(2-piperidin-1-ylethoxy)phenyl]methanone (aka raloxifene) and {2-[4-(1,2-diphenylbut-1-enyl)-phenoxy]ethyl}dimethylamine (aka tamoxifen). A non-limiting subclass of estrogen receptor agonists suitable for administration in combination with the compounds of Formula I include estrogen receptor partial agonists (i.e., estrogen receptor agonists with mixed agonist/antagonist properties), sometimes referred to as estrogen receptor modulators. Estrogen receptor partial agonists can exert tissue-selective estrogen agonist effects. Tamoxifen, for example, selectively exerts an estrogen agonist effect on the bone, in humans. Additional suitable estrogen receptor partial agonists are described in Tissue-Selective Actions Of Estrogen Analogs, Bone Vol. 17, No. 4, October 1995, 181S–190S. Certain 3-[4-(2-phenylindol-1-ylmethyl) phenyl]acrylamides, described in U.S. Pat. No. 5,985,910 to Miller et al., Nov. 16, 1999; benzothiphene compounds, described in U.S. Pat. No. 5,985,897 to Meuhl et al., Nov. 16, 1999; naphthyl compounds, described in U.S. Pat. No. 5,952,350 to Cullinan et al., Sep. 14, 1999; substituted benzothiophene compounds, described in U.S. Pat. No. 5,962,475 to Schmid et al., Oct. 4, 1999, are suitable estrogen receptor partial agonists for administration with the compounds of Formula I; all of which patents and other documents referred to above are incorporated by reference herein in their entirety.

More particularly a pharmaceutical composition of this invention may comprise a therapeutically effect amount of a compound of Formula I in combination with one or more active ingredient(s) selected from the group consisting of (i) a therapeutically effect amount of a bisphosphonic acid or acid ester thereof or a pharmaceutically acceptable salt thereof and (ii) a therapeutically effect amount of an estrogen receptor agonist or a pharmaceutically acceptable salt thereof; and one or more pharmaceutically acceptable excipient(s). Non-limiting examples of such bisphosphonic acids include 1,1-dichloromethylene-1,1-diphosphonic acid, 1-hydroxy-3-pyrrolidin-1-ylpropylidene-1,1-bisphosphonic acid, 1-hydroxyethylidene-1,1-diphosphonic acid, 1-hydroxy-3-(N-methyl-N-pentylamino)propylidene-1,1-bisphosphonic acid, 6-amino-1-hydroxyhexylidene-1,1-bisphosphonic acid, 3-(dimethylamino)-1-hydroxypropylidene-1,1-bisphosphonic acid, 3-amino-1-hydroxypropylidene-1,1-bisphosphonic acid, 2-pyrid-2-ylethylidene-1,1-bisphosphonic acid, 1-hydroxy-2-pyrid-3-ylethylidene-1,1-bisphosphonic acid, 4-chlorophenylthiomethylenebisphosphonic acid and 1-hydroxy-2-(1H-imidazol-1-yl)ethylidene-1,1-bisphosphonic acid or acid ester thereof or a pharmaceutically acceptable salt thereof; particularly 1,1-dichloromethylene-1,1-diphosphonic acid or a pharmaceutically acceptable salt thereof and preferably 1,1-dichloromethylene-1,1-diphosphonate monosodium trihydrate.

EXAMPLES

The following preparations of intermediates (References) and compounds of Formula I (Examples) are given to enable those skilled in the art to more clearly understand and to practice the present invention. They should not be considered as limiting the scope of the invention, but merely as being illustrative and representative thereof.

Reference 1

Synthesis of tert-butyl 1S-(4-methoxyphenylsulfamoylmethyl)-3-phenylpropylcarbamate, i.e., a compound of formula 3 in which PG is tert-butoxycarbonyl, $R^1$ is 4-methoxyphenyl and $R^3$ is 2-phenylethyl

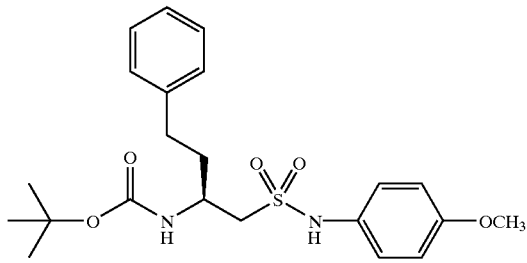

A mixture of 1S-chlorosulfonylmethyl-3-phenylpropylcarbamate (0.96 g, 2.76 mmol) and 4-methoxyaniline (0.34 g, 2.76 mmol) in DCM (15 mL) was cooled to 0° C. and triethylamine (0.846 mL, 6.07 mmol) was added. The mixture was stirred at room temperature for approximately 12 hours and then diluted with DCM (30 mL). The dilution was washed with 1N hydrochloric acid (30 mL), saturated aqueous sodium bicarbonate (30 mL), dried over magnesium sulfate, filtered and concentrated to dryness to provide tert-butyl 1S-(4-methoxyphenylsulfamoylmethyl)-3-phenylpropylcarbamate (0.60 g, 50% yield). $R_f$ 0.4, 30% ethyl acetate/hexane. $^1$H NMR (CDCl$_3$): 1.42 (9H, s); 1.75–1.85 (2H, m); 2.52–2.75 (2H, m); 3.08 (2H, m); 3.75 (3H, s); 4.05 (1H, m); 5.02 (1H, d, J=9 Hz); 6.75 (2H, d, J=8 Hz) 7.07–7.28 (8H, m*).

Proceeding as in Reference 1 and using appropriate starting materials provided the following compounds of Formula 3:

tert-butyl 1S-(4-hydroxyphenylsulfamoylmethyl)-3-phenylpropylcarbamate; $R_f$ 0.45 (10% methanol/DCM);

tert-butyl 1S-(3-acetylphenylsulfamoylmethyl)-3-phenylpropylcarbamate; $R_f$ 0.25 (30% ethyl acetate/hexane);

benzyl 5S-tert-butoxycarbonylamino-6-(4-methoxyphenylsulfamoyl)hexylcarbamate; MS: (M+1) 536; and benzyl 2-(4-methoxyphenylsulfamoyl)ethylcarbamate; $^1$H NMR (chloroform-d): 3.20 (2H, t, J=6 Hz); 3.67 (2H, q, J=6 Hz); 3.78 (3H, s); 5.08 (2H, s); 5.39 (1H, t, J=6 Hz); 6.76 (1H, s); 6.82 (2H, d, J=9 Hz); 7.17 (2H, d, J=9 Hz); 7.32 (5H, s).

Reference 2

Synthesis of 2S-amino-N-(4-methoxyphenyl)-4-phenylbutane-1-sulfonamide hydrochloride, i.e., a compound of formula 4 in which $R^1$ is 4-methoxyphenyl and $R^3$ is phenethyl

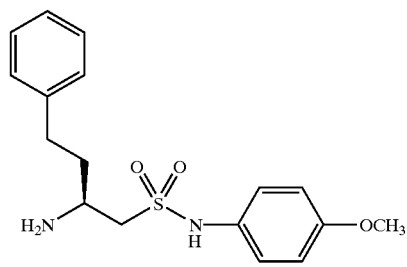

A solution comprised of crude tert-butyl 1-(4-methoxyphenylsulfamoylmethyl)-3-phenylpropylcarbamate (1.92 g, 4.42 mmol), prepared as in Reference 1, in DCM (10 mL) was treated with a 4M solution of hydrogen chloride in dioxane (11 mL). The mixture was stirred for 16 hours at room temperature and diluted with diethyl ether. A resulting precipitate was collected by filtration, washed several times with diethyl ether and hexane and pumped dry to provide 2S-amino-N-4-methoxyphenyl-4-phenylbutane-1-sulfonamide hydrochloride with quantitative mass recovery. $^1$H NMR (DMSO): 2.05 (2H, m); 2.6–2.7 (2H, m); 3.4 (3H, m*); 3.72 (3H, s); 6.9 (2H, d, J=7 Hz); 7.25 (5H, m); 7.3 (2H, d, J=7 Hz); 8.5 (br. s); 10.0 (1H, s).

Proceeding as in Reference 2 provided the following compounds of Formula 4:

2S-amino-N-(4-hydroxyphenyl)-4-phenylbutane-1-sulfonamide hydrochloride; $^1$H NMR (DMSO): 2.09 (2H, m); 2.72 (2H, m*); 3.68 (1H, m); 3.91–3.94 (2H, 2×dd); 7.22 (7H, m*); 7.67 (2H, d, J=7 Hz); 8.64 (2H, d, J=7 Hz); 8.7 (m*); and benzyl 5S-amino-6-(4-methoxyphenylsulfamoyl)hexylcarbamate hydrochloride.

Reference 3

Synthesis of N-(3-acetylphenyl)-2S-amino-4-phenylbutane-1-sulfonamide p-toluenesulfonate, ie., a compound of formula 4 in which $R^1$ is 3-acetylphenyl and $R^3$ is 2-phenylethyl:

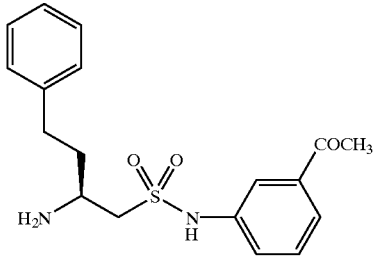

A solution comprised of crude tert-butyl 1S-(3-acetylphenylsulfamoylmethyl)-3-phenylpropylcarbamate, prepared as in Reference 1, in DCM (3 mL) was treated with azeotropically dried anhydrous p-toluenesulfonic acid (1.3 g, 6.83 mmol) in ether (3 mL). The mixture was stirred at room temperature for approximately 12 hours, diluted with diethyl ether (100 mL), washed with diethyl ether (2×30 mL) and pumped dry to provide N-(3-acetylphenyl)-2S-amino-4-phenylbutane-1-sulfonamide-p-toluenesulfonate (1.59 g, 59% yield). $^1$H NMR (DMSO-d$^6$): 1.99 (2H, m*); 2.28 (3H, s); 2.56 (3H, s*); 2.61 (2H, m*); 3.42–3.54 (3H, m*); 7.09–7.77 (13H, m*); 8.01 (2H, br. s); 10.4 (1H, s). MS (M+1, free amine): 347.

Reference 4

Synthesis of 2-amino-N-(4-methoxyphenyl) ethanesulfonamide, i.e., a compound of formula 4 in which R$^1$ is 4-methoxyphenyl and R$^3$ is hydrogen

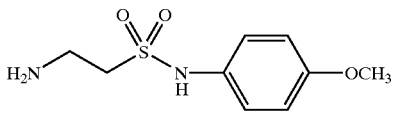

A solution comprised of benzyl 2-(4-methoxyphenylsulfamoyl)ethylcarbamate (2.78 g, 7.63 mmol), prepared as in Reference 1, in ethanol (20 mL) and cyclohexene (20 mL) was treated with 20% palladium hydroxide (0.95 g). The mixture was heated at reflux for 2 hours, cooled, and concentrated to dryness. The solid was triturated with ether, filtered and dried to provide 2-amino-N-(4-methoxyphenyl)ethanesulfonamide (1.08 grams, 61% yield). $^1$H NMR (DMSO-d$^6$): 2.86 (2H, t, J=6.4 Hz); 3.04 (2H, t, J=6.4 Hz); 3.72 (3H, s); 4.16 (2H, br. s); 6.87 (2H, d, J=9 Hz); 7.05 (2H, d, J=9 Hz).

Reference 5

Synthesis of tert-butyl 1S-chlorosulfonylmethyl-3-phenylpropylcarbamate, i.e., a compound of formula 2 in which R$^3$ is phenethyl and PG is tert-butoxycarbonyl

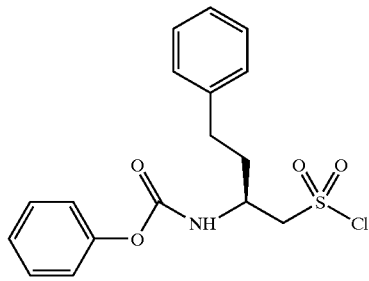

A solution comprised of 2S-tert-butoxycarbonylamino-4-phenylbutyric acid (20.27 g, 72.56 mmol) in THF (100 mL) was cooled to 0° C. and then 4-methylmorpholine (7.98 mL, 72.56 mmol) and isobutyl chloroformate (9.41 mL, 72.56 mmol) were added. The mixture was allowed to stand for 10 minutes and then filtered. The filter was washed through with THF (100 mL) and the combined filtrates were added, with rapid stirring, to a solution of sodium borohydride (5.45 g, 145.1 mmol) in water (200 mL) at 0° C. The mixture was stirred for 30 minutes and then diluted with saturated aqueous sodium bicarbonate (400 mL) and ethyl acetate (200 mL). The mixture was stirred vigorously for 20 minutes, separated, and the organic phase was washed with brine (100 mL). The solution was dried over magnesium sulfate, filtered, and evaporated to dryness to provide tert-butyl 1S-hydroxymethyl-3-phenylpropylcarbamate.

The tert-butyl 1S-hydroxymethyl-3-phenylpropylcarbamate was dissolved in DCM (200 mL). The solution was cooled to 0° C. and then triethylamine (27.31 mL, 195.9 mmol) was added. The mixture was stirred vigorously while methanesulfonyl chloride (13.48 mL, 174.1 mmol) was added over 5 minutes. The mixture was stirred for an additional 30 minutes and then diluted with water (200 mL). The dilution was stirred for an additional 30 minutes and then the organic phase was separated, dried over magnesium sulfate, filtered, and evaporated to dryness to provide tert-butyl 1S-methanesulfonyloxymethyl-3-phenylpropylcarbamate.

A solution of cesium thiolacetate was prepared by treating a solution of thiolacetic acid (10.36 mL, 145.1 mmol) in methanol (100 mL) with cesium carbonate (23.64 g, 72.56 mmol), concentrating the mixture and dissolving the residue in DMF (50 mL). The tert-butyl 1S-methanesulfonyloxymethyl-3-phenylpropylcarbamate was dissolved in DMF (50 mL) and added to the cesium thiolacetate solution. The mixture was stirred at room temperature for approximately 12 hours and diluted with water (500 mL) and then ethyl acetate (300 mL). The mixture was stirred vigorously for 20 minutes and the organic phase was separated, washed with 1N hydrochloric acid (200 mL), saturated aqueous sodium bicarbonate (200 mL) and brine (200 mL), dried over a mixture of magnesium sulfate and decolorizing charcoal, filtered, and concentrated to dryness to provide tert-butyl 1S-acetylsulfanylmethyl-3-phenylpropyl)carbamate.

The tert-butyl 1S-acetylsulfanylmethyl-3-phenylpropyl) carbamate (14.73 g, 45.54 mmol) was dissolved in a 1:1 mixture of DCM:water (500 mL). The biphasic mixture was stirred rapidly and cooled to 0° C. Chlorine gas was bubbled into the solution for approximately 30 minutes (to the saturation point). The organic layer was separated, dried over magnesium sulfate, filtered, concentrated and the residue was recrystallized from DCM/hexane to provide tert-butyl 1S-chlorosulfonylmethyl-3-phenylpropylcarbamate (9.80 g, 62% yield).

Proceeding as in Reference 5 and using appropriate starting materials provided the following compounds of Formula 2:

(2-chlorosulfonylethyl)-carbamic acid tert-butyl ester;

(5-tert-butoxycarbonylamino-6-chlorosulfonylhexyl)-carbamic acid benzyl ester; and (5-amino-1-chlorosulfonylmethylpentyl)-carbamic acid tert-butyl ester.

Reference 6

Synthesis of 2S-amino-N-[1S-(4-methoxyphenylsulfamoylmethyl)-3-phenylpropyl]-4-methyl-pentanamide hydrochloride, i.e., a compound of formula 6 in which $R^1$ is 4-methoxyphenyl, $R^3$ is 2-phenethyl and $R^4$ is 2-methylpropyl and $R^5$ is hydrogen

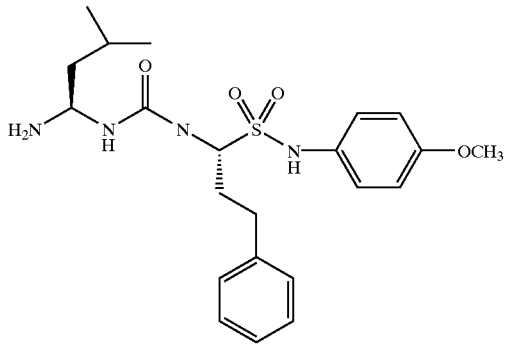

A solution of tert-butyl 1S-[1S-(4-methoxyphenylsulfamoylmethyl)-3-phenylpropylcarbamoyl]-3-methylbutylcarbamate (1.1 g, 2 mmol) in dichloromethane (5 mL) was treated with a 1M solution of hydrogen chloride in diethyl ether (20 mL), with stirring, at room temperature for 5 hours and then concentrated to provide 2S-amino-N-[1S-(4-methoxyphenylsulfamoylmethyl)-3-phenylpropyl]-4-methylpentanamide hydrochloride (810 mg, 84% yield).

Example 1

Synthesis of benzyl 1S-[1S-(4-methoxyphenylsulfamoylmethyl)-3-phenylpropylcarbamoyl]-3-methylbutylcarbamate (Compound 1)

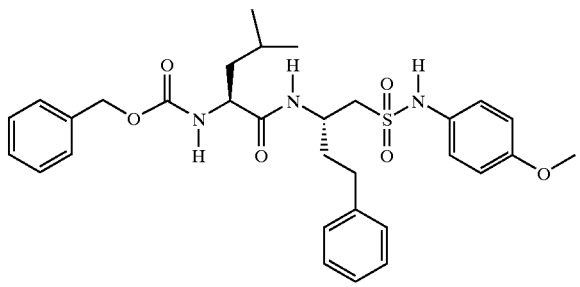

A solution comprised of 2S-benzyloxycarbonylamino-4-methylpentanoic acid (0.25 g, 0.944 mmol) in THF (10 mL) was cooled to −10° C. and then 4-methylmorpholine (0.104 mL, 0.944 mmol) and isobutyl chloroformate (0.122 mL, 0.944 mmol) were added. The reaction mixture was allowed 5 minutes and then 2S-amino-N-(4-methoxyphenyl)-4-phenylbutane-1-sulfonamide hydrochloride (0.35 g, 0.944 mmol), prepared as in Reference 2, and 4-methylmorpholine (0.104 mL, 0.944 mmol) were added sequentially. The reaction mixture was stirred for 45 minutes and then ethyl acetate (50 mL) was added. The reaction mixture was washed with 1N hydrochloric acid, saturated sodium bicarbonate and brine (10 mL each), dried over $MgSO_4$, filtered and concentrated. Product was purified from the residue on a silica gel column, mobile phase 30–50% ethyl acetate/hexane and crystallized from DCM/diethyl ether/hexane to provide benzyl 1S-[1S-(4-methoxyphenylsulfamoylmethyl)-3-phenylpropylcarbamoyl]-3-methylbutylcarbamate (0.172 g, 31% yield). $^1$H NMR (CDCl$_3$): 0.91 (6H, 2×d*); 1.4–1.81 (4H, m*); 1.93 (1H, m); 2.55 (2H, m); 3.1–3.26 (2H, 2×dd); 3.74 (3H, s); 4.18 (1H, m); 4.22 (1H, m); 5.07 (2H, dd); 5.48 (1H, d, J=7 Hz); 6.76 (2H, d, J=9 Hz); 6.89 (1H, d); 7.04–7.28 (12H, m); 7.87 (1H, s). MS (M+1) 582.

Proceeding as in Example 1 provided the following compounds of Formula I:

benzyl 1S-[1S-(4-methoxyphenylsulfamoylmethyl)-3-phenylpropylcarbamoyl]-2-methyl-butyl-carbamate (Compound 2); $^1$H NMR (CDCl$_3$): 0.85 (3H, t, J=6.5 Hz); 0.91 (3H, d, J=6.5 Hz); 1.12 (1H, m); 1.52 (1H, m); 1.8–2.05 (4H, m*); 2.55 (2H, m*); 3.18 (2H, m); 3.73 (3H, s); 4.03 (1H, m); 4.31 (1H, m); 5.09 (2H, dd); 5.31 (1H, br d); 6.76 (3H, d+m); 7.05–7.31 (12H, m); 7.62 (1H, s). MS (M+1): 582;

tert-butyl 1S-[1S-(4-methoxyphenylsulfamoylmethyl)-3-phenylpropylcarbamoyl]-3-methyl-butylcarbamate (Compound 3); $^1$H NMR (CDCl$_3$): 0.85 (6H, 2×d*); 0.93 (1H, m*); 1.44 (9H, s); 1.37–1.62 (3H, m*). 2.07 (2H, m); 2.64 (2H, m); 3.62 (1H, dd, J=13.6, 3.7 Hz); 3.79 (3H, s); 3.91 (1H, dd*); 3.96 (1H, m*); 4.31 (1H, m); 4.81 (1H, m); 6.5 (1H, d, J=7.4 Hz); 7.1–7.26 (7H);

benzyl 1S-[1S-(3-acetylphenylsulfamoylmethyl)-3-phenylpropylcarbamoyl]-3-methylbutyl-carbamate (Compound 4); $R_f$ (TLC, 20% ethyl acetate/$CH_2Cl_2$): 0.65; $^1$H NMR (CDCl$_3$); 0.93 (6H, 2×d, J=6 Hz); 1.52 (1H, m); 1.67 (2H, m); 1.83 (1H, m); 1.98 (1H, m); 2.54–2.59 (5H, s, m*); 3.14–3.37 (2H, 2×dd); 4.11 (1H, m); 4.25 (1H, m); 5.07–5.11 (3H, s, d*); 6.59 (1H, d, J=8.4 Hz); 7.04–7.38 (13 H); 7.69 (1H, d); 7.82 (1H, s); 8.14 (1H, s). MS (M+1): 594;

N-{1S-[1S-(4-methoxyphenylsulfamoylmethyl)-3-phenylpropylcarbamoyl]-2-methylbutyl}-4-methylpiperazine-1-carboxamide (Compound 5); $^1$H NMR (CDCl$_3$): 0.9 (3H, t, J=6 Hz); 1.00 (3H, d, J=6 Hz); 1.19 (1H, m); 1.56 (1H, m); 1.85 (1H, m); 2.01 (2H, m); 2.30 (3H, s); 2.42 (4H, m); 2.56 (2H, m); 3.15–3.32 (2H, 2×dd); 3.43 (4H, m); 3.77 (3H, s); 4.07 (1H, t, J=6 Hz); 4.23 (1H, m); 4.89 (1H, br d); 6.78 (2H, d); 7.00 (1H, d); 7.05–7.25 (7H, m); 8.28 (1H, br s). MS (M$^+$) 574; and benzyl 1S-[2-(4-methoxyphenylsulfamoyl)ethylcarbamoyl]-2-methylbutylcarbamate (Compound 6); $R_f$ (TLC: 50% ethyl acetate/$CH_2Cl_2$): 0.65; $^1$H NMR (CDCl$_3$): 0.84–0.92 (6H, d, t*); 1.09 (1H, m); 1.46 (1H, m); 1.89 (1H, m); 3.22 (2H, m); 3.68 (2H, m*); 3.74 (3H, s); 4.01 (1H, t, J=6 Hz); 5.02 (2H, dd); 5.35 (1H, d, J=8 Hz); 6.85 (2H, d, J=7.5 Hz); 7.24 (2H, 7.5 Hz); 7.30 (6H, s, d*).

(2-cyclohexyl-1S-{3-phenyl-1S-[(2-phenylaminoethylsulfamoyl)-methyl]-propylcarbamoyl}ethyl)-carbamic acid tert-butyl ester (Compound 7);

Example 2

Synthesis of 4-dimethylamino-N-{1S-[1S-(4-methoxyphenylsulfamoylmethyl)-3-phenylpropylcarbamoyl]-3-methylbutyl}benzamide (Compound 8)

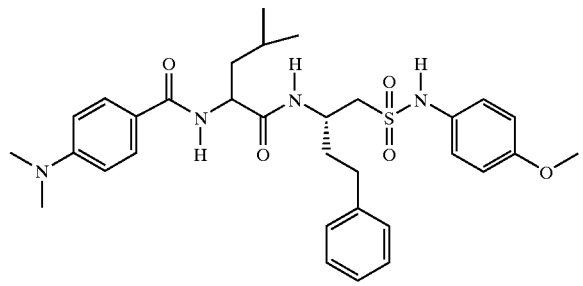

A solution comprised of 2S-amino-N-(4-methoxyphenyl)-4-phenylbutane-1-sulfonamide hydrochloride (0.371 g, 1 mmol), prepared as in Reference 2,2S-(4-dimethylaminobenzoylamino)-4-methylpentanoic acid (0.278 g, 1 mmol) and PyBOP (0.52 g, 1 mmol) in DMF (10 mL) was treated with triethylamine (0.418 mL, 3 mmol). The mixture was stirred at room temperature for approximately 12 hours and then diluted with ethyl acetate (30 mL), washed with 1N hydrochloric acid (10 mL) and saturated aqueous sodium bicarbonate (10 mL), dried (MgSO$_4$), filtered and concentrated to dryness. The product was crystallized twice from DCM/diethyl ether/hexane to provide 4-dimethylamino-N-{1S-[1S-(4-methoxyphenyl-sulfamoylmethyl)-3-phenylpropylcarbamoyl]-3-methylbutyl}benzamide (50 mg, 8.4% yield) as a diastereomeric/rotameric mixture. $^1$H NMR (CDCl$_3$): 0.85–1.1 (6H, 2×d, t); 1.25 (1H, m); 1.5–2.2 (5H, 5×m*); 2.56 (2H, m); 3.02 (6H, s); 3.04–3.19 (2H, m*); 3.72 (3H, 2×s) 4.2–4.44 (1H, m*); 4.45, 4.67 (1H total, 2×dd); 6.7 (4H, 2×d*); 7.06–7.24 (8H, m*); 7.69 (2H, d, J=8.7 Hz); 7.92, 8.0 (1H total, 2×s).

Proceeding as in Example 2 provide the following compounds of Formula I:

quinoline-6-carboxylic acid (1-{1-[(4-methoxyphenylsulfamoyl)-methyl]-3-phenyl-propylcarbamoyl}-3-methylbutyl)-amide (Compound 9);

morpholine-4-carboxylic acid (2-cyclohexyl-1S-{3-phenyl-1S-[(2-phenylamino-ethylsulfamoyl)methyl]-propylcarbamoyl}-ethyl)-amide (Compound 10);

4-(2-dimethylaminothiazol-4-yl)-N-{1S-[2-(4-methoxyphenylsulfamoyl)-ethylcarbamoyl]-3-methyl-butyl}benzamide (Compound 11);

(S)-2-acetylamino-3-cyclohexyl-N-{1-[(4-methoxyphenylsulfamoyl)-methyl]-3-phenyl-propyl}-propionamide (Compound 12);

(R)-2-acetylamino-3-cyclohexyl-N-{1-[(4-methoxyphenylsulfamoyl)methyl]-3-phenyl-propyl}-propionamide (Compound 13);

2(RS)-acetylamino-3-cyclohexyl-N-{1-[(4-hydroxyphenylsulfamoyl)methyl]-3-phenyl-propyl}-propionamide (Compound 14).

Example 3

Synthesis of benzyl 6-(4-methoxyphenylsulfamoyl)-5S-{4-methyl-2S-[4-(2-pyridin-3-ylaminothiazol-4-yl)-benzoylamino]pentanoylamino}hexylcarbamate (Compound 15)

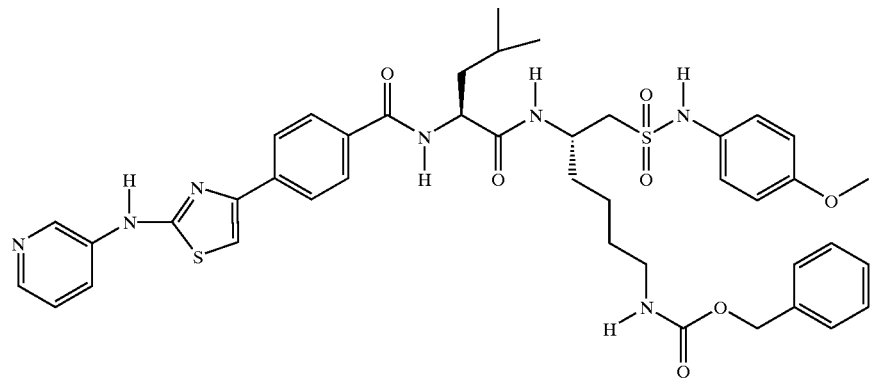

A solution comprised of benzyl 5S-amino-6-(4-methoxyphenylsulfamoyl)-hexylcarbamate hydrochloride (0.254 g, 0.539 mmol), prepared as in Reference 2,4-methyl-2S-[4-(2-pyridin-3-ylaminothiazol-4-yl)benzoylamino] pentanoic acid hydrochloride (0.232 g, 0.539 mmol) and PyBOP (0.281 g, 0.539 mmol) in DMF (5 mL) was treated with triethylamine (0.226 mL, 1.62 mmol). The reaction mixture was stirred at room temperature for 90 minutes and then diluted with ethyl acetate (30 mL), washed with saturated aqueous sodium bicarbonate (20 mL), brine (5 mL), dried (MgSO$_4$), filtered and concentrated to dryness. The residue was triturated with 5:1 ether/dichloromethane. Solids were collected by filtration and product was purified on a short path of silica gel using 50% ethyl acetate/DCM followed by 5% methanol/DCM to provide benzyl 6-(4-methoxyphenylsulfamoyl)-5S-{4-methyl-2S-[4-(2-pyridin-3-ylaminothiazol-4-yl)benzoylamino]-pentanoylamino}hexylcarbamate. R$_f$ (TLC: 10% methanol/DCM): 0.45. $^1$H NMR (DMSO-d$^6$): 0.88 (6H, 2×d); 0.9–1.75 (9H, m*); 2.93 (2H, m); 3.09 (2H, m); 3.69 (3H, s); 4.19 (1H, m); 4.39 (1H, m); 4.99 (2H, s). 6.88 (2H, m); 7.13–7.7.45 (9H, m); 7.57 (1H, s); 7.98 (5H, m*); 8.19 (1H, d, J=5 Hz); 8.29 (1H, d, J=7 Hz); 8.43 (1H, d, J=6 Hz); 8.86 (1H, d, J=2.4 Hz); 9.45 (1H, s); 10.6 (1H, s). MS (M+1): 8.28.

Proceeding as in Example 3 the following compounds of Formula I were prepared:

N-{1S-[1S-(4-methoxyphenylsulfamoylmethyl)-3-phenylpropylcarbamoyl]-3-methy-butyl}-4-(2-pyridin-3-ylaminothiazol-4-yl)benzamide (Compound 16); $^1$H NMR (DMSO-d$^6$) 0.87 (6H, 2×d); 1.23 (1H, m*); 1.5–1.86 (3H, m*); 1.99 (1H, m); 2.59 (2H, m); 3.15 (2H, m); 3.70 (3H, s); 4.24 (1H, m); 4.47 (1H, m); 6.87 (2H, d, J=9 Hz); 7.14–7.25 (7H, m); 7.43 (1H, dd); 7.58 (1H, s); 7.99 (4H, 2×d); 8.14 (1H, d); 8.19 (1H, d); 8.3 (1H, d); 8.53 (1H, d); 8.86 (1H, d); 9.48 (1H, s); 10.55 (1H, s). MS (M+1): 727.

Example 4

Synthesis of N-{1S-[1S-(4-methoxyphenylsulfamoylmethyl)-3-phenylpropylcarbamoyl]-3-methylbutyl}nicotinamide (Compound 19)

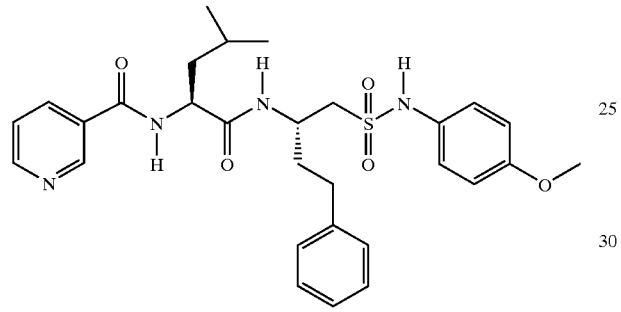

A mixture comprised of 2S-amino-N-[1S-(4-methoxyphenylsulfamoylmethyl)-3-phenylpropyl]-4-methylpentanamide hydrochloride (110 mg, 0.227 mmol), prepared as in Reference 6, and nicotinyl chloride hydrochloride (44 mg, 0.227 mmol) in THF (2 mL) and DCM (2 mL) was treated with triethylamine (0.095 mL, 0.682 mmol). The mixture was stirred at room temperature for 3 hours and then diluted with ethyl acetate (25 mL). The dilution was washed with saturated sodium bicarbonate (5 mL), dried (MgSO$_4$), filtered and concentrated to dryness. The residue was dissolved in DCM/diethyl ether/hexane and product was crystallized to provide N-{1S-[1S-(4-methoxyphenylsulfamoylmethyl)-3-phenylpropylcarbamoyl]-3-methylbutyl}nicotinamide (63 mg, 50% yield). R$_f$(TLC, 50% ethyl acetate/DCM): 0.25. $^1$H NMR (CDCl$_3$): 0.92–0.97 (6H, 2×d); 1.7–1.81 (4H, m*); 1.95 (1H, m); 2.54 (2H, m); 3.16 (2H, dd); 3.78 (3H, s); 4.30 (1H, m); 4.59 (1H, m); 6.74 (2H, d, J=9 Hz); 6.89 (1H, d, J=8 Hz); 7.02–7.24 (8H, m); 7.37 (1H, dd); 7.96 (1H, br s); 8.12 (1H, d, J=8 Hz); 8.71 (1H, br s); 9.06 (1H, br s). MS (M+1): 553.

Proceeding as in Example 4 provided:

N-{1S-[1S-(4-methoxyphenylsulfamoyl-methyl)-3-phenylpropylcarbamoyl]-3-methylbutyl}-isonicotinamide (Compound 20); R$_f$(TLC, 20% ethyl acetate/DCM); 0.1; $^1$H NMR (CDCl$_3$): 0.96 (6H, 2×d); 1.65–1.89 (4H, m*); 1.98 (1H, m); 2.57 (2H, m); 3.16 (2H, 2×dd); 3.75 (3H, s); 4.30 (1H, m); 4.59 (1H, m); 6.75 (3H, d, m*); 6.85 (1H, d, J=8 Hz); 7.05–7.24 (7H, m); 7.59 (3H, m); 8.71 (2H, d); MS (M+1): 553.

Example 5

Synthesis of N-{1-[1-(4-methoxyphenylsulfamoylmethyl)-3-phenylpropylcarbamoyl]-3-methylbutyl}-1H-indole-5-carboxamide (Compound 21)

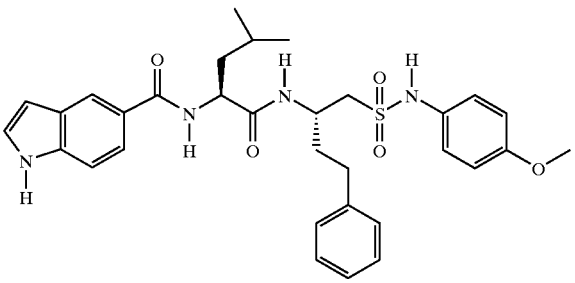

A mixture comprised of and 2S-amino-N-[1S-(4-methoxyphenylsulfamoyl-methyl)-3-phenylpropyl]-4-methylpentanamide hydrochloride (0.100 g, 0.206 mmol), prepared as in Reference 6, and 5-indolecarboxylic acid (33.3 mg, 0.206 mmol) in DCM (2 mL) was treated with triethylamine (0.029 mL, 0.206 mmol) and DCC (0.206 mL of a 1.0 M DCM solution). The reaction mixture was stirred at room temperature overnight and then eluted directly through a silica gel column (0–50% ethyl acetate/CH$_2$Cl$_2$ gradient). Product was crystallized from DCM/diethyl ether/hexane to provide N-{1-[1-(4-methoxyphenylsulfamoylmethyl)-3-phenylpropylcarbamoyl]-3-methylbutyl}-1H-indole-5-carboxamide (58 mg, 48% yield). R$_f$ (TLC, 20% ethyl acetate/CH$_2$Cl$_2$): 0.2; NMR (CDCl$_3$): 0.97–1.02 (6H, 2×d, J=6 Hz); 1.64–1.98 (5H, m*); 2.54 (2H, m); 3.02–3.19 (2H, 2×dd); 3.74 (3H, s); 4.27 (1H, m); 6.48 (1H, d, J=7 Hz); 6.61 (1H, s, t); 6.75 (2H, d, J=9 Hz); 6.94–7.27 (9H, m*); 7.41 (1H, d); 7.61 (1H, dd); 7.87 (1H, s); 8.10 (1H, s); 8.47 (1H, br s); MS (M+1): 591.

Proceeding as in Example 5 provided:

tert-Butyl 3-{1S-[1S-(4-methoxyphenyl-sulfamoylmethyl)-3-phenylpropylcarbamoyl]-3-methyl-butylcarbamoylphenyl}carbamate (Compound 22); R$_f$ (TLC, 20% ethyl acetate/CH$_2$Cl$_2$): 0.35; $^1$H NMR (CDCl$_3$): 0.93–0.99 (6H, 2×d, J=6 Hz); 1.50 (9H, s); 1.42–1.85 (4H, m*); 1.98 (1H, m); 2.58 (2H, m); 3.13 (2H, m); 3.75 (3H, s); 4.30 (1H. m); 4.60 (1H, m); 6.53 (1H, d, J=7 Hz); 6.73 (2H, d, J=9 Hz); 7.0–7.4 (11H, m*); 7.62 (1H, d, J=7,5 Hz); 7.72 (1H, s); 7.78 (1H, s); MS (M+1): 667.

Example 6

Synthesis of 3-amino-N-{1S-[1S-(4-methoxyphenylsulfamoylmethyl)-3-phenylpropylcarbamoyl]-3-methylbutyl}benzamide (Compound 23)

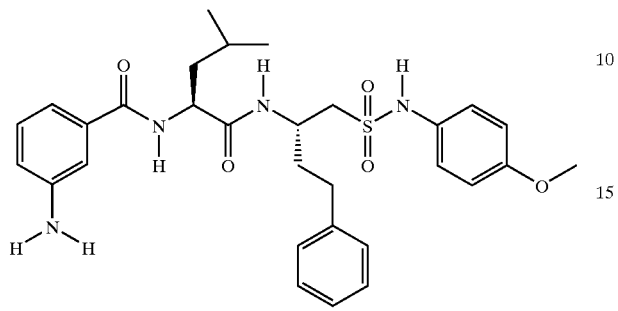

A solution comprised of tert-butyl 3-{1S-[1S-(4-methoxyphenylsulfamoyl-methyl)-3-phenylpropylcarbamoyl]-3-methylbutylcarbamoyl}phenylcarbamate (20 mg, 30 μmol), prepared as in Example 6, in methylene chloride (2 mL) was treated with a 4M solution of hydrochloric acid in dioxane (1 mL) at room temperature for 16 hours and then diluted with diethyl ether (100 mL) to form a precipitate. The precipitate was collected by filtration, washed with ether and dried in vacuo to provide 3-amino-N-{1S-[1S-(4-methoxyphenyl-sulfamoylmethyl)-3-phenylpropylcarbamoyl]-3-methylbutyl}benzamide (14.3 mg, 79% yield). MS (M+1, free base): 567.

Example 7

Synthesis of N-{1S-[5-amino-1S-(4-methoxyphenylsulfamoylmethyl)pentylcarbamoyl]-3-methyl-butyl}-4-(2-pyridin-3-ylaminothiazol-4-yl)benzamide hydrobromide

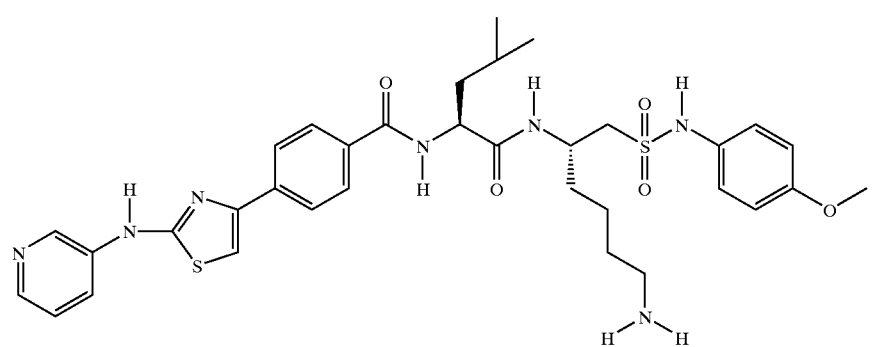

A solution of benzyl 6-(4-methoxyphenylsulfamoyl)-5S-{4-methyl-2S-[4-(2-pyridin-3-ylamino-thiazol-4-yl)benzoylamino]pentanoylamino}hexylcarbamate (0.1 g, 0.121 mmol), prepared as in Example 3, in DCM (3 mL) was treated with 30% (0.1 g, 0.3 mL) solution of hydrogen bromide in glacial acetic acid for 3 hours. The solution was diluted with methanol/ether to form a precipitate which was isolated to provide N-{1S-[5-amino-1S-(4-methoxyphenylsulfamoylmethyl)pentylcarbamoyl]-3-methylbutyl}-4-(2-pyridin-3-ylaminothiazol-4-yl)benzamide hydrobromide (90 mg, 0.1 mmol). $^1$H NMR (DMSO-d$^6$): 9.88 (6H, 2×d); 1.2–1.71 (9H, m); 2.72 (2H, m); 3.12 (2H, m); 3.71 (3H, s); 4.22 (1H, m); 4.43 (1H. m); 6.89 (2H, d, J=9 Hz); 7.14 (2H, d, J=9 Hz);.75 (3H, s, m*); 8.00–8.06 (7H, m); 8.53–8.66 (3H, d, d, m*); 9.47 (1H, s); 9.56 (1H, d, J=2 Hz); 11.55 (1H, s). MS (M+1, free base): 6.94.

Example 8

Synthesis of benzyl 1S-{1S-[3-(1-hydroxyethyl)phenylsulfamoylmethyl]-3-phenylpropylcarbamoyl}-3-methylbutyl-carbamate (Compound 26)

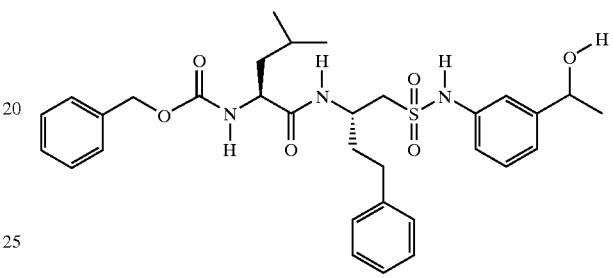

A solution comprised of benzyl 1S-[1S-(3-acetylphenylsulfamoylmethyl)-3-phenylpropyl-carbamoyl]-3-methylbutylcarbamate (85 mg, 0.143 mmol), prepared as in Example 1, in THF (5 mL) was treated with sodium borohydride (10 mg, 0.266 mmol). Water (0.5 mL) was added and the mixture was stirred for 30 minutes. Saturated aqueous sodium bicarbonate (5 mL) and ethyl acetate (25 mL) were added and the mixture was stirred for 15 minutes. The organic phase was separated, dried (MgSO$_4$), filtered and concentrated to dryness to provide benzyl 1S-{1S-[3-(1-hydroxyethyl)-phenylsulfamoylmethyl]-3-phenylpropyl-carbamoyl}-3-methylbutylcarbamate (70 mg, 82% yield). R$_f$ (TLC, 20% ethyl acetate/CH$_2$Cl$_2$): 0.2–0.3 (2 spots, corresponding to diastereomers at the hydroxyethyl group). MS(M+1): 596.

Example 9

Cathepsin B Assay

Solutions of test compounds in varying concentrations were prepared in 10 μL of dimethyl sulfoxide (DMSO) and then diluted into assay buffer (40 μL, comprising: N,N-bis (Compound 24)

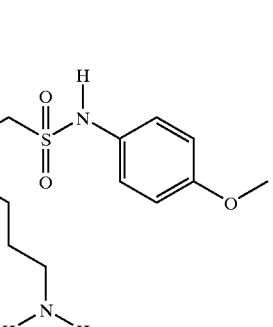

(2-hydroxyethyl)-2-aminoethanesulfonic acid (BES), 50 mM (pH 6); polyoxyethylenesorbitan monolaurate, 0.05%; and dithiothreitol (DTT), 2.5 mM). Human cathepsin B (0.025 pMoles in 25 μL of assay buffer) was added to the dilutions. The assay solutions were mixed for 5–10 seconds on a shaker plate, covered and incubated for 30 minutes at room temperature. Z-FR-AMC (20 nMoles in 25 μL of assay buffer) was added to the assay solutions and hydrolysis was followed spectrophotometrically at (λ 460 nm) for 5 minutes. Apparent inhibition constants ($K_i$) were calculated from the enzyme progress curves using standard mathematical models.

Compounds of the invention were tested by the above-described assay and observed to exhibit cathepsin B inhibitory activity.

Example 10

Cathepsin K Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin K (0.0906 pMoles in 25 μL of assay buffer) was added to the dilutions. The assay solutions were mixed for 5–10 seconds on a shaker plate, covered and incubated for 30 minutes at room temperature. Z-Phe-Arg-AMC (4 nMoles in 25 μL of assay buffer) was added to the assay solutions and hydrolysis was followed spectrophotometrically at (λ 460 nm) for 5 minutes. Apparent inhibition constants ($K_i$) were calculated from the enzyme progress curves using standard mathematical models.

Compounds of the invention were tested by the above-described assay and observed to exhibit cathepsin K inhibitory activity.

Example 11

Cathepsin L Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin L (0.05 pMoles in 25 μL of assay buffer) was added to the dilutions. The assay solutions were mixed for 5–10 seconds on a shaker plate, covered and incubated for 30 minutes at room temperature. Z-Phe-Arg-AMC (1 nMoles in 25 μL of assay buffer) was added to the assay solutions and hydrolysis was followed spectrophotometrically at (λ 460 nm) for 5 minutes. Apparent inhibition constants ($K_i$) were calculated from the enzyme progress curves using standard mathematical models.

Compounds of the invention were tested by the above-described assay and observed to exhibit cathepsin L inhibitory activity.

Example 12

Cathepsin S Assay

Solutions of test compounds in varying concentrations were prepared in 10 μL of dimethyl sulfoxide (DMSO) and then diluted into assay buffer (40 μL, comprising: MES, 50 mM (pH 6.5); EDTA, 2.5 mM; and NaCl, 100 mM). Human cathepsin S (0.158 pMoles in 25 μL of assay buffer) was added to the dilutions. The assay solutions were mixed for 5–10 seconds on a shaker plate, covered and incubated for 30 minutes at room temperature. Z-Val-Val-Arg-AMC (9 nMoles in 25 μL of assay buffer) was added to the assay solutions and hydrolysis was followed spectrophotometrically at (λ 460 nm) for 5 minutes. Apparent inhibition constants ($K_i$) were calculated from the enzyme progress curves using standard mathematical models.

Compounds of the invention were tested by the above-described assay and observed to exhibit cathepsin S inhibitory activity.

Example 13

Representative Pharmaceutical Formulations Containing a Compound of Formula I:

Oral Formulation

| | |
|---|---|
| Compound of Formula I | 10–100 mg |
| Citric Acid Monohydrate | 105 mg |
| Sodium Hydroxide | 18 mg |
| Flavoring | |
| Water | q.s. to 100 mL |

Intravenous Formulation

| | |
|---|---|
| Compound of Formula I | 0.1–10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

Tablet Formulation

| | |
|---|---|
| Compound of Formula I | 1% |
| Microcrystalline Cellulose | 73% |
| Stearic Acid | 25% |
| Colloidal Silica | 1% |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

I claim:

1. A compound of Formula I:

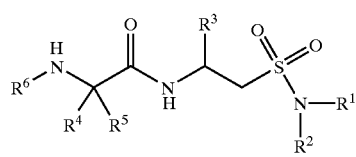

in which:

$R^1$ and $R^2$ independently are —$R^8$, —$X^2OR^8$, —$X^2SR^8$, —$X^2S(O)R^8$, —$X^2S(O)_2R^8$, —$X^2C(O)R^8$, —$X^2C$ $(OR^7)R^7R^8$, —$X^2C(O)OR^8$, —$X^2NR^7R^8$, —$X^2NR^7C(O)OR^8$, —$X^2C(O)NR^7R^8$, —$X^2S(O)_2NR^7R^8$, —$X^2NR^7C(O)NR^7R^8$ or —$X^2NR^7C(NR^7)NR^7R^8$, wherein $X^2$ is $(C_{1-6})$alkylene, $R^7$ is hydrogen or $(C_{1-6})$alkyl; $R^8$ is hydrogen, $(C_{1-6})$alkyl, $(C_{3-12})$cycloalkyl$(C_{0-3})$alkyl, hetero$(C_{5-12})$cycloalkyl$(C_{0-3})$alkyl, $(C_{6-12})$aryl$(C_{0-3})$alkyl, hetero$(C_{5-12})$aryl$(C_{0-3})$alkyl, $(C_{9-12})$bicycloaryl$(C_{0-3})$alkyl or hetero$(C_{8-12})$bicyclo-aryl$(C_{0-3})$alkyl; wherein within $R^8$ said cycloalkyl, heterocycloalkyl, aryl, heteroaryl, bicycloaryl or heterobicycloaryl ring may be substituted with halo, —$R^9$, —$X^3OR^9$, —$X^3SR^9$, —$X^3S(O)R^9$, —$X^3S(O)_2R^9$, —$X^3C(O)R^9$, —$X^3C(OR^9)R^9$, —$X^3C(O)OR^9$, —$X^3NR^9R^{10}$, —$X^3NR^9C(O)OR^9$, —$X^3C(O)NR^9R^{10}$, —$X^3S(O)_2NR^9R^{10}$, —$X^3NR^9C(O)NR^9R^{10}$ or —$X^3NR^9C(NR^9)NR^9R^{10}$; wherein $X^3$ is a bond or $(C_{1-6})$alkylene, $R^9$ is hydrogen or $(C_{1-6})$alkyl and $R^{10}$ is cycloalkyl;

$R^3$ is —$R^{11}$, —$X^3OR^{11}$, —$X^3SR^{11}$, —$X^3S(O)R^{11}$, —$X^3S(O)_2R^{11}$, —$X^3C(O)R^{11}$, —$X^3C(O)OR^{11}$, —$X^3NR^{11}R^{12}$, —$X^3NR^{12}C(O)OR^{11}$, —$X^3C(O)NR^{11}R^{12}$, —$X^3S(O)_2NR^{11}R^{12}$, —$X^3NR^{12}C(O)NR^{11}R^{12}$ or —$X^3NR^{12}C(NR^{12})NR^{11}R^{12}$, wherein $X^3$ is as described above, $R^{11}$ is hydrogen, $(C_{1-6})$alkyl, halo$(C_{1-6})$alkyl, $(C_{3-12})$cycloalkyl$(C_{0-3})$alkyl, hetero$(C_{5-12})$cycloalkyl-$(C_{0-3})$alkyl, $(C_{6-12})$aryl$(C_{0-3})$alkyl, hetero$(C_{5-12})$aryl$(C_{0-3})$alkyl, $(C_{9-12})$bicycloaryl$(C_{0-3})$alkyl or hetero$(C_{8-12})$bicycloaryl$(C_{0-3})$alkyl and $R^{12}$ is hydrogen or $(C_{1-6})$alkyl, wherein any 1 to 3 annular atoms of any aromatic ring with available valences comprising $R^3$ are optionally independently substituted with halo, nitro, cyano, $(C_{1-6})$alkyl, halo-substituted $(C_{1-6})$alkyl, —$OR^7$, —$C(O)R^7$, —$C(O)OR^7$, —$C(O)NR^7R^7$, —$S(O)_2NR^7R^7$, —$X^2NR^7R^7$, —$X^2NR^7C(O)OR^7$, —$X^2NR^7C(O)NR^7R^7$ or —$X^2NR^7C(NR^7NR^7R^7$, wherein $X^2$ and $R^7$ are as defined above;

$R^4$ is hydrogen or $(C_{1-6})$alkyl;

$R^5$ is $(C_{1-6})$alkyl, halo$(C_{1-6})$alkyl, $(C_{3-12})$cycloalkyl$(C_{0-3})$alkyl, or —$X^2S(O)R^{14}$ where $X^2$ is as defined above and $R^{14}$ is $(C_{3-12})$cycloalkyl$(C_{0-3})$alkyl, hetero$(C_{5-12})$cycloalkyl$(C_{0-3})$alkyl, $(C_{6-12})$aryl$(C_{0-3})$alkyl, hetero$(C_{5-12})$aryl$(C_{0-3})$alkyl, $(C_{9-12})$bicycloaryl$(C_{0-3})$alkyl or hetero$(C_{8-12})$bicycloaryl$(C_{0-3})$alkyl; or $R^4$ and $R^5$ together with the carbon atom to which $R^4$ and $R^5$ are attached form $(C_{3-7})$cycloalkylene;

$R^6$ is hydrogen or —$X^4X^5R^{13}$, wherein $X$ is —$C(O)$—, $X^5$ is a bond, —O— or —$NR^{12}$—, wherein $R^{12}$ is as defined above, and $R^{13}$ is $(C_{1-6})$alkyl, —$R^{14}$, —$X^3OR^{14}$, —$X^3SR^{14}$, —$X^3S(O)R^{14}$, —$X^3S(O)_2R^{14}$, —$X^3C(O)R^{14}$, —$X^3C(O)OR^{14}$, —$X^3NR^{14}R^{15}$, —$X^3NR^{15}C(O)OR^{14}$, —$X^3C(O)NR^{14}R^{15}$, —$X^3S(O)_2NR^{14}R^{15}$, —$X^3NR^{15}C(O)NR^{14}R^{15}$ or —$X^3NR^{15}C(NR^{15})NR^{14}R^{15}$, wherein $X^3$ is as defined above; $R^{14}$ is $(C_{3-12})$cycloalkyl$(C_{0-3})$alkyl, hetero$(C_{5-12})$cycloalkyl$(C_{0-3})$alkyl, $(C_{6-12})$aryl$(C_{0-3})$alkyl, hetero$(C_{5-12})$aryl$(C_{0-3})$alkyl, $(C_{9-12})$bicycloaryl$(C_{0-3})$alkyl or hetero$(C_{8-12})$bicycloaryl$(C_{0-3})$alkyl; $R^{15}$ is hydrogen or $(C_{1-6})$alkyl; and within $R^{14}$ said cycloalkyl, heterocycloalkyl, aryl, heteroaryl, bicycloaryl or heterobicycloaryl ring may be substituted with —$OCF_3$, —$CF_3$, —OH, halo, —$R^{16}$, —$X^3OR^{16}$, —$X^3OR^{15}$, —$X^3C(O)R^{15}$, —$X^3SR^{16}$, —$X^3S(O)R^{16}$, —$R^{15}$, —$X^3S(O)_2R^{16}$, —$X^3C(O)OR^{15}$, —$X^3NR^{15}R^{15}$, —$X^3NR^{15}C(O)OR^{15}$, —$X^3C(O)NR^{15}R^{16}$, —$X^3S(O)_2NR^{15}R^{16}$, —$X^3NR^{15}C(O)NR^{15}R^{15}$ or —$X^3NR^{15}C(NR^{15})NR^{15}R^{16}$, wherein $X^3$ and $R^{15}$ are as defined above and $R^{16}$ is $(C_{3-12})$cycloalkyl$(C_{0-3})$alkyl, hetero$(C_{5-12})$cycloalkyl$(C_{0-3})$alkyl, $(C_{6-12})$aryl$(C_{0-3})$alkyl, hetero$(C_{5-12})$aryl$(C_{0-3})$alkyl, $(C_{9-12})$bicycloaryl$(C_{0-3})$alkyl or hetero$(C_{8-12})$bicycloaryl-$C_{0-3})$alkyl and within $R^{16}$ said cycloalkyl, heterocycloalkyl, aryl, heteroaryl, bicycloaryl or heterobicycloaryl ring may be substituted with —$R^{15}$, —$R^{17}$, —$X^3OR^{17}$, —$X^3SR^{17}$, —$X^3S(O)R^{17}$, —$X^3S(O)_2R^{17}$, —$X^3C(O)R^{17}$, —$X^3C(O)OR^{17}$, —$X^3NR^{15}R^{17}$, —$X^3NR^{15}R^{15}$, —$X^3NR^{15}C(O)OR^{17}$, —$X^3C(O)NR^{15}R^{17}$, —$X^3S(O)_2NR^{15}R^{17}$, —$X^3NR^{15}C(O)NR^{15}R^{17}$ or —$X^3NR^{15}C(NR^{15})NR^{15}R^{17}$, wherein $X^3$ and $R^{15}$ are as defined above and $R^{17}$ is $(C_{3-12})$cycloalkyl$(C_{0-3})$alkyl, hetero$(C_{5-12})$cycloalkyl$(C_{0-3})$alkyl, $(C_{6-12})$aryl$(C_{0-3})$alkyl, hetero$(C_{5-12})$aryl$(C_{0-3})$alkyl, $(C_{9-12})$bicycloaryl$(C_{0-3})$alkyl or hetero$(C_{8-12})$bicycloaryl$(C_{0-3})$alkyl and within $R^{17}$ said cycloalkyl, heterocycloalkyl, aryl, heteroaryl, bicycloaryl or heterobicycloaryl ring may be substituted with —$R^{18}$, —$X^3OR^{18}$, —$X^3SR^{18}$, —$X^3S(O)R^{18}$, —$X^3S(O)_2R^{18}$, —$X^3C(O)R^{18}$, —$X^3C(O)OR^{18}$, —$X^3NR^{15}R^{18}$, —$X^3NR^{15}C(O)OR^{18}$, —$X^3C(O)NR^{15}R^{18}$, —$X^3S(O)_2NR^{15}R^{18}$, —$X^3NR^{15}C(O)NR^{15}R^{18}$ or —$X^3NR^{15}C(NR^{15})NR^{15}R^{18}$, wherein $X^3$ and $R^{15}$ are as defined above and $R^{18}$ is $(C_{3-12})$cycloalkyl$(C_{0-3})$alkyl, hetero$(C_{5-12})$cycloalkyl$(C_{0-3})$alkyl, $(C_{6-12})$aryl$(C_{0-3})$alkyl, hetero$(C_{5-12})$aryl$(C_{0-3})$alkyl, $(C_{9-12})$bicycloaryl$(C_{0-3})$alkyl or hetero$(C_{8-12})$bicycloaryl$(C_{0-3})$alkyl; with the proviso that only one $(C_{9-12})$bicycloaryl$(C_{0-3})$alkyl or hetero$(C_{8-12})$bicycloaryl$(C_{0-3})$alkyl is present within $R^6$, or a pharmaceutically acceptable salt thereof.

2. The compound of claim 1 in which:

$R^2$ is hydrogen;

$R^1$ is —$R^8$, —$X^2OR^8$, —$X^2C(O)R^8$, —$X^2C(OR^7)R^7R^8$, —$X^2NR^7R^8$ or —$X^2NR^7C(O)OR^8$ wherein $X^2$ is $(C_{1-6})$alkylene; $R^7$ is hydrogen or $(C_{1-6})$alkyl; $R^8$ is hydrogen, $(C_{1-6})$alkyl, $(C_{3-12})$cycloalkyl$(C_{0-3})$alkyl, hetero$(C_{5-12})$cycloalkyl$(C_{0-3})$alkyl, $(C_{6-12})$aryl$(C_{0-3})$alkyl or hetero$(C_{5-12})$aryl$(C_{0-3})$alkyl; wherein within $R^8$ said cycloalkyl, heterocycloalkyl, aryl or heteroaryl ring may be substituted with halo, —$R^9$, —$X^3OR^9$, —$X^3C(O)R^9$, —$X^3C(OR^9)R^9$, —$X^3NR^9R^{10}$ or —$X^3NR^9C(O)OR^9$; wherein $X^3$ is a bond or $(C_{1-6})$alkylene, $R^9$ is hydrogen or $(C_{1-6})$alkyl and $R^{10}$ is cycloalkyl;

$R^3$ is —$R^{11}$, —$X^3NR^{11}R^{12}$ or —$X^3NR^{12}C(O)OR^{11}$ where $R^{11}$ is hydrogen, $(C_{1-6})$alkyl, halo$(C_{1-6})$alkyl, $(C_{3-12})$cycloalkyl$(C_{0-3})$alkyl, hetero$(C_{5-12})$cycloalkyl-$(C_{0-3})$alkyl, $(C_{6-12})$aryl$(C_{0-3})$alkyl, hetero$(C_{5-12})$aryl$(C_{0-3})$alkyl, $(C_{9-12})$bicycloaryl$(C_{0-3})$alkyl or hetero$(C_{8-12})$bicycloaryl$(C_{0-3})$alkyl;

$R^4$ is hydrogen or $(C_{1-6})$alkyl;

$R^5$ is $(C_{1-6})$alkyl or $(C_{3-12})$cycloalkyl$(C_{0-3})$alkyl; or $R^4$ and $R^5$ together with the carbon atom to which $R^4$ and $R^5$ are attached form $(C_{3-7})$cycloalkylene;

$R^6$ is hydrogen or —$X^4X^5R^{13}$, wherein $X^4$ is —$C(O)$—, $X^5$ is a bond, —O— or —$NR^{12}$—, wherein $R^{12}$ is as defined above, and $R^{13}$ is $(C_{1-6})$alkyl or —$R^{14}$ wherein $R^{14}$ is $(C_{3-12})$cycloalkyl$(C_{0-3})$alkyl, hetero$(C_{5-12})$cycloalkyl$(C_{0-3})$alkyl, $(C_{6-12})$aryl$(C_{0-3})$alkyl, hetero$(C_{5-12})$aryl$(C_{0-3})$alkyl, $(C_{9-12})$bicycloaryl$(C_{0-3})$alkyl or hetero$(C_{8-12})$bicycloaryl$(C_{0-3})$alkyl; and within $R^{14}$ said cycloalkyl, heterocycloalkyl, aryl, heteroaryl, bicycloaryl or heterobicycloaryl ring may be substituted with —$OCF_3$, —$CF_3$, —OH, halo, —$R^{16}$, —$X^3OR^{16}$, —$X^3OR^{15}$, —$X^3C(O)R^{15}$, —$R^{15}$, —$X^3C(O)R^{16}$, —$X^3C(O)OR^{15}$, —$X^3NR^{15}R^{15}$, —$X^3NR^{15}C(O)OR^{15}$, wherein $X^3$ and $R^{15}$ are as defined above and $R^{16}$ is $(C_{3-12})$cycloalkyl$(C_{0-3})$alkyl, hetero$(C_{5-12})$cycloalkyl$(C_{0-3})$alkyl, $(C_{6-12})$aryl$(C_{0-3})$alkyl or hetero$(C_{5-12})$aryl$(C_{0-3})$alkyl, and within $R^{16}$ said cycloalkyl, heterocycloalkyl, aryl or heteroaryl ring may be substituted with —$R^{15}$, —$R^{17}$, —$X^3NR^{15}R^{17}$, or —$X^3NR^{15}R^{15}$ wherein $X^3$ and $R^{15}$ are as defined above and $R^{17}$ is $(C_{3-12})$cycloalkyl$(C_{0-3})$alkyl, hetero$(C_{5-12})$cycloalkyl$(C_{0-3})$alkyl, $(C_{6-12})$aryl$(C_{0-3})$alkyl or hetero$(C_{5-12})$aryl$(C_{0-3})$alkyl.

3. The compound of claim 1 wherein $R^1$ is 4-methoxyphenyl, 3-methoxyphenyl, 2-methoxyphenyl, 4-chlorophenyl, 3-chlorophenyl, 2-chlorophenyl, 4-hydroxyphenyl, 2-acetyl-phenyl, 2-(1-hydroxyethyl)-phenyl, 2-phenylaminoethyl, pyridin-4-ylphenyl, pyridin-3-yl-phenyl, pyridin-2-ylphenyl, 1H-imidazol-2-yl, piperidin-4-yl or 1-methyl-piperidin-4-yl; and $R^2$ is hydrogen.

4. The compound of claim 3 in which $R^3$ is hydrogen, phenethyl, 4-amino-butyl, butyl or 4-benzyloxycarbonylaminobutyl.

5. The compound of claim 4 in which $R^5$ is isobutyl, sec-butyl or cyclohexylmethyl; and $R^4$ is hydrogen, or $R^4$ and $R^5$ together with the carbon atom to which $R^4$ and $R^5$ are attached form cyclohexyl.

6. The compound of claim 5 in which $R^6$ is selected from the group consisting of benzoyl, morpholin-4-ylcarbonyl, acetyl, furan-3-ylcarbonyl, 2-methoxybenzoyl, 3-methoxybenzoyl, naphthalen-2-ylcarbonyl, benzo[1,3]dioxol-5-ylcarbonyl, 3-pyridin-3-ylacryloyl, benzofuran-2-ylcarbonyl, furan-2-ylcarbonyl, tert-butoxycarbonyl, biphenyl-4-carbonyl, quinolin-2-ylcarbonyl, quinolin-3-ylcarbonyl, 3-acetylbenzoyl, 4-phenoxybenzoyl, 3-hydroxybenzoyl, 4-hydroxybenzoyl, pyridin-3-ylcarbonyl, 3-(tert-butoxycarbonylaminomethyl)benzoyl, 4-carbonylpiperazin-1-ylcarboxylic acid tert-butyl ester, 4-carbonylpiperazin-1-ylcarboxylic acid ethyl ester, 4-(furan-2-ylcarbonyl)piperazin-1-ylcarbonyl, pyridin-4-ylcarbonyl, 1-oxypyridin-4-ylcarbonyl, 1-oxypyridin-3-ylcarbonyl, thiophen-2-ylcarbonyl, thiophen-3-ylcarbonyl, 4-benzoylbenzoyl, 5-methylthiophen-2-ylcarbonyl, 3-chlorothiophen-2-ylcarbonyl, 3-bromothiophen-2-ylcarbonyl, 4-chlorobenzoyl, 3-flouro-4-methoxybenzoyl, 4-methoxy-benzoyl, 4-triflouromethoxybenzoyl, 3,4-diflourobenzoyl, 4-fluorobenzoyl, 3,4-dimethoxy-benzoyl, 3-methylbenzoyl, 4-bromobenzoyl, 4-triflouromethylbenzoyl, 3-benzoylbenzoyl, cyclopentanecarbonyl, benzo[b]thiophen-2-ylcarbonyl, 3-chlorobenzo[b]thiophen-2-ylcarbonyl, formamylmethyl ester, 4-methylpentanoyl, formamylisobutyl ester, formamylmonoallyl ester, formamylisopropyl ester, N,N-dimethylformamyl, N-isopropylformamyl, N-pyridin-4-ylformamyl, N-pyridin-3-ylformamyl, 3-phenylacryloyl, 1H-indol-5-ylcarbonyl, pyridin-2-ylcarbonyl, pyrazin-2-ylcarbonyl, 3-hydroxypyridin-2-ylcarbonyl, 2-aminopyridin-3-ylcarbonyl, 2-hydroxypyridin-3-ylcarbonyl, 6-aminopyridin-3-ylcarbonyl, 6-hydroxypyridin-3-ylcarbonyl, pyridazin-4-ylcarbonyl, 3-phenoxybenzoyl, 1-oxo-1,3-dihydroisoindol-2-ylcarbonyl, 4-(4-methylpiperazin-1-yl)benzoyl, 4-morpholin-4-ylbenzoyl, 4-[2-(pyridin-3-ylamino)thiazol-4-yl]-benzoyl, 4-(2-dimethylaminothiazol-4-yl)benzoyl, quinolin-6-ylcarbonyl, 4-dimethylamino-benzoyl, 3-aminobenzoyl, 4-methylpiperazin-1-ylcarbonyl and benzylacetyl.

7. The compound of claim 1 wherein:
$R^1$ is 4-methoxyphenyl, 3-acetylphenyl, 3-(1-hydroxyethyl)-phenyl, 2-(phenylamino)ethyl or 4-hydroxyphenyl;

$R^2$ is hydrogen;
$R^3$ is hydrogen, 2-phenethyl, 4-aminobutyl, or 4-benzyloxycarbonylaminobutyl;
$R^4$ is hydrogen;
$R^5$ is isobutyl, sec-butyl or cyclohexylmethyl; or $R^4$ and $R^5$ together with the carbon atom to which $R^4$ and $R^5$ are attached form cyclohexyl; and
$R^6$ is selected from the group consisting of acetyl, pyridin-3-ylcarbonyl, 3-(tert-butoxycarbonylamino)benzoyl, pyridin-4-ylcarbonyl, 1H-indol-5-ylcarbonyl, benzyloxycarbonyl, 3-aminobenzoyl, 4-methylpiperazin-1-ylcarbonyl, quinolin-6-ylcarbonyl, 4-[2-(pyridin-3-ylamino)thiazol-4-yl]benzoyl, 4-dimethylaminobenzoyl, morpholin-4-ylcarbonyl, 4-(2-dimethylaminothiazol-4-yl)benzoyl, tert-butoxycarbonyl, 4-(4-ethylpiperazin-1-yl)-benzoyl, and 4-[2-(4-methylpiperazin-1-yl)thiazol-4-yl]benzoyl.

8. The compound of claim 1 in which $R^6$ is selected from the group consisting of benzoyl, morpholin-4-ylcarbonyl, acetyl, furan-3-ylcarbonyl, 2-methoxybenzoyl, 3-methoxybenzoyl, naphthalen-2-ylcarbonyl, benzo[1,3]dioxol-5-ylcarbonyl, 3-pyridin-3-ylacryloyl, benzofuran-2-ylcarbonyl, furan-2-ylcarbonyl, tert-butoxycarbonyl, biphenyl-4-carbonyl, quinolin-2-ylcarbonyl, quinolin-3-ylcarbonyl, 3-acetylbenzoyl, 4-phenoxybenzoyl, 3-hydroxybenzoyl, 4-hydroxybenzoyl, pyridin-3-ylcarbonyl, 3-(tert-butoxycarbonylaminomethyl)benzoyl, 4-carbonylpiperazin-1-ylcarboxylic acid tert-butyl ester, 4-carbonylpiperazin-1-ylcarboxylic acid ethyl ester, 4-(furan-2-ylcarbonyl)piperazin-1-ylcarbonyl, pyridin-4-ylcarbonyl, 1-oxypyridin-4-ylcarbonyl, 1-oxypyridin-3-ylcarbonyl, thiophen-2-ylcarbonyl, thiophen-3-ylcarbonyl, 4-benzoylbenzoyl, 5-methylthiophen-2-ylcarbonyl, 3-chlorothiophen-2-ylcarbonyl, 3-bromothiophen-2-ylcarbonyl, 4-chlorobenzoyl, 3-flouro-4-methoxybenzoyl, 4-methoxy-benzoyl, 4-triflouromethoxybenzoyl, 3,4-diflourobenzoyl, 4-fluorobenzoyl, 3,4-dimethoxy-benzoyl, 3-methylbenzoyl, 4-bromobenzoyl, 4-triflouromethylbenzoyl, 3-benzoylbenzoyl, cyclopentanecarbonyl, benzo[b]thiophen-2-ylcarbonyl, 3-chlorobenzo[b]thiophen-2-ylcarbonyl, formamylmethyl ester, 4-methylpentanoyl, formamylisobutyl ester, formamylmonoallyl ester, formamylisopropyl ester, N,N-dimethylformamyl, N-isopropylformamyl, N-pyridin-4-ylformamyl, N-pyridin-3-ylformamyl, 3-phenylacryloyl, 1H-indol-5-ylcarbonyl, pyridin-2-ylcarbonyl, pyrazin-2-ylcarbonyl, 3-hydroxypyridin-2-ylcarbonyl, 2-aminopyridin-3-ylcarbonyl, 2-hydroxypyridin-3-ylcarbonyl, 6-aminopyridin-3-ylcarbonyl, 6-hydroxypyridin-3-ylcarbonyl, pyridazin-4-ylcarbonyl, 3-phenoxybenzoyl, 1-oxo-1,3-dihydroisoindol-2-ylcarbonyl, 4-(4-methylpiperazin-1-yl)benzoyl, 4-morpholin-4-ylbenzoyl, 4-[2-(pyridin-3-ylamino)thiazol-4-yl]-benzoyl, 3-aminobenzoyl, 4-methylpiperazin-1-ylcarbonyl and benzylacetyl.

9. A compound selected from the group consisting of:
benzyl (1S-{1S-[(4-methoxyphenylsulfamoyl)-methyl]-3-phenyl-propylcarbamoyl}-3-methyl-butyl)-carbamate;
benzyl (1S-{1S-[(4-methoxyphenylsulfamoyl)-methyl]-3-phenyl-propylcarbamoyl}-2-methyl-butyl)-carbamate;
tert-butyl (1S-{1S-[(4-methoxyphenylsulfamoyl)-methyl]-3-phenyl-propylcarbamoyl}-3-methyl-butyl)-carbamate;

benzyl (1S-{1S-[(3-acetyl-phenylsulfamoyl)-methyl]-3-phenyl-propylcarbamoyl}-3-methyl-butyl)-carbamate;

N-{1S-[1S-(4-methoxyphenylsulfamoylmethyl)-3-phenylpropylcarbamoyl]-2-methylbutyl}-4-methylpiperazine-1-carboxamide;

benzyl {1S-[2-(4-methoxyphenylsulfamoyl)-ethylcarbamoyl]-2-methyl-butyl}-carbamate;

(2-cyclohexyl-1S-{3-phenyl-1S-[(2-phenylaminoethylsulfamoyl)-methyl]-propylcarbamoyl}ethyl)-carbamic acid tert-butyl ester;

4-dimethylamino-N-(1S-{1S-[(4-methoxyphenylsulfamoyl)methyl]-3-phenyl-propylcarbamoyl}-3-methylbutyl)-benzamide;

quinoline-6-carboxylic acid (1S-{1S-[(4-methoxyphenylsulfamoyl)methyl]-3-phenyl-propylcarbamoyl}-3-methyl-butyl)-amide;

morpholine-4-carboxylic acid (2-cyclohexyl-1S-{3-phenyl-1S-[(2-phenylamino-ethylsulfamoyl)methyl]-propylcarbamoyl}ethyl)amide;

4-(2-dimethylaminothiazol-4-yl)-N-{1S-[2-(4-methoxyphenylsulfamoyl)-ethylcarbamoyl]-3-methyl-butyl}benzamide;

2S-acetylamino-3-cyclohexyl-N-{1-[(4-methoxyphenylsulfamoyl)-methyl]-3-phenyl-propyl}propionamide;

2R-acetylamino-3-cyclohexyl-N-{1-[(4-methoxyphenylsulfamoyl)methyl]-3-phenyl-propyl}propionamide;

2RS-acetylamino-3-cyclohexyl-N-{1-[(4-hydroxyphenylsulfamoyl)methyl]-3-phenyl-propyl}-propionamide;

benzyl [6-(4-methoxyphenylsulfamoyl)-5S-(4-methyl-2S-{4-[2-(pyridin-3-ylamino)thiazol-4-yl]-benzoylamino}pentanoylamino)hexyl]carbamate;

N-(1S-{1S-[(4-methoxyphenylsulfamoyl)methyl]-3-phenylpropylcarbamoyl}-3-methyl-butyl)-4-[2-(pyridin-3-ylamino)thiazol-4-yl]-benzamide;

N-(1S-{1S-[(4-methoxyphenylsulfamoyl)methyl]-3-phenyl-propylcarbamoyl}-3-methyl-butyl)-nicotinamide;

N-(1S-{1S-[(4-methoxyphenylsulfamoyl)-methyl]-3-phenylpropylcarbamoyl}-3-methyl-butyl)-isonicotinamide;

N-{1-[1-(4-methoxyphenylsulfamoylmethyl)-3-phenylpropylcarbamoyl]-3-methylbutyl}-1H-indole-5-carboxamide;

tert-butyl [3-(1S-{1S-[(4-methoxyphenylsulfamoyl)-methyl]-3-phenylpropylcarbamoyl}-3-methyl-butylcarbamoyl)phenyl]-carbamate;

3-amino-N-(1S-{1S-[(4-methoxyphenylsulfamoyl)-methyl]-3-phenylpropylcarbamoyl}-3-methyl-butyl)-benzamide;

N-(1S-{5-amino-1S-[(4-methoxyphenylsulfamoyl)methyl]pentylcarbamoyl}-3-methyl-butyl)-4-[2-(pyridin-3-ylamino)-thiazol-4-yl]-benzamide;

benzyl [1S-(1S-{[3-(1-hydroxyethyl)phenylsulfamoyl]methyl}-3-phenylpropyl-carbamoyl)-3-methylbutyl]-carbamate;

morpholine 4-carboxylic acid (1S-{5-amino-1S-[(4-methoxyphenylsulfamoyl)methyl]-pentylcarbamoyl}-2-phenylmethanesulfonylethyl)amide;

(5S-[2S-(morpholin-4-ylcarbonyl)amino]-3-phenylmethanesulfonylpropionylamino}-6-phenylsulfamoylhexyl)carbamic acid benzyl ester;

morpholine 4-carboxylic acid (1S-{1S-[(4-methoxyphenylsulfamoyl)methyl]-3-phenylpropylcarbamoyl}-2-phenylmethanesulfonylethyl)amide;

N-(1S-{1S-[(4-methoxy-phenylsulfamoyl)-methyl]-3-phenyl-propylcarbamoyl}-cyclohexyl)-4-[2-(4-methylpiperazin-1-yl)thiazol-4-yl]benzamide; and N-(1S-{1S-[(4-methoxy-phenylsulfamoyl)-methyl]-3-phenyl-propylcarbamoyl}-cyclohexyl)-4-(4-propylpiperazin-1-yl)-benzamide; or a pharmaceutically acceptable salt thereof.

10. A pharmaceutical composition comprising a therapeutically effective amount of a compound of claim 1 in combination with one or more pharmaceutically acceptable excipient(s).

11. The composition of claim 10 which further comprises one or more active ingredient(s) selected from a therapeutically effective amount of a bisphosphonic acid or acid ester thereof or a pharmaceutically acceptable salt thereof.

12. The composition of claim 11 wherein the bisphosphonic acid is selected from the group consisting of 1,1-dichloromethylene-1,1-diphosphonic acid, 1-hydroxy-3-pyrrolidin-1-ylpropylidene-1,1-bisphosphonic acid, 1-hydroxyethylidene-1,1-diphosphonic acid, 1-hydroxy-3-(N-methyl-N-pentylamino)propylidene-1,1-bisphosphonic acid, 6-amino-1-hydroxyhexylidene-1,1-bisphosphonic acid, 3-(dimethylamino)-1-hydroxypropylidene-1,1-bisphosphonic acid, 3-amino-1-hydroxypropylidene-1,1-bisphosphonic acid, 2-pyrid-2-ylethylidene-1,1-bisphosphonic acid, 1-hydroxy-2-pyrid-3-ylethylidene-1,1-bisphosphonic acid, 4-chlorophenylthiomethylenebisphosphonic acid and 1-hydroxy-2-(1H-imidazol-1-yl)ethylidene-1,1-bisphosphonic acid or acid ester thereof or a pharmaceutically acceptable salt thereof.

13. The composition of claim 11 wherein the bisphosphonic acid is 1,1-dichloromethylene-1,1-diphosphonic acid or a pharmaceutically acceptable salt thereof.

14. The composition of claim 11 which comprises 1,1-dichloromethylene-1,1-diphosphonate monosodium trihydrate.

15. A method for treating a disease in an animal in which inhibition of a cysteine protease can inhibit or ameliorate the pathology and/or symptomatology of the disease, which method comprises administering to the animal a therapeutically effective amount of compound of claim 1 or a pharmaceutically acceptable salt thereof.

16. The method of claim 15 wherein the disease is osteoporosis.

17. The method of claim 16 wherein the animal is a human.

18. The method of claim 17 wherein the human is a post-menopausal woman.

19. The method of claim 18 wherein the cysteine protease activity is cathepsin K activity.

20. A process for preparing a compound of claim 1 comprising:

(A) reacting a compound of formula 4

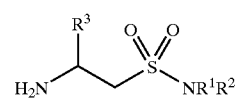

4 where $R^1$, $R^2$, and $R^3$ are as defined in claim 1 above; with a compound of formula 5:

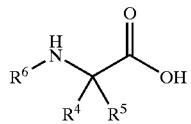

where $R^6$ is as defined in claim 1 above; or (B) reacting a compound of formula 7:

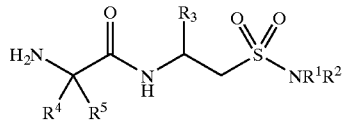

with an acid compound of formula $R^6OH$ or an acid derivative thereof, wherein $R^1$, $R^2$, $R^3$, $R^4$, $R^5$ and $R^6$ are as defined in claim 1 above; and (C) optionally converting a compound of Formula I into a pharmaceutically acceptable salt;

(D) optionally converting a salt form of a compound of Formula I to non-salt form;

(E) optionally converting an unoxidized form of a compound of Formula I into a pharmaceutically acceptable N-oxide;

(F) optionally converting an N-oxide form of a compound of Formula I its unoxidized form;

(G) optionally resolving an individual isomer of a compound of Formula I from a mixture of isomers;

(H) optionally converting a non-derivatized compound of Formula I into a pharmaceutically prodrug derivative;

(I) optionally converting a prodrug derivative of a compound of Formula I to its non-derivatized form; and (J) optionally modifying any of the $R^1$, $R^2$, $R^3$, $R^4$, $R^5$ and $R^6$ groups.

* * * * *